United States Patent
Cheng et al.

(10) Patent No.: US 12,091,406 B2
(45) Date of Patent: *Sep. 17, 2024

(54) LYSINE ACETYLTRANSFERASE 6A (KAT6A) INHIBITORS AND USES THEREOF

(71) Applicant: Insilico Medicine IP Limited, Hong Kong (HK)

(72) Inventors: Xin Cheng, Shanghai (CN); Luoheng Qin, Shanghai (CN); Feng Ren, Shanghai (CN)

(73) Assignee: INSILICO MEDICINE IP LIMITED, Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 18/507,566

(22) Filed: Nov. 13, 2023

(65) Prior Publication Data

US 2024/0150374 A1    May 9, 2024

Related U.S. Application Data

(63) Continuation of application No. PCT/CN2022/131893, filed on Nov. 15, 2022.

(30) Foreign Application Priority Data

Nov. 16, 2021  (WO) ............... PCT/CN2021/130956
Mar. 8, 2022   (WO) ............... PCT/CN2022/079709
Oct. 21, 2022  (WO) ............... PCT/CN2022/126722

(51) Int. Cl.
| | | |
|---|---|---|
| *C07D 413/14* | (2006.01) |
| *C07D 413/06* | (2006.01) |
| *C07D 413/12* | (2006.01) |
| *C07D 417/06* | (2006.01) |
| *C07D 417/12* | (2006.01) |
| *C07D 417/14* | (2006.01) |
| *C07D 498/04* | (2006.01) |

(52) U.S. Cl.
CPC ......... *C07D 413/14* (2013.01); *C07D 413/06* (2013.01); *C07D 413/12* (2013.01); *C07D 417/06* (2013.01); *C07D 417/12* (2013.01); *C07D 417/14* (2013.01); *C07D 498/04* (2013.01)

(58) Field of Classification Search
CPC .. C07D 498/04; C07D 413/06; C07D 413/12; C07D 413/14; C07D 417/12; C07D 417/14
USPC .................................................... 514/252.06
See application file for complete search history.

(56) References Cited

U.S. PATENT DOCUMENTS

2024/0109880 A1    4/2024   Cheng et al.

FOREIGN PATENT DOCUMENTS

| WO | WO-2009012312 A1 | 1/2009 |
| WO | WO-2014144545 A2 | 9/2014 |
| WO | WO-2016198507 A1 | 12/2016 |
| WO | WO-2018102419 A1 | 6/2018 |
| WO | WO-2019108824 A1 | 6/2019 |
| WO | WO-2019243491 A1 | 12/2019 |
| WO | WO-2020002587 A1 | 1/2020 |
| WO | WO-2020216701 A1 | 10/2020 |
| WO | WO-2020254946 A1 | 12/2020 |
| WO | WO-2020254989 A1 | 12/2020 |
| WO | WO-2022013369 A1 | 1/2022 |
| WO | WO-2022081807 A1 | 4/2022 |
| WO | WO-2022081842 A1 | 4/2022 |
| WO | WO-2022243983 A1 | 11/2022 |
| WO | WO-2023280182 A1 | 1/2023 |
| WO | WO-2023016484 A1 | 2/2023 |
| WO | WO-2023088233 A1 | 5/2023 |
| WO | WO-2023114710 A1 | 6/2023 |
| WO | WO-2023192817 A1 | 10/2023 |

OTHER PUBLICATIONS

Co-pending U.S. Appl. No. 18/486,369, inventors Cheng; Xin et al., filed Oct. 13, 2023.
Liang et al. Identification of MYST3 as a novel epigenetic activator of ERα frequently amplified in breast cancer. Oncogene 36(20):2910-2918 (2017).
PCT/CN2022/131893 International Search Report and Written Opinion dated Dec. 28, 2022.

*Primary Examiner* — Kahsay Habte
(74) *Attorney, Agent, or Firm* — WILSON SONSINI GOODRICH & ROSATI

(57) ABSTRACT

Described herein are KAT6A inhibitors of Formula (Ia) and pharmaceutical compositions comprising said inhibitors. The subject compounds of Formula (Ia) and compositions are useful for the treatment of a disease or disorder associated with KAT6A

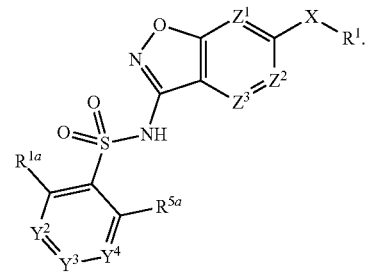

20 Claims, No Drawings

LYSINE ACETYLTRANSFERASE 6A (KAT6A) INHIBITORS AND USES THEREOF

CROSS REFERENCE TO RELATED APPLICATIONS

This patent application is a continuation of International Application No. PCT/CN2022/131893, filed Nov. 15, 2022, which claims the benefit of International Application No. PCT/CN2021/130956, filed Nov. 16, 2021, International Application No. PCT/CN2022/079709, filed Mar. 8, 2022, and International Application No. PCT/CN2022/126722, filed Oct. 21, 2022, each of which is incorporated herein by reference in its entirety.

BACKGROUND

Lysine acetyltransferase 6A (KAT6A) belongs to the MYST family of acetyltransferases and was first discovered approximately 25 years ago. KAT6A controls fundamental cellular processes, including gene transcription, cellular senescence, cardiac septum development, memory T-cell diversity, and maintenance of normal hematopoietic stem cells. Dysregulation of KAT6A acetyltransferase activity or aberrant expression of KAT6A has been associated with oncogenic function in a number of cancers, including leukemia, glioma, endometrial serous carcinoma, and breast cancer. As such, compounds that inhibit KAT6A are potential agents for treating a variety of cancers.

SUMMARY

In one aspect disclosed herein is a compound of Formula (I), or a pharmaceutically acceptable salt or solvate thereof:

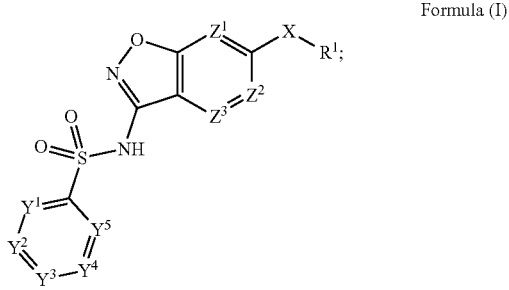

Formula (I)

wherein:
$Y^1$ is $CR^{1a}$ or N;
$Y^2$ is $CR^{2a}$ or N;
$Y^3$ is $CR^{3a}$ or N;
$Y^4$ is $CR^{4a}$ or N;
$Y^5$ is $CR^{5a}$ or N;
$Z^1$ is $CR^{1b}$ or N;
$Z^2$ is $CR^{2b}$ or N;
$Z^3$ is $CR^{3b}$ or N; wherein at least one of $Y^1$, $Y^2$, $Y^3$, $Y^4$, $Y^5$, $Z^1$, $Z^2$, and $Z^3$ is N;
X is selected from —$C(R^6)(R^{6a})$—, —O—, and —$N(R^7)$—;
$R^1$ is $C_{1-9}$heteroaryl optionally substituted with one, two, or three groups selected from $R^{15a}$;
$R^{1a}$, $R^{2a}$, $R^{3a}$, $R^{4a}$, $R^{5a}$, $R^{5b}$, $R^{2b}$, and $R^{3b}$ are independently selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15b}$;

$R^6$ and $R^{6a}$ are independently selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

$R^7$ is selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-4}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{10}$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-4}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; and each $R^{15a}$ and each $R^{15b}$ are each independently selected from halogen, oxo, —CN, $C_{1-6}$alkyl, $C_{1-6}$haloalkyl, $C_{2-6}$alkenyl, $C_{2-6}$alkynyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(=O)(=NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, —CH$_2$—C$_{3-10}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, —CH$_2$—C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^2$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(=O)(=NH)N(R$^{10}$)(R$^{11}$), —CH$_2$C(O)N(R$^{10}$)(R$^{11}$), —CH$_2$N(R$^{12}$)C(O)R$^3$, —CH$_2$S(O)$_2$R$^{13}$, and —CH$_2$S(O)$_2$N(R$^{10}$)(R$^{11}$).

In some embodiments, provided herein is a compound of Formula (I'), or a pharmaceutically acceptable salt or solvate thereof

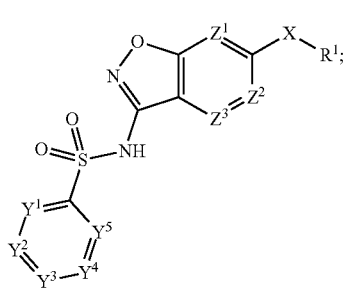

Formula (I')

wherein:
Y$^1$ is CR$^{1a}$ or N;
Y$^2$ is CR$^{2a}$ or N;
Y$^3$ is CR$^{3a}$ or N;
Y$^4$ is CR$^{4a}$ or N;
Y$^5$ is CR$^{5a}$ or N;
Z$^1$ is CR$^{1b}$ or N;
Z$^2$ is CR$^{2b}$ or N;
Z$^3$ is CR$^{3b}$ or N;
X is —O— or —S—; or
X is selected from —C(R$^6$)(R$^{6a}$)— and —N(R$^7$)—, and wherein at least one of Y$^1$, Y$^2$, Y$^3$, Y$^4$, Y$^5$, Z$^1$, Z$^2$, and Z$^3$ is N;
R$^1$ is C$_{1-9}$heteroaryl optionally substituted with one, two, or three groups selected from R$^{15a}$;
R$^{1a}$, R$^{2a}$, R$^{3a}$, R$^{4a}$, R$^{5a}$, R$^{1b}$, R$^{2b}$, and R$^{3b}$ are independently selected from hydrogen, halogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(=O)(=NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15b}$;

each R$^{10}$ is independently selected from hydrogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-4}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

each R$^{11}$ is independently selected from hydrogen, C$_{1-6}$alkyl, and C$_{1-6}$haloalkyl;

each R$^{12}$ is independently selected from hydrogen, C$_{1-6}$alkyl, and C$_{1-6}$haloalkyl;

each R$^{13}$ is independently selected C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-4}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl; and each R$^{15a}$ and each R$^{15b}$ are each independently selected from halogen, oxo, —CN, C$_{1-6}$alkyl, C$_{1-6}$haloalkyl, C$_{2-6}$alkenyl, C$_{2-6}$alkynyl, C$_{3-10}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, C$_{1-9}$heteroaryl, —CH$_2$—C$_{1-9}$heteroaryl, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(=O)(=NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, —CH$_2$—C$_{3-10}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, —CH$_2$—C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(=O)(=NH)N(R$^{10}$)(R$^{11}$), —CH$_2$C(O)N(R$^{10}$)(R$^{11}$), —CH$_2$N(R$^{12}$)C(O)R.

In some embodiments, provided herein is a compound of Formula (I'), or a pharmaceutically acceptable salt or solvate thereof,

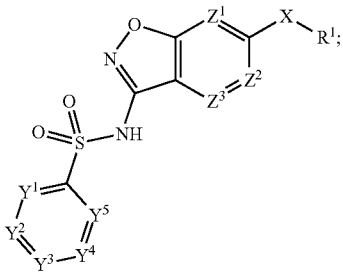

Formula (I')

wherein:
Y$^1$ is CR$^{1a}$ or N;
Y$^2$ is CR$^{2a}$ or N;
Y$^3$ is CR$^{3a}$ or N;
Y$^4$ is CR$^{4a}$ or N;
Y$^5$ is CR$^{5a}$ or N;
Z$^1$ is CR$^{1b}$ or N;
Z$^2$ is CR$^{2b}$ or N;
Z$^3$ is CR$^{3b}$ or N;
X is —O—;
R$^1$ is C$_{1-9}$heteroaryl optionally substituted with one, two, or three groups selected from R$^{15a}$;
R$^{1a}$, R$^{2a}$, R$^{3a}$, R$^{4a}$, R$^{5a}$, R$^{1b}$, R$^{2b}$, and R$^{3b}$ are independently selected from hydrogen, halogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^3$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(=O)(=NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15b}$;
each R$^{10}$ is independently selected from hydrogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;
each R$^{11}$ is independently selected from hydrogen, C$_{1-6}$alkyl, and C$_{1-6}$haloalkyl;
each R$^{12}$ is independently selected from hydrogen, C$_{1-6}$alkyl, and C$_{1-6}$haloalkyl;
each R$^{13}$ is independently selected C$_{1-6}$alkyl, C$_{2-4}$alkenyl, C$_{2-4}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl; and
each R$^{15a}$ and each R$^{15b}$ are each independently selected from halogen, oxo, —CN, C$_{1-6}$alkyl, C$_{1-6}$haloalkyl, C$_{2-6}$alkenyl, C$_{2-6}$alkynyl, C$_{3-10}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, C$_{1-9}$heteroaryl, —CH$_2$—C$_{1-9}$heteroaryl, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(=O)(=NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, —CH$_2$—C$_{3-10}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, —CH$_2$—C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(=O)(=NH)N(R$^{10}$)(R$^{11}$), —CH$_2$C(O)N(R$^{10}$)(R$^{11}$), —CH$_2$N(R$^{12}$)C(O)R$^3$, —CH$_2$S(O)$_2$R$^{13}$, and —CH$_2$S(O)$_2$N(R$^{10}$)(R$^{11}$).

In some embodiments, a compound of Formula (I) or (I'), or a pharmaceutically acceptable salt or solvate thereof, having the structure of Formula (Ia), or a pharmaceutically acceptable salt or solvate thereof:

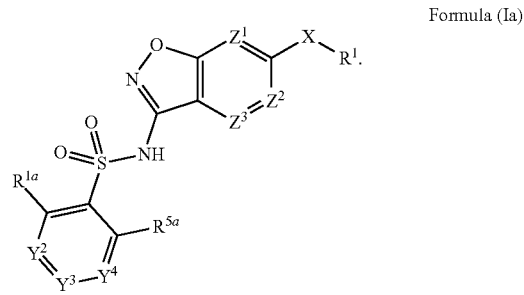

Formula (Ia)

In some embodiments, provided herein is a compound of Formula (I), (I'), or (Ia), or a pharmaceutically acceptable salt or solvate thereof, wherein R$^{1a}$ and R$^{5a}$ are independently selected from hydrogen, halogen, C$_{1-6}$alkyl, C$_{1-6}$haloalkyl, and —OR$^{10}$. In some embodiments, provided herein is a compound of Formula (I), (I'), or (Ia), or a pharmaceutically acceptable salt or solvate thereof, wherein R$^{1a}$ and R$^{5a}$ are independently selected from hydrogen and —OR$^{10}$. In some embodiments, provided herein is a compound of Formula (I), (I'), or (Ia), or a pharmaceutically acceptable salt or solvate thereof, wherein R$^{1a}$ and R$^{5a}$ are —OR$^{10}$. In some embodiments, provided herein is a compound of Formula (I), (I'), or (Ia), or a pharmaceutically acceptable salt or solvate thereof, wherein R$^{10}$ is C$_{1-6}$alkyl. In some embodiments, provided herein is a compound of Formula (I), (I'), or (Ia), or a pharmaceutically acceptable salt or solvate thereof, wherein R$^{10}$ is —CH$_3$. In some embodiments, provided herein is a compound of Formula (I), (I'), or (Ia), or a pharmaceutically acceptable salt or solvate thereof, wherein Y$^2$ is N; Y$^3$ is CR$^{3a}$; and Y$^4$ is CR$^{4a}$. In some embodiments, provided herein is a compound of Formula (I), (I'), or (Ia), or a pharmaceutically acceptable salt or solvate thereof, wherein $Y^2$ is $CR^{2a}$; $Y^3$ is N; and $Y^4$ is $CR^{4a}$. In some embodiments, provided herein is a compound of Formula (I), (I'), or (Ia), or a pharmaceutically acceptable salt or solvate thereof, wherein $Y^2$ is N; $Y^3$ is $CR^{3a}$; and $Y^4$ is N. In some embodiments, provided herein is a compound of Formula (I), (I'), or (Ia), or a pharmaceutically acceptable salt or solvate thereof, wherein $Y^2$ is $CR^{2a}$; $Y^3$ is $CR^{3a}$; and $Y^4$ is $CR^{4a}$. In some embodiments, provided herein is a compound of Formula (I), (I'), or (Ia), or a pharmaceutically acceptable salt or solvate thereof, wherein $Z^1$ is $CR^{1b}$; $Z^2$ is $CR^{2b}$; and $Z^3$ is $CR^{3b}$. In some embodiments, provided herein is a compound of Formula (I), (I'), or (Ia), or a pharmaceutically acceptable salt or solvate thereof, wherein $Z^1$ is N; $Z^2$ is $CR^{2b}$; and $Z^3$ is $CR^{3b}$. In some embodiments, provided herein is a compound of Formula (I), (I'), or (Ia), or a pharmaceutically acceptable salt or solvate thereof, wherein $Z^1$ is $CR^{1b}$; $Z^2$ is N; and $Z^3$ is $CR^{3b}$. In some embodiments, provided herein is a compound of Formula (I), (I'), or (Ia), or a pharmaceutically acceptable salt or solvate thereof, wherein $Z^1$ is $CR^{1b}$; $Z^2$ is $CR^{2b}$; and $Z^3$ is N. In some embodiments, provided herein is a compound of Formula (I), (I'), or (Ia), or a pharmaceutically acceptable salt or solvate thereof, wherein $R^{2a}$, $R^{3a}$, $R^{4a}$, $R^{1b}$, $R^{2b}$, and $R^{3b}$ are independently selected from hydrogen, halogen, $C_{1-6}$alkyl, $C_{1-6}$haloalkyl, and —$OR^{10}$. In some embodiments, provided herein is a compound of Formula (I), (I'), or (Ia), or a pharmaceutically acceptable salt or solvate thereof, wherein $R^{2a}$, $R^{3a}$, $R^{4a}$, $R^{1b}$, $R^{2b}$, and $R^{3b}$ are independently selected from hydrogen, halogen, and $C_{1-6}$alkyl. In some embodiments, provided herein is a compound of Formula (I), (I'), or (Ia), or a pharmaceutically acceptable salt or solvate thereof, wherein $R^{2a}$, $R^{3a}$, $R^{4a}$, $R^{1b}$, $R^{2b}$, and $R^{3b}$ are hydrogen.

In another aspect disclosed herein is a compound of Formula (II), or a pharmaceutically acceptable salt or solvate thereof:

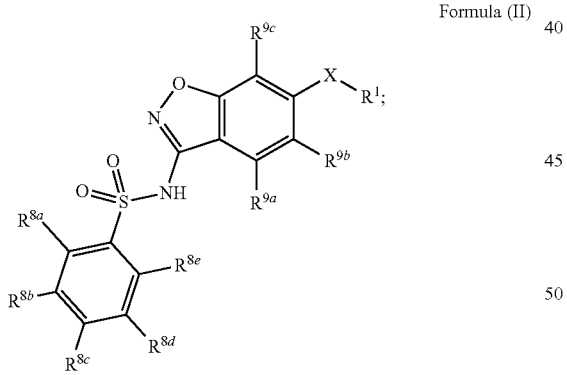

Formula (II)

wherein:

X is selected from —$C(R^6)(R^{6a})$—, —O—, and —$N(R^7)$—;

$R^1$ is $C_{1-9}$heteroaryl optionally substituted with one, two, or three groups selected from $R^{15a}$;

$R^6$ and $R^{6a}$ are independently selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)OR^{13}$, —$N(R^{12})S(O)_2 R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

$R^7$ is selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

$R^{8a}$, $R^{8b}$, $R^{8c}$, $R^{8d}$, $R^{8e}$, $R^{9b}$, and $R^{9c}$ are each independently selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15b}$;

$R^{9a}$ is selected from $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{14}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^2)C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl and $C_{3-6}$cycloalkyl are substituted with one, two, or three groups selected from $R^{15c}$, and wherein $C_{2-6}$alkenyl, $C_{2-6}$alkynyl, $C_{2-9}$heterocycloalkyl, $C_{6-10}$aryl, and $C_{1-9}$heteroaryl are optionally substituted with one, two, or three groups selected from $R^{15d}$; or $R^{9a}$ and $R^{9b}$ are combined to form a $C_{3-6}$cycloalkyl, $C_{2-9}$heterocycloalkyl, or $C_{2-9}$heteroaryl, wherein $C_{3-6}$cycloalkyl, $C_{2-9}$heterocycloalkyl, and $C_{2-9}$heteroaryl are optionally substituted with one, two, or three groups selected from $R^{15e}$; each $R^{10}$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-4}$alkenyl, $C_{2-4}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

$R^{14}$ is independently selected from hydrogen, $C_{1-6}$haloalkyl, $C_{2-6}$alkenyl, $C_{2-6}$alkynyl, $C_{2-9}$heterocycloalkyl, $C_{6-10}$aryl, and $C_{1-9}$heteroaryl, wherein $C_{2-6}$alkenyl, $C_{2-6}$alkynyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; and each $R^{15a}$, each $R^{15b}$, each $R^{15c}$, each $R^{15d}$, and each $R^{15e}$ are each independently selected from halogen, oxo, —CN, $C_{1-6}$alkyl, $C_{1-6}$haloalkyl, $C_{2-6}$alkenyl, $C_{2-6}$alkynyl, $C_{3-10}$cycloalkyl, —CH$_2$—$C_{1-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-9}$heteroaryl, —CH$_2$—$C_{1-9}$heteroaryl, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(=O)(=NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$), wherein $C_{1-6}$alkyl, $C_{2-6}$alkenyl, $C_{2-6}$alkynyl, $C_{3-6}$cycloalkyl, —CH$_2$—$C_{3-10}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, —CH$_2$—$C_{1-9}$heteroaryl, and $C_{1-6}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(=O)(=NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$).

In some embodiments, provided herein is a compound of Formula (II), or a pharmaceutically acceptable salt or solvate thereof, wherein $R^{9b}$ is selected from hydrogen, halogen, and $C_{1-6}$alkyl. In some embodiments, provided herein is a compound of Formula (II), or a pharmaceutically acceptable salt or solvate thereof, wherein $R^{9b}$ is hydrogen. In some embodiments, provided herein is a compound of Formula (II), or a pharmaceutically acceptable salt or solvate thereof, wherein $R^{9a}$ is —OR$^{14}$. In some embodiments, provided herein is a compound of Formula (II), or a pharmaceutically acceptable salt or solvate thereof, wherein $R^{14}$ is $C_{1-6}$haloalkyl. In some embodiments, provided herein is a compound of Formula (II), or a pharmaceutically acceptable salt or solvate thereof, wherein $R^{9a}$ and $R^{9b}$ are combined to form a $C_{3-6}$cycloalkyl, $C_{2-9}$heterocycloalkyl, or $C_{2-9}$heteroaryl, wherein $C_{3-6}$cycloalkyl, $C_{2-9}$heterocycloalkyl, and $C_{2-9}$heteroaryl are optionally substituted with one, two, or three groups selected from $R^{15e}$. In some embodiments, provided herein is a compound of Formula (II), or a pharmaceutically acceptable salt or solvate thereof, wherein $R^{9a}$ and $R^{9b}$ are combined to form a $C_{2-9}$heterocycloalkyl optionally substituted with one, two, or three groups selected from $R^{15e}$. In some embodiments, provided herein is a compound of Formula (II), or a pharmaceutically acceptable salt or solvate thereof, wherein $R^{9a}$ and $R^{9b}$ are combined to form a $C_{2-9}$heterocycloalkyl optionally substituted with one, two, or three groups selected from halogen, $C_{1-6}$alkyl, and $C_{1-6}$haloalkyl.

In some embodiments, provided herein is a compound of Formula (I), (I'), (Ia), or (II), or a pharmaceutically acceptable salt or solvate thereof, wherein X is —C(R$^6$)(R$^{6a}$)—. In some embodiments, provided herein is a compound of Formula (I), (I'), (Ia), or (II), or a pharmaceutically acceptable salt or solvate thereof, wherein $R^6$ and $R^{6a}$ are independently selected from hydrogen, halogen, $C_{1-6}$alkyl, and —OH. In some embodiments, provided herein is a compound of Formula (I), (I'), (Ia), or (II), or a pharmaceutically acceptable salt or solvate thereof, wherein $R^6$ and $R^{6a}$ are hydrogen. In some embodiments, provided herein is a compound of Formula (I), (I'), (Ia), or (II), or a pharmaceutically acceptable salt or solvate thereof, wherein X is —O—.

In another aspect disclosed herein is a compound of Formula (III), or a pharmaceutically acceptable salt or solvate thereof:

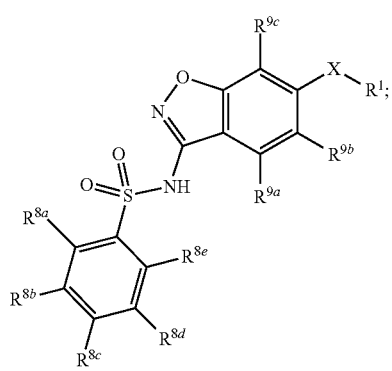

Formula (III)

wherein:
X is selected from —O— and —N(R$^7$)—;
$R^1$ is $C_{1-9}$heteroaryl optionally substituted with one, two, or three groups selected from $R^{15a}$;
$R^7$ is selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;
$R^{8a}$, $R^{8b}$, $R^{8c}$, $R^{8d}$, $R^{8e}$, $R^{9b}$, and $R^{9c}$ are each independently selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^3$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(=O)(=NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15b}$;

R$^{9a}$ is selected from hydrogen, C$_{1-6}$alkyl, C$_{3-6}$cycloalkyl, and —OR$^{14}$;

each R$^{10}$ is independently selected from hydrogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

each R$^{11}$ is independently selected from hydrogen, C$_{1-6}$alkyl, and C$_{1-6}$haloalkyl;

each R$^{12}$ is independently selected from hydrogen, C$_{1-6}$alkyl, and C$_{1-6}$haloalkyl;

each R$^{13}$ is independently selected C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

R$^{14}$ is selected from C$_{1-6}$alkyl and C$_{3-6}$cycloalkyl; and each R$^{15a}$ and each R$^{15b}$ are each independently selected from halogen, oxo, —CN, C$_{1-6}$alkyl, C$_{1-6}$haloalkyl, C$_{2-6}$alkenyl, C$_{2-6}$alkynyl, C$_{3-10}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, C$_{1-9}$heteroaryl, —CH$_2$—C$_{1-9}$heteroaryl, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^2$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(=O)(=NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, —CH$_2$—C$_{3-10}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, —CH$_2$—C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(=O)(=NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$).

In some embodiments, provided herein is a compound of Formula (III), or a pharmaceutically acceptable salt or solvate thereof, wherein R$^{9a}$ is selected from hydrogen, halogen, and C$_{1-6}$alkyl. In some embodiments, provided herein is a compound of Formula (III), or a pharmaceutically acceptable salt or solvate thereof, wherein R$^{9b}$ is hydrogen.

In some embodiments, provided herein is a compound of Formula (III), or a pharmaceutically acceptable salt or solvate thereof, wherein R$^{9a}$ is —OR$^{14}$. In some embodiments, provided herein is a compound of Formula (III), or a pharmaceutically acceptable salt or solvate thereof, wherein R$^{14}$ is C$_{1-6}$alkyl. In some embodiments, provided herein is a compound of Formula (III), or a pharmaceutically acceptable salt or solvate thereof, wherein R$^1$ is —OCH$_3$.

In some embodiments, provided herein is a compound of Formula (III), or a pharmaceutically acceptable salt or solvate thereof, wherein X is —O—.

In some embodiments, provided herein is a compound of Formula (II) or (III), or a pharmaceutically acceptable salt or solvate thereof, wherein R$^{8a}$ and R$^{8e}$ are independently selected from hydrogen, halogen, C$_{1-6}$alkyl, C$_{1-6}$haloalkyl, and —OR$^{10}$. In some embodiments, provided herein is a compound of Formula (II) or (III), or a pharmaceutically acceptable salt or solvate thereof, wherein R$^{8a}$ and R$^{8e}$ are independently selected from hydrogen and —OR$^{10}$. In some embodiments, provided herein is a compound of Formula (II) or (III), or a pharmaceutically acceptable salt or solvate thereof, wherein R$^{8a}$ and R$^{8e}$ are —OR$^{10}$. In some embodiments, provided herein is a compound of Formula (II) or (III), or a pharmaceutically acceptable salt or solvate thereof, wherein R$^{10}$ is C$_{1-6}$alkyl. In some embodiments, provided herein is a compound of Formula (II) or (III), or a pharmaceutically acceptable salt or solvate thereof, wherein R$^{10}$ is —CH$_3$. In some embodiments, provided herein is a compound of Formula (II) or (III), or a pharmaceutically acceptable salt or solvate thereof, wherein R$^{8b}$, R$^{8c}$, R$^{8d}$, and R$^{9c}$ are independently selected from hydrogen, halogen, C$_{1-6}$alkyl, C$_{1-6}$haloalkyl, and —OR$^{10}$. In some embodiments, provided herein is a compound of Formula (II) or (III), or a pharmaceutically acceptable salt or solvate thereof, wherein R$^{8b}$, R$^{8c}$, R$^{8d}$, and R$^{9c}$ are independently selected from hydrogen, halogen, and C$_{1-6}$alkyl. In some embodiments, provided herein is a compound of Formula (II) or (III), or a pharmaceutically acceptable salt or solvate thereof, wherein R$^{8b}$, R$^{8c}$, R$^{8d}$, and R$^{9c}$ are hydrogen.

In some embodiments disclosed herein is a compound of Formula (IV), or a pharmaceutically acceptable salt or solvate thereof:

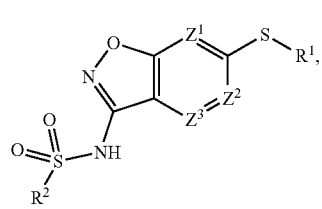

Formula (IV)

wherein:
R$^2$ is C$_{3-6}$cycloalkyl, C$_{2-9}$heterocycloalkyl, C$_{6-10}$aryl, or C$_{1-9}$heteroaryl; each optionally substituted with one, two, three, or four groups selected from R$^{15c}$;
Z$^1$ is CR$^{1b}$ or N;
Z$^2$ is CR$^{2b}$ or N;
Z$^3$ is CR$^{3b}$ or N;
R$^1$ is C$_{3-6}$cycloalkyl, C$_{2-9}$heterocycloalkyl, C$_{6-10}$aryl, or C$_{1-9}$heteroaryl; each optionally substituted with one, two, or three groups selected from R$^{15a}$;
R$^{1b}$, R$^{2b}$, and R$^{3b}$ are independently hydrogen, halogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, $C_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$), wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from R$^{15b}$;

or R$^{2b}$ and R$^{3b}$ are taken together to form a $C_{3-6}$cycloalkyl, $C_{2-9}$heterocycloalkyl, $C_{6-10}$aryl, or $C_{1-9}$heteroaryl; wherein $C_{3-6}$cycloalkyl, $C_{2-9}$heterocycloalkyl, $C_{6-10}$aryl, and $C_{1-9}$heteroaryl are optionally substituted with one, two, three, or four groups selected from R$^{15e}$;

each R$^{15a}$, each R$^{15b}$, and each R$^{15c}$ are independently halogen, oxo, —CN, $C_{1-6}$alkyl, $C_{1-6}$haloalkyl, $C_{2-6}$alkenyl, $C_{2-6}$alkynyl, $C_{3-10}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-9}$heteroaryl, —CH$_2$—$C_{1-9}$heteroaryl, —OR$^{10}$, —SR$^{10}$, —N(R$^{10}$)(R$^{11}$), —C(O)OR$^{10}$, —OC(O)N(R$^{10}$)(R$^{11}$), —N(R$^2$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, or —CH$_2$S(O)$_2$N(R$^{10}$)(R$^{11}$), wherein $C_{1-6}$alkyl, $C_{2-6}$alkenyl, $C_{2-6}$alkynyl, $C_{3-6}$cycloalkyl, —CH$_2$—$C_{3-10}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, —CH$_2$—$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

each R$^{15e}$ are independently halogen, oxo, —CN, $C_{1-6}$alkyl, $C_{1-6}$haloalkyl, $C_{2-6}$alkenyl, $C_{2-6}$alkynyl, $C_{3-10}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-9}$heteroaryl, —CH$_2$—$C_{2-9}$heteroaryl, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, or —CH$_2$S(O)$_2$N(R$^{10}$)(R$^{11}$), wherein $C_{1-6}$alkyl, $C_{2-6}$alkenyl, $C_{2-6}$alkynyl, $C_{3-6}$cycloalkyl, —CH$_2$—$C_{3-10}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, —CH$_2$—$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

or two R$^{15e}$ on the adjacent carbon are taken together to form a $C_{2-6}$alkenylene;

or two R$^{15e}$ on the same atom are taken together to form a $C_{3-6}$cycloalkyl or $C_{2-9}$heterocycloalkyl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

or two R$^{15e}$ on the different atom are taken together to form a $C_{3-6}$cycloalkyl, $C_{2-9}$heterocycloalkyl, $C_{6-10}$aryl, or $C_{1-9}$heteroaryl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

each R$^{10}$ is independently hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, or $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each R$^{11}$ is independently hydrogen, $C_{1-6}$alkyl, or $C_{1-6}$haloalkyl;

each R$^{12}$ is independently hydrogen, $C_{1-6}$alkyl, or $C_{1-6}$haloalkyl; and each R$^{13}$ is independently hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, or $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl.

Also disclosed herein is a compound of Formula (V), or a pharmaceutically acceptable salt or solvate thereof:

Formula (V)

wherein:

$R^2$ is $C_{1-9}$heteroaryl optionally substituted with one, two, three, or four groups selected from $R^{15c}$;

$Z^1$ is $CR^{1b}$ or N;

$R^1$ is $C_{3-6}$cycloalkyl, $C_{2-9}$heterocycloalkyl, $C_{6-10}$aryl, or $C_{1-9}$heteroaryl; each optionally substituted with one, two, or three groups selected from $R^{15a}$;

$R^{1b}$ is hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, $-OR^{10}$, $-SR^{10}$, $-SF_5$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $S(O)(NH)N(R^{10})(R^{11})$, $-CH_2C(O)N(R^{10})(R^{11})$, $-CH_2N(R^{12})C(O)R^{13}$, $-CH_2S(O)_2R^{13}$, or $-CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-6}$heteroaryl are optionally substituted with one, two, or three groups selected from $R^{15b}$;

X is $-C(R^6)(R^{6a})-$, $-S-$, $-O-$, or $-N(R^7)-$;

$R^6$ and $R^{6a}$ are independently hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, $-OR^{10}$, $-SR^{10}$, $-N(R^{10})(R^{11})$, $-C(O)OR^{10}$, $-OC(O)N(R^{10})(R^{11})$, $-N(R^{12})C(O)N(R^{10})(R^{11})$, $-N(R^2)C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $S(O)(NH)N(R^{10})(R^{11})$, $-CH_2C(O)N(R^{10})(R^{11})$, $-CH_2N(R^{12})C(O)R^{13}$, $-CH_2S(O)_2R^{13}$, or $-CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, $-CN$, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

or $R^6$ and $R^{6a}$ are taken together to form an oxo;

$R^7$ is hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, or $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, $-CN$, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

Ring A is $C_{3-6}$cycloalkyl, $C_{2-9}$heterocycloalkyl, $C_{6-10}$aryl, or $C_{1-9}$heteroaryl;

each $R^{15a}$, each $R^{15b}$, and each $R^{15c}$ are independently halogen, oxo, $-CN$, $C_{1-6}$alkyl, $C_{1-6}$haloalkyl, $C_{2-6}$alkenyl, $C_{2-6}$alkynyl, $C_{3-10}$cycloalkyl, $-CH_2-C_{3-6}$cycloalkyl, $C_{2-9}$heterocycloalkyl, $-CH_2-C_{2-9}$heterocycloalkyl, $C_{6-10}$aryl, $-CH_2-C_{6-10}$aryl, $C_{1-9}$heteroaryl, $-CH_2-C_{1-9}$heteroaryl, $-OR^{10}$, $-SR^{10}$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $S(O)(NH)N(R^{10})(R^{11})$, $-CH_2C(O)N(R^{10})(R^{11})$, $-CH_2N(R^{12})C(O)R^{13}$, $-CH_2S(O)_2R^{13}$, or $-CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, $-CH_2-C_{1-9}$heteroaryl, and $C_{1-9}$heteroaryl are optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{10}$, $-SR^{10}$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $S(O)(NH)N(R^{10})(R^{11})$, $-CH_2C(O)N(R^{10})(R^{11})$, $-CH_2N(R^{12})C(O)R^{13}$, $-CH_2S(O)_2R^{13}$, and $-CH_2S(O)_2N(R^{10})(R^{11})$;

each $R^{15e}$ are independently halogen, oxo, $-CN$, $C_{1-6}$alkyl, $C_{1-6}$haloalkyl, $C_{2-6}$alkenyl, $C_{2-6}$alkynyl, $C_{3-10}$cycloalkyl, $-CH_2-C_{3-6}$cycloalkyl, $C_{2-9}$heterocycloalkyl, $-CH_2-C_{2-9}$heterocycloalkyl, $C_{6-10}$aryl, $-CH_2-C_{6-10}$aryl, $C_{1-9}$heteroaryl, $-CH_2-C_{1-9}$heteroaryl, $-OR^{10}$, $-SR^{10}$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $S(O)(NH)N(R^{10})(R^{11})$, $-CH_2C(O)N(R^{10})(R^{11})$, $-CH_2N(R^{12})C(O)R^{13}$, $-CH_2S(O)_2R^{13}$, or $-CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, $-CH_2-C_{1-9}$heteroaryl, and $C_{1-9}$heteroaryl are optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{10}$, $-SR^{10}$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $S(O)(NH)N(R^{10})(R^{11})$, $-CH_2C(O)N(R^{10})(R^{11})$, $-CH_2N(R^{12})C(O)R^{13}$, $-CH_2S(O)_2R^{13}$, and $-CH_2S(O)_2N(R^{10})(R^{11})$;

or two $R^{15e}$ on the adjacent carbon are taken together to form a $C_{2-6}$alkenylene;

or two $R^{15e}$ on the same atom are taken together to form a $C_{3-6}$cycloalkyl or $C_{2-9}$heterocycloalkyl; each optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{10}$, $-SR^{10}$, $-N(R^{10})(R^{11})$, $-C(O)OR^{10}$, $-OC(O)N(R^{10})(R^{11})$, $-N(R^{12})C(O)N(R^{10})(R^{11})$, $-N(R^2)C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $S(O)(NH)N(R^{10})(R^{11})$, $-CH_2C(O)N(R^{10})(R^{11})$, $-CH_2N(R^{12})C(O)R^{13}$, $-CH_2S(O)_2R^{13}$, and $-CH_2S(O)_2N(R^{10})(R^{11})$;

or two $R^{15e}$ on the different atom are taken together to form a $C_{3-6}$cycloalkyl, $C_{2-9}$heterocycloalkyl, $C_{6-10}$aryl, or $C_{1-9}$heteroaryl; each optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{10}$, $-SR^{10}$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $S(O)(NH)N(R^{10})$ ($R^{11}$), —$CH_2C(O)N(R^{10})(R^{11})$, —$CH_2N(R^{12})C(O)$$R^{13}$, —$CH_2S(O)_2R^{13}$, and —$CH_2S(O)_2N(R^{10})(R^{11})$;

n is 0-6;

each $R^{10}$ is hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is hydrogen, $C_{1-6}$alkyl, or $C_{1-6}$haloalkyl;

each $R^{12}$ is hydrogen, $C_{1-6}$alkyl, or $C_{1-6}$haloalkyl; and each $R^{13}$ is hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, or $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl.

Also disclosed herein is a compound of Formula (VI), or a pharmaceutically acceptable salt or solvate thereof:

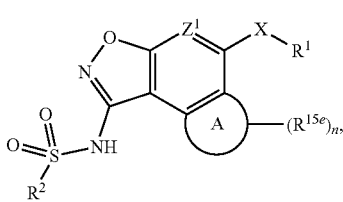

Formula (VI)

wherein:

$R^2$ is $C_{3-6}$cycloalkyl, $C_{2-9}$heterocycloalkyl, $C_{6-10}$aryl, or $C_{1-9}$heteroaryl; each optionally substituted with one, two, three, or four groups selected from $R^{15e}$;

$Z^1$ is $CR^{1b}$ or N;

$R^1$ is $C_{3-6}$cycloalkyl, $C_{2-9}$heterocycloalkyl, $C_{6-10}$aryl, or $C_{1-9}$heteroaryl; each optionally substituted with one, two, or three groups selected from $R^{15a}$;

$R^{1b}$ is hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(O)(NH)N(R^{10})(R^{11})$, —$CH_2C(O)N(R^{10})(R^{11})$, —$CH_2N(R^{12})C(O)R^{13}$, —$CH_2S(O)_2R^{13}$, or —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15b}$;

X is —$C(R^6)(R^{6a})$—, —S—, —O—, or —$N(R^7)$—;

$R^6$ and $R^{6a}$ are independently hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(O)(NH)N(R^{10})(R^{11})$, —$CH_2C(O)N(R^{10})(R^{11})$, —$CH_2N(R^{12})C(O)R^{13}$, —$CH_2S(O)_2R^{13}$, or —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

or $R^6$ and $R^{6a}$ are taken together to form an oxo;

$R^7$ is selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-4}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

Ring B is $C_{3-6}$cycloalkyl, $C_{6-9}$heterocycloalkyl, $C_{6-10}$aryl, or $C_{1-9}$heteroaryl;

each $R^{15a}$, each $R^{15a}$, and each $R^{15c}$ are independently halogen, oxo, —CN, $C_{1-6}$alkyl, $C_{1-6}$haloalkyl, $C_{2-6}$alkenyl, $C_{2-6}$alkynyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-6}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(O)(NH)N(R^{10})(R^{11})$, —$CH_2C(O)N(R^{10})(R^{11})$, —$CH_2N(R^{12})C(O)R^{13}$, —$CH_2S(O)_2R^{13}$, or —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, —$CH_2$—$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(O)(NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$;

each $R^{15e}$ are independently halogen, oxo, —CN, $C_{1-6}$alkyl, $C_{1-6}$haloalkyl, $C_{2-6}$alkenyl, $C_{2-6}$alkynyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(O)(NH)N(R^{10})(R^{11})$, —$CH_2C(O)N(R^{10})(R^{11})$, —$CH_2N(R^{12})C(O)R^{13}$, —$CH_2S(O)_2R^{13}$, or —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —CH$_2$—C$_{6-10}$aryl, —CH$_2$—C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

or two R$^{15e}$ on the adjacent carbon are taken together to form a C$_{2-6}$alkenylene;

or two R$^{15e}$ on the same atom are taken together to form a C$_{3-6}$cycloalkyl or C$_{2-9}$heterocycloalkyl; each optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

or two R$^{15e}$ on the different atom are taken together to form a C$_{3-6}$cycloalkyl, C$_{2-9}$heterocycloalkyl, C$_{6-10}$aryl, or C$_{1-9}$heteroaryl; each optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

n is 0-6;

each R$^{15e}$ is hydrogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

each R$^{11}$ is hydrogen, C$_{1-6}$alkyl, or C$_{1-6}$haloalkyl;

each R$^{12}$ is hydrogen, C$_{1-6}$alkyl, or C$_{1-6}$haloalkyl; and each R$^{13}$ is hydrogen, C$_{1-6}$alkyl, C$_{2-6}$alkenyl, C$_{2-4}$alkynyl, C$_{3-6}$cycloalkyl, C$_{2-9}$heterocycloalkyl, C$_{6-10}$aryl, or C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl.

In some embodiments, provided herein is a compound of Formula (I), (I'), (Ia), (II), (III), (IV), (V) or (VI), or a pharmaceutically acceptable salt or solvate thereof, wherein R$^1$ is C$_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are optionally substituted with one, two, or three groups selected from R$^{15a}$. In some embodiments, provided herein is a compound of Formula (I), (I'), (Ia), (II), (III), (IV), (V) or (VI), or a pharmaceutically acceptable salt or solvate thereof, wherein R$^1$ is C$_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are unsubstituted. In some embodiments, provided herein is a compound of Formula (I), (I'), (Ia), (II), or (III), or a pharmaceutically acceptable salt or solvate thereof, wherein R$^1$ is unsubstituted pyrazolyl. In some embodiments, provided herein is a compound of Formula (I), (I'), (Ia), (II), (III), (IV), (V) or (VI), or a pharmaceutically acceptable salt or solvate thereof, wherein R$^1$ is unsubstituted pyridinyl.

In some embodiments, provided herein is a compound of Formula (I), (I'), (Ia), (II), (III), (IV), (V) or (VI), or a pharmaceutically acceptable salt or solvate thereof, wherein R$^1$ is C$_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are optionally substituted with one, two, or three groups selected from R$^{15a}$. In some embodiments, provided herein is a compound of Formula (I), (I'), (Ia), (II), (III), (IV), (V) or (VI), or a pharmaceutically acceptable salt or solvate thereof, wherein R$^1$ is C$_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are unsubstituted. In some embodiments, provided herein is a compound of Formula (I), (I'), (Ia), (II), or (III), or a pharmaceutically acceptable salt or solvate thereof, wherein R$^1$ is unsubstituted pyrazolyl. In some embodiments, provided herein is a compound of Formula (I), (I'), (Ia), (II), (III), (IV), (V) or (VI), or a pharmaceutically acceptable salt or solvate thereof, wherein R$^1$ is unsubstituted pyridinyl.

In one aspect, disclosed herein are compounds of Table 1A, Table 1B and Table 1C, or a pharmaceutically acceptable salt or solvate thereof. In one aspect, disclosed herein is a pharmaceutical composition comprising a compound of Table 1A, Table 1B and Table 1C, or a pharmaceutically acceptable salt or solvate thereof, and at least one pharmaceutically acceptable excipient.

In another aspect is a pharmaceutical composition comprising a compound of Formula (I), (I'), (Ia), (II), (III), (IV), (V) or (VI), or a pharmaceutically acceptable salt or solvate thereof, and at least one pharmaceutically acceptable excipient.

In another aspect is a method of treating cancer in a mammal in need thereof, comprising administering to the mammal a compound of Formula (I), (I'), (Ia), (II), (III), (IV), (V) or (VI), or a pharmaceutically acceptable salt or solvate thereof.

In some embodiments is a method of treating cancer in a mammal in need thereof, comprising administering to the mammal a compound of Formula (I), (I'), (Ia), (II), (III), (IV), (V) or (VI), or a pharmaceutically acceptable salt or solvate thereof, wherein the cancer is selected from lung cancer, mesothelioma, bone cancer, pancreatic cancer, skin cancer, cancer of the head or neck, cutaneous or intraocular melanoma, uterine cancer, ovarian cancer, rectal cancer, stomach cancer, hepatocellular carcinoma, colon cancer, breast cancer, carcinoma of the endometrium, carcinoma of the cervix, carcinoma of the vagina, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, hematology malignancy, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, glioblastoma, brain stem glioma, pituitary adenoma, or a combination of two or more of the foregoing cancers.

In some embodiments is a method of treating cancer in a mammal in need thereof, comprising administering to the mammal a compound of Formula (I), (I'), (Ia), (II), (III), (IV), (V) or (VI), or a pharmaceutically acceptable salt or solvate thereof, wherein the cancer is selected from ER-positive breast cancer, glioblastoma, non-small cell lung cancer (NSCLC), small cell lung cancer (SCLC), melanoma, ovarian cancer, prostate cancer, pancreatic cancer, colorectal cancer (CRC), hepatocellular carcinoma (HCC), renal cell carcinoma (RCC), leukemia, lymphoma or multiple myeloma, acute lymphocytic leukemia (ALL), acute myeloid leukemia (AML), chronic lymphocytic leukemia (CLL), chronic myeloid leukemia (CML), and non-Hodgkin's lymphoma.

In some embodiments is a method of treating cancer in a mammal in need thereof, comprising administering to the mammal a compound of Formula (I), (I'), (Ia), (II), (III), (IV), (V) or (VI), or a pharmaceutically acceptable salt or solvate thereof, wherein the cancer is a solid tumor with KAT6A/6B amplification or overexpression, or leukemia or solid tumor with KAT6A/6B fusion protein resulting from chromosomal translocation.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Definitions

In the following description, certain specific details are set forth in order to provide a thorough understanding of various embodiments. However, one skilled in the art will understand that the disclosure may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "some embodiments" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"oxo" refers to =O.

"Carboxyl" refers to —COOH.

"Cyano" refers to —CN.

"Alkyl" refers to a straight-chain, or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$alkyl. In some embodiments, the alkyl is a $C_{1-6}$alkyl. In some embodiments, the alkyl is a $C_{1-5}$alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —NH$_2$, or —NO$_2$. In some embodiments, the alkyl is optionally substituted with halogen, —CN, —OH, or —OMe. In some embodiments, the alkyl is optionally substituted with halogen.

"Alkenyl" refers to a straight-chain, or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "$C_2$-$C_6$ alkenyl" or "$C_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —NH$_2$, or —NO$_2$. In some embodiments, the alkenyl is optionally substituted with halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, —NH$_2$, or —NO$_2$. In some embodiments, the alkynyl is optionally substituted with halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, —NH$_2$, or —NO$_2$. In some embodiments, the alkylene is optionally substituted with halogen, —CN, —OH, or —OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —NH$_2$, or —NO$_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, —CF$_3$, —OH, —OMe, —NH$_2$, or —NO$_2$. In some embodiments, the aryl is optionally substituted with halogen, methyl, ethyl, —CN, —CF$_3$, —OH, or —OMe. In some embodiments, the aryl is optionally substituted with halogen.

"Cycloalkyl" refers to a partially or fully saturated, monocyclic or polycyclic carbocyclic ring, which may include fused (when fused with an aryl or a heteroaryl ring, the cycloalkyl is bonded through a non-aromatic ring atom), spiro, or bridged ring systems. In some embodiments, the cycloalkyl is fully saturated. Representative cycloalkyls include, but are not limited to, cycloalkyls having from three to fifteen carbon atoms ($C_3$-$C_{15}$ fully saturated cycloalkyl or $C_3$-$C_{15}$ cycloalkenyl), from three to ten carbon atoms ($C_3$-$C_{10}$ fully saturated cycloalkyl or $C_3$-$C_{10}$ cycloalkenyl), from three to eight carbon atoms ($C_3$-$C_8$ fully saturated cycloalkyl or $C_3$-$C_8$ cycloalkenyl), from three to six carbon atoms ($C_3$-$C_6$ fully saturated cycloalkyl or $C_3$-$C_6$ cycloalkenyl), from three to five carbon atoms ($C_3$-$C_5$ fully saturated cycloalkyl or $C_3$-$C_5$ cycloalkenyl), or three to four carbon atoms ($C_3$-$C_4$ fully saturated cycloalkyl or $C_3$-$C_4$ cycloalkenyl). In some embodiments, the cycloalkyl is a 3- to 10-membered fully saturated cycloalkyl or a 3- to 10-membered cycloalkenyl. In some embodiments, the cycloalkyl is a 3- to 6-membered fully saturated cycloalkyl or a 3- to 6-membered cycloalkenyl. In some embodiments, the cycloalkyl is a 5- to 6-membered fully saturated cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, —$CH_2OCH_3$, —$CH_2CH_2OCH_3$, —$CH_2CH_2OCH_2CH_2OCH_3$, —$CH(CH_3)OCH_3$, —$CH_2NHCH_3$, —$CH_2N(CH_3)_2$, —$CH_2CH_2NHCH_3$, or —$CH_2CH_2N(CH_3)_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —$CF_3$, —OH, —OMe, —$NH_2$, or —$NO_2$. In some embodiments, a heteroalkyl is optionally substituted with oxo, halogen, methyl, ethyl, —CN, —$CF_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous, silicon, and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom), spiro, or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms ($C_2$-$C_{15}$ fully saturated heterocycloalkyl or $C_2$-$C_{15}$ heterocycloalkenyl), from two to ten carbon atoms ($C_2$-$C_{10}$ fully saturated heterocycloalkyl or $C_2$-$C_{10}$ heterocycloalkenyl), from two to eight carbon atoms ($C_2$-$C_8$ fully saturated heterocycloalkyl or $C_2$-$C_8$ heterocycloalkenyl), from two to seven carbon atoms ($C_2$-$C_7$ fully saturated heterocycloalkyl or $C_2$-$C_7$ heterocycloalkenyl), from two to six carbon atoms ($C_2$-$C_6$ fully saturated heterocycloalkyl or $C_2$-$C_7$ heterocycloalkenyl), from two to five carbon atoms ($C_2$-$C_5$ fully saturated heterocycloalkyl or $C_2$-$C_5$ heterocycloalkenyl), or two to four carbon atoms ($C_2$-$C_4$ fully saturated heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. In some embodiments, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered fully saturated heterocycloalkyl. In some embodiments, the heterocycloalkyl is a 3- to 7-membered fully saturated heterocycloalkyl. In some embodiments, the heterocycloalkyl is a 3- to 6-membered fully saturated heterocycloalkyl. In some embodiments, the heterocycloalkyl is a 4- to 6-membered fully saturated heterocycloalkyl. In some embodiments, the heterocycloalkyl is a 5- to 6-membered fully saturated heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, —$CF_3$, —OH, —OMe, —$NH_2$, or —$NO_2$. In some embodiments, the heterocycloalkyl is optionally substituted with halogen, methyl, ethyl, —CN, —$CF_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, —CF$_3$, —OH, —OMe, —NH$_2$, or —NO$_2$. In some embodiments, the heteroaryl is optionally substituted with halogen, methyl, ethyl, —CN, —CF$_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). It will be understood by those skilled in the art with respect to any group containing one or more substituents that such groups are not intended to introduce any substitution or substitution patterns that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition.

Compounds

Described herein are compounds of Formula (I), (I'), (Ia), (II), (III), (IV), (V) or (VI), or a pharmaceutically acceptable salt or solvate thereof, which are KAT6A inhibitors and useful in the treatment of a disease or disorder associated with KAT6A inhibition. In some embodiments, the compounds of Formula (I), (I'), (Ia), (II), (III), (IV), (V) or (VI), or a pharmaceutically acceptable salt or solvate thereof, are useful in the treatment of cancer.

In some embodiments disclosed herein is a compound of Formula (I), or a pharmaceutically acceptable salt or solvate thereof:

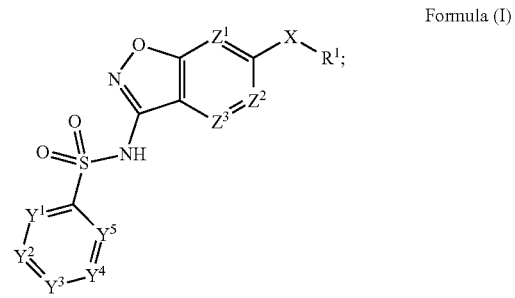

Formula (I)

wherein:
$Y^1$ is $CR^{1a}$ or N;
$Y^2$ is $CR^{2a}$ or N;
$Y^3$ is $CR^{3a}$ or N;
$Y^4$ is $CR^{4a}$ or N;
$Y^5$ is $CR^{5a}$ or N;
$Z^1$ is $CR^{1b}$ or N;
$Z^2$ is $CR^{2b}$ or N;
$Z^3$ is $CR^{3b}$ or N; wherein at least one of $Y^1$, $Y^2$, $Y^3$, $Y^4$, $Y^5$, $Z^1$, $Z^2$, and $Z^3$ is N;
X is selected from —C($R^6$)($R^{6a}$)—, —O—, and —N($R^7$)—;
$R^1$ is $C_{1-9}$heteroaryl optionally substituted with one, two, or three groups selected from $R^{15a}$;
$R^{1a}$, $R^{2a}$, $R^{3b}$, $R^{4a}$, $R^{5a}$, $R^{1b}$, $R^{2b}$, and $R^{3b}$ are independently selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(=O)(=NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$), wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15b}$;
$R^6$ and $R^{6a}$ are independently selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

$R^7$ is selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-4}$alkenyl, $C_{2-4}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{10}$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-4}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-4}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; and each $R^{15a}$ and each $R^{15b}$ are each independently selected from halogen, oxo, —CN, $C_{1-6}$alkyl, $C_{1-6}$haloalkyl, $C_{2-6}$alkenyl, $C_{2-6}$alkynyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, —$CH_2$—$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^3$, —$CH_2S(O)_2R^{13}$, and —$CH_2S(O)_2N(R^{10})(R^{11})$).

In some embodiments of a compound of Formula (I), or a pharmaceutically acceptable salt or solvate thereof, $Y^1$ is $CR^{1a}$. In some embodiments of a compound of Formula (I), or a pharmaceutically acceptable salt or solvate thereof, $Y^1$ is N.

In some embodiments of a compound of Formula (I), or a pharmaceutically acceptable salt or solvate thereof, $Y^2$ is $CR^{2a}$. In some embodiments of a compound of Formula (I), or a pharmaceutically acceptable salt or solvate thereof, $Y^2$ is N.

In some embodiments of a compound of Formula (I), or a pharmaceutically acceptable salt or solvate thereof, $Y^3$ is $CR^{3a}$. In some embodiments of a compound of Formula (I), or a pharmaceutically acceptable salt or solvate thereof, $Y^3$ is N.

In some embodiments of a compound of Formula (I), or a pharmaceutically acceptable salt or solvate thereof, $Y^4$ is $CR^{4a}$. In some embodiments of a compound of Formula (I), or a pharmaceutically acceptable salt or solvate thereof, $Y^4$ is N.

In some embodiments of a compound of Formula (I), or a pharmaceutically acceptable salt or solvate thereof, $Y^5$ is $CR^{5a}$. In some embodiments of a compound of Formula (I), or a pharmaceutically acceptable salt or solvate thereof, $Y^5$ is N.

In some embodiments of a compound of Formula (I), or a pharmaceutically acceptable salt or solvate thereof, $Y^1$ is $CR^{1a}$ and $Y^5$ is $CR^{5a}$.

In some embodiments of a compound of Formula (I), or a pharmaceutically acceptable salt or solvate thereof, $Y^1$ is $CR^{1a}$, $Y^5$ is $CR^{5a}$, and $R^{1a}$ and $R^{5a}$ are independently selected from hydrogen, halogen, $C_{1-6}$alkyl, $C_{1-4}$haloalkyl, and —$OR^{10}$. In some embodiments of a compound of Formula (I), or a pharmaceutically acceptable salt or solvate thereof, $Y^1$ is $CR^{1a}$, $Y^5$ is $CR^{5a}$, and $R^{1a}$ and $R^{5a}$ are independently selected from hydrogen and —$OR^{10}$. In some embodiments of a compound of Formula (I), or a pharmaceutically acceptable salt or solvate thereof, $Y^1$ is $CR^{1a}$, $Y^5$ is $CR^{5a}$, and $R^{1a}$ and $R^{5a}$ are —$OR^{10}$. In some embodiments of a compound of Formula (I), or a pharmaceutically acceptable salt or solvate thereof, $Y^1$ is $CR^{1a}$, $Y^5$ is $CR^{5a}$, $R^{1a}$ and $R^{5a}$ are —$OR^{10}$, and $R^{10}$ is $C_{1-6}$alkyl. In some embodiments of a compound of Formula (I), or a pharmaceutically acceptable salt or solvate thereof, $Y^1$ is $CR^{1a}$, $Y^5$ is $CR^{5a}$, $R^{1a}$ and $R^{5a}$ are —$OR^{10}$, and $R^{10}$ is —$CH_3$.

In some embodiments of a compound of Formula (I), or a pharmaceutically acceptable salt or solvate thereof, $Z^1$ is $CR^{1b}$. In some embodiments of a compound of Formula (I), or a pharmaceutically acceptable salt or solvate thereof, $Z^3$ is N.

In some embodiments of a compound of Formula (I), or a pharmaceutically acceptable salt or solvate thereof, $Z^2$ is $CR^{2b}$. In some embodiments of a compound of Formula (I), or a pharmaceutically acceptable salt or solvate thereof, $Z^2$ is N.

In some embodiments of a compound of Formula (I), or a pharmaceutically acceptable salt or solvate thereof, $Z^3$ is $CR^{3b}$. In some embodiments of a compound of Formula (I), or a pharmaceutically acceptable salt or solvate thereof, $Z^3$ is N.

In some embodiments of a compound of Formula (I), or a pharmaceutically acceptable salt or solvate thereof, $Y^1$ is $CR^{1a}$; $Y^2$ is $CR^{2b}$; $Y^3$ is $CR^{3a}$; $Y^4$ is $CR^{4a}$; $Y^5$ is $CR^{5a}$; $Z^1$ is $CR^{1b}$; $Z^2$ is $CR^{2b}$; and $Z^3$ is $CR^{3b}$. In some embodiments of a compound of Formula (I), or a pharmaceutically acceptable salt or solvate thereof, $Y^1$ is $CR^{1a}$; $Y^2$ is N; $Y^3$ is $CR^{3b}$; $Y^4$ is $CR^{4a}$; $Y^5$ is $CR^{5a}$; $Z^1$ is $CR^{1b}$; $Z^2$ is $CR^{2b}$; and $Z^3$ is $CR^{3b}$. In some embodiments of a compound of Formula (I), or a pharmaceutically acceptable salt or solvate thereof, among $Y^1$, $Y^2$, $Y^3$, $Y^4$, $Y^5$, $Z^1$, $Z^2$, and $Z^3$, only $Y^2$ is N. In some embodiments of a compound of Formula (I), or a pharmaceutically acceptable salt or solvate thereof, only one of $Y^1$, $Y^2$, $Y^3$, $Y^4$, $Y^5$, $Z^1$, $Z^2$, and $Z^3$ is N. In some embodiments, when $Y^2$ is N, then $R^{1a}$ and $R^{5a}$ are $-OR^{10}$. In some embodiments, when $Y^2$ is N, then $R^{1a}$ and $R^{5a}$ are independently selected from $-O-C_{1-6}$alkyl and $-O-C_{1-6}$haloalkyl. In some embodiments, when $Y^2$ is N, then $R^{1a}$ and $R^{5a}$ are $-OCH_3$.

In some embodiments of a compound of Formula (I), or a pharmaceutically acceptable salt or solvate thereof, $Y^2$ is N; $Y^3$ is $CR^{3a}$; and $Y^4$ is $CR^{4a}$. In some embodiments of a compound of Formula (I), or a pharmaceutically acceptable salt or solvate thereof, $Y^2$ is $CR^{2a}$; $Y^3$ is N; and $Y^4$ is $CR^{4a}$. In some embodiments of a compound of Formula (I), or a pharmaceutically acceptable salt or solvate thereof, $Y^2$ is N; $Y^3$ is $CR^{3a}$; and $Y^4$ is N. In some embodiments of a compound of Formula (I), or a pharmaceutically acceptable salt or solvate thereof, $Y^2$ is $CR^{2a}$; $Y^3$ is $CR^{3a}$; and $Y^4$ is $CR^{4a}$.

In some embodiments of a compound of Formula (I), or a pharmaceutically acceptable salt or solvate thereof, $Y^1$ is $CR^{1a}$; $Y^5$ is $CR^{5a}$; $Y^2$ is N; $Y^3$ is $CR^{3a}$; and $Y^4$ is $CR^{4a}$. In some embodiments of a compound of Formula (I), or a pharmaceutically acceptable salt or solvate thereof, $Y^1$ is $CR^{1a}$; $Y^5$ is $CR^{5a}$; $Y^2$ is $CR^{2a}$; $Y^3$ is N; and $Y^4$ is $CR^{4a}$. In some embodiments of a compound of Formula (I), or a pharmaceutically acceptable salt or solvate thereof, $Y^1$ is $CR^{1a}$; $Y^4$ is $CR^{4a}$; $Y^2$ is N; $Y^3$ is $CR^{3a}$; and $Y^4$ is N. In some embodiments of a compound of Formula (I), or a pharmaceutically acceptable salt or solvate thereof, $Y^1$ is $CR^{1a}$; $Y^5$ is $CR^{5a}$; $Y^2$ is $CR^{2a}$; $Y^3$ is $CR^{3a}$; and $Y^4$ is $CR^{4a}$.

In some embodiments of a compound of Formula (I), or a pharmaceutically acceptable salt or solvate thereof, $Z^1$ is $CR^{1b}$; $Z^2$ is $CR^{2b}$; and $Z^3$ is $CR^{3b}$. In some embodiments of a compound of Formula (I), or a pharmaceutically acceptable salt or solvate thereof, $Z^1$ is N; $Z^2$ is $CR^{2b}$; and $Z^3$ is $CR^{3b}$. In some embodiments of a compound of Formula (I), or a pharmaceutically acceptable salt or solvate thereof, $Z^1$ is $CR^{1b}$; $Z^2$ is N; and $Z^3$ is $CR^{3b}$. In some embodiments of a compound of Formula (I), or a pharmaceutically acceptable salt or solvate thereof, $Z^1$ is $CR^{1b}$; $Z^2$ is $CR^{2b}$; and $Z^3$ is N.

In some embodiments of a compound of Formula (I), or a pharmaceutically acceptable salt or solvate thereof, $R^{2a}$, $R^{3a}$, $R^{4a}$, $R^{1b}$, $R^{2b}$, and $R^{3b}$ are independently selected from hydrogen, halogen, $C_{1-6}$alkyl, $C_{1-6}$haloalkyl, and $-OR^{10}$. In some embodiments of a compound of Formula (I), or a pharmaceutically acceptable salt or solvate thereof, $R^{2a}$, $R^{3a}$, $R^{4a}$, $R^{1b}$, $R^{2b}$, and $R^{3b}$ are independently selected from hydrogen, halogen, and $C_{1-6}$alkyl. In some embodiments of a compound of Formula (I), or a pharmaceutically acceptable salt or solvate thereof, $R^{2a}$, $R^{3a}$, $R^{4a}$, $R^{1b}$, $R^{2b}$, and $R^{3b}$ are hydrogen. In some embodiments of a compound of Formula (I), or a pharmaceutically acceptable salt or solvate thereof, $R^{1b}$ and $R^{2b}$ are hydrogen, $R^{3b}$ is $-OR^{10}$, and $R^{10}$ is $C_{1-6}$alkyl. In some embodiments of a compound of Formula (I), or a pharmaceutically acceptable salt or solvate thereof, $R^{1b}$ and $R^{2b}$ are hydrogen, $R^{3b}$ is $-OR^{10}$, $R^{10}$ is $C_{1-6}$alkyl substituted with one, two, or three halogen.

In some embodiments of a compound of Formula (I), or a pharmaceutically acceptable salt or solvate thereof, $R^{1a}$ is hydrogen, halogen, $C_{1-6}$alkyl, $C_{1-6}$haloalkyl, or $-OR^{10}$. In some embodiments, $R^{1a}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{1a}$ is hydrogen. In some embodiments, $R^{1a}$ is $C_{1-6}$alkyl. In some embodiments, $R^{1a}$ is $C_{1-6}$alkoxyl, wherein the alkoxyl is optionally substituted with 1, 2 or 3 halogen. In some embodiments, $R^{1a}$ is $C_{1-6}$alkoxyl. In some $^{1a}$ is $-OCF_3$.

In some embodiments of a compound of Formula (I), or a pharmaceutically acceptable salt or solvate thereof, $R^{2a}$ is hydrogen, halogen, $C_{1-6}$alkyl, $C_{1-6}$haloalkyl, or $-OR^{10}$. In some embodiments, $R^{2a}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{2a}$ is hydrogen. In some embodiments, $R^2$ is $C_{1-6}$alkyl. In some embodiments, $R^{2a}$ is $C_{1-6}$alkoxyl, wherein the alkoxyl is optionally substituted with 1, 2 or 3 halogen.

In some embodiments of a compound of Formula (I), or a pharmaceutically acceptable salt or solvate thereof, $R^{3a}$ is hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $-OR^{10}$, $-SR^{10}$, or $-SF_5$, wherein $C_{1-6}$alkyl, $C_{2-6}$alkenyl, $C_{2-6}$alkynyl, $C_{3-6}$cycloalkyl, are $C_{2-9}$heterocycloalkyl are optionally substituted with one, two, or three groups selected from $R^{15b}$. In some embodiments, $R^{3a}$ is hydrogen, halogen, $C_{1-6}$alkyl, $C_{1-6}$haloalkyl, $C_{2-6}$alkenyl, $C_{2-6}$alkynyl, or $C_{3-6}$cycloalkyl, wherein the $C_{1-6}$alkyl, $C_{2-6}$alkenyl, $C_{2-6}$alkynyl, and $C_{3-6}$cycloalkyl are optionally substituted. In some embodiments, $R^{3a}$ is hydrogen, $C_{1-6}$alkyl, $C_{1-6}$haloalkyl, $C_{2-6}$alkenyl, or $C_{2-6}$alkynyl. In some embodiments, $R^{3a}$ is hydrogen. In some embodiments, $R^{3a}$ is $C_{1-6}$alkyl. In some embodiments, $R^{3a}$ is $C_{1-6}$alkyl. In some embodiments, $R^{3a}$ is $C_{1-6}$haloalkyl. In some embodiments, $R^{3a}$ is $C_{2-6}$alkenyl. In some embodiments, $R^{3a}$ is $C_{2-6}$alkynyl.

In some embodiments of a compound of Formula (I), or a pharmaceutically acceptable salt or solvate thereof, $R^{4a}$ is hydrogen, halogen, $C_{1-6}$alkyl, $C_{1-6}$haloalkyl, or $-OR^{10}$. In some embodiments, $R^{4a}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{4a}$ is hydrogen. In some embodiments, $R^{4a}$ is $C_{1-6}$alkyl. In some embodiments, $R^{4a}$ is $C_{1-6}$alkoxyl, wherein the alkoxyl is optionally substituted with 1, 2 or 3 halogen.

In some embodiments of a compound of Formula (I), or a pharmaceutically acceptable salt or solvate thereof, $R^{5a}$ is hydrogen, halogen, $C_{1-6}$alkyl, $C_{1-6}$haloalkyl, or $-OR^{10}$. In some embodiments, $R^{5a}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{5a}$ is hydrogen. In some embodiments, $R^{5a}$ is $C_{1-6}$alkoxyl, wherein the alkoxyl is optionally substituted with 1, 2 or 3 halogen. In some embodiments, $R^{5a}$ is $C_{1-6}$alkoxyl. In some embodiments, $R^{5a}$ is $C_{1-6}$alkoxyl. In some embodiments, $R^{5a}$ is $-OCH_3$.

In some embodiments of a compound of Formula (I), or a pharmaceutically acceptable salt or solvate thereof, $R^{1b}$ is hydrogen, halogen, $C_{1-6}$alkyl, or $C_{1-6}$haloalkyl, wherein $C_{1-6}$alkyl is optionally substituted with one, two, or three groups selected from $R^{15b}$. In some embodiments, $R^{1b}$ is hydrogen. In some embodiments, $R^{1b}$ is halogen. In some embodiments, $R^{1b}$ is $C_{1-6}$alkyl. In some embodiments, $R^{1b}$ is $C_{1-6}$haloalkyl.

In some embodiments of a compound of Formula (I), or a pharmaceutically acceptable salt or solvate thereof, $R^{2b}$ is hydrogen, halogen, $C_{1-6}$alkyl, or $C_{1-6}$haloalkyl, wherein $C_{1-6}$alkyl is optionally substituted with one, two, or three groups selected from $R^{15b}$. In some embodiments, $R^{2b}$ is hydrogen. In some embodiments, $R^{2b}$ is halogen. In some embodiments, $R^{1b}$ is $C_{1-6}$alkyl. In some embodiments, $R^{1b}$ is $C_{1-6}$haloalkyl.

In some embodiments of a compound of Formula (I), or a pharmaceutically acceptable salt or solvate thereof, $R^{3b}$ is hydrogen, halogen, $C_{1-6}$alkyl, $C_{1-6}$haloalkyl, or —$OR^{10}$. In some embodiments, $R^{3b}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{3b}$ is hydrogen. In some embodiments, $R^{3b}$ is $C_{1-6}$alkoxyl, wherein the alkoxyl is optionally substituted with 1, 2 or 3 halogen. In some embodiments, $R^{3b}$ is $C_{1-6}$alkoxyl. In some embodiments, $R^{3b}$ is $C_{1-3}$alkoxyl. In some embodiments, $R^{3b}$ is $C_{1-3}$alkoxyl, wherein the alkoxyl is optionally substituted with 1, 2 or 3 halogen. In some embodiments, $R^{3b}$ is —$OCH_3$. In some embodiments, $R^{3b}$ is —$OCH_2F$. In some embodiments, $R^{3b}$ is —$OCF_3$. In some embodiments, $R^{3b}$ is —$OCHF_2$. In some embodiments, $R^{3b}$ is —$OCH_2CF_3$.

In some embodiments of a compound of Formula (I), or a pharmaceutically acceptable salt or solvate thereof, X is —$C(R^6)(R^{6a})$—. In some embodiments of a compound of Formula (I), or a pharmaceutically acceptable salt or solvate thereof, X is —$C(R^6)(R^{6a})$— and $R^6$ and $R^{6a}$ are independently selected from hydrogen, halogen, $C_{1-6}$alkyl, and —OH. In some embodiments of a compound of Formula (I), or a pharmaceutically acceptable salt or solvate thereof, X is —$C(R^6)(R^{6a})$— and $R^6$ and $R^{6a}$ are hydrogen.

In some embodiments of a compound of Formula (I), or a pharmaceutically acceptable salt or solvate thereof, X is —O—.

In some embodiments of a compound of Formula (I), or a pharmaceutically acceptable salt or solvate thereof, X is —$N(R^7)$—. In some embodiments of a compound of Formula (I), or a pharmaceutically acceptable salt or solvate thereof, X is —$N(R^7)$— and $R^7$ is hydrogen. In some embodiments of a compound of Formula (I), or a pharmaceutically acceptable salt or solvate thereof, X is —$N(R^7)$— and $R^7$ is $C_{1-6}$alkyl.

In some embodiments of a compound of Formula (I), or a pharmaceutically acceptable salt or solvate thereof, $R^1$ is optionally substituted $C_{1-9}$heteroaryl. In some embodiments of a compound of Formula (I), or a pharmaceutically acceptable salt or solvate thereof, $R^1$ is optionally substituted 5 or 6 membered heteroaryl. In some embodiments of a compound of Formula (I), or a pharmaceutically acceptable salt or solvate thereof, $R^1$ is optionally substituted 5 membered heteroaryl. In some embodiments of a compound of Formula (I), or a pharmaceutically acceptable salt or solvate thereof, $R^1$ is optionally substituted 6 membered heteroaryl. In some embodiments of a compound of Formula (I), or a pharmaceutically acceptable salt or solvate thereof, $R^1$ is monocyclic heteroaryl. In some embodiments of a compound of Formula (I), or a pharmaceutically acceptable salt or solvate thereof, $R^1$ is bicyclic heteroaryl. In some embodiments, $R^1$ is optionally substituted with one, two, or three groups selected from $R^{15a}$. In some embodiments, $R^1$ is optionally substituted with one, two, or three groups selected from halogen, $C_{1-6}$alkyl, $C_{1-6}$haloalkyl, and $C_{1-6}$alkoxyl. In some embodiments, $R^1$ is optionally substituted with one, two, or three groups selected from oxo, —CN, amino, OH, halogen, $C_{1-6}$alkyl, $C_{1-6}$haloalkyl, $C_{1-6}$alkoxyl, and $C_{3-6}$cycloalkyl.

In some embodiments of a compound of Formula (I), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are optionally substituted with one, two, or three groups selected from $R^{15a}$. In some embodiments of a compound of Formula (I), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from $R^{15a}$. In some embodiments of a compound of Formula (I), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from $R^{15a}$ and each $R^{15a}$ is independently selected from halogen, $C_{1-6}$alkyl, $C_{1-6}$haloalkyl, and —$OR^{10}$. In some embodiments of a compound of Formula (I), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, pyrazolyl, imidazolyl, isoxazolyl, thiazolyl, oxazolyl, pyrimidinyl, pyridazinyl, and pyridinyl are substituted with one group selected from $R^{15a}$ and $R^{15a}$ is selected from halogen, $C_{1-6}$alkyl, $C_{1-6}$haloalkyl, and —$OR^{10}$.

In some embodiments of a compound of Formula (I), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are optionally substituted with one, two, or three groups selected from $R^{15a}$. In some embodiments of a compound of Formula (I), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are substituted with one, two, or three groups selected from $R^{15a}$. In some embodiments of a compound of Formula (I), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are substituted with one, two, or three groups selected from $R^{15a}$ and each $R^{15a}$ is independently selected from halogen, $C_{1-6}$alkyl, $C_{1-6}$haloalkyl, and —$OR^{10}$. In some embodiments of a compound of Formula (I), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are substituted with one group selected from $R^{15a}$ and $R^{15a}$ is selected from halogen, $C_{1-6}$alkyl, $C_{1-6}$haloalkyl, and —$OR^{10}$.

In some embodiments of a compound of Formula (I), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are unsubstituted. In some embodiments of a compound of Formula (I), or a pharmaceutically acceptable salt or solvate thereof, $R^1$ is C$_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are unsubstituted. In some embodiments of a compound of Formula (I), or a pharmaceutically acceptable salt or solvate thereof, R$^1$ is unsubstituted pyrazolyl. In some embodiments of a compound of Formula (I), or a pharmaceutically acceptable salt or solvate thereof, R$^1$ is unsubstituted imidazolyl. In some embodiments of a compound of Formula (I), or a pharmaceutically acceptable salt or solvate thereof, R$^1$ is unsubstituted isoxazolyl. In some embodiments of a compound of Formula (I), or a pharmaceutically acceptable salt or solvate thereof, R$^1$ is unsubstituted oxazolyl. In some embodiments of a compound of Formula (I), or a pharmaceutically acceptable salt or solvate thereof, R$^1$ is unsubstituted pyridinyl. In some embodiments of a compound of Formula (I), or a pharmaceutically acceptable salt or solvate thereof, R$^1$ is unsubstituted thiazolyl. In some embodiments of a compound of Formula (I), or a pharmaceutically acceptable salt or solvate thereof, R$^1$ is unsubstituted pyrimidinyl. In some embodiments of a compound of Formula (I), or a pharmaceutically acceptable salt or solvate thereof, R$^1$ is unsubstituted pyridazinyl.

In some embodiments of a compound of Formula (I), or a pharmaceutically acceptable salt or solvate thereof, R$^1$ is selected from

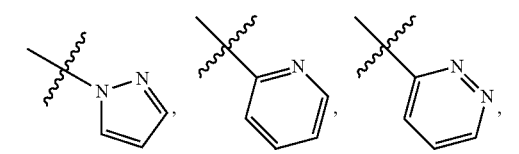

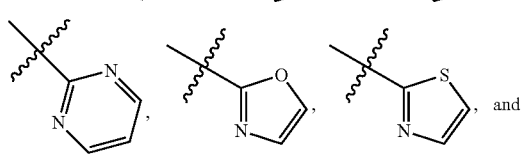

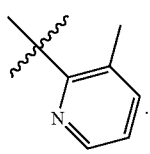

In some embodiments of a compound of Formula (I), or a pharmaceutically acceptable salt or solvate thereof, R$^1$ is selected from

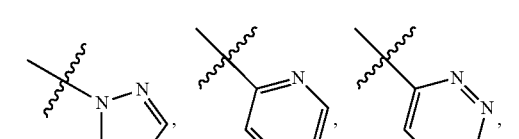

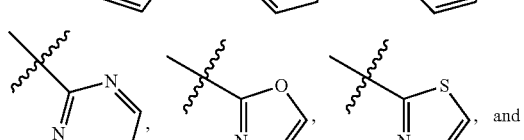

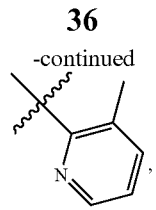

wherein each is optionally substituted with 1, 2 or 3 R$^{15a}$. In some embodiments, R$^1$ is

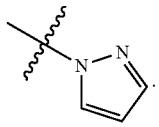 [SMILES: *n1cccn1]

In some embodiments, R$^1$ is

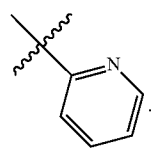 [SMILES: *c1ccccn1]

In some embodiments, R$^1$ is

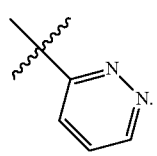 [SMILES: *c1cccnn1]

In some embodiments, R$^1$ is

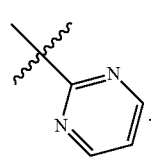 [SMILES: *c1ncccn1]

In some embodiments, R$^1$ is

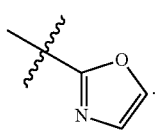 [SMILES: *c1ncco1]

In some embodiments, R$^1$ is

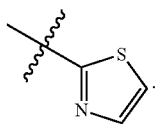

In some embodiments, $R^1$ is

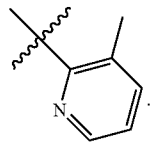 [SMILES: *c1ncccc1C]

In some embodiments, $R^1$ is

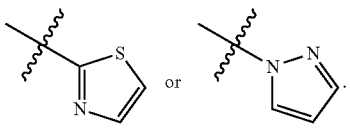 [SMILES: *c1nccs1 ; *n1cccn1]

In some embodiments of a compound of Formula (I), or a pharmaceutically acceptable salt or solvate thereof,

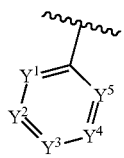

is selected from

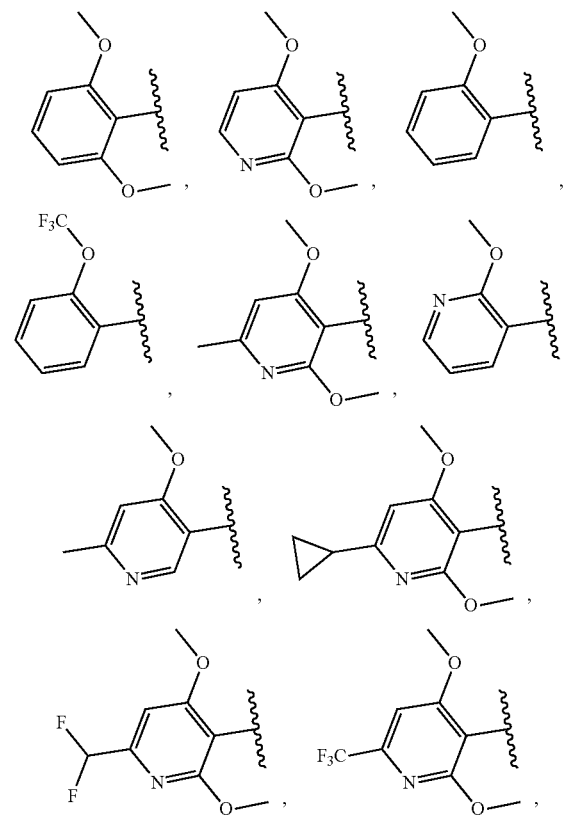

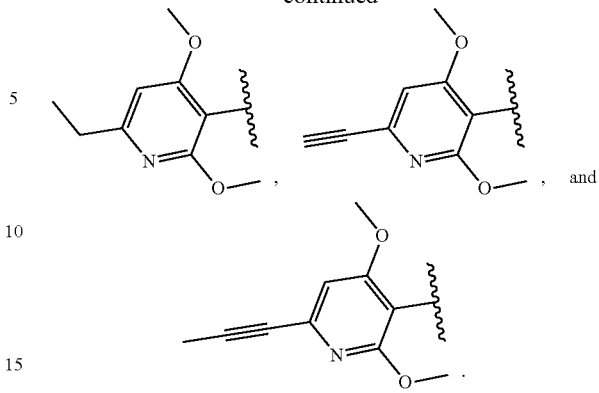

In some embodiments of a compound of Formula (I), or a pharmaceutically acceptable salt or solvate thereof, $R^{10}$ is hydrogen, $C_{1-6}$alkyl, $C_{1-6}$haloalkyl, or $C_{3-6}$cycloalkyl. In some embodiments, $R^{10}$ is hydrogen, $C_{1-6}$alkyl, $C_{1-6}$haloalkyl, or $C_{3-6}$cycloalkyl, wherein $C_{1-6}$alkyl and $C_{3-6}$cycloalkyl are optionally substituted with one, two, or three groups selected from halogen. hydrogen. In some embodiments, $R^{10}$ is hydrogen, $C_{1-6}$alkyl, or $C_{1-6}$haloalkyl. In some embodiments, $R^{10}$ is $C_{1-6}$alkyl or $C_{1-6}$haloalkyl. In some embodiments, $R^{10}$ is hydrogen. In some embodiments, $R^{10}$ is —$CH_3$. In some embodiments, $R^{10}$ is —$CH_2F$. In some embodiments, $R^{10}$ is —$CHF_2$. In some embodiments, $R^{10}$ is —$CH_2CF_3$. In some embodiments, $R^{10}$ is —$CF_3$.

In some embodiments of a compound of Formula (I), or a pharmaceutically acceptable salt or solvate thereof, $R^{11}$ is hydrogen, $C_{1-6}$alkyl, and $C_{1-6}$haloalkyl. In some embodiments, $R^{11}$ is hydrogen. In some embodiments of a compound of Formula (I), or a pharmaceutically acceptable salt or solvate thereof, $R^{11}$ is $C_{1-6}$alkyl.

In some embodiments of a compound of Formula (I), or a pharmaceutically acceptable salt or solvate thereof, $R^{12}$ is hydrogen, $C_{1-6}$alkyl, and $C_{1-6}$haloalkyl. In some embodiments, $R^{12}$ is hydrogen. In some embodiments of a compound of Formula (I), or a pharmaceutically acceptable salt or solvate thereof, $R^{12}$ is $C_{1-6}$alkyl.

In some embodiments of a compound of Formula (I), or a pharmaceutically acceptable salt or solvate thereof, $R^{13}$ is $C_{1-6}$alkyl, $C_{1-6}$haloalkyl, or $C_{3-6}$cycloalkyl. In some embodiments of a compound of Formula (I), or a pharmaceutically acceptable salt or solvate thereof, $R^{13}$ is $C_{1-6}$alkyl or $C_{1-6}$haloalkyl.

In some embodiments of a compound of Formula (I), or a pharmaceutically acceptable salt or solvate thereof, each $R^{15a}$, each $R^{15b}$, and each $R^{15c}$ are independently halogen, oxo, —CN, $C_{1-6}$alkyl, $C_{1-6}$haloalkyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$N(R^{10})(R^{11})$, —$C(O)OR^{10}$, —$C(O)R^{13}$, or —$C(O)N(R^{10})(R^{11})$. In some embodiments of a compound of Formula (I), each $R^{15a}$, each $R^{15b}$, and each $R^{15c}$ are independently halogen, oxo, —CN, $C_{1-6}$alkyl, $C_{1-6}$haloalkyl, $C_{3-10}$cycloalkyl, —$OR^{10}$, or —$N(R^{10})(R^{11})$. In some embodiments of a compound of Formula (I), each $R^{15a}$, each $R^{15b}$, and each $R^{15c}$ are independently halogen, oxo, —CN, $C_{1-6}$alkyl, $C_{1-6}$haloalkyl, —$OR^{10}$, or —$N(R^{10})(R^{11})$. In some embodiments of a compound of Formula (I), each $R^{15a}$, each $R^{15b}$, and each $R^{15c}$ are independently halogen, $C_{1-6}$alkyl, $C_{1-6}$haloalkyl, $C_{3-10}$cycloalkyl, or —$OR^{10}$.

In some embodiments of a compound of Formula (I), each $R^{15a}$, each $R^{15b}$, and each $R^{15c}$ are independently halogen, $C_{1-6}$alkyl, $C_{1-6}$haloalkyl, or —$OR^{10}$. In some embodiments of a compound of Formula (I), each $R^{15a}$, each $R^{15b}$, and each $R^{15c}$ are independently halogen, $C_{1-6}$alkyl, $C_{3-10}$cycloalkyl, or —$OR^{10}$. In some embodiments of a compound of Formula (I), each $R^{15a}$, each $R^{15b}$, and each $R^{15c}$ are independently halogen, $C_{1-6}$alkyl, or —$OR^{10}$. In some embodiments of a compound of Formula (I), each $R^{15a}$, each $R^{15b}$, and each $R^{15c}$ are independently $C_{1-6}$alkyl, $C_{3-10}$cycloalkyl, or —$OR^{10}$. In some embodiments of a compound of Formula (I), each $R^{15a}$, each $R^{15b}$, and each $R^{15c}$ are independently $C_{1-6}$alkyl or —$OR^{10}$. In some embodiments of a compound of Formula (I), each $R^{15a}$, each $R^{15b}$, and each $R^{15c}$ are independently $C_{3-10}$cycloalkyl or —$OR^{10}$. In some embodiments of a compound of Formula (I), each $R^{15a}$, each $R^{15b}$, and each $R^{15c}$ are independently —$OR^{10}$.

In some embodiments disclosed herein is a compound of Formula (Ia), or a pharmaceutically acceptable salt or solvate thereof:

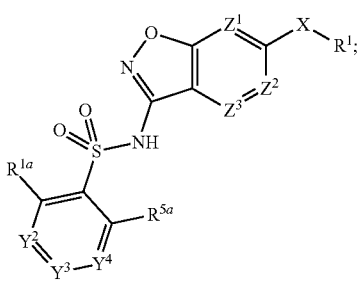

Formula (Ia)

wherein:
$Y^2$ is $CR^{2a}$ or N;
$Y^3$ is $CR^{3a}$ or N;
$Y^4$ is $CR^{4a}$ or N;
$Z^1$ is $CR^{1b}$ or N;
$Z^2$ is $CR^{2b}$ or N;
$Z^3$ is $CR^{3b}$ or N; wherein at least one of $Y^2$, $Y^3$, $Y^4$, $Z^1$, $Z^2$, and $Z^3$ is N;
X is selected from —$C(R^6)(R^{6a})$—, —O—, and —$N(R^7)$—;
$R^1$ is $C_{1-9}$heteroaryl optionally substituted with one, two, or three groups selected from $R^{15a}$;
$R^{1a}$, $R^{2a}$, $R^{3a}$, $R^{4a}$, $R^{5a}$, $R^{1b}$, $R^{2b}$, and $R^{3b}$ are independently selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15b}$;
$R^6$ and $R^{6a}$ are independently selected from hydrogen, halogen, $C_{1-6}$alkyl, $C_{1-6}$haloalkyl, $C_{2-6}$alkenyl, $C_{2-6}$alkynyl, $C_{2-9}$heterocycloalkyl, $C_{6-10}$aryl, $C_{1-9}$heteroaryl, —$OR^{10}$, —$SR^{10}$, —$N(R^{10})$ $(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-4}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-6}$heteroaryl;

$R^7$ is selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{10}$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-6}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-6}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-4}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; and each $R^{15a}$ and each $R^{15b}$ are each independently selected from halogen, oxo, —CN, $C_{1-6}$alkyl, $C_{1-6}$haloalkyl, $C_{2-6}$alkenyl, $C_{2-6}$alkynyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N$ $(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, —$CH_2$—$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, —$SR^{10}$, —$N(R^{10})(R^{11})$, —$C(O)OR^{10}$, —OC (O)N($R^{10}$)($R^{11}$), —N($R^{12}$)C(O)N($R^{10}$)($R^{11}$), —N($R^2$)C(O)O$R^{13}$, —N($R^{12}$)S(O)$_2R^{13}$, —C(O)$R^{13}$, —S(O)$R^{13}$, —OC(O)$R^{13}$, —C(O)N($R^{10}$)($R^{11}$), —C(O)C(O)N($R^{10}$)($R^{11}$), —N($R^{12}$)C(O)$R^{13}$, —S(O)$_2R^{13}$, —S(O)$_2$N($R^{10}$)($R^{11}$)—, S(=O)(=NH)N($R^{10}$)($R^{11}$), —CH$_2$C(O)N($R^{10}$)($R^{11}$), —CH$_2$N($R^{12}$)C(O)$R^3$, —CH$_2$S(O)$_2R^{13}$, and —CH$_2$S(O)$_2$N($R^{10}$)($R^{11}$)).

In some embodiments of a compound of Formula (Ia), or a pharmaceutically acceptable salt or solvate thereof, $R^{1a}$ and $R^{5a}$ are independently selected from hydrogen, halogen, $C_{1-6}$alkyl, $C_{1-6}$haloalkyl, and —O$R^{10}$. In some embodiments of a compound of Formula (Ia), or a pharmaceutically acceptable salt or solvate thereof, $R^{1a}$ and $R^{5a}$ are independently selected from hydrogen and —O$R^{10}$. In some embodiments of a compound of Formula (Ia), or a pharmaceutically acceptable salt or solvate thereof, $R^{1a}$ and $R^{5a}$ are —O$R^{10}$. In some embodiments of a compound of Formula (Ia), or a pharmaceutically acceptable salt or solvate thereof, $R^{1a}$ and $R^{5a}$ are —O$R^{10}$, and $R^{10}$ is $C_{1-6}$alkyl. In some embodiments of a compound of Formula (Ia), or a pharmaceutically acceptable salt or solvate thereof, $R^{1a}$ and $R^{5a}$ are —O$R^{10}$, and $R^{10}$ is —CH$_3$.

In some embodiments of a compound of Formula (Ia), or a pharmaceutically acceptable salt or solvate thereof, $Y^2$ is N; $Y^3$ is C$R^{3a}$; and $Y^4$ is C$R^{4a}$. In some embodiments of a compound of Formula (Ia), or a pharmaceutically acceptable salt or solvate thereof, $Y^2$ is C$R^{2a}$; $Y^3$ is N; and $Y^4$ is C$R^{4a}$. In some embodiments of a compound of Formula (Ia), or a pharmaceutically acceptable salt or solvate thereof, $Y^2$ is N; $Y^3$ is C$R^{3a}$; and $Y^4$ is N. In some embodiments of a compound of Formula (Ia), or a pharmaceutically acceptable salt or solvate thereof, $Y^2$ is C$R^{2a}$; $Y^3$ is C$R^{3a}$; and $Y^4$ is C$R^{4a}$.

In some embodiments of a compound of Formula (Ia), or a pharmaceutically acceptable salt or solvate thereof, $Y^2$ is C$R^{2a}$. In some embodiments of a compound of Formula (Ia), or a pharmaceutically acceptable salt or solvate thereof, $Y^2$ is N.

In some embodiments of a compound of Formula (Ia), or a pharmaceutically acceptable salt or solvate thereof, $Y^3$ is C$R^{3a}$. In some embodiments of a compound of Formula (Ia), or a pharmaceutically acceptable salt or solvate thereof, $Y^3$ is N.

In some embodiments of a compound of Formula (Ia), or a pharmaceutically acceptable salt or solvate thereof, $Y^4$ is C$R^{4a}$. In some embodiments of a compound of Formula (I), or a pharmaceutically acceptable salt or solvate thereof, $Y^4$ is N.

In some embodiments of a compound of Formula (Ia), or a pharmaceutically acceptable salt or solvate thereof, $Y^2$ is N; $Y^3$ is C$R^{3a}$; and $Y^4$ is C$R^{4a}$. In some embodiments of a compound of Formula (Ia), or a pharmaceutically acceptable salt or solvate thereof, $Y^2$ is C$R^{2a}$; $Y^3$ is N; and $Y^4$ is C$R^{4a}$. In some embodiments of a compound of Formula (Ia), or a pharmaceutically acceptable salt or solvate thereof, $Y^2$ is N; $Y^3$ is C$R^{3a}$; and $Y^4$ is N. In some embodiments of a compound of Formula (Ia), or a pharmaceutically acceptable salt or solvate thereof, $Y^2$ is C$R^{2a}$; $Y^3$ is C$R^{3a}$; and $Y^4$ is C$R^{4a}$.

In some embodiments of a compound of Formula (Ia), or a pharmaceutically acceptable salt or solvate thereof, $Z^1$ is C$R^{1b}$; $Z^2$ is C$R^{2b}$; and $Z^3$ is C$R^{3b}$. In some embodiments of a compound of Formula (Ia), or a pharmaceutically acceptable salt or solvate thereof, $Z^1$ is N; $Z^2$ is C$R^{2b}$; and $Z^3$ is C$R^{3b}$. In some embodiments of a compound of Formula (Ia), or a pharmaceutically acceptable salt or solvate thereof, $Z^1$ is C$R^{1b}$; $Z^2$ is N; and $Z^3$ is C$R^{3b}$. In some embodiments of a compound of Formula (Ia), or a pharmaceutically acceptable salt or solvate thereof, $Z^1$ is C$R^{1b}$; $Z^2$ is C$R^{2b}$; and $Z^3$ is N.

In some embodiments of a compound of Formula (Ia), or a pharmaceutically acceptable salt or solvate thereof, $Z^1$ is C$R^{1b}$. In some embodiments of a compound of Formula (Ia), or a pharmaceutically acceptable salt or solvate thereof, $Z^3$ is N.

In some embodiments of a compound of Formula (Ia), or a pharmaceutically acceptable salt or solvate thereof, $Z^2$ is C$R^{2b}$. In some embodiments of a compound of Formula (Ia), or a pharmaceutically acceptable salt or solvate thereof, $Z^2$ is N.

In some embodiments of a compound of Formula (Ia), or a pharmaceutically acceptable salt or solvate thereof, $Z^3$ is C$R^{3b}$. In some embodiments of a compound of Formula (Ia), or a pharmaceutically acceptable salt or solvate thereof, $Z^3$ is N.

In some embodiments of a compound of Formula (Ia), or a pharmaceutically acceptable salt or solvate thereof, $Y^1$ is C$R^{1a}$; $Y^2$ is C$R^{2a}$; $Y^3$ is C$R^{3a}$; $Y^4$ is C$R^{4a}$; $Y^5$ is C$R^{5a}$; $Z^1$ is C$R^{1b}$; $Z^2$ is C$R^{2b}$; and $Z^3$ is C$R^{3b}$. In some embodiments of a compound of Formula (Ia), or a pharmaceutically acceptable salt or solvate thereof, $Y^1$ is C$R^{1a}$; $Y^2$ is N; $Y^3$ is C$R^{3a}$; $Y^4$ is C$R^{4a}$a; $Y^5$ is C$R^{5a}$; $Z^1$ is C$R^{1b}$; $Z^2$ is C$R^{2b}$; and $Z^3$ is C$R^{3b}$. In some embodiments of a compound of Formula (Ia), or a pharmaceutically acceptable salt or solvate thereof, among $Y^1$, $Y^2$, $Y^3$, $Y^4$, $Y^5$, $Z^1$, $Z^2$, and $Z^3$, only $Y^2$ is N. In some embodiments of a compound of Formula (Ia), or a pharmaceutically acceptable salt or solvate thereof, only one of $Y^1$, $Y^2$, $Y^3$, $Y^4$, $Y^5$, $Z^1$, $Z^2$, and $Z^3$ is N. In some embodiments, when $Y^2$ is N, then $R^{1a}$ and $R^{5a}$ are —O$R^{10}$. In some embodiments, when $Y^2$ is N, then $R^{1a}$ and $R^{5a}$ are independently selected from —O—$C_{1-6}$alkyl and —O—$C_{1-6}$haloalkyl. In some embodiments, when $Y^2$ is N, then $R^{1a}$ and $R^{5a}$ are —OCH$_3$.

In some embodiments of a compound of Formula (Ia), or a pharmaceutically acceptable salt or solvate thereof, $R^{2a}$, $R^{3a}$, $R^{4a}$, $R^{1b}$, $R^{2b}$, and $R^{3b}$ are independently selected from hydrogen, halogen, $C_{1-6}$alkyl, $C_{1-6}$haloalkyl, and —O$R^{10}$. In some embodiments of a compound of Formula (Ia), or a pharmaceutically acceptable salt or solvate thereof, $R^{2a}$, $R^{3a}$, $R^{4a}$, $R^{1b}$, $R^{2b}$, and $R^{3b}$ are independently selected from hydrogen, halogen, and $C_{1-6}$alkyl. In some embodiments of a compound of Formula (Ia), or a pharmaceutically acceptable salt or solvate thereof, $R^{2a}$, $R^{3a}$, $R^{4a}$, $R^{1b}$, $R^{2b}$, and $R^{3b}$ are hydrogen. In some embodiments of a compound of Formula (Ia), or a pharmaceutically acceptable salt or solvate thereof, $R^{1b}$ and $R^{2b}$ are hydrogen, $R^{3b}$ is —O$R^{10}$, and $R^{10}$ is $C_{1-6}$alkyl. In some embodiments of a compound of Formula (Ia), or a pharmaceutically acceptable salt or solvate thereof, $R^{1b}$ and $R^{2a}$ are hydrogen, $R^1$ is —O$R^{10}$, $R^{10}$ is $C_{1-6}$alkyl substituted with one, two, or three halogen.

In some embodiments of a compound of Formula (Ia), or a pharmaceutically acceptable salt or solvate thereof, $R^{1a}$ is hydrogen, halogen, $C_{1-6}$alkyl, $C_{1-6}$haloalkyl, or —O$R^{11}$. In some embodiments, $R^{1a}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{1a}$ is hydrogen. In some embodiments, $R^{1a}$ is $C_{1-6}$alkyl. In some embodiments, $R^{1a}$ is $C_{1-6}$alkoxyl, wherein the alkoxyl is optionally substituted with 1, 2 or 3 halogen. In some embodiments, $R^{1a}$ is $C_{1-6}$alkoxyl. In some $^{1a}$ is —OCF$_3$.

In some embodiments of a compound of Formula (Ia), or a pharmaceutically acceptable salt or solvate thereof, $R^{2a}$ is hydrogen, halogen, $C_{1-6}$alkyl, $C_{1-6}$haloalkyl, or —O$R^{10}$. In some embodiments, $R^{2a}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{2a}$ is hydrogen. In some embodiments, $R^{2a}$ is $C_{1-6}$alkyl. In some embodiments, $R^{2a}$ is $C_{1-6}$alkoxyl, wherein the alkoxyl is optionally substituted with 1, 2 or 3 halogen.

In some embodiments of a compound of Formula (Ia), or a pharmaceutically acceptable salt or solvate thereof, $R^{3a}$ is hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, —$OR^{10}$, —$SR^{10}$, or —$SF_5$, wherein $C_{1-6}$alkyl, $C_{2-6}$alkenyl, $C_{2-6}$alkynyl, $C_{3-6}$cycloalkyl, are $C_{2-9}$heterocycloalkyl are optionally substituted with one, two, or three groups selected from $R^{15b}$. In some embodiments, $R^{3a}$ is hydrogen, halogen, $C_{1-6}$alkyl, $C_{1-6}$haloalkyl, $C_{2-6}$alkenyl, $C_{2-6}$alkynyl, or $C_{3-6}$cycloalkyl, wherein the $C_{1-6}$alkyl, $C_{2-6}$alkenyl, $C_{2-6}$alkynyl, and $C_{3-6}$cycloalkyl are optionally substituted. In some embodiments, $R^{3a}$ is hydrogen, $C_{1-6}$alkyl, $C_{1-6}$haloalkyl, $C_{2-6}$alkenyl, or $C_{2-6}$alkynyl. In some embodiments, $R^{3a}$ is hydrogen. In some embodiments, $R^3$ is $C_{1-6}$alkyl. In some embodiments, $R^{3a}$ is $C_{1-6}$alkyl. In some embodiments, $R^{3a}$ is $C_{1-6}$haloalkyl. In some embodiments, $R^{3a}$ is $C_{2-6}$alkenyl. In some embodiments, $R^{3a}$ is $C_{2-6}$alkynyl.

In some embodiments of a compound of Formula (Ia), or a pharmaceutically acceptable salt or solvate thereof, $R^{4a}$ is hydrogen, halogen, $C_{1-6}$alkyl, $C_{1-6}$haloalkyl, or —$OR^{10}$. In some embodiments, $R^{4a}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{4a}$ is hydrogen. In some embodiments, $R^{4a}$ is $C_{1-6}$alkyl. In some embodiments, $R^{4a}$ is $C_{1-6}$alkoxyl, wherein the alkoxyl is optionally substituted with 1, 2 or 3 halogen.

In some embodiments of a compound of Formula (Ia), or a pharmaceutically acceptable salt or solvate thereof, $R^{5a}$ is hydrogen, halogen, $C_{1-6}$alkyl, $C_{1-6}$haloalkyl, or —$OR^{10}$. In some embodiments, $R^{5a}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{5a}$ is hydrogen. In some embodiments, $R^{5a}$ is $C_{1-6}$alkoxyl, wherein the alkoxyl is optionally substituted with 1, 2 or 3 halogen. In some embodiments, $R^{5a}$ is $C_{1-6}$alkoxyl. In some embodiments, $R^{5a}$ is $C_{1-6}$alkoxyl. In some embodiments, $R^{5a}$ is —$OCH_3$.

In some embodiments of a compound of Formula (Ia), or a pharmaceutically acceptable salt or solvate thereof, $R^{1b}$ is hydrogen, halogen, $C_{1-6}$alkyl, or $C_{1-6}$haloalkyl, wherein $C_{1-6}$alkyl is optionally substituted with one, two, or three groups selected from $R^{1b}$. In some embodiments, $R^{1b}$ is hydrogen. In some embodiments, $R^{1b}$ is halogen. In some embodiments, $R^{1b}$ is $C_{1-6}$alkyl. In some embodiments, $R^{1b}$ is $C_{1-6}$haloalkyl.

In some embodiments of a compound of Formula (Ia), or a pharmaceutically acceptable salt or solvate thereof, $R^{2b}$ is hydrogen, halogen, $C_{1-6}$alkyl, or $C_{1-6}$haloalkyl, wherein $C_{1-6}$alkyl is optionally substituted with one, two, or three groups selected from $R^{2b}$. In some embodiments, $R^{2b}$ is hydrogen. In some embodiments, $R^{2b}$ is halogen. In some embodiments, $R^{2b}$ is $C_{1-6}$alkyl. In some embodiments, $R^{1b}$ is $C_{1-6}$haloalkyl.

In some embodiments of a compound of Formula (Ia), or a pharmaceutically acceptable salt or solvate thereof, $R^{3b}$ is hydrogen, halogen, $C_{1-6}$alkyl, $C_{1-6}$haloalkyl, or —$OR^{10}$. In some embodiments, $R^{3b}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{3b}$ is hydrogen. In some embodiments, $R^{3b}$ is $C_{1-6}$alkoxyl, wherein the alkoxyl is optionally substituted with 1, 2 or 3 halogen. In some embodiments, $R^{3b}$ is $C_{1-6}$alkoxyl. In some embodiments, $R^{3b}$ is $C_{1-3}$alkoxyl. In some embodiments, $R^{3b}$ is $C_{1-3}$alkoxyl, wherein the alkoxyl is optionally substituted with 1, 2 or 3 halogen. In some embodiments, $R^{3b}$ is —$OCH_3$. In some embodiments, $R^{3b}$ is —$OCH_2F$. In some embodiments, $R^{3b}$ is —$OCF_3$. In some embodiments, $R^{3b}$ is —$OCHF_2$. In some embodiments, $R^{3b}$ is —$OCH_2CF_3$.

In some embodiments of a compound of Formula (Ia), or a pharmaceutically acceptable salt or solvate thereof, X is —$C(R^6)(R^{6a})$—. In some embodiments of a compound of Formula (Ia), or a pharmaceutically acceptable salt or solvate thereof, X is —$C(R^6)(R^{6a})$— and $R^6$ and $R^{6a}$ are independently selected from hydrogen, halogen, $C_{1-6}$alkyl, and —OH. In some embodiments of a compound of Formula (Ia), or a pharmaceutically acceptable salt or solvate thereof, X is —$C(R^6)(R^{6a})$— and $R^6$ and $R^{6a}$ are hydrogen.

In some embodiments of a compound of Formula (Ia), or a pharmaceutically acceptable salt or solvate thereof, X is —O—.

In some embodiments of a compound of Formula (Ia), or a pharmaceutically acceptable salt or solvate thereof, X is —$N(R^7)$—. In some embodiments of a compound of Formula (Ia), or a pharmaceutically acceptable salt or solvate thereof, X is —$N(R^7)$— and $R^7$ is hydrogen. In some embodiments of a compound of Formula (Ia), or a pharmaceutically acceptable salt or solvate thereof, X is —$N(R^7)$— and $R^7$ is $C_{1-6}$alkyl.

In some embodiments of a compound of Formula (Ia), or a pharmaceutically acceptable salt or solvate thereof, $R^1$ is optionally substituted $C_{1-9}$heteroaryl. In some embodiments of a compound of Formula (Ia), or a pharmaceutically acceptable salt or solvate thereof, $R^1$ is optionally substituted 5 or 6 membered heteroaryl. In some embodiments of a compound of Formula (Ia), or a pharmaceutically acceptable salt or solvate thereof, $R^1$ is optionally substituted 5 membered heteroaryl. In some embodiments of a compound of Formula (Ia), or a pharmaceutically acceptable salt or solvate thereof, $R^1$ is optionally substituted 6 membered heteroaryl. In some embodiments of a compound of Formula (Ia), or a pharmaceutically acceptable salt or solvate thereof, $R^1$ is monocyclic heteroaryl. In some embodiments of a compound of Formula (Ia), or a pharmaceutically acceptable salt or solvate thereof, $R^1$ is bicyclic heteroaryl. In some embodiments, $R^1$ is optionally substituted with one, two, or three groups selected from $R^1$. In some embodiments, $R^1$ is optionally substituted with one, two, or three groups selected from halogen, $C_{1-6}$alkyl, $C_{1-6}$haloalkyl, and $C_{1-6}$alkoxyl. In some embodiments, $R^1$ is optionally substituted with one, two, or three groups selected from oxo, —CN, amino, OH, halogen, $C_{1-6}$alkyl, $C_{1-6}$haloalkyl, $C_{1-6}$alkoxyl, and $C_{3-6}$cycloalkyl.

In some embodiments of a compound of Formula (Ia), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are optionally substituted with one, two, or three groups selected from $R^{15a}$. In some embodiments of a compound of Formula (Ia), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from $R^{15a}$. In some embodiments of a compound of Formula (Ia), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from $R^{15a}$ and each $R^{15a}$ is independently selected from halogen, $C_{1-6}$alkyl, $C_{1-6}$haloalkyl, and —$OR^{10}$. In some embodiments of a compound of Formula (Ia), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, pyrazolyl, imidazolyl, isoxazolyl, thiazolyl, oxazolyl, pyrimidinyl, pyridazinyl, and pyridinyl are substituted with one group selected from $R^{15a}$ and $R^{15a}$ is selected from halogen, $C_{1-6}$alkyl, $C_{1-6}$haloalkyl, and —$OR^{10}$.

In some embodiments of a compound of Formula (Ia), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are optionally substituted with one, two, or three groups selected from $R^{15a}$. In some embodiments of a compound of Formula (Ia), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are substituted with one, two, or three groups selected from $R^{15a}$. In some embodiments of a compound of Formula (Ia), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are substituted with one, two, or three groups selected from $R^{15a}$ and each $R^{15a}$ is independently selected from halogen, $C_{1-6}$alkyl, $C_{1-6}$haloalkyl, and —$OR^{10}$. In some embodiments of a compound of Formula (Ia), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are substituted with one group selected from $R^{15a}$ and $R^{15a}$ is selected from halogen, $C_{1-6}$alkyl, $C_{1-6}$haloalkyl, and —$OR^{10}$.

In some embodiments of a compound of Formula (Ia), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are unsubstituted. In some embodiments of a compound of Formula (Ia), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are unsubstituted. In some embodiments of a compound of Formula (Ia), or a pharmaceutically acceptable salt or solvate thereof, $R^1$ is unsubstituted pyrazolyl. In some embodiments of a compound of Formula (Ia), or a pharmaceutically acceptable salt or solvate thereof, $R^1$ is unsubstituted imidazolyl. In some embodiments of a compound of Formula (Ia), or a pharmaceutically acceptable salt or solvate thereof, $R^1$ is unsubstituted isoxazolyl. In some embodiments of a compound of Formula (Ia), or a pharmaceutically acceptable salt or solvate thereof, $R^1$ is unsubstituted oxazolyl. In some embodiments of a compound of Formula (Ia), or a pharmaceutically acceptable salt or solvate thereof, $R^1$ is unsubstituted pyridinyl. In some embodiments of a compound of Formula (Ia), or a pharmaceutically acceptable salt or solvate thereof, $R^1$ is unsubstituted thiazolyl. In some embodiments of a compound of Formula (Ia), or a pharmaceutically acceptable salt or solvate thereof, $R^1$ is unsubstituted pyrimidinyl. In some embodiments of a compound of Formula (Ia), or a pharmaceutically acceptable salt or solvate thereof, $R^1$ is unsubstituted pyridazinyl.

In some embodiments of a compound of Formula (Ia), or a pharmaceutically acceptable salt or solvate thereof, $R^1$ is selected from

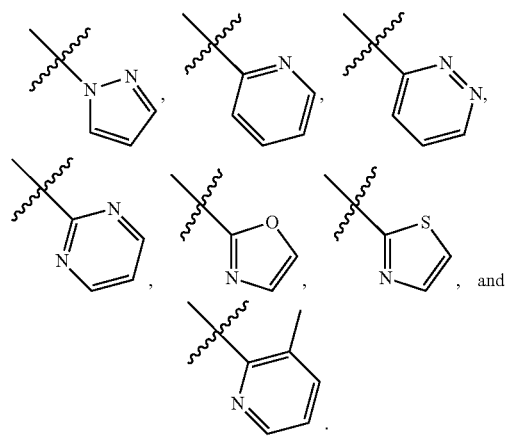

In some embodiments of a compound of Formula (Ia), or a pharmaceutically acceptable salt or solvate thereof, $R^1$ is

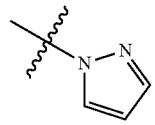

In some embodiments of a compound of Formula (Ia), or a pharmaceutically acceptable salt or solvate thereof, $R^1$ is

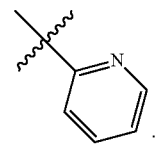 [SMILES: *c1ccccn1]

In some embodiments of a compound of Formula Ia or a pharmaceutically acceptable salt or solvate thereof, $R^1$ is selected from

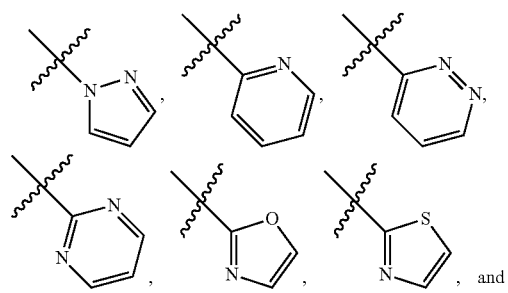

-continued

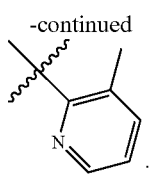

wherein each is optionally substituted with 1, 2 or 3 $R^{15a}$. In some embodiments, $R^1$ is

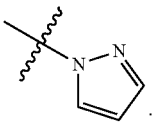

In some embodiments, $R^1$ is

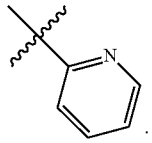

In some embodiments, $R^1$ is

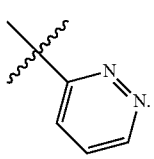

In some embodiments, $R^1$ is

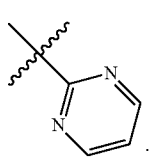 [SMILES: *c1ncccn1]

In some embodiments, $R^1$ is

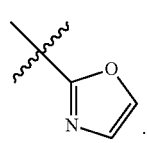

In some embodiments, $R^1$ is

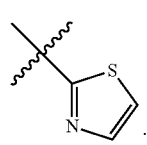

In some embodiments, $R^1$ is

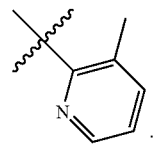

In some embodiments, $R^1$ is

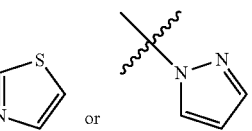

or

In some embodiments of a compound of Formula (Ia), or a pharmaceutically acceptable salt or solvate thereof,

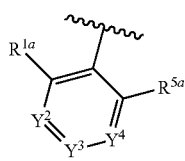

is selected from

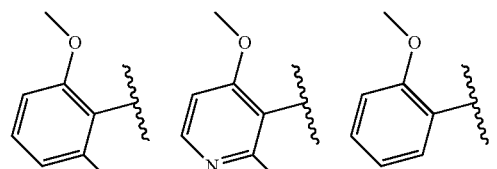

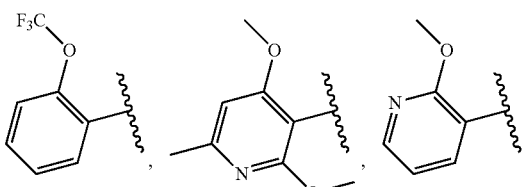

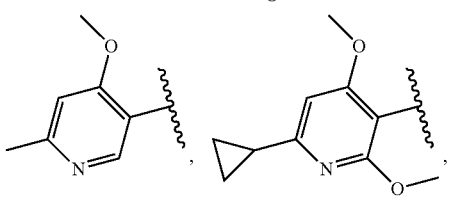

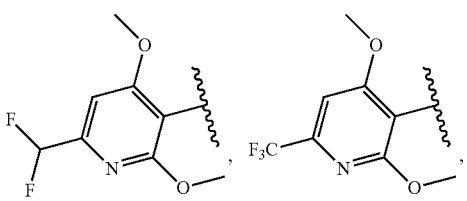

-continued

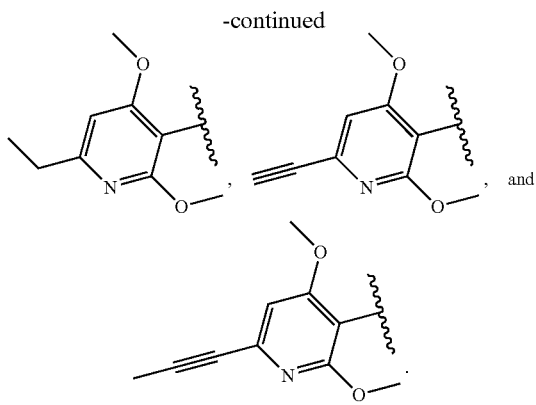

In some embodiments of a compound of Formula (Ia), or a pharmaceutically acceptable salt or solvate thereof, $R^{10}$ is hydrogen, $C_{1-6}$alkyl, $C_{1-6}$haloalkyl, or $C_{3-6}$cycloalkyl. In some embodiments, $R^{10}$ is hydrogen, $C_{1-6}$alkyl, $C_{1-6}$haloalkyl, or $C_{3-6}$cycloalkyl, wherein $C_{1-6}$alkyl and $C_{3-6}$cycloalkyl are optionally substituted with one, two, or three groups selected from halogen. hydrogen. In some embodiments, $R^{10}$ is hydrogen, $C_{1-6}$alkyl, or $C_{1-6}$haloalkyl. In some embodiments, $R^{10}$ is $C_{1-6}$alkyl or $C_{1-6}$haloalkyl. In some embodiments, $R^{10}$ is hydrogen. In some embodiments, $R^{10}$ is —$CH_3$. In some embodiments, $R^{10}$ is —$CH_2F$. In some embodiments, $R^{10}$ is —$CHF_2$. In some embodiments, $R^{10}$ is —$CH_2CF_3$. In some embodiments, $R^{10}$ is —$CF_3$.

In some embodiments of a compound of Formula (Ia), or a pharmaceutically acceptable salt or solvate thereof, $R^{11}$ is hydrogen, $C_{1-6}$alkyl, and $C_{1-6}$haloalkyl. In some embodiments, $R^{11}$ is hydrogen. In some embodiments of a compound of Formula (Ia), or a pharmaceutically acceptable salt or solvate thereof, $R^{11}$ is $C_{1-6}$alkyl.

In some embodiments of a compound of Formula (Ia), or a pharmaceutically acceptable salt or solvate thereof, $R^{12}$ is hydrogen, $C_{1-6}$alkyl, and $C_{1-6}$haloalkyl. In some embodiments, $R^{12}$ is hydrogen. In some embodiments of a compound of Formula (Ia), or a pharmaceutically acceptable salt or solvate thereof, $R^{12}$ is $C_{1-6}$alkyl.

In some embodiments of a compound of Formula (Ia), or a pharmaceutically acceptable salt or solvate thereof, $R^{13}$ is $C_{1-6}$alkyl, $C_{1-6}$haloalkyl, or $C_{3-6}$cycloalkyl. In some embodiments of a compound of Formula (Ia), or a pharmaceutically acceptable salt or solvate thereof, $R^{13}$ is $C_{1-6}$alkyl or $C_{1-6}$haloalkyl.

In some embodiments of a compound of Formula (Ia), or a pharmaceutically acceptable salt or solvate thereof, each $R^{15a}$, each $R^{15b}$, and each $R^{15c}$ are independently halogen, oxo, —CN, $C_{1-6}$alkyl, $C_{1-6}$haloalkyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$N(R^{10})(R^{11})$, —$C(O)OR^{10}$, —$C(O)R^{13}$, or —$C(O)N(R^{10})(R^{11})$. In some embodiments of a compound of Formula (Ia), each $R^{15a}$, each $R^{15b}$, and each $R^{15b}$ are independently halogen, oxo, —CN, $C_{1-6}$alkyl, $C_{1-6}$haloalkyl, $C_{3-10}$cycloalkyl, —$OR^{10}$, or —$N(R^{11})(R^{11})$. In some embodiments of a compound of Formula (Ia), each $R^{15a}$, each $R^{15b}$, and each $R^{15c}$ are independently halogen, oxo, —CN, $C_{1-6}$alkyl, $C_{1-6}$haloalkyl, —$OR^{10}$, or —$N(R^{10})(R^{11})$. In some embodiments of a compound of Formula (Ia), each $R^{15a}$, each $R^{15b}$, and each $R^{15c}$ are independently halogen, $C_{1-6}$alkyl, $C_{1-6}$haloalkyl, $C_{3-10}$cycloalkyl, or —$OR^{10}$.

In some embodiments of a compound of Formula (Ia), each $R^{15a}$, each $R^{15b}$, and each $R^{15c}$ are independently halogen, $C_{1-6}$alkyl, $C_{1-6}$haloalkyl, or —$OR^{10}$. In some embodiments of a compound of Formula (Ia), each $R^{15a}$, each $R^{15b}$, and each $R^{15c}$ are independently halogen, $C_{1-6}$alkyl, $C_{3-10}$cycloalkyl, or —$OR^{10}$. In some embodiments of a compound of Formula (Ia), each $R^{15a}$, each $R^{15b}$, and each $R^{15c}$ are independently halogen, $C_{1-6}$alkyl, or —$OR^{10}$. In some embodiments of a compound of Formula (Ia), each $R^{15a}$, each $R^{15b}$, and each $R^{15c}$ are independently $C_{1-6}$alkyl, $C_{3-10}$cycloalkyl, or —$OR^{10}$. In some embodiments of a compound of Formula (Ia), each $R^{15a}$, each $R^{15b}$, and each $R^{15c}$ are independently $C_{1-6}$alkyl or —$OR^{10}$. In some embodiments of a compound of Formula (Ia), each $R^{15a}$, each $R^{15b}$, and each $R^{15c}$ are independently $C_{3-10}$cycloalkyl or —$OR^{10}$. In some embodiments of a compound of Formula (Ia), each $R^{15a}$, each $R^{15b}$, and each $R^{15c}$ are independently —$OR^{10}$.

In some embodiments disclosed herein is a compound of Formula (I'), or a pharmaceutically acceptable salt or solvate thereof:

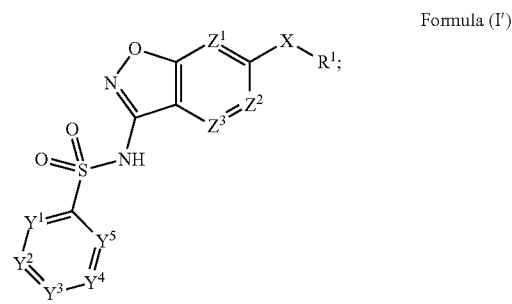

Formula (I')

wherein:
$Y^1$ is $CR^{1a}$ or N;
$Y^2$ is $CR^{1a}$ or N;
$Y^3$ is $CR^{3a}$ or N;
$Y^4$ is $CR^{4a}$ or N;
$Y^5$ is $CR^{5a}$ or N;
$Z^1$ is $CR^{1b}$ or N;
$Z^2$ is $CR^{2b}$ or N;
$Z^3$ is $CR^{3b}$ or N;
X is —O— or —S—; or
X is selected from —C($R^6$)($R^{6a}$)— and —N($R^7$)—, wherein at least one of $Y^1$, $Y^2$, $Y^3$, $Y^4$, $Y^5$, $Z^1$, $Z^2$, and $Z^3$ is N;
$R^1$ is $C_{1-9}$heteroaryl optionally substituted with one, two, or three groups selected from $R^{15a}$;
$R^{1a}$, $R^{2a}$, $R^{3a}$, $R^{4a}$, $R^{5a}$, $R^{1b}$, $R^{2b}$, and $R^{3b}$ are independently selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15b}$;

$R^6$ and $R^{6a}$ are independently selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-6}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

$R^7$ is selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-6}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{10}$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; and each $R^{15a}$ and each $R^{15b}$ are each independently selected from halogen, oxo, —CN, $C_{1-6}$alkyl, $C_{1-6}$haloalkyl, $C_{2-4}$alkenyl, $C_{2-6}$alkynyl, $C_{3-10}$cycloalkyl, —$CH_2$—$C_{3-6}$cycloalkyl, $C_{2-6}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{10}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, —$CH_2$—$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^2)C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^3$, —$CH_2S(O)_2R^{13}$, and —$CH_2S(O)_2N(R^{10})(R^{11})$.

In some embodiments of a compound of Formula (I'), or a pharmaceutically acceptable salt or solvate thereof, X is —O—. In some embodiments of a compound of Formula (I'), or a pharmaceutically acceptable salt or solvate thereof, X is —S—. In some embodiments of a compound of Formula (I'), or a pharmaceutically acceptable salt or solvate thereof, X is —O— or —S—. In some embodiments of a compound of Formula (I'), or a pharmaceutically acceptable salt or solvate thereof, X is —$C(R^6)(R^{6a})$—, wherein at least one of $Y^1$, $Y^2$, $Y^3$, $Y^4$, $Y^5$, $Z^1$, $Z^2$, and $Z^3$ is N. In some embodiments of a compound of Formula (I'), or a pharmaceutically acceptable salt or solvate thereof, X is —$N(R^7)$—, wherein at least one of $Y^1$, $Y^2$, $Y^3$, $Y^4$, $Y^5$, $Z^1$, $Z^2$, and $Z^3$ is N.

In some embodiments disclosed herein is a compound of Formula (I'), or a pharmaceutically acceptable salt or solvate thereof:

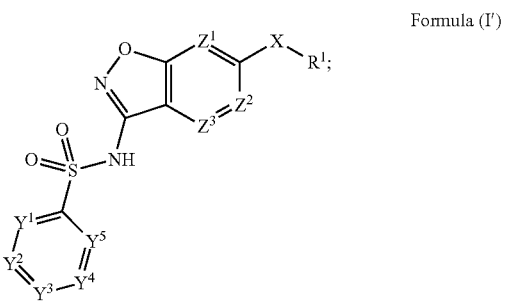

Formula (I')

wherein:
$Y^1$ is $CR^{1a}$ or N;
$Y^2$ is $CR^{2a}$ or N;
$Y^3$ is $CR^{3b}$ or N;
$Y^4$ is $CR^{4a}$ or N;
$Y^5$ is $CR^{5a}$ or N;
$Z^1$ is $CR^{1b}$ or N;
$Z^2$ is $CR^{2b}$ or N;
$Z^3$ is $CR^{3b}$ or N;
X is —O—;
$R^1$ is $C_{1-9}$heteroaryl optionally substituted with one, two, or three groups selected from $R^{15a}$;
$R^{1a}$, $R^{2a}$, $R^{3a}$, $R^{4a}$, $R^{5a}$, $R^{1b}$, $R^{2b}$, and $R^{3b}$ are independently selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15b}$;

each $R^{10}$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-4}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-4}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; and each $R^{15a}$ and each $R^{15b}$ are each independently selected from halogen, oxo, —CN, $C_{1-6}$alkyl, $C_{1-6}$haloalkyl, $C_{2-6}$alkenyl, $C_{2-6}$alkynyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-4}$alkenyl, $C_{2-6}$alkynyl, $C_{3-6}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, —$CH_2$—$C_{1-9}$heteroaryl, and $C_{1-9}$heteroaryl are optionally substituted with one, two or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^3$, —$CH_2S(O)_2R^{13}$, and —$CH_2S(O)_2N(R^{10})(R^{11})$.

In some embodiments, a compound of Formula (I') has a structure of Formula (Ia).

In some embodiments of a compound of Formula (I'), or a pharmaceutically acceptable salt or solvate thereof, X is —O—. In some embodiments of a compound of Formula (I'), or a pharmaceutically acceptable salt or solvate thereof, X is —S—. In some embodiments of a compound of Formula (I'), or a pharmaceutically acceptable salt or solvate thereof, X is —$C(R^{10})(R^{11})$—. In some embodiments of a compound of Formula (I'), or a pharmaceutically acceptable salt or solvate thereof, X is —$N(R^7)$—.

In some embodiments of a compound of Formula (I'), or a pharmaceutically acceptable salt or solvate thereof, $Y^1$ is $CR^{1a}$. In some embodiments of a compound of Formula (I'), or a pharmaceutically acceptable salt or solvate thereof, $Y^1$ is N.

In some embodiments of a compound of Formula (I'), or a pharmaceutically acceptable salt or solvate thereof, $Y^2$ is $CR^{2a}$. In some embodiments of a compound of Formula (I'), or a pharmaceutically acceptable salt or solvate thereof, $Y^2$ is N.

In some embodiments of a compound of Formula (I'), or a pharmaceutically acceptable salt or solvate thereof, $Y^3$ is $CR^{3a}$. In some embodiments of a compound of Formula (I'), or a pharmaceutically acceptable salt or solvate thereof, $Y^3$ is N.

In some embodiments of a compound of Formula (I'), or a pharmaceutically acceptable salt or solvate thereof, $Y^4$ is $CR^{4a}$. In some embodiments of a compound of Formula (I'), or a pharmaceutically acceptable salt or solvate thereof, $Y^4$ is N.

In some embodiments of a compound of Formula (I'), or a pharmaceutically acceptable salt or solvate thereof, $Y^5$ is $CR^{5a}$. In some embodiments of a compound of Formula (I'), or a pharmaceutically acceptable salt or solvate thereof, $Y^5$ is N.

In some embodiments of a compound of Formula (I'), or a pharmaceutically acceptable salt or solvate thereof, $Y^1$ is $CR^{1a}$ and $Y^5$ is $CR^{5a}$.

In some embodiments of a compound of Formula (I'), or a pharmaceutically acceptable salt or solvate thereof, $Y^1$ is $CR^{1a}$, $Y^5$ is $CR^{5a}$, and $R^{1a}$ and $R^{5a}$ are independently selected from hydrogen, halogen, $C_{1-6}$alkyl, $C_{1-6}$haloalkyl, and —$OR^{10}$. In some embodiments of a compound of Formula (I'), or a pharmaceutically acceptable salt or solvate thereof, $Y^1$ is $CR^{1a}$, $Y^5$ is $CR^{5a}$, and $R^{1a}$ and $R^{5a}$ are independently selected from hydrogen and —$OR^{10}$. In some embodiments of a compound of Formula (I'), or a pharmaceutically acceptable salt or solvate thereof, $Y^1$ is $CR^{1a}$, $Y^5$ is $CR^{5a}$, and $R^{1a}$ and $R^{5a}$ are —$OR^{10}$. In some embodiments of a compound of Formula (I'), or a pharmaceutically acceptable salt or solvate thereof, $Y^1$ is $CR^{1a}$, $Y^5$ is $CR^{5a}$, $R^{1a}$ and $R^{5a}$ are —$OR^{10}$, and $R^{10}$ is $C_{1-6}$alkyl. In some embodiments of a compound of Formula (I'), or a pharmaceutically acceptable salt or solvate thereof, $Y^1$ is $CR^{1a}$, $Y^5$ is $CR^{5a}$, $R^{1a}$ and $R^{5a}$ are —$OR^{10}$, and $R^{10}$ is —$CH_3$.

In some embodiments of a compound of Formula (I'), or a pharmaceutically acceptable salt or solvate thereof, $Y^2$ is N; $Y^3$ is $CR^{3a}$; and $Y^4$ is $CR^{4a}$. In some embodiments of a compound of Formula (I'), or a pharmaceutically acceptable salt or solvate thereof, $Y^2$ is $CR^{2a}$; $Y^3$ is N; and $Y^4$ is $CR^{4a}$. In some embodiments of a compound of Formula (I'), or a pharmaceutically acceptable salt or solvate thereof, $Y^2$ is N; $Y^3$ is $CR^{3a}$; and $Y^4$ is N. In some embodiments of a compound of Formula (I'), or a pharmaceutically acceptable salt or solvate thereof, $Y^2$ is $CR^{2b}$; $Y^3$ is $CR^{3a}$; and $Y^4$ is $CR^{4a}$.

In some embodiments of a compound of Formula (I'), or a pharmaceutically acceptable salt or solvate thereof, $Y^1$ is $CR^{1a}$; $Y^5$ is $CR^{5a}$; $Y^2$ is N; $Y^3$ is $CR^{3a}$; and $Y^4$ is $CR^{4a}$. In some embodiments of a compound of Formula (I'), or a pharmaceutically acceptable salt or solvate thereof, $Y^1$ is $CR^{1a}$; $Y^5$ is $CR^{5a}$; $Y^2$ is $CR^{2a}$; $Y^3$ is N; and $Y^4$ is $CR^{4a}$. In some embodiments of a compound of Formula (I'), or a pharmaceutically acceptable salt or solvate thereof, $Y^1$ is $CR^{1a}$; $Y^5$ is $CR^{5a}$; $Y^2$ is N; $Y^3$ is $CR^{3a}$; and $Y^4$ is N. In some embodiments of a compound of Formula (I'), or a pharmaceutically acceptable salt or solvate thereof, $Y^1$ is $CR^{1a}$; $Y^5$ is $CR^{5a}$; $Y^2$ is $CR^{2a}$; $Y^3$ is $CR^{3a}$; and $Y^4$ is $CR^{4a}$.

In some embodiments of a compound of Formula (I'), or a pharmaceutically acceptable salt or solvate thereof, $Z^1$ is $CR^{1b}$; $Z^2$ is $CR^{2b}$; and $Z^3$ is $CR^{3b}$. In some embodiments of a compound of Formula (I'), or a pharmaceutically acceptable salt or solvate thereof, $Z^1$ is N; $Z^2$ is $CR^{2b}$; and $Z^3$ is $CR^{3b}$. In some embodiments of a compound of Formula (I'), or a pharmaceutically acceptable salt or solvate thereof, $Z^1$ is $CR^{1b}$; $Z^2$ is N; and $Z^3$ is $CR^{3b}$. In some embodiments of a compound of Formula (I'), or a pharmaceutically acceptable salt or solvate thereof, $Z^1$ is $CR^{1b}$; $Z^2$ is $CR^{2b}$; and $Z^3$ is N.

In some embodiments of a compound of Formula (I'), or a pharmaceutically acceptable salt or solvate thereof, $Z^1$ is $CR^{1b}$. In some embodiments of a compound of Formula (I'), or a pharmaceutically acceptable salt or solvate thereof, $Z^3$ is N.

In some embodiments of a compound of Formula (I'), or a pharmaceutically acceptable salt or solvate thereof, $Z^2$ is $CR^{2b}$. In some embodiments of a compound of Formula (I'), or a pharmaceutically acceptable salt or solvate thereof, $Z^2$ is N.

In some embodiments of a compound of Formula (I'), or a pharmaceutically acceptable salt or solvate thereof, $Z^3$ is $CR^{3b}$. In some embodiments of a compound of Formula (I'), or a pharmaceutically acceptable salt or solvate thereof, $Z^3$ is N.

In some embodiments of a compound of Formula (I'), or a pharmaceutically acceptable salt or solvate thereof, $Y^1$ is $CR^{1a}$; $Y^2$ is $CR^{2a}$; $Y^3$ is $CR^{3a}$; $Y^4$ is $CR^{4a}$; $Y^5$ is $CR^{5a}$; $Z^1$ is $CR^{1b}$; $Z^2$ is $CR^{2b}$; and $Z^3$ is $CR^{3b}$. In some embodiments of a compound of Formula (I'), or a pharmaceutically acceptable salt or solvate thereof, $Y^1$ is $CR^{1a}$; $Y^2$ is N; $Y^3$ is $CR^{3a}$; $Y^4$ is $CR^{4a}$; $Y^5$ is $CR^{5a}$; $Z^1$ is $CR^{1b}$; $Z^2$ is $CR^{2b}$; and $Z^3$ is $CR^{3b}$. In some embodiments of a compound of Formula (I'), or a pharmaceutically acceptable salt or solvate thereof, among $Y^1$, $Y^2$, $Y^3$, $Y^4$, $Y^5$, $Z^1$, $Z^2$, and $Z^3$, only $Y^2$ is N. In some embodiments of a compound of Formula (I'), or a pharmaceutically acceptable salt or solvate thereof, only one of $Y^1$, $Y^2$, $Y^3$, $Y^4$, $Y^5$, $Z^1$, $Z^2$, and $Z^3$ is N. In some embodiments, when $Y^2$ is N, then $R^{1a}$ and $R^{5a}$ are —$OR^{10}$. In some embodiments, when $Y^2$ is N, then $R^{1a}$ and $R^{5a}$ are independently selected from —O—$C_{1-6}$alkyl and —O—$C_{1-6}$haloalkyl. In some embodiments, when $Y^2$ is N, then $R^{1a}$ and $R^{5a}$ are —$OCH_3$.

In some embodiments of a compound of Formula (I'), or a pharmaceutically acceptable salt or solvate thereof, $R^{2a}$, $R^{3a}$, $R^{4a}$, $R^{1b}$, $R^{2b}$, and $R^{3b}$ are independently selected from hydrogen, halogen, $C_{1-6}$alkyl, $C_{1-6}$haloalkyl, and —$OR^{10}$. In some embodiments of a compound of Formula (I'), or a pharmaceutically acceptable salt or solvate thereof, $R^{2a}$, $R^{3a}$, $R^{4a}$, $R^{1b}$, $R^{2b}$, and $R^{3b}$ are independently selected from hydrogen, halogen, and $C_{1-6}$alkyl. In some embodiments of a compound of Formula (I'), or a pharmaceutically acceptable salt or solvate thereof, $R^{2a}$, $R^{3a}$, $R^{4a}$, $R^{1b}$, $R^{2b}$, and $R^{3b}$ are hydrogen. In some embodiments of a compound of Formula (I'), or a pharmaceutically acceptable salt or solvate thereof, $R^{1b}$ and $R^{2b}$ are hydrogen, $R^{3b}$ is —$OR^{10}$, and $R^{10}$ is $C_{1-6}$alkyl. In some embodiments of a compound of Formula (I'), or a pharmaceutically acceptable salt or solvate thereof, $R^{1b}$ and $R^{2b}$ are hydrogen, $R^1$ is —$OR^{10}$, $R^{10}$ is $C_{1-6}$alkyl substituted with one, two, or three halogen.

In some embodiments of a compound of Formula (I'), or a pharmaceutically acceptable salt or solvate thereof, $R^{1a}$ is hydrogen, halogen, $C_{1-6}$alkyl, $C_{1-6}$haloalkyl, or —$OR^{10}$. In some embodiments, $R^{1a}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{1a}$ is hydrogen. In some embodiments, $R^{1a}$ is $C_{1-6}$alkyl. In some embodiments, $R^{1a}$ is $C_{1-6}$alkoxyl, wherein the alkoxyl is optionally substituted with 1, 2 or 3 halogen. In some embodiments, $R^{1a}$ is $C_{1-6}$alkoxyl. In some a is —$OCF_3$.

In some embodiments of a compound of Formula (I'), or a pharmaceutically acceptable salt or solvate thereof, $R^{2a}$ is hydrogen, halogen, $C_{1-6}$alkyl, $C_{1-6}$haloalkyl, or —$OR^{10}$. In some embodiments, $R^{2a}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{2a}$ is hydrogen. In some embodiments, $R^{2a}$ is $C_{1-6}$alkyl. In some embodiments, $R^2$ is $C_{1-6}$alkoxyl, wherein the alkoxyl is optionally substituted with 1, 2 or 3 halogen.

In some embodiments of a compound of Formula (I'), or a pharmaceutically acceptable salt or solvate thereof, $R^{3a}$ is hydrogen, halogen, $C_{1-6}$alkyl, $C_{1-6}$haloalkyl, $C_{2-6}$alkenyl, $C_{2-6}$alkynyl, $C_{3-10}$cycloalkyl, $C_{2-9}$heterocycloalkyl, —$OR^{10}$, —$SR^{10}$, or —$SF_5$, wherein $C_{1-6}$alkyl, $C_{2-6}$alkenyl, $C_{2-6}$alkynyl, $C_{3-6}$cycloalkyl, are $C_{2-9}$heterocycloalkyl are optionally substituted with one, two, or three groups selected from $R^{15b}$. In some embodiments, $R^{3a}$ is hydrogen, halogen, $C_{1-6}$alkyl, $C_{1-6}$haloalkyl, $C_{2-6}$alkenyl, $C_{2-6}$alkynyl, or $C_{3-6}$cycloalkyl, wherein the $C_{1-6}$alkyl, $C_{2-6}$alkenyl, $C_{2-6}$alkynyl, and $C_{3-6}$cycloalkyl are optionally substituted. In some embodiments, $R^{3a}$ is hydrogen, $C_{1-6}$alkyl, $C_{1-6}$haloalkyl, $C_{2-6}$alkenyl, or $C_{2-6}$alkynyl. In some embodiments, $R^{3a}$ is hydrogen. In some embodiments, $R^3$ is $C_{1-6}$alkyl. In some embodiments, $R^3$ is $C_{1-6}$alkyl. In some embodiments, $R^{3a}$ is $C_{1-6}$haloalkyl. In some embodiments, $R^{3a}$ is $C_{2-6}$alkenyl. In some embodiments, $R^{3a}$ is $C_{2-6}$alkynyl.

In some embodiments of a compound of Formula (I'), or a pharmaceutically acceptable salt or solvate thereof, $R^{4a}$ is hydrogen, halogen, $C_{1-6}$alkyl, $C_{1-6}$haloalkyl, or —$OR^{10}$. In some embodiments, $R^{4a}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{4a}$ is hydrogen. In some embodiments, $R^{4a}$ is $C_{1-6}$alkyl. In some embodiments, $R^{4a}$ is $C_{1-6}$alkoxyl, wherein the alkoxyl is optionally substituted with 1, 2 or 3 halogen.

In some embodiments of a compound of Formula (I'), or a pharmaceutically acceptable salt or solvate thereof, $R^{5a}$ is hydrogen, halogen, $C_{1-6}$alkyl, $C_{1-6}$haloalkyl, or —$OR^{10}$. In some embodiments, $R^{5a}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{5a}$ is hydrogen. In some embodiments, $R^{5a}$ is $C_{1-6}$alkoxyl, wherein the alkoxyl is optionally substituted with 1, 2 or 3 halogen. In some embodiments, $R^{5a}$ is $C_{1-6}$alkoxyl. In some embodiments, $R^{5a}$ is $C_{1-6}$alkoxyl. In some embodiments, $R^{5a}$ is —$OCH_3$.

In some embodiments of a compound of Formula (I'), or a pharmaceutically acceptable salt or solvate thereof, $R^{2b}$ is hydrogen, halogen, $C_{1-6}$alkyl, or $C_{1-6}$haloalkyl, wherein $C_{1-6}$alkyl is optionally substituted with one, two, or three groups selected from $R^{15b}$. In some embodiments, $R^{2b}$ is hydrogen. In some embodiments, $R^{2b}$ is halogen. In some embodiments, $R^{1b}$ is $C_{1-6}$alkyl. In some embodiments, $R^{1b}$ is $C_{1-6}$haloalkyl.

In some embodiments of a compound of Formula (I'), or a pharmaceutically acceptable salt or solvate thereof, $R^{1b}$ is hydrogen, halogen, $C_{1-6}$alkyl, or $C_{1-6}$haloalkyl, wherein $C_{1-6}$alkyl is optionally substituted with one, two, or three groups selected from $R^{15b}$. In some embodiments, $R^{1b}$ is hydrogen. In some embodiments, $R^{2b}$ is halogen. In some embodiments, $R^{1b}$ is $C_{1-6}$alkyl. In some embodiments, $R^{1b}$ is $C_{1-6}$haloalkyl.

In some embodiments of a compound of Formula (I'), or a pharmaceutically acceptable salt or solvate thereof, $R^{3b}$ is hydrogen, halogen, $C_{1-6}$alkyl, $C_{1-6}$haloalkyl, or —$OR^{10}$. In some embodiments, $R^{3b}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{3b}$ is hydrogen. In some embodiments, $R^{3b}$ is $C_{1-6}$alkoxyl, wherein the alkoxyl is optionally substituted with 1, 2 or 3 halogen. In some embodiments, $R^{3b}$ is $C_{1-6}$alkoxyl. In some embodiments, $R^{3b}$ is $C_{1-3}$alkoxyl. In some embodiments, $R^{3b}$ is $C_{1-3}$alkoxyl, wherein the alkoxyl is optionally substituted with 1, 2 or 3 halogen. In some embodiments, $R^{3b}$ is —$OCH_3$. In some embodiments, $R^{3b}$ is —$OCH_2F$. In some embodiments, $R^{3b}$ is —$OCF_3$. In some embodiments, $R^{3b}$ is —$OCHF_2$. In some embodiments, $R^{3b}$ is —$OCH_2CF_3$.

In some embodiments of a compound of Formula (I'), or a pharmaceutically acceptable salt or solvate thereof, X is —$C(R^6)(R^{6a})$—. In some embodiments of a compound of Formula (I'), or a pharmaceutically acceptable salt or solvate thereof, X is —$C(R^6)(R^{6a})$— and $R^6$ and $R^{6a}$ are independently selected from hydrogen, halogen, $C_{1-6}$alkyl, and —OH. In some embodiments of a compound of Formula (I'), or a pharmaceutically acceptable salt or solvate thereof, X is —$C(R^6)(R^{6a})$— and $R^6$ and $R^{6a}$ are hydrogen.

In some embodiments of a compound of Formula (I'), or a pharmaceutically acceptable salt or solvate thereof, X is —O—.

In some embodiments of a compound of Formula (I'), or a pharmaceutically acceptable salt or solvate thereof, X is —$N(R^7)$—. In some embodiments of a compound of Formula (I'), or a pharmaceutically acceptable salt or solvate thereof, X is —$N(R^7)$— and $R^7$ is hydrogen. In some embodiments of a compound of Formula (I'), or a pharmaceutically acceptable salt or solvate thereof, X is —$N(R^7)$— and $R^7$ is $C_{1-6}$alkyl.

In some embodiments of a compound of Formula (I'), or a pharmaceutically acceptable salt or solvate thereof, $R^1$ is optionally substituted $C_{1-9}$heteroaryl. In some embodiments of a compound of Formula (I'), or a pharmaceutically acceptable salt or solvate thereof, $R^1$ is optionally substituted 5 or 6 membered heteroaryl. In some embodiments of a compound of Formula (I'), or a pharmaceutically acceptable salt or solvate thereof, $R^1$ is optionally substituted 5 membered heteroaryl. In some embodiments of a compound of Formula (I'), or a pharmaceutically acceptable salt or solvate thereof, $R^1$ is optionally substituted 6 membered heteroaryl. In some embodiments of a compound of Formula (I'), or a pharmaceutically acceptable salt or solvate thereof, $R^1$ is monocyclic heteroaryl. In some embodiments of a compound of Formula (I'), or a pharmaceutically acceptable salt or solvate thereof, $R^1$ is bicyclic heteroaryl. In some embodiments, $R^1$ is optionally substituted with one, two, or three groups selected from $R^{15a}$. In some embodiments, $R^1$ is optionally substituted with one, two, or three groups selected from halogen, $C_{1-6}$alkyl, $C_{1-6}$haloalkyl, and $C_{1-6}$alkoxyl. In some embodiments, $R^1$ is optionally substituted with one, two, or three groups selected from oxo, —CN, amino, OH, halogen, $C_{1-6}$alkyl, $C_{1-6}$haloalkyl, $C_{1-6}$alkoxyl, and $C_{3-6}$cycloalkyl.

In some embodiments of a compound of Formula (I'), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are optionally substituted with one, two, or three groups selected from $R^{15a}$. In some embodiments of a compound of Formula (I'), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from $R^{15}$. In some embodiments of a compound of Formula (I'), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from $R^{15a}$ and each $R^{15a}$ is independently selected from halogen, $C_{1-6}$alkyl, $C_{1-6}$haloalkyl, and —$OR^{10}$. In some embodiments of a compound of Formula (I'), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, pyrazolyl, imidazolyl, isoxazolyl, thiazolyl, oxazolyl, pyrimidinyl, pyridazinyl, and pyridinyl are substituted with one group selected from $R^{15a}$ and $R^{15a}$ is selected from halogen, $C_{1-6}$alkyl, $C_{1-6}$haloalkyl, and —$OR^{10}$.

In some embodiments of a compound of Formula (I'), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are optionally substituted with one, two, or three groups selected from $R^{15a}$. In some embodiments of a compound of Formula (I'), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are substituted with one, two, or three groups selected from $R^{15a}$. In some embodiments of a compound of Formula (I'), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are substituted with one, two, or three groups selected from $R^{15a}$ and each $R^{15a}$ is independently selected from halogen, $C_{1-6}$alkyl, $C_{1-6}$haloalkyl, and —$OR^{10}$. In some embodiments of a compound of Formula (I'), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are substituted with one group selected from $R^{15a}$ and $R^{15a}$ is selected from halogen, $C_{1-6}$alkyl, $C_{1-6}$haloalkyl, and —$OR^{10}$.

In some embodiments of a compound of Formula (I'), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are unsubstituted. In some embodiments of a compound of Formula (I'), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are unsubstituted. In some embodiments of a compound of Formula (I'), or a pharmaceutically acceptable salt or solvate thereof, $R^1$ is unsubstituted pyrazolyl. In some embodiments of a compound of Formula (I'), or a pharmaceutically acceptable salt or solvate thereof, $R^1$ is unsubstituted imidazolyl. In some embodiments of a compound of Formula (I'), or a pharmaceutically acceptable salt or solvate thereof, $R^1$ is unsubstituted isoxazolyl. In some embodiments of a compound of Formula (I'), or a pharmaceutically acceptable salt or solvate thereof, $R^1$ is unsubstituted oxazolyl. In some embodiments of a compound of Formula (I'), or a pharmaceutically acceptable salt or solvate thereof, $R^1$ is unsubstituted pyridinyl. In some embodiments of a compound of Formula (I'), or a pharmaceutically acceptable salt or solvate thereof, $R^1$ is unsubstituted thiazolyl. In some embodiments of a compound of Formula (I'), or a pharmaceutically acceptable salt or solvate thereof, $R^1$ is unsubstituted pyrimidinyl. In some embodiments of a compound of Formula (I'), or a pharmaceutically acceptable salt or solvate thereof, $R^1$ is unsubstituted pyridazinyl.

In some embodiments of a compound of Formula (I'), or a pharmaceutically acceptable salt or solvate thereof, $R^1$ is selected from

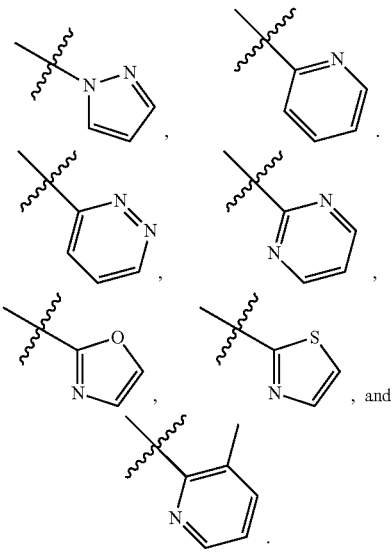

In some embodiments of a compound of Formula (I'), or a pharmaceutically acceptable salt or solvate thereof, $R^1$ is selected from

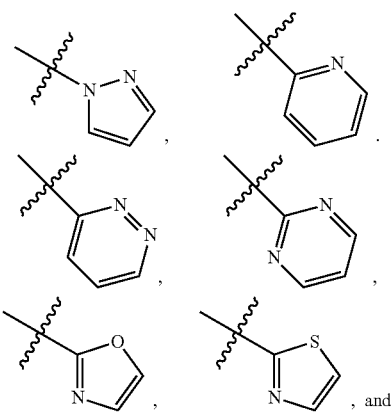

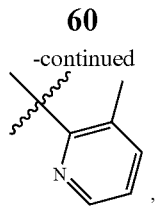

wherein each is optionally substituted with 1, 2 or 3 $R^{15a}$. In some embodiments, $R^1$ is

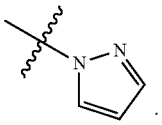

In some embodiments, $R^1$ is

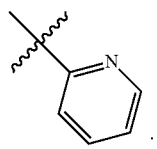

In some embodiments, $R^1$ is

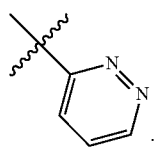

In some embodiments, $R^1$ is

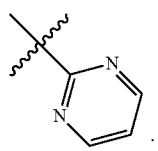

In some embodiments, $R^1$ is

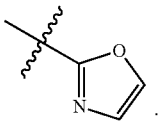 [SMILES: *c1ncco1]

In some embodiments, $R^1$ is

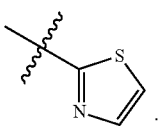 [SMILES: *c1nccs1]

In some embodiments, $R^1$ is

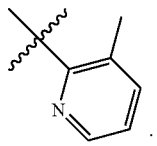 [SMILES: *c1ncccc1C]

In some embodiments, $R^1$ is

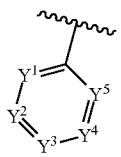

In some embodiments of a compound of Formula (I'), or a pharmaceutically acceptable salt or solvate thereof,

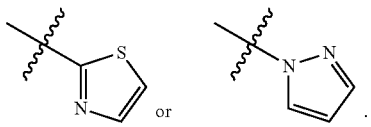 [SMILES: *c1nccs1 ; *n1cccn1]

is selected from

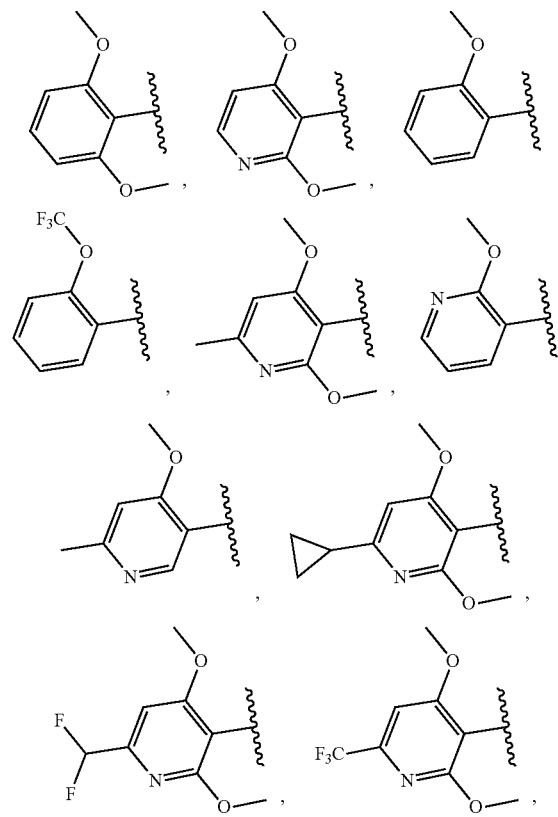

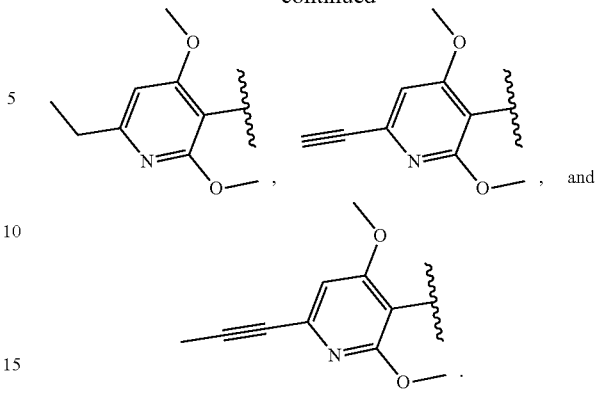

In some embodiments of a compound of Formula (I'), or a pharmaceutically acceptable salt or solvate thereof, $R^{10}$ is hydrogen, $C_{1-6}$alkyl, $C_{1-6}$haloalkyl, or $C_{3-6}$cycloalkyl. In some embodiments, $R^{1b}$ is hydrogen, $C_{1-6}$alkyl, $C_{1-6}$haloalkyl, or $C_{3-6}$cycloalkyl, wherein $C_{1-6}$alkyl and $C_{3-6}$cycloalkyl are optionally substituted with one, two, or three groups selected from halogen. hydrogen. In some embodiments, $R^{10}$ is hydrogen, $C_{1-6}$alkyl, or $C_{1-6}$haloalkyl. In some embodiments, $R^{10}$ is $C_{1-6}$alkyl or $C_{1-6}$haloalkyl. In some embodiments, $R^{10}$ is hydrogen. In some embodiments, $R^{10}$ is —$CH_3$. In some embodiments, $R^{10}$ is —$CH_2F$. In some embodiments, $R^{10}$ is —$CHF_2$. In some embodiments, $R^{10}$ is —$CH_2CF_3$. In some embodiments, $R^{10}$ is —$CF_3$.

In some embodiments of a compound of Formula (I'), or a pharmaceutically acceptable salt or solvate thereof, $R^{10}$ is hydrogen, $C_{1-6}$alkyl, and $C_{1-6}$haloalkyl. In some embodiments, $R^{10}$ is hydrogen. In some embodiments of a compound of Formula (I'), or a pharmaceutically acceptable salt or solvate thereof, $R^{10}$ is $C_{1-6}$alkyl.

In some embodiments of a compound of Formula (I'), or a pharmaceutically acceptable salt or solvate thereof, $R^2$ is hydrogen, $C_{1-6}$alkyl, and $C_{1-6}$haloalkyl. In some embodiments, $R^{12}$ is hydrogen. In some embodiments of a compound of Formula (I'), or a pharmaceutically acceptable salt or solvate thereof, $R^{12}$ is $C_{1-6}$alkyl.

In some embodiments of a compound of Formula (I'), or a pharmaceutically acceptable salt or solvate thereof, $R^{13}$ is $C_{1-6}$alkyl, $C_{1-6}$haloalkyl, or $C_{3-6}$cycloalkyl. In some embodiments of a compound of Formula (I'), or a pharmaceutically acceptable salt or solvate thereof, $R^{13}$ is $C_{1-6}$alkyl or $C_{1-6}$haloalkyl.

In some embodiments of a compound of Formula (I'), or a pharmaceutically acceptable salt or solvate thereof, each $R^{15a}$, each $R^{15b}$, and each $R^{15c}$ are independently halogen, oxo, —CN, $C_{1-6}$alkyl, $C_{1-6}$haloalkyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$N(R^{10})(R^{11})$, —$C(O)OR^{10}$, —$C(O)R^{13}$, or —$C(O)N(R^{10})(R^{11})$. In some embodiments of a compound of Formula (I'), each $R^{15a}$, each $R^{15b}$, and each $R^{15c}$ are independently halogen, oxo, —CN, $C_{1-6}$alkyl, $C_{1-6}$haloalkyl, $C_{3-10}$cycloalkyl, —$OR^{10}$, or —$N(R^{10})(R^{11})$. In some embodiments of a compound of Formula (I'), each $R^{15a}$, each $R^{15b}$, and each $R^{15c}$ are independently halogen, oxo, —CN, $C_{1-6}$alkyl, $C_{1-6}$haloalkyl, —$OR^{10}$, or —$N(R^{10})(R^{11})$. In some embodiments of a compound of Formula (I'), each $R^{15a}$, each $R^{15b}$, and each $R^{15c}$ are independently halogen, $C_{1-6}$alkyl, $C_{1-6}$haloalkyl, $C_{3-10}$cycloalkyl, or —$OR^{10}$.

In some embodiments of a compound of Formula (I'), each $R^{15a}$, each $R^{15b}$, and each $R^{15c}$ are independently halogen, $C_{1-6}$alkyl, $C_{1-6}$haloalkyl, or —$OR^{10}$. In some embodiments of a compound of Formula (I'), each $R^{15a}$, each $R^{15b}$, and each $R^{15c}$ are independently halogen, $C_{1-6}$alkyl, $C_{3-10}$cycloalkyl, or —$OR^{10}$. In some embodiments of a compound of Formula (I'), each $R^{15a}$, each $R^{15b}$, and each $R^{15c}$ are independently halogen, $C_{1-6}$alkyl, or —$OR^{10}$. In some embodiments of a compound of Formula (I'), each $R^{15a}$, each $R^{15b}$, and each $R^{15c}$ are independently $C_{1-6}$alkyl, $C_{3-10}$cycloalkyl, or —$OR^{10}$. In some embodiments of a compound of Formula (I'), each $R^{15a}$, each $R^{15b}$, and each $R^{15c}$ are independently $C_{1-6}$alkyl or —$OR^{10}$. In some embodiments of a compound of Formula (I'), each $R^{15a}$, each $R^{15b}$, and each $R^{15c}$ are independently $C_{3-10}$cycloalkyl or —$OR^{10}$. In some embodiments of a compound of Formula (I'), each $R^{15a}$, each $R^{15b}$, and each $R^{15c}$ are independently —$OR^{10}$.

In some embodiments of a compound of Formula (I), (I'), or (Ia), or a pharmaceutically acceptable salt or solvate thereof, $Z^1$ is $CR^{1b}$, $Z^2$ is $CR^{2b}$, $Z^3$ is $CR^{3b}$, each $R^{1a}$ and each $R^{5a}$ are independently selected from hydrogen, halogen, $C_{1-6}$alkyl, $C_{1-4}$haloalkyl, and —$OR^{10}$, and each $R^{2a}$, each $R^{3a}$, each $R^{4a}$, each $R^{1b}$, each $R^{2b}$, and each $R^{3b}$ are independently selected from hydrogen, halogen, $C_{1-6}$alkyl, $C_{1-6}$haloalkyl, and —$OR^{10}$, wherein $R^{10}$ is hydrogen, $C_{1-6}$alkyl, $C_{1-6}$haloalkyl, $C_{3-6}$cycloalkyl, or $C_{2-4}$heterocycloalkyl. In some embodiments of a compound of Formula (I), (I'), or (Ia), or a pharmaceutically acceptable salt or solvate thereof, $R^1$ is an optionally substituted 5 or 6 membered heteroaryl. In some embodiments of a compound of Formula (I), (I'), or (Ia), or a pharmaceutically acceptable salt or solvate thereof, $R^1$ is an optionally substituted 5 membered heteroaryl. In some embodiments of a compound of Formula (I), (I'), or (Ia), or a pharmaceutically acceptable salt or solvate thereof, $R^1$ is pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from $R^{15a}$. In some embodiments of a compound of Formula (I), (I'), or (Ia), or a pharmaceutically acceptable salt or solvate thereof, $R^1$ is selected from

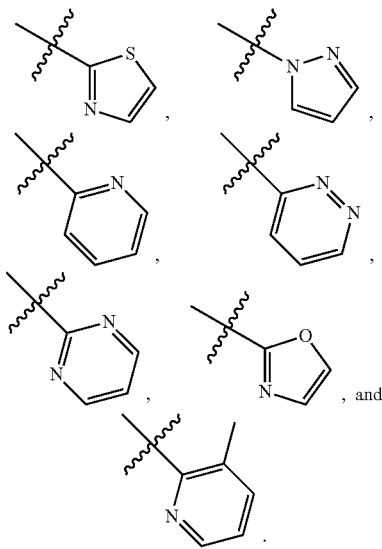

In some embodiments of a compound of Formula (I), (I'), or (Ia), or a pharmaceutically acceptable salt or solvate thereof, $R^{10}$ is $C_{1-6}$alkyl or $C_{1-6}$haloalkyl.

In some embodiments disclosed herein is a compound of Formula (II), or a pharmaceutically acceptable salt or solvate thereof:

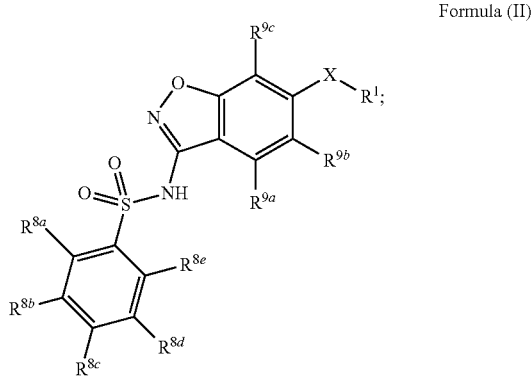

Formula (II)

wherein:

X is selected from —$C(R^6)(R^{6a})$—, —O—, and —$N(R^7)$—;

$R^1$ is $C_{1-9}$heteroaryl optionally substituted with one, two, or three groups selected from $R^{15a}$;

$R^6$ and $R^{6a}$ are independently selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

$R^7$ is selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-4}$alkenyl, $C_{2-4}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

$R^{8a}$, $R^{8b}$, $R^{8c}$, $R^{8d}$, $R^{8e}$, $R^{9b}$, and $R^{9c}$ are each independently selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15*}$;

$R^{9a}$ is selected from $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl and $C_{3-6}$cycloalkyl are substituted with one, two, or three groups selected from $R^{15c}$, and wherein $C_{2-6}$alkenyl, $C_{2-6}$alkynyl, $C_{2-9}$heterocycloalkyl, $C_{6-10}$aryl, and $C_{1-9}$heteroaryl are optionally substituted with one, two, or three groups selected from $R^{15d}$; or $R^{9a}$ and $R^{9b}$ are combined to form a $C_{3-6}$cycloalkyl, $C_{2-9}$heterocycloalkyl, or $C_{2-9}$heteroaryl, wherein $C_{3-6}$cycloalkyl, $C_{2-9}$heterocycloalkyl, and $C_{2-9}$heteroaryl are optionally substituted with one, two, or three groups selected from $R^{15e}$;

each $R^{10}$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-4}$alkenyl, $C_{2-4}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

$R^{14}$ is independently selected from hydrogen, $C_{1-6}$haloalkyl, $C_{2-6}$alkenyl, $C_{2-6}$alkynyl, $C_{2-9}$heterocycloalkyl, $C_{6-10}$aryl, and $C_{1-9}$heteroaryl, wherein $C_{2-6}$alkenyl, $C_{2-6}$alkynyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl; and each $R^{15a}$, each $R^{15b}$, each $R^{15c}$, each $R^{15d}$, and each $R^{15e}$ are each independently selected from halogen, oxo, —CN, $C_{1-6}$alkyl, $C_{1-6}$haloalkyl, $C_{2-6}$alkenyl, $C_{2-6}$alkynyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, —$CH_2$—$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$.

In some embodiments of a compound of Formula (II), or a pharmaceutically acceptable salt or solvate thereof, $R^{8a}$ and $R^{8e}$ are independently selected from hydrogen, halogen, $C_{1-6}$alkyl, $C_{1-6}$haloalkyl, and —$OR^{10}$. In some embodiments of a compound of Formula (II), or a pharmaceutically acceptable salt or solvate thereof, $R^{8a}$ and $R^{8e}$ are independently selected from hydrogen and —$OR^{10}$. In some embodiments of a compound of Formula (II), or a pharmaceutically acceptable salt or solvate thereof, $R^{8a}$ and $R^{8e}$ are —$OR^{10}$. In some embodiments of a compound of Formula (II), or a pharmaceutically acceptable salt or solvate thereof, $R^{8a}$ and $R^{8e}$ are —$OR^{10}$ and $R^{10}$ is $C_{1-6}$alkyl. In some embodiments of a compound of Formula (II), or a pharmaceutically acceptable salt or solvate thereof, $R^{8a}$ and $R^{8e}$ are —$OR^{10}$ and $R^{10}$ is —$CH_3$.

In some embodiments of a compound of Formula (II), or a pharmaceutically acceptable salt or solvate thereof, $R^{8a}$ is hydrogen, halogen, $C_{1-6}$alkyl, $C_{1-6}$haloalkyl, or —$OR^{10}$. In some embodiments, $R^{8a}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{8a}$ is hydrogen. In some embodiments, $R^{8a}$ is $C_{1-6}$alkyl. In some embodiments, $R^{8a}$ is $C_{1-6}$alkoxyl, wherein the alkoxyl is optionally substituted with 1, 2 or 3 halogen. In some embodiments, $R^{8a}$ is $C_{1-6}$alkoxyl. In some embodiments, $R^{8a}$ is —$OCF_3$.

In some embodiments of a compound of Formula (II), or a pharmaceutically acceptable salt or solvate thereof, $R^{8e}$ is hydrogen, halogen, $C_{1-6}$alkyl, $C_{1-6}$haloalkyl, or —$OR^{10}$. In some embodiments, $R^{8e}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{8e}$ is hydrogen. In some embodiments, $R^{8e}$ is $C_{1-6}$alkoxyl, wherein the alkoxyl is optionally substituted with 1, 2 or 3 halogen. In some embodiments, $R^{8e}$ is $C_{1-6}$alkoxyl. In some embodiments, $R^{8e}$ is —$OCH_3$.

In some embodiments of a compound of Formula (II), or a pharmaceutically acceptable salt or solvate thereof, $R^{8b}$, $R^{8c}$, $R^{8d}$, and $R^{9c}$ are independently selected from hydrogen, halogen, $C_{1-6}$alkyl, $C_{1-6}$haloalkyl, and —$OR^{10}$. In some embodiments of a compound of Formula (II), or a pharmaceutically acceptable salt or solvate thereof, $R^{8b}$, $R^{8c}$, $R^{8d}$, and $R^{9c}$ are independently selected from hydrogen, halogen, and $C_{1-6}$alkyl. In some embodiments of a compound of Formula (II), or a pharmaceutically acceptable salt or solvate thereof, $R^{8b}$, $R^{8c}$, $R^{8d}$, and $R^{9c}$ are hydrogen.

In some embodiments of a compound of Formula (II), or a pharmaceutically acceptable salt or solvate thereof, $R^{8b}$ is hydrogen, halogen, $C_{1-6}$alkyl, $C_{1-6}$haloalkyl, or —$OR^{10}$. In some embodiments, $R^{8b}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^1$ is hydrogen. In some embodiments, $R^1$ is $C_{1-6}$alkyl. In some embodiments, $R^1$ is $C_{1-6}$alkoxyl, wherein the alkoxyl is optionally substituted with 1, 2 or 3 halogen.

In some embodiments of a compound of Formula (II), or a pharmaceutically acceptable salt or solvate thereof, $R^{8c}$ is hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, —$OR^{10}$, —$SR^{10}$, or —$SF_5$, wherein $C_{1-6}$alkyl, $C_{2-6}$alkenyl, $C_{2-6}$alkynyl, $C_{3-6}$cycloalkyl, are $C_{2-9}$heterocycloalkyl are optionally substituted with one, two, or three groups selected from $R^{15b}$. In some embodiments, $R^{8c}$ is hydrogen, halogen, $C_{1-6}$alkyl, $C_{1-6}$haloalkyl, $C_{2-6}$alkenyl, $C_{2-6}$alkynyl, or $C_{3-6}$cycloalkyl, wherein the $C_{1-6}$alkyl, $C_{2-6}$alkenyl, $C_{2-6}$alkynyl, and $C_{3-6}$cycloalkyl are optionally substituted. In some embodiments, $R^{8c}$ is hydrogen, $C_{1-6}$alkyl, $C_{1-6}$haloalkyl, $C_{2-6}$alkenyl, or $C_{2-6}$alkynyl. In some embodiments, $R^{8c}$ is hydrogen. In some embodiments, $R^{8c}$ is $C_{1-6}$alkyl. In some embodiments, $R^{8c}$ is $C_{1-6}$alkyl. In some embodiments, $R^{8c}$ is $C_{1-6}$haloalkyl. In some embodiments, $R^{8c}$ is $C_{2-6}$alkenyl. In some embodiments, $R^{8c}$ is $C_{2-6}$alkynyl.

In some embodiments of a compound of Formula (II), or a pharmaceutically acceptable salt or solvate thereof, $R^{8d}$ is hydrogen, halogen, $C_{1-6}$alkyl, $C_{1-6}$haloalkyl, or —$OR^{10}$. In some embodiments, $R^{8d}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{8d}$ is hydrogen. In some embodiments, $R^{8d}$ is $C_{1-6}$alkyl. In some embodiments, $R^{8d}$ is $C_{1-6}$alkoxyl, wherein the alkoxyl is optionally substituted with 1, 2 or 3 halogen.

In some embodiments of a compound of Formula (II), or a pharmaceutically acceptable salt or solvate thereof, $R^{9c}$ is hydrogen, halogen, $C_{1-6}$alkyl, or $C_{1-6}$haloalkyl, wherein $C_{1-6}$alkyl is optionally substituted with one, two, or three groups selected from $R^{15b}$. In some embodiments, $R^{9c}$ is hydrogen. In some embodiments, $R^{9c}$ is halogen. In some embodiments, $R^{9c}$ is $C_{1-6}$alkyl. In some embodiments, $R^{9c}$ is $C_{1-6}$haloalkyl.

In some embodiments of a compound of Formula (II), or a pharmaceutically acceptable salt or solvate thereof, $R^{9b}$ is selected from hydrogen, halogen, and $C_{1-6}$alkyl. In some embodiments of a compound of Formula (II), or a pharmaceutically acceptable salt or solvate thereof, $R^{9b}$ is hydrogen. In some embodiments of a compound of Formula (II), or a pharmaceutically acceptable salt or solvate thereof, $R^{9b}$ is halogen. In some embodiments of a compound of Formula (II), or a pharmaceutically acceptable salt or solvate thereof, $R^{9b}$ is $C_{1-6}$alkyl. In some embodiments of a compound of Formula (II), or a pharmaceutically acceptable salt or solvate thereof, $R^{9b}$ is —$CH_3$.

In some embodiments of a compound of Formula (II), or a pharmaceutically acceptable salt or solvate thereof, $R^{9b}$ is hydrogen, halogen, $C_{1-6}$alkyl, or $C_{1-6}$haloalkyl, wherein $C_{1-6}$alkyl is optionally substituted with one, two, or three groups selected from $R^{15b}$. In some embodiments, $R^{9b}$ is hydrogen. In some embodiments, $R^{9b}$ is halogen. In some embodiments, $R^{9b}$ is $C_{1-6}$alkyl. In some embodiments, $R^{9b}$ is $C_{1-6}$haloalkyl.

In some embodiments of a compound of Formula (II), or a pharmaceutically acceptable salt or solvate thereof, $R^{9a}$ is —$OR^{14}$. In some embodiments of a compound of Formula (II), or a pharmaceutically acceptable salt or solvate thereof, $R^9$ is —$OR^{14}$ and $R^{14}$ is $C_{1-6}$haloalkyl. In some embodiments of a compound of Formula (II), or a pharmaceutically acceptable salt or solvate thereof, $R^9$ is —$OR^{14}$ and $R^{14}$ is —$CF_3$. In some embodiments of a compound of Formula (II), or a pharmaceutically acceptable salt or solvate thereof, $R^9$ is —$OR^{14}$ and $R^{14}$ is —$CHF_2$.

In some embodiments of a compound of Formula (II), or a pharmaceutically acceptable salt or solvate thereof, $R^{9a}$ is $C_{3-6}$cycloalkyl are substituted with one, two, or three groups selected from $R^{15c}$. In some embodiments of a compound of Formula (II), or a pharmaceutically acceptable salt or solvate thereof, $R^{9a}$ is $C_{3-6}$cycloalkyl are substituted with one, two, or three groups selected from $R^{15c}$ and each $R^{15c}$ is independently selected from halogen, $C_{1-6}$alkyl, $C_{1-6}$haloalkyl. In some embodiments of a compound of Formula (II), or a pharmaceutically acceptable salt or solvate thereof, $R^{9a}$ is $C_{3-6}$cycloalkyl are substituted with one, two, or three groups selected from $R^{15c}$ and each $R^{15c}$ is halogen.

In some embodiments of a compound of Formula (II), or a pharmaceutically acceptable salt or solvate thereof, $R^{9a}$ is $C_{1-6}$alkyl, $C_{1-6}$haloalkyl, or —$OR^{14}$. In some embodiments, $R^{9a}$ is $C_{1-6}$alkyl, $C_{1-6}$haloalkyl, or —O—$C_{1-6}$haloalkyl. In some embodiments, $R^{9a}$ is —O—$C_{1-6}$haloalkyl. In some embodiments, $R^{9a}$ is —O—$C_{1-6}$haloalkyl. In some embodiments, $R^{9a}$ is —$OCH_2F$.

In some embodiments of a compound of Formula (II), or a pharmaceutically acceptable salt or solvate thereof, $R^{9a}$ and $R^{9b}$ are combined to form a $C_{3-6}$cycloalkyl, $C_{2-9}$heterocycloalkyl, or $C_{2-9}$heteroaryl, wherein $C_{3-6}$cycloalkyl, $C_{2-9}$heterocycloalkyl, and $C_{2-9}$heteroaryl are optionally substituted with one, two, or three groups selected from $R^{15e}$. In some embodiments of a compound of Formula (II), or a pharmaceutically acceptable salt or solvate thereof, $R^{9a}$ and $R^{9b}$ are combined to form a $C_{2-9}$heterocycloalkyl optionally substituted with one, two, or three groups selected from $R^{15e}$. In some embodiments of a compound of Formula (II), or a pharmaceutically acceptable salt or solvate thereof, $R^{9a}$ and $R^{9b}$ are combined to form a $C_{2-9}$heterocycloalkyl optionally substituted with one, two, or three groups selected from halogen, $C_{1-6}$alkyl, and $C_{1-6}$haloalkyl. In some embodiments of a compound of Formula (II), or a pharmaceutically acceptable salt or solvate thereof, $R^{10}$ is hydrogen, $C_{1-6}$alkyl, $C_{1-6}$haloalkyl, or $C_{3-6}$cycloalkyl. In some embodiments, $R^{10}$ is hydrogen, $C_{1-6}$alkyl, $C_{1-6}$haloalkyl, or $C_{3-6}$cycloalkyl, wherein $C_{1-6}$alkyl and $C_{3-6}$cycloalkyl are optionally substituted with one, two, or three groups selected from halogen. hydrogen. In some embodiments, $R^{10}$ is hydrogen, $C_{1-6}$alkyl, or $C_{1-6}$haloalkyl. In some embodiments, $R^{10}$ is $C_{1-6}$alkyl or $C_{1-6}$haloalkyl. In some embodiments, $R^{10}$ is hydrogen. In some embodiments, $R^{10}$ is —$CH_3$. In some embodiments, $R^{10}$ is —$CH_2F$. In some embodiments, $R^{10}$ is —$CHF_2$. In some embodiments, $R^{10}$ is —$CH_2CF_3$. In some embodiments, $R^{11}$ is —$CF_3$.

In some embodiments of a compound of Formula (II), or a pharmaceutically acceptable salt or solvate thereof, $R^{9a}$ and $R^{9b}$ are combined to form a 5 to 7-membered ring. In some embodiments, $R^{9a}$ and $R^{9b}$ are combined to form a 6-membered ring. In some embodiments, $R^{9a}$ and $R^{9b}$ are combined to form a cycloalkyl. In some embodiments, $R^{9a}$ and $R^{9b}$ are combined to form a heterocycloalkyl. In some embodiments, $R^{9a}$ and $R^{9b}$ are combined to form a ring containing 1 or 2 oxygen and 0-2 nitrogen. In some embodiments, $R^{9a}$ and $R^{9b}$ are combined to form a ring containing 1 oxygen.

In some embodiments of a compound of Formula (II), or a pharmaceutically acceptable salt or solvate thereof, is

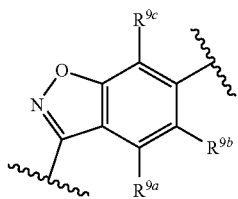

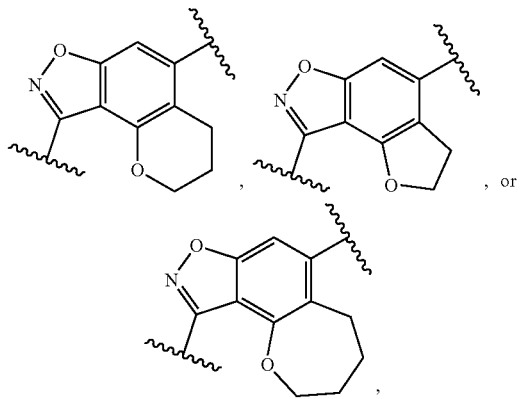

In some embodiments of compound of Formula (II), or a pharmaceutically acceptable salt or solvate thereof,

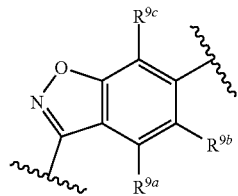

is

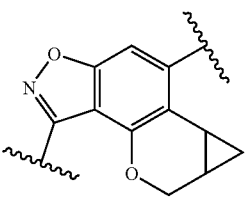 [SMILES: *c1cc2onc(*)c2c2c1C1CC1CO2]

In some embodiments of a compound of Formula (II), or a pharmaceutically acceptable salt or solvate thereof, $R^{11}$ is hydrogen, $C_{1-6}$alkyl, and $C_{1-6}$haloalkyl. In some embodiments, $R^{11}$ is hydrogen. In some embodiments of a compound of Formula (II), or a pharmaceutically acceptable salt or solvate thereof, $R^{11}$ is $C_{1-6}$alkyl.

In some embodiments of a compound of Formula (II), or a pharmaceutically acceptable salt or solvate thereof, $R^{12}$ is hydrogen, $C_{1-6}$alkyl, and $C_{1-6}$haloalkyl. In some embodiments, $R^{12}$ is hydrogen. In some embodiments of a compound of Formula (II), or a pharmaceutically acceptable salt or solvate thereof, $R^{12}$ is $C_{1-6}$alkyl.

In some embodiments of a compound of Formula (II), or a pharmaceutically acceptable salt or solvate thereof, $R^{11}$ is $C_{1-6}$haloalkyl, $C_{1-6}$alkyl or $C_{3-6}$cycloalkyl. In some embodiments of a compound of Formula (II), or a pharmaceutically acceptable salt or solvate thereof, $R^{13}$ is $C_{1-6}$alkyl.

In some embodiments of a compound of Formula (II), or a pharmaceutically acceptable salt or solvate thereof, $R^4$ is hydrogen, $C_{1-6}$haloalkyl, or $C_{3-6}$cycloalkyl. In some embodiments, $R^{14}$ is hydrogen, or $C_{1-6}$haloalkyl. In some embodiments, $R^{14}$ is $C_{1-6}$haloalkyl. In some embodiments, $R^{14}$ is hydrogen. In some embodiments, $R^{14}$ is —CH$_2$F. In some embodiments, $R^{14}$ is —CH$_2$CF$_3$. In some embodiments, $R^{14}$ is —CF$_3$.

In some embodiments of a compound of Formula (II), or a pharmaceutically acceptable salt or solvate thereof, each $R^{15a}$, each $R^{15b}$, and each $R^{15c}$ are independently halogen, oxo, —CN, $C_{1-6}$alkyl, $C_{1-6}$haloalkyl, $C_{3-10}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-9}$heteroaryl, —CH$_2$—$C_{1-9}$heteroaryl, —OR$^{10}$, —N(R$^{10}$)(R$^{11}$), —C(O)OR$^{10}$, —C(O)R$^{13}$, or —C(O)N(R$^{10}$)(R$^{11}$). In some embodiments of a compound of Formula (II), each $R^{15a}$, each $R^{15b}$, and each $R^{15c}$ are independently halogen, oxo, —CN, $C_{1-6}$alkyl, $C_{1-6}$haloalkyl, $C_{3-10}$cycloalkyl, —OR$^{10}$, or —N(R$^{10}$)(R$^{11}$). In some embodiments of a compound of Formula (II), each $R^{15a}$, each $R^{15b}$, and each $R^{15c}$ are independently halogen, oxo, —CN, $C_{1-6}$alkyl, $C_{1-6}$haloalkyl, —OR$^{10}$, or —N(R$^{11}$)(R$^{11}$). In some embodiments of a compound of Formula (II), each $R^{15a}$, each $R^{15b}$, and each $R^{15c}$ are independently halogen, $C_{1-6}$alkyl, $C_{1-6}$haloalkyl, $C_{3-10}$cycloalkyl, or —OR$^{10}$.

In some embodiments of a compound of Formula (II), each $R^{15a}$, each $R^{15b}$, and each $R^{15c}$ are independently halogen, $C_{1-6}$alkyl, $C_{1-6}$haloalkyl, or —OR$^{10}$. In some embodiments of a compound of Formula (II), each $R^{15a}$, each $R^{15b}$, and each $R^{15c}$ are independently halogen, $C_{1-6}$alkyl, $C_{3-10}$cycloalkyl, or —OR$^{10}$. In some embodiments of a compound of Formula (II), each $R^{15a}$, each $R^{15b}$, and each $R^{15c}$ are independently halogen, $C_{1-6}$alkyl, or —OR$^{10}$. In some embodiments of a compound of Formula (II), each $R^{15a}$, each $R^{15b}$, and each $R^{15c}$ are independently $C_{1-6}$alkyl, $C_{3-10}$cycloalkyl, or —OR$^{10}$. In some embodiments of a compound of Formula (II), each $R^{15a}$, each $R^{15b}$, and each $R^{15c}$ are independently $C_{1-6}$alkyl or —OR$^{10}$. In some embodiments of a compound of Formula (II), each $R^{15a}$, each $R^{15b}$, and each $R^{15c}$ are independently $C_{3-10}$cycloalkyl or —OR$^{10}$. In some embodiments of a compound of Formula (II), each $R^{15a}$, each $R^{15b}$, and each $R^{15c}$ are independently —OR$^{10}$.

In some embodiments of a compound of Formula (II), or a pharmaceutically acceptable salt or solvate thereof, X is —C(R$^6$)(R$^{6a}$)—. In some embodiments of a compound of Formula (II), or a pharmaceutically acceptable salt or solvate thereof, X is —C(R$^6$)(R$^{6a}$)— and R$^6$ and R$^{6a}$ are independently selected from hydrogen, halogen, $C_{1-6}$alkyl, and —OH. In some embodiments of a compound of Formula (II), or a pharmaceutically acceptable salt or solvate thereof, X is —C(R$^6$)(R$^{6a}$)— and R$^6$ and R$^{6a}$ are hydrogen.

In some embodiments of a compound of Formula (II), or a pharmaceutically acceptable salt or solvate thereof, X is —O—.

In some embodiments of a compound of Formula (II), or a pharmaceutically acceptable salt or solvate thereof, X is —N(R$^7$)—. In some embodiments of a compound of Formula (II), or a pharmaceutically acceptable salt or solvate thereof, X is —N(R$^7$)— and R$^7$ is hydrogen. In some embodiments of a compound of Formula (II), or a pharmaceutically acceptable salt or solvate thereof, X is —N(R$^7$)— and R$^7$ is C$_{1-6}$alkyl.

In some embodiments of a compound of Formula (II), or a pharmaceutically acceptable salt or solvate thereof, R$^1$ is optionally substituted C$_{1-9}$heteroaryl. In some embodiments of a compound of Formula (II), or a pharmaceutically acceptable salt or solvate thereof, R$^1$ is optionally substituted 5 or 6 membered heteroaryl. In some embodiments of a compound of Formula (II), or a pharmaceutically acceptable salt or solvate thereof, R$^1$ is optionally substituted 5 membered heteroaryl. In some embodiments of a compound of Formula (II), or a pharmaceutically acceptable salt or solvate thereof, R$^1$ is optionally substituted 6 membered heteroaryl. In some embodiments of a compound of Formula (II), or a pharmaceutically acceptable salt or solvate thereof, R$^1$ is monocyclic heteroaryl. In some embodiments of a compound of Formula (II), or a pharmaceutically acceptable salt or solvate thereof, R$^1$ is bicyclic heteroaryl. In some embodiments, R$^1$ is optionally substituted with one, two, or three groups selected from R$^{15a}$. In some embodiments, R$^1$ is optionally substituted with one, two, or three groups selected from halogen, C$_{1-6}$alkyl, C$_{1-6}$haloalkyl, and C$_{1-6}$alkoxyl. In some embodiments, R$^1$ is optionally substituted with one, two, or three groups selected from oxo, —CN, amino, OH, halogen, C$_{1-6}$alkyl, C$_{1-6}$haloalkyl, C$_{1-6}$alkoxyl, and C$_{3-6}$cycloalkyl.

In some embodiments of a compound of Formula (II), or a pharmaceutically acceptable salt or solvate thereof, R$^1$ is C$_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are optionally substituted with one, two, or three groups selected from R$^{15a}$. In some embodiments of a compound of Formula (II), or a pharmaceutically acceptable salt or solvate thereof, R$^1$ is C$_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from R$^{15a}$. In some embodiments of a compound of Formula (II), or a pharmaceutically acceptable salt or solvate thereof, R$^1$ is C$_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from R$^{15a}$ and each R$^{15a}$ is independently selected from halogen, C$_{1-6}$alkyl, C$_{1-6}$haloalkyl, and —OR$^{10}$. In some embodiments of a compound of Formula (II), or a pharmaceutically acceptable salt or solvate thereof, R$^1$ is C$_{1-9}$heteroaryl selected from pyrazolyl, imidazolyl, isoxazolyl, thiazolyl, oxazolyl, pyrimidinyl, pyridazinyl, and pyridinyl, pyrazolyl, imidazolyl, isoxazolyl, thiazolyl, oxazolyl, pyrimidinyl, pyridazinyl, and pyridinyl are substituted with one group selected from R$^{15a}$ and R$^{15a}$ is selected from halogen, C$_{1-6}$alkyl, C$_{1-6}$haloalkyl, and —OR$^{10}$.

In some embodiments of a compound of Formula (II), or a pharmaceutically acceptable salt or solvate thereof, R$^1$ is C$_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are optionally substituted with one, two, or three groups selected from R$^{15a}$. In some embodiments of a compound of Formula (II), or a pharmaceutically acceptable salt or solvate thereof, R$^1$ is C$_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are substituted with one, two, or three groups selected from R$^{15a}$. In some embodiments of a compound of Formula (II), or a pharmaceutically acceptable salt or solvate thereof, R$^1$ is C$_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are substituted with one, two, or three groups selected from R$^{15a}$ and each R$^{15a}$ is independently selected from halogen, C$_{1-6}$alkyl, C$_{1-6}$haloalkyl, and —OR$^{10}$. In some embodiments of a compound of Formula (II), or a pharmaceutically acceptable salt or solvate thereof, R$^1$ is C$_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are substituted with one group selected from R$^{15a}$ and R$^{15a}$ is selected from halogen, C$_{1-6}$alkyl, C$_{1-6}$haloalkyl, and —OR$^{10}$.

In some embodiments of a compound of Formula (II), or a pharmaceutically acceptable salt or solvate thereof, R$^1$ is C$_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are unsubstituted. In some embodiments of a compound of Formula (II), or a pharmaceutically acceptable salt or solvate thereof, R$^1$ is C$_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are unsubstituted. In some embodiments of a compound of Formula (II), or a pharmaceutically acceptable salt or solvate thereof, R$^1$ is unsubstituted pyrazolyl. In some embodiments of a compound of Formula (II), or a pharmaceutically acceptable salt or solvate thereof, R$^1$ is unsubstituted imidazolyl. In some embodiments of a compound of Formula (II), or a pharmaceutically acceptable salt or solvate thereof, R$^1$ is unsubstituted isoxazolyl. In some embodiments of a compound of Formula (II), or a pharmaceutically acceptable salt or solvate thereof, R$^1$ is unsubstituted oxazolyl. In some embodiments of a compound of Formula (II), or a pharmaceutically acceptable salt or solvate thereof, R$^1$ is unsubstituted pyridinyl. In some embodiments of a compound of Formula (II), or a pharmaceutically acceptable salt or solvate thereof, R$^1$ is unsubstituted thiazolyl. In some embodiments of a compound of Formula (II), or a pharmaceutically acceptable salt or solvate thereof, R$^1$ is unsubstituted pyrimidinyl. In some embodiments of a compound of Formula (II), or a pharmaceutically acceptable salt or solvate thereof, R$^1$ is unsubstituted pyridazinyl.

In some embodiments of a compound of Formula (II), or a pharmaceutically acceptable salt or solvate thereof, R$^1$ is selected from

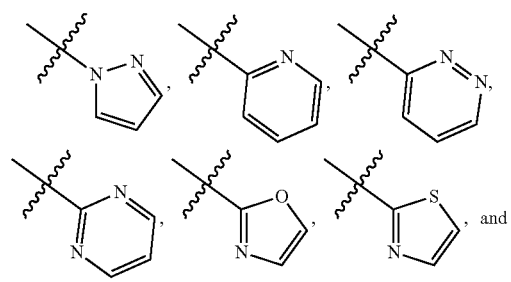

-continued

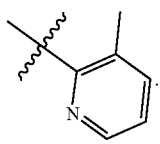

In some embodiments of a compound of Formula (II), or a pharmaceutically acceptable salt or solvate thereof, $R^1$ is selected from

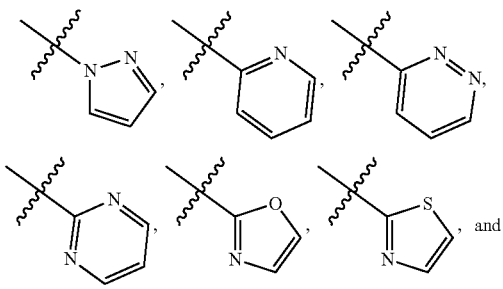, and wherein each is optionally substituted with 1, 2 or 3 $R^{15a}$. In some embodiments, $R^1$ is

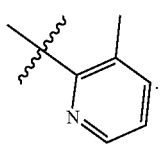

In some embodiments, $R^1$ is

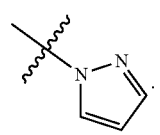 [SMILES: *n1cccn1]

In some embodiments, $R^1$ is

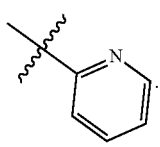 [SMILES: *c1ccccn1]

In some embodiments, $R^1$ is

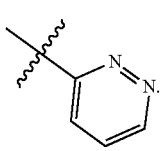 [SMILES: *c1cccnn1]

In some embodiments, $R^1$ is

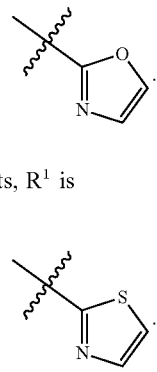

In some embodiments, $R^1$ is

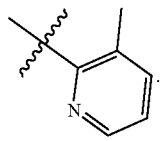 [SMILES: *c1ncccc1C]

In some embodiments, $R^1$ is

In some embodiments, $R^1$ is

In some embodiments, $R^1$ is

In some embodiments disclosed herein is a compound of Formula (III), or a pharmaceutically acceptable salt or solvate thereof:

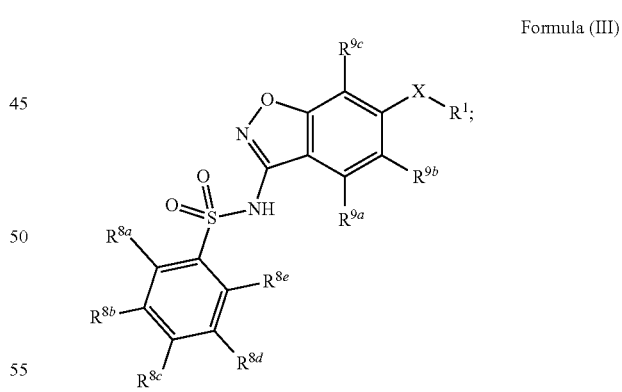

Formula (III)

wherein:
X is selected from —O— and —N($R^7$)—;
$R^1$ is $C_{1-9}$heteroaryl optionally substituted with one, two, or three groups selected from $R^{15a}$;
$R^7$ is selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

$R^{8a}$, $R^{8b}$, $R^{8c}$, $R^{8d}$, $R^{8e}$, $R^{9b}$, and $R^{9c}$ are each independently selected from hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^3$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15b}$;

$R^{9a}$ is selected from hydrogen, $C_{1-6}$alkyl, $C_{3-6}$cycloalkyl, and —$OR^{14}$;

each $R^{10}$ is independently selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently selected from hydrogen, $C_{1-6}$alkyl, and $C_{1-6}$haloalkyl;

each $R^{12}$ is independently selected from hydrogen, $C_{1-6}$alkyl, and $C_{1-6}$haloalkyl;

each $R^{13}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

$R^{14}$ is selected from $C_{1-6}$alkyl and $C_{3-6}$cycloalkyl; and each $R^{15a}$ and each $R^{15b}$ are each independently selected from halogen, oxo, —CN, $C_{1-6}$alkyl, $C_{1-6}$haloalkyl, $C_{2-6}$alkenyl, $C_{2-6}$alkynyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, —$CH_2$—$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(=O)(=NH)N(R^{10})(R^{11})$, —$CH_2C(O)N(R^{10})(R^{11})$, —$CH_2N(R^{12})C(O)R^3$, —$CH_2S(O)_2R^{13}$, and —$CH_2S(O)_2N(R^{10})(R^{11})$.

In some embodiments of a compound of Formula (III), or a pharmaceutically acceptable salt or solvate thereof, $R^{8a}$ and $R^{8e}$ are independently selected from hydrogen, halogen, $C_{1-6}$alkyl, $C_{1-6}$haloalkyl, and —$OR^{10}$. In some embodiments of a compound of Formula (III), or a pharmaceutically acceptable salt or solvate thereof, $R^{8a}$ and $R^{8e}$ are independently selected from hydrogen and —$OR^{10}$. In some embodiments of a compound of Formula (III), or a pharmaceutically acceptable salt or solvate thereof, $R^{8a}$ and $R^{8e}$ are —$OR^{10}$. In some embodiments of a compound of Formula (III), or a pharmaceutically acceptable salt or solvate thereof, $R^{8a}$ and $R^{8e}$ are —$OR^{10}$ and $R^{10}$ is $C_{1-6}$alkyl. In some embodiments of a compound of Formula (III), or a pharmaceutically acceptable salt or solvate thereof, $R^{8a}$ and $R^{8e}$ are —$OR^{10}$ and $R^{10}$ is —$CH_3$.

In some embodiments of a compound of Formula (III), or a pharmaceutically acceptable salt or solvate thereof, $R^{8a}$ is hydrogen, halogen, $C_{1-6}$alkyl, $C_{1-6}$haloalkyl, or —$OR^{10}$. In some embodiments, $R^{8a}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{8a}$ is hydrogen. In some embodiments, $R^{8a}$ is $C_{1-6}$alkyl. In some embodiments, $R^{8a}$ is $C_{1-6}$alkoxyl, wherein the alkoxyl is optionally substituted with 1, 2 or 3 halogen. In some embodiments, $R^{8a}$ is $C_{1-6}$alkoxyl. In some embodiments, $R^{8a}$ is —$OCF_3$.

In some embodiments of a compound of Formula (III), or a pharmaceutically acceptable salt or solvate thereof, $R^{8e}$ is hydrogen, halogen, $C_{1-6}$alkyl, $C_{1-6}$haloalkyl, or —$OR^{10}$. In some embodiments, $R^{8e}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{8e}$ is hydrogen. In some embodiments, $R^{8e}$ is $C_{1-6}$alkoxyl, wherein the alkoxyl is optionally substituted with 1, 2 or 3 halogen. In some embodiments, $R^{8e}$ is $C_{1-6}$alkoxyl. In some embodiments, $R^{8e}$ is $C_{1-6}$alkoxyl. In some embodiments, $R^{8e}$ is —$OCH_3$.

In some embodiments of a compound of Formula (III), or a pharmaceutically acceptable salt or solvate thereof, $R^{8b}$, $R^{8c}$, $R^{8d}$, and $R^{8e}$ are independently selected from hydrogen, halogen, $C_{1-6}$alkyl, $C_{1-6}$haloalkyl, and —$OR^{10}$. In some embodiments of a compound of Formula (III), or a pharmaceutically acceptable salt or solvate thereof, $R^{8b}$, $R^{8c}$, $R^{8d}$, and $R^{9c}$ are independently selected from hydrogen, halogen, and $C_{1-6}$alkyl. In some embodiments of a compound of Formula (III), or a pharmaceutically acceptable salt or solvate thereof, $R^{8b}$, $R^{8c}$, $R^{8d}$, and $R^{9c}$ are hydrogen.

In some embodiments of a compound of Formula (III), or a pharmaceutically acceptable salt or solvate thereof, $R^{8b}$ is hydrogen, halogen, $C_{1-6}$alkyl, $C_{1-6}$haloalkyl, or —$OR^{10}$. In some embodiments, $R^{8b}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^1$ is hydrogen. In some embodiments, $R^{8b}$ is $C_{1-6}$alkyl. In some embodiments, $R^{8b}$ is $C_{1-6}$alkoxyl, wherein the alkoxyl is optionally substituted with 1, 2 or 3 halogen.

In some embodiments of a compound of Formula (III), or a pharmaceutically acceptable salt or solvate thereof, $R^{8c}$ is hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, —$OR^{10}$, —$SR^{10}$, or —$SF_5$, wherein $C_{1-6}$alkyl, $C_{2-6}$alkenyl, $C_{2-6}$alkynyl, $C_{3-6}$cycloalkyl, are $C_{2-9}$heterocycloalkyl are optionally substituted with one, two, or three groups selected from $R^{15b}$. In some embodiments, $R^{8c}$ is hydrogen, halogen, $C_{1-6}$alkyl, $C_{1-6}$haloalkyl, $C_{2-6}$alkenyl, $C_{2-6}$alkynyl, or $C_{3-6}$cycloalkyl, wherein the $C_{1-6}$alkyl, $C_{2-6}$alkenyl, $C_{2-6}$alkynyl, and $C_{3-6}$cycloalkyl are optionally substituted. In some embodiments, $R^{8c}$ is hydrogen, $C_{1-6}$alkyl, $C_{1-6}$haloalkyl, $C_{2-6}$alkenyl, or $C_{2-6}$alkynyl. In some embodiments, $R^{8c}$ is hydrogen. In some embodiments, $R^{8c}$ is $C_{1-6}$alkyl. In some embodiments, $R^{8c}$ is $C_{1-6}$alkyl. In some embodiments, $R^{8c}$ is $C_{1-6}$haloalkyl. In some embodiments, $R^{8c}$ is $C_{2-6}$alkenyl. In some embodiments, $R^{8c}$ is $C_{2-6}$alkynyl.

In some embodiments of a compound of Formula (III), or a pharmaceutically acceptable salt or solvate thereof, $R^{8d}$ is hydrogen, halogen, $C_{1-6}$alkyl, $C_{1-6}$haloalkyl, or —$OR^{10}$. In some embodiments, $R^{8d}$ is hydrogen, $C_{1-6}$alkyl, $C_{1-6}$haloalkyl, or $C_{1-6}$alkoxyl, wherein the alkoxyl is optionally substituted with 1, 2 or 3 halogen. In some embodiments, $R^{8d}$ is hydrogen. In some embodiments, $R^{8d}$ is $C_{1-6}$alkyl. In some embodiments, $R^{8d}$ is $C_{1-6}$alkoxyl, wherein the alkoxyl is optionally substituted with 1, 2 or 3 halogen.

In some embodiments of a compound of Formula (III), or a pharmaceutically acceptable salt or solvate thereof, $R^{9c}$ is hydrogen, halogen, $C_{1-6}$alkyl, or $C_{1-6}$haloalkyl, wherein $C_{1-6}$alkyl is optionally substituted with one, two, or three groups selected from $R^{15b}$. In some embodiments, $R^{9c}$ is hydrogen. In some embodiments, $R^{9c}$ is halogen. In some embodiments, $R^{9c}$ is $C_{1-6}$alkyl. In some embodiments, $R^{9c}$ is $C_{1-6}$haloalkyl.

In some embodiments of a compound of Formula (III), or a pharmaceutically acceptable salt or solvate thereof, $R^{9b}$ is selected from hydrogen, halogen, and $C_{1-6}$alkyl. In some embodiments of a compound of Formula (III), or a pharmaceutically acceptable salt or solvate thereof, $R^{9b}$ is hydrogen. In some embodiments of a compound of Formula (III), or a pharmaceutically acceptable salt or solvate thereof, $R^{9b}$ is halogen. In some embodiments of a compound of Formula (III), or a pharmaceutically acceptable salt or solvate thereof, $R^{9b}$ is $C_{1-6}$alkyl. In some embodiments of a compound of Formula (III), or a pharmaceutically acceptable salt or solvate thereof, $R^{9b}$ is —$CH_3$.

In some embodiments of a compound of Formula (III), or a pharmaceutically acceptable salt or solvate thereof, $R^{9b}$ is hydrogen, halogen, $C_{1-6}$alkyl, or $C_{1-6}$haloalkyl, wherein $C_{1-6}$alkyl is optionally substituted with one, two, or three groups selected from $R^{15b}$. In some embodiments, $R^{9b}$ is hydrogen. In some embodiments, $R^{9b}$ is halogen. In some embodiments, $R^{9b}$ is $C_{1-6}$alkyl. In some embodiments, $R^{9b}$ is $C_{1-6}$haloalkyl.

In some embodiments of a compound of Formula (III), or a pharmaceutically acceptable salt or solvate thereof, $R^{9a}$ is —$OR^{14}$. In some embodiments of a compound of Formula (III), or a pharmaceutically acceptable salt or solvate thereof, $R^9$ is —$OR^{14}$ and $R^{14}$ is $C_{1-6}$alkyl. In some embodiments of a compound of Formula (III), or a pharmaceutically acceptable salt or solvate thereof, $R^{9a}$ is —$OR^{14}$ and $R^{14}$ is —$CH_3$. In some embodiments of a compound of Formula (III), or a pharmaceutically acceptable salt or solvate thereof, $R^{9a}$ is —$OR^{14}$ and $R^{14}$ is $C_{3-6}$cycloalkyl. In some embodiments, $R^{9a}$ is —$OCH_2F$.

In some embodiments of a compound of Formula (III), or a pharmaceutically acceptable salt or solvate thereof, $R^{9a}$ is $C_{1-6}$alkyl, $C_{3-6}$cycloalkyl, or —$OR^{14}$. In some embodiments, $R^{9a}$ is $C_{1-6}$alkyl, $C_{1-6}$cycloalkyl, or $C_{1-6}$alkoxyl, In some embodiments, $R^{9a}$ is $C_{1-6}$alkoxyl. In some embodiments, $R^{9a}$ is $C_{1-3}$alkoxyl.

In some embodiments of a compound of Formula (III), or a pharmaceutically acceptable salt or solvate thereof, $R^{9a}$ is hydrogen. In some embodiments of a compound of Formula (III), or a pharmaceutically acceptable salt or solvate thereof, $R^{9a}$ is $C_{1-6}$alkyl. In some embodiments of a compound of Formula (III), or a pharmaceutically acceptable salt or solvate thereof, $R^{9a}$ is $C_{3-6}$cycloalkyl. In some embodiments of a compound of Formula (III), or a pharmaceutically acceptable salt or solvate thereof, X is —O—.

In some embodiments of a compound of Formula (III), or a pharmaceutically acceptable salt or solvate thereof, X is —$N(R^7)$—. In some embodiments of a compound of Formula (III), or a pharmaceutically acceptable salt or solvate thereof, X is —$N(R^7)$— and $R^7$ is hydrogen. In some embodiments of a compound of Formula (III), or a pharmaceutically acceptable salt or solvate thereof, X is —$N(R^7)$— and $R^7$ is $C_{1-6}$alkyl.

In some embodiments of a compound of Formula (III), or a pharmaceutically acceptable salt or solvate thereof, $R^{10}$ is hydrogen, $C_{1-6}$alkyl, $C_{1-6}$haloalkyl, or $C_{3-6}$cycloalkyl. In some embodiments, $R^{10}$ is hydrogen, $C_{1-6}$alkyl, $C_{1-6}$haloalkyl, or $C_{3-6}$cycloalkyl, wherein $C_{1-6}$alkyl and $C_{3-6}$cycloalkyl are optionally substituted with one, two, or three groups selected from halogen. hydrogen. In some embodiments, $R^{10}$ is hydrogen, $C_{1-6}$alkyl, or $C_{1-6}$haloalkyl. In some embodiments, $R^{10}$ is $C_{1-6}$alkyl or $C_{1-6}$haloalkyl. In some embodiments, $R^{10}$ is hydrogen. In some embodiments, $R^{10}$ is —$CH_3$. In some embodiments, $R^{10}$ is —$CH_2F$. In some embodiments, $R^{10}$ is —$CHF_2$. In some embodiments, $R^{10}$ is —$CH_2CF_3$. In some embodiments, $R^{10}$ is —$CF_3$.

In some embodiments of a compound of Formula (III), or a pharmaceutically acceptable salt or solvate thereof, $R^{11}$ is hydrogen, $C_{1-6}$alkyl, and $C_{1-6}$haloalkyl. In some embodiments, $R^{11}$ is hydrogen. In some embodiments of a compound of Formula (III), or a pharmaceutically acceptable salt or solvate thereof, $R^{11}$ is $C_{1-6}$alkyl.

In some embodiments of a compound of Formula (III), or a pharmaceutically acceptable salt or solvate thereof, $R^{12}$ is hydrogen, $C_{1-6}$alkyl, and $C_{1-6}$haloalkyl. In some embodiments, $R^{12}$ is hydrogen. In some embodiments of a compound of Formula (III), or a pharmaceutically acceptable salt or solvate thereof, $R^{12}$ is $C_{1-6}$alkyl.

In some embodiments of a compound of Formula (III), or a pharmaceutically acceptable salt or solvate thereof, $R^{13}$ is $C_{1-6}$haloaoalkyl, $C_{1-6}$alkyl or $C_{3-6}$cycloalkyl. In some embodiments of a compound of Formula (III), or a pharmaceutically acceptable salt or solvate thereof, $R^{13}$ is $C_{1-6}$alkyl. In some embodiments of a compound of Formula (III), or a pharmaceutically acceptable salt or solvate thereof, $R^{13}$ is $C_{1-6}$haloaoalkyl.

In some embodiments of a compound of Formula (III), or a pharmaceutically acceptable salt or solvate thereof, $R^{14}$ is $C_{1-6}$alkyl or $C_{3-6}$cycloalkyl. In some embodiments, $R^{14}$ is $C_{1-6}$alkyl. In some embodiments, $R^{14}$ is $C_{3-6}$cycloalkyl. In some embodiments, $R^{14}$ is —$CH_3$.

In some embodiments of a compound of Formula (III), or a pharmaceutically acceptable salt or solvate thereof, each $R^{15a}$ and each $R^{15b}$ are independently halogen, oxo, —CN, $C_{1-6}$alkyl, $C_{1-6}$haloalkyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$N(R^{10})(R^{11})$, —$C(O)OR^{10}$, —$C(O)R^{13}$, or —$C(O)N(R^{10})(R^{11})$. In some embodiments of a compound of Formula (III), each $R^{15a}$ and each $R^{15b}$ are independently halogen, oxo, —CN, $C_{1-6}$alkyl, $C_{1-6}$haloalkyl, $C_{3-10}$cycloalkyl, —$OR^{10}$, or —$N(R^{10})(R^{11})$. In some embodiments of a compound of Formula (III), each $R^{15a}$ and each $R^{15b}$ are independently halogen, oxo, —CN, $C_{1-6}$alkyl, $C_{1-6}$haloalkyl, —$OR^{10}$, or —$N(R^{10})(R^{11})$. In some embodiments of a compound of Formula (III), each $R^{15a}$ and each $R^{15b}$ are independently halogen, $C_{1-6}$alkyl, $C_{1-6}$haloalkyl, $C_{3-10}$cycloalkyl, or —$OR^{10}$. In some embodiments of a compound of Formula (III), each $R^{15a}$ and each $R^{15b}$ are independently halogen, $C_{1-6}$alkyl, $C_{1-6}$haloalkyl, or —$OR^{10}$. In some embodiments of a compound of Formula (III), each $R^{15a}$ and each $R^{15b}$ are independently halogen, $C_{1-6}$alkyl, $C_{3-10}$cycloalkyl, or —$OR^{10}$. In some embodiments of a compound of Formula (III), each $R^{15a}$ and each $R^{15b}$ are independently halogen, $C_{1-6}$alkyl, or —$OR^{10}$. In some embodiments of a compound of Formula (III), each $R^{15a}$ and each $R^{15b}$ are independently $C_{1-6}$alkyl, $C_{3-10}$cycloalkyl, or —$OR^{10}$. In some embodiments of a compound of Formula (III), each $R^{15a}$ and each $R^{15b}$ are independently $C_{1-6}$alkyl or —$OR^{10}$. In some embodiments of a compound of Formula (III), each $R^{15a}$ and each $R^{15b}$ are independently $C_{3-10}$cycloalkyl or —$OR^{10}$. In some embodiments of a compound of Formula (III), each $R^{15a}$ and each $R^{15b}$ are independently —$OR^{10}$.

In some embodiments of a compound of Formula (III), or a pharmaceutically acceptable salt or solvate thereof, $R^1$ is optionally substituted $C_{1-9}$heteroaryl. In some embodiments of a compound of Formula (III), or a pharmaceutically acceptable salt or solvate thereof, $R^1$ is optionally substituted 5 or 6 membered heteroaryl. In some embodiments of a compound of Formula (III), or a pharmaceutically acceptable salt or solvate thereof, $R^1$ is optionally substituted 5 membered heteroaryl. In some embodiments of a compound of Formula (III), or a pharmaceutically acceptable salt or solvate thereof, $R^1$ is optionally substituted 6 membered heteroaryl. In some embodiments of a compound of Formula (III), or a pharmaceutically acceptable salt or solvate thereof, $R^1$ is monocyclic heteroaryl. In some embodiments of a compound of Formula (III), or a pharmaceutically acceptable salt or solvate thereof, $R^1$ is bicyclic heteroaryl. In some embodiments, $R^1$ is optionally substituted with one, two, or three groups selected from $R^{15a}$. In some embodiments, $R^1$ is optionally substituted with one, two, or three groups selected from halogen, $C_{1-6}$alkyl, $C_{1-6}$haloalkyl, and $C_{1-6}$alkoxyl. In some embodiments, $R^1$ is optionally substituted with one, two, or three groups selected from oxo, —CN, amino, OH, halogen, $C_{1-6}$alkyl, $C_{1-6}$haloalkyl, $C_{1-6}$alkoxyl, and $C_{3-6}$cycloalkyl.

In some embodiments of a compound of Formula (III), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are optionally substituted with one, two, or three groups selected from $R^{15a}$. In some embodiments of a compound of Formula (III), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from $R^{15a}$. In some embodiments of a compound of Formula (III), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from $R^{15a}$ and each $R^{15b}$ is independently selected from halogen, $C_{1-6}$alkyl, $C_{1-6}$haloalkyl, and —$OR^{10}$. In some embodiments of a compound of Formula (III), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, pyrazolyl, imidazolyl, isoxazolyl, thiazolyl, oxazolyl, pyrimidinyl, pyridazinyl, and pyridinyl are substituted with one group selected from $R^{15a}$ and $R^{15b}$ is selected from halogen, $C_{1-6}$alkyl, $C_{1-6}$haloalkyl, and —$OR^{10}$.

In some embodiments of a compound of Formula (III), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are optionally substituted with one, two, or three groups selected from $R^{15a}$. In some embodiments of a compound of Formula (III), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are substituted with one, two, or three groups selected from $R^{15a}$. In some embodiments of a compound of Formula (III), or a pharmaceutically acceptable salt or solvate thereof, $R^1$ is $C_{1-6}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are substituted with one, two, or three groups selected from $R^{15a}$ and each $R^{15a}$ is independently selected from halogen, $C_{1-6}$alkyl, $C_{1-6}$haloalkyl, and —$OR^{10}$. In some embodiments of a compound of Formula (III), or a pharmaceutically acceptable salt or solvate thereof, $R^1$ is $C_{1-6}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are substituted with one group selected from $R^{15a}$ and $R^{15a}$ is selected from halogen, $C_{1-6}$alkyl, $C_{1-6}$haloalkyl, and —$OR^{10}$.

In some embodiments of a compound of Formula (III), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are unsubstituted. In some embodiments of a compound of Formula (III), or a pharmaceutically acceptable salt or solvate thereof, $R^1$ is $C_{1-9}$heteroaryl selected from pyrazolyl, imidazolyl, isoxazolyl, oxazolyl, and pyridinyl, wherein pyrazolyl, imidazolyl, isoxazolyl, oxazolyl, and pyridinyl are unsubstituted. In some embodiments of a compound of Formula (III), or a pharmaceutically acceptable salt or solvate thereof, $R^1$ is unsubstituted pyrazolyl. In some embodiments of a compound of Formula (III), or a pharmaceutically acceptable salt or solvate thereof, $R^1$ is unsubstituted imidazolyl. In some embodiments of a compound of Formula (III), or a pharmaceutically acceptable salt or solvate thereof, $R^1$ is unsubstituted isoxazolyl. In some embodiments of a compound of Formula (III), or a pharmaceutically acceptable salt or solvate thereof, $R^1$ is unsubstituted oxazolyl. In some embodiments of a compound of Formula (III), or a pharmaceutically acceptable salt or solvate thereof, $R^1$ is unsubstituted pyridinyl. In some embodiments of a compound of Formula (III), or a pharmaceutically acceptable salt or solvate thereof, $R^1$ is unsubstituted thiazolyl. In some embodiments of a compound of Formula (III), or a pharmaceutically acceptable salt or solvate thereof, $R^1$ is unsubstituted pyrimidinyl. In some embodiments of a compound of Formula (III), or a pharmaceutically acceptable salt or solvate thereof, $R^1$ is unsubstituted pyridazinyl.

In some embodiments of a compound of Formula (III), or a pharmaceutically acceptable salt or solvate thereof, $R^1$ is selected from

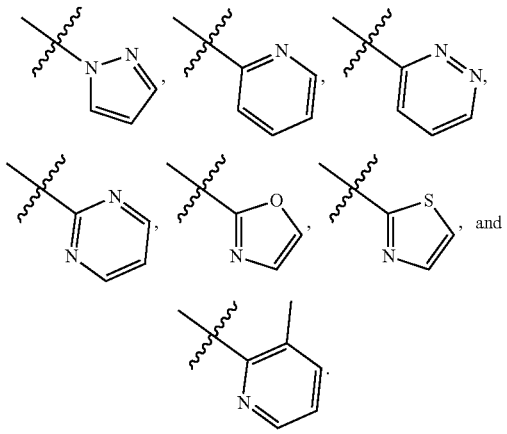

In some embodiments of a compound of Formula (III), or a pharmaceutically acceptable salt or solvate thereof, $R^1$ is selected from

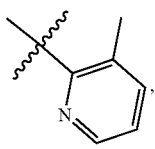

wherein each is optionally substituted with 1, 2 or 3 $R^{15a}$. In some embodiments, $R^1$ is

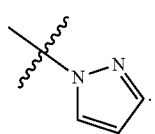 [SMILES: *n1cccn1]

In some embodiments, $R^1$ is

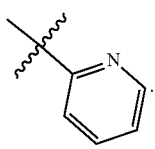 [SMILES: *c1ccccn1]

In some embodiments, $R^1$ is

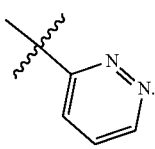 [SMILES: *c1cccnn1]

In some embodiments, $R^1$ is

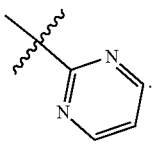 [SMILES: *c1ncccn1]

In some embodiments, $R^1$ is

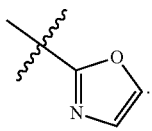 [SMILES: *c1ncco1]

In some embodiments, $R^1$ is

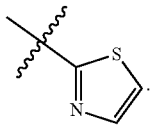 [SMILES: *c1nccs1]

In some embodiments, $R^1$ is

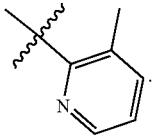 [SMILES: *c1ncccc1C]

Any combination of the groups described above for the various variables is contemplated herein. Throughout the specification, groups and substituents thereof are chosen by one skilled in the field to provide stable moieties and compounds.

In some embodiments, provided herein is a compound, or a pharmaceutically acceptable salt or solvate thereof, selected from:

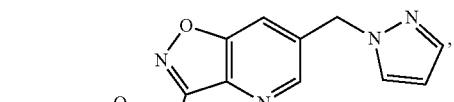

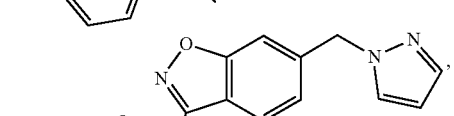

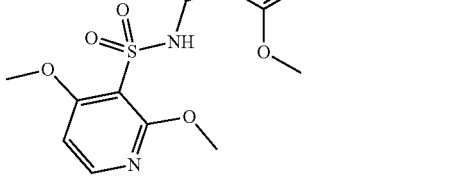

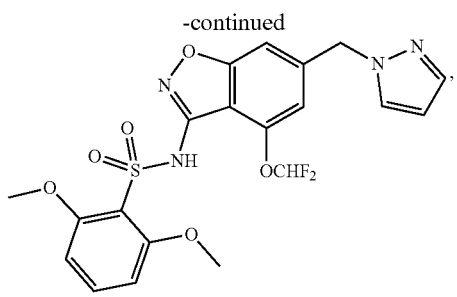
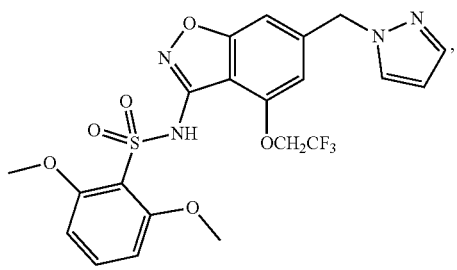
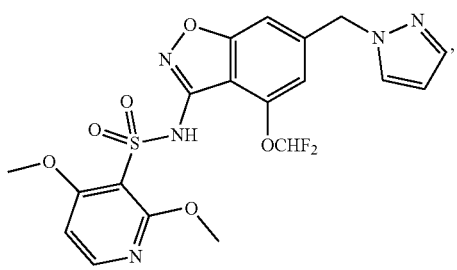
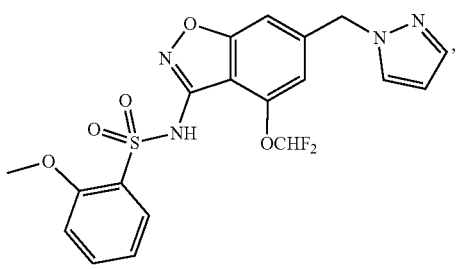
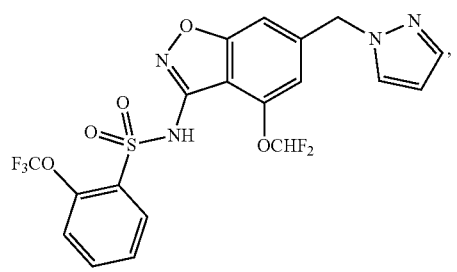
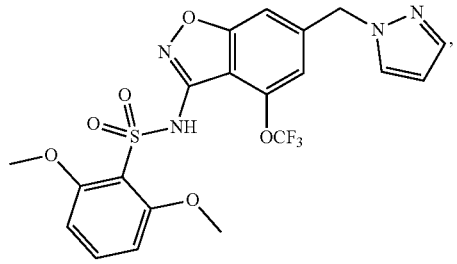
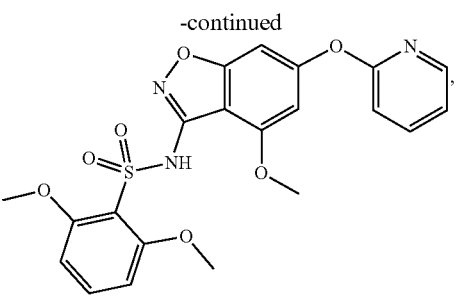
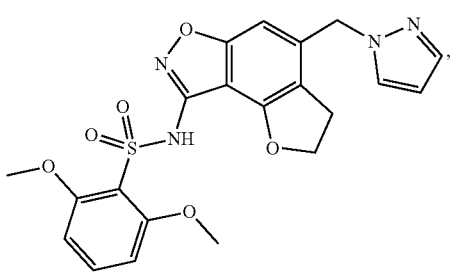
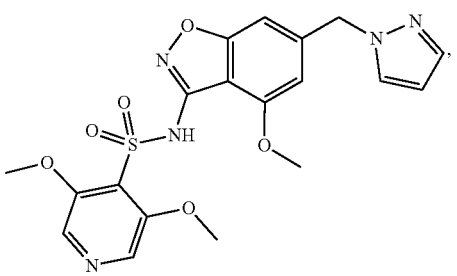
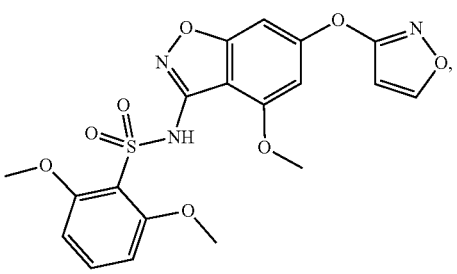
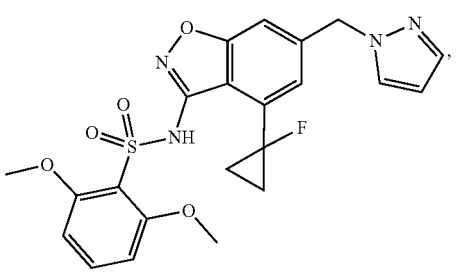
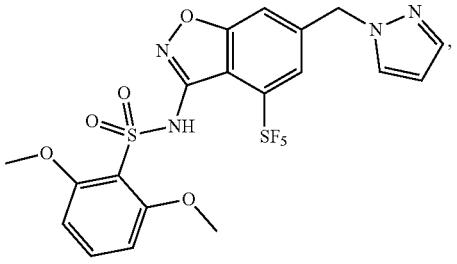

-continued
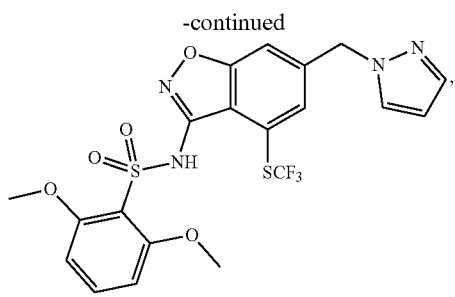
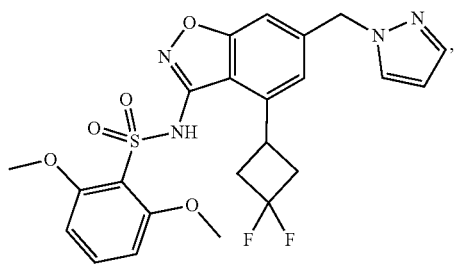
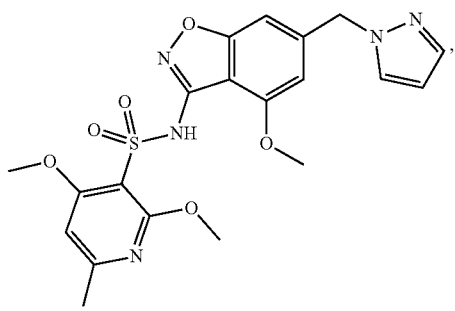
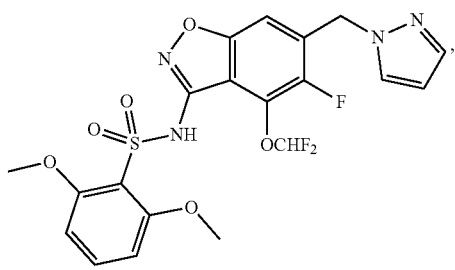
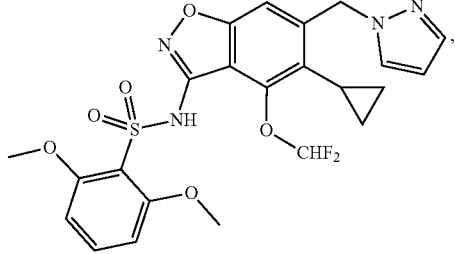
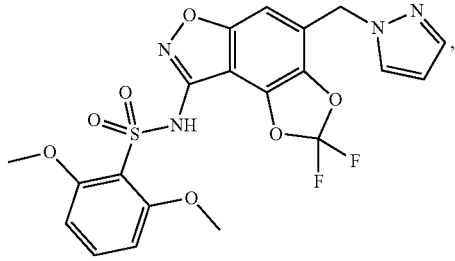
-continued
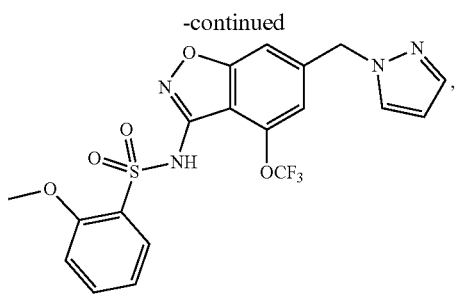
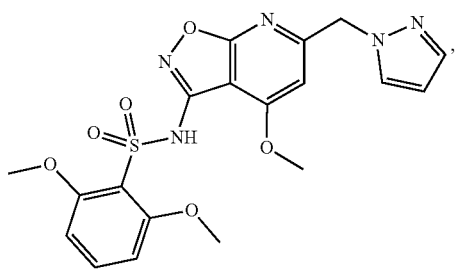
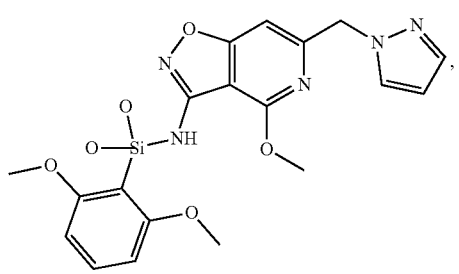
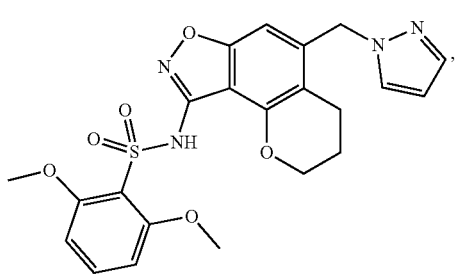
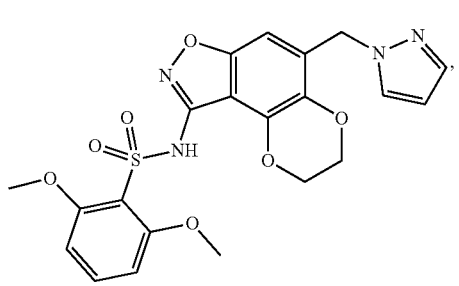
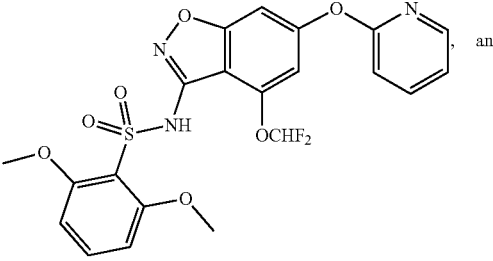

-continued
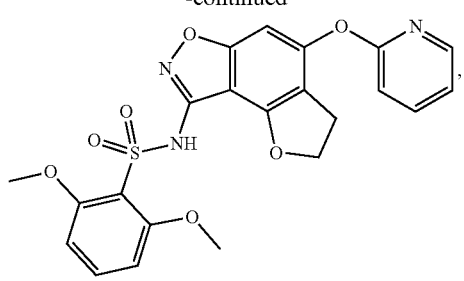
In some embodiments, described herein is a compound, or a pharmaceutically acceptable salt or solvate thereof, wherein the compound is selected from a compound of Table 1A:
TABLE 1A
Exemplary Compounds
| Compound | Structure |
|---|---|
| 1 | 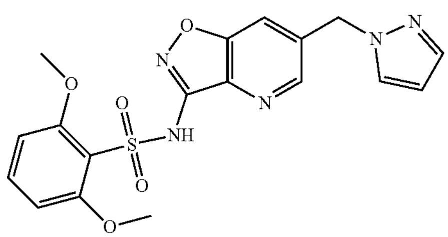 [SMILES: COc1cccc(OC)c1S(=O)(=O)Nc1noc2cc(Cn3cccn3)cnc12] |
| 2 | 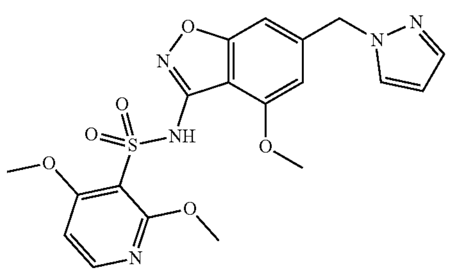 [SMILES: COc1ccnc(OC)c1S(=O)(=O)Nc1noc2cc(Cn3cccn3)cc(OC)c12] |
| 3 | 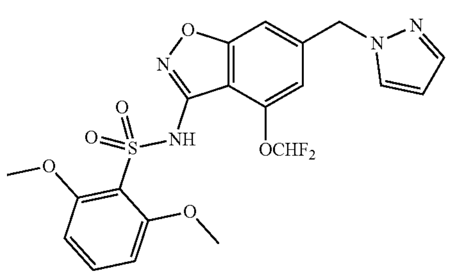 [SMILES: COc1cccc(OC)c1S(=O)(=O)Nc1noc2cc(Cn3cccn3)cc(OC(F)F)c12] |
| 4 | 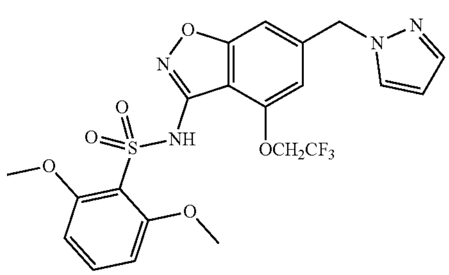 |
TABLE 1A-continued
Exemplary Compounds
| Compound | Structure |
|---|---|
| 5 | 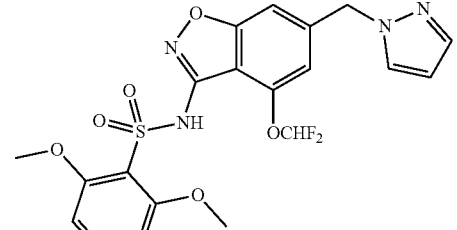 |
| 6 | 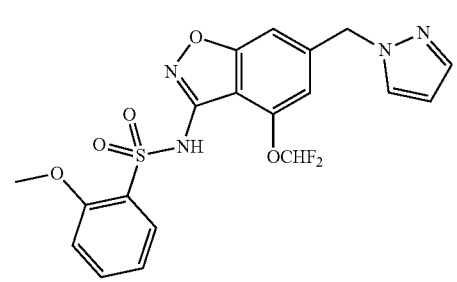 [SMILES: COc1ccccc1S(=O)(=O)Nc1noc2cc(Cn3cccn3)cc(OC(F)F)c12] |
| 7 | 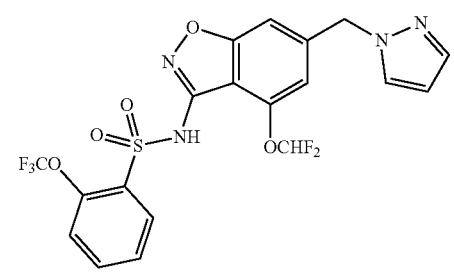 [SMILES: O=S(=O)(Nc1noc2cc(Cn3cccn3)cc(OC(F)F)c12)c1ccccc1OC(F)(F)F] |
| 8 | 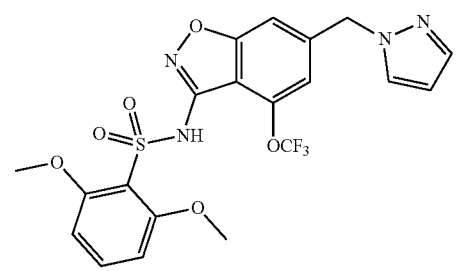 [SMILES: COc1cccc(OC)c1S(=O)(=O)Nc1noc2cc(Cn3cccn3)cc(OC(F)(F)F)c12] |
| 9 | 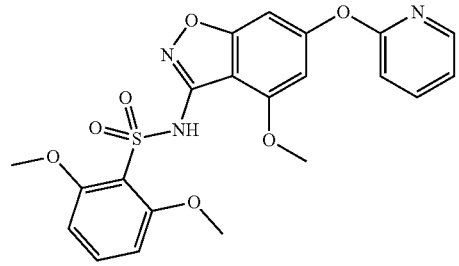 [SMILES: COc1cccc(OC)c1S(=O)(=O)Nc1noc2cc(Oc3ccccn3)cc(OC)c12] |

TABLE 1A-continued

Exemplary Compounds

| Compound | Structure |
|---|---|
| 10 | 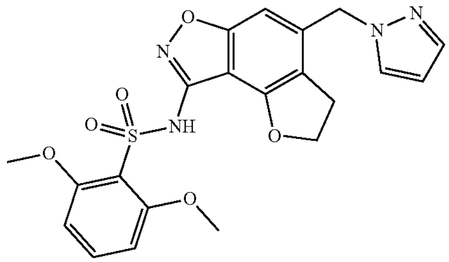 [SMILES: COc1cccc(OC)c1S(=O)(=O)Nc1noc2cc(Cn3cccn3)c3c(c12)OCC3] |
| 11 | 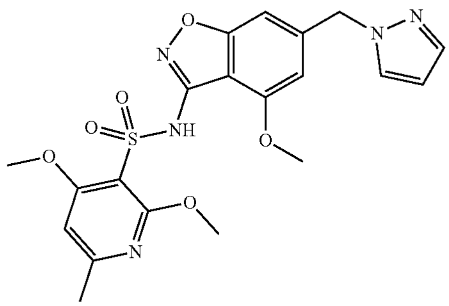 [SMILES: COc1cc(C)nc(OC)c1S(=O)(=O)Nc1noc2cc(Cn3cccn3)cc(OC)c12] |
| 12 | 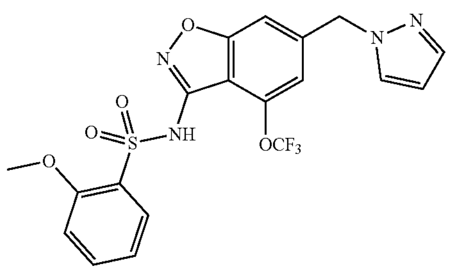 [SMILES: COc1ccccc1S(=O)(=O)Nc1noc2cc(Cn3cccn3)cc(OC(F)(F)F)c12] |
| 13 | 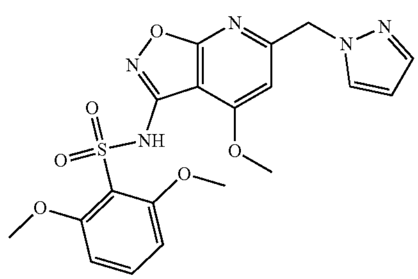 [SMILES: COc1cccc(OC)c1S(=O)(=O)Nc1noc2nc(Cn3cccn3)cc(OC)c12] |
| 14 | 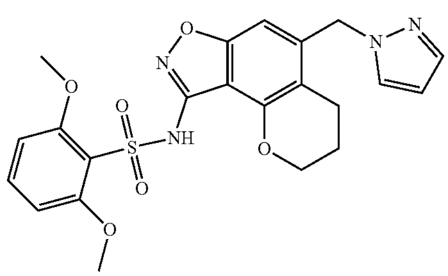 [SMILES: COc1cccc(OC)c1S(=O)(=O)Nc1noc2cc(Cn3cccn3)c3c(c12)OCCC3] |
| 15 | 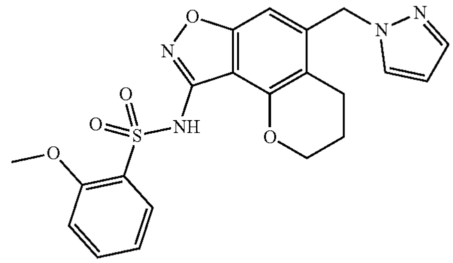 [SMILES: COc1ccccc1S(=O)(=O)Nc1noc2cc(Cn3cccn3)c3c(c12)OCCC3] |
| 16 | 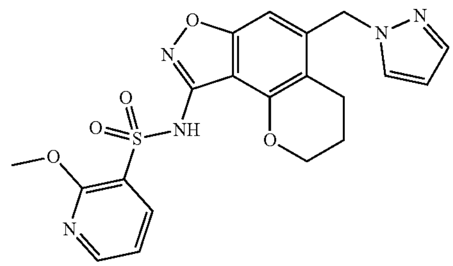 [SMILES: COc1ncccc1S(=O)(=O)Nc1noc2cc(Cn3cccn3)c3c(c12)OCCC3] |
| 17 | 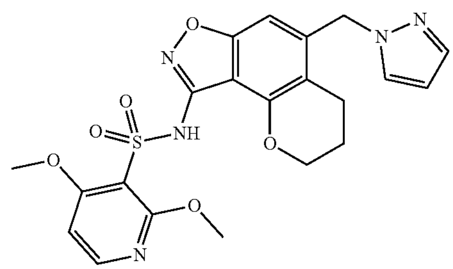 [SMILES: COc1ccnc(OC)c1S(=O)(=O)Nc1noc2cc(Cn3cccn3)c3c(c12)OCCC3] |
| 18 | 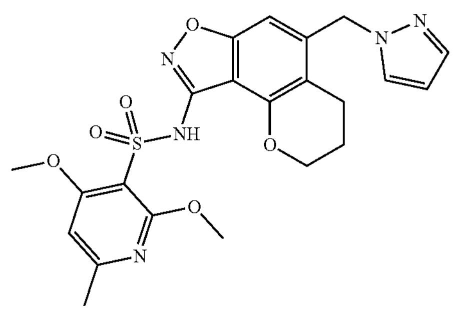 [SMILES: COc1cc(C)nc(OC)c1S(=O)(=O)Nc1noc2cc(Cn3cccn3)c3c(c12)OCCC3] |
| 19 | 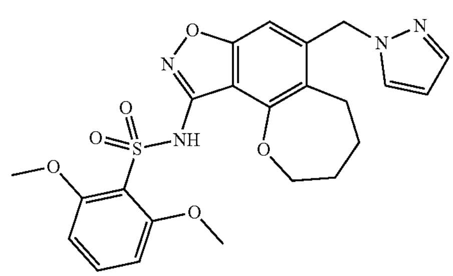 [SMILES: COc1cccc(OC)c1S(=O)(=O)Nc1noc2cc(Cn3cccn3)c3c(c12)OCCCC3] |

TABLE 1A-continued
Exemplary Compounds
| Compound | Structure |
|---|---|
| 20 | 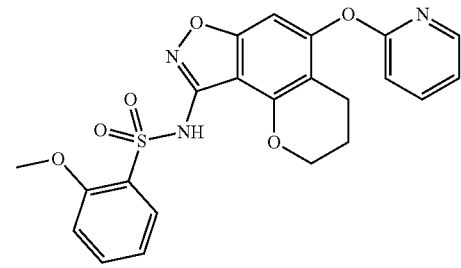 [SMILES: COc1ccccc1S(=O)(=O)Nc1noc2cc(Oc3ccccn3)c3c(c12)OCCC3] |
| 21 | 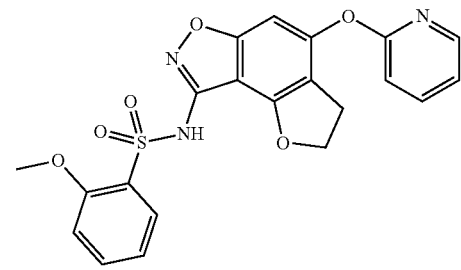 [SMILES: COc1ccccc1S(=O)(=O)Nc1noc2cc(Oc3ccccn3)c3c(c12)OCC3] |
| 22 | 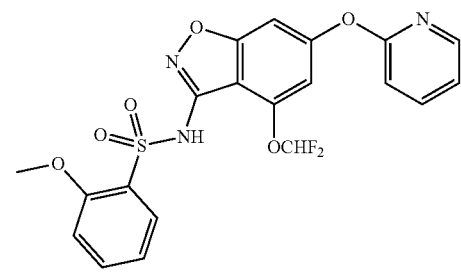 [SMILES: COc1ccccc1S(=O)(=O)Nc1noc2cc(Oc3ccccn3)cc(OC(F)F)c12] |
| 23 | 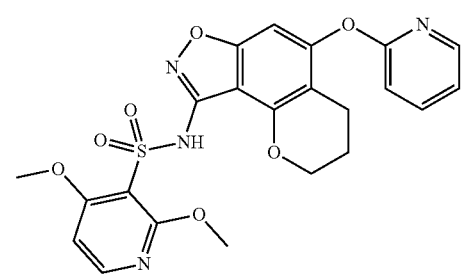 [SMILES: COc1ccnc(OC)c1S(=O)(=O)Nc1noc2cc(Oc3ccccn3)c3c(c12)OCCC3] |
| 24 | 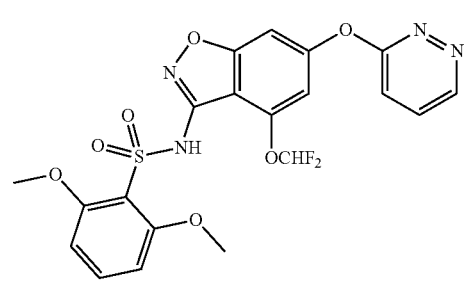 [SMILES: COc1cccc(OC)c1S(=O)(=O)Nc1noc2cc(Oc3cccnn3)cc(OC(F)F)c12] |
| 25 | |
| 26 | |
| 27 | |
| 28 | |
| 29 | |

TABLE 1A-continued

Exemplary Compounds

| Compound | Structure |
|---|---|
| 30 | 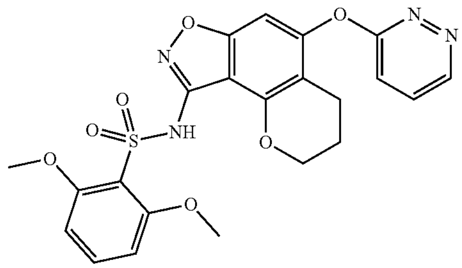 [SMILES: COc1cccc(OC)c1S(=O)(=O)Nc1noc2cc(Oc3cccnn3)c3c(c12)OCCC3] |
| 31 | 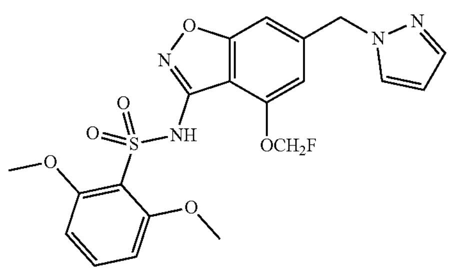 |
| 32 | 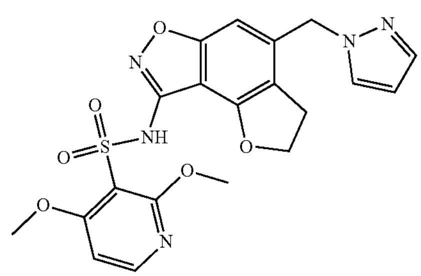 [SMILES: COc1ccnc(OC)c1S(=O)(=O)Nc1noc2cc(Cn3cccn3)c3c(c12)OCC3] |
| 33 | 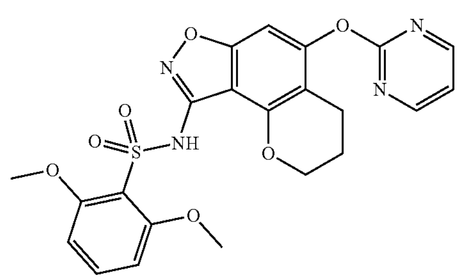 [SMILES: COc1cccc(OC)c1S(=O)(=O)Nc1noc2cc(Oc3ncccn3)c3c(c12)OCCC3] |
| 34 | 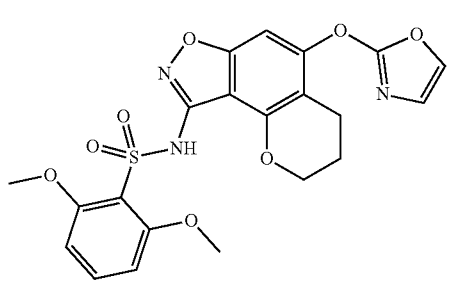 [SMILES: COc1cccc(OC)c1S(=O)(=O)Nc1noc2cc(Oc3ncco3)c3c(c12)OCCC3] |
| 35 | 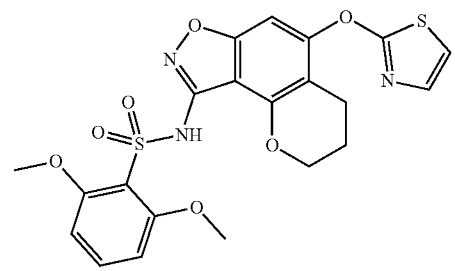 [SMILES: COc1cccc(OC)c1S(=O)(=O)Nc1noc2cc(Oc3nccs3)c3c(c12)OCCC3] |
| 36 | 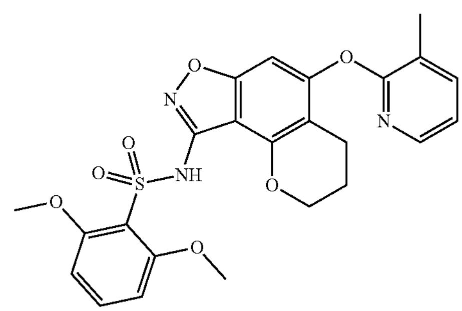 [SMILES: COc1cccc(OC)c1S(=O)(=O)Nc1noc2cc(Oc3ncccc3C)c3c(c12)OCCC3] |
| 37 | 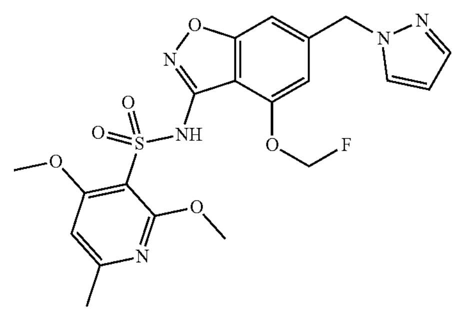 [SMILES: COc1cc(C)nc(OC)c1S(=O)(=O)Nc1noc2cc(Cn3cccn3)cc(OCF)c12] |
| 38 | 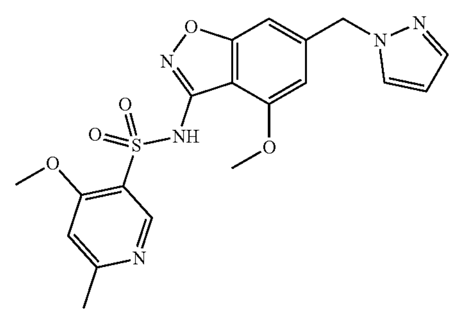 [SMILES: COc1cc(C)ncc1S(=O)(=O)Nc1noc2cc(Cn3cccn3)cc(OC)c12] |
| 39 | 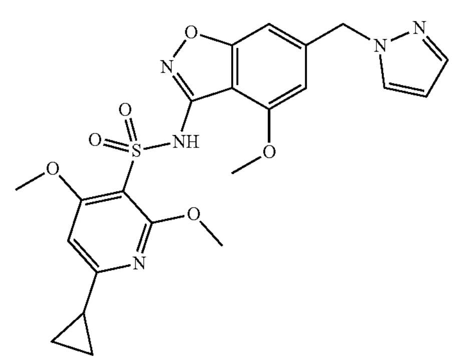 [SMILES: COc1cc(C2CC2)nc(OC)c1S(=O)(=O)Nc1noc2cc(Cn3cccn3)cc(OC)c12] |

TABLE 1A-continued
Exemplary Compounds
| Compound | Structure |
|---|---|
| 40 | 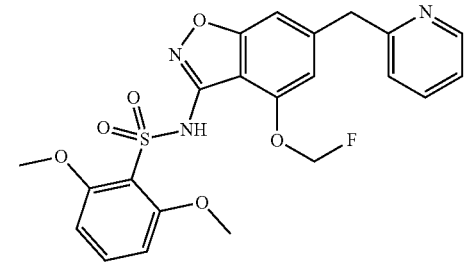 |
| 41 | 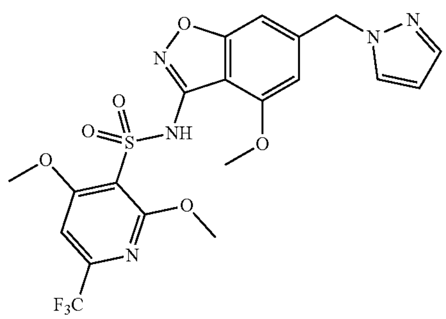 [SMILES: COc1cc(C(F)(F)F)nc(OC)c1S(=O)(=O)Nc1noc2cc(Cn3cccn3)cc(OC)c12] |
| 42 | 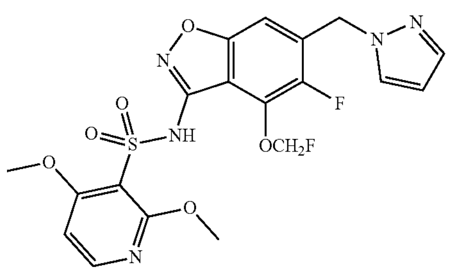 |
| 43 | 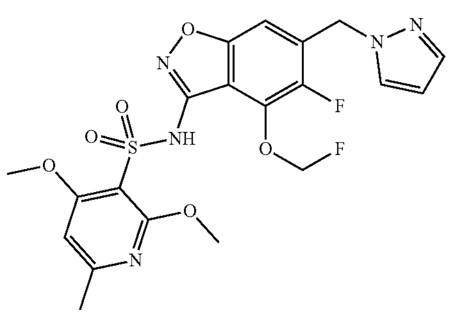 [SMILES: COc1cc(C)nc(OC)c1S(=O)(=O)Nc1noc2cc(Cn3cccn3)c(F)c(OCF)c12] |
| 44 | 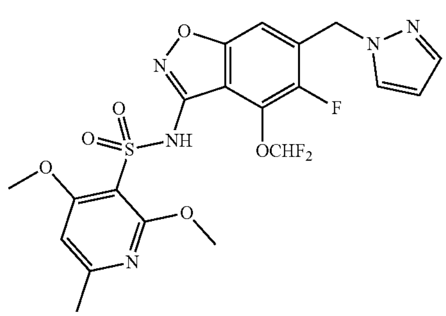 [SMILES: COc1cc(C)nc(OC)c1S(=O)(=O)Nc1noc2cc(Cn3cccn3)c(F)c(OC(F)F)c12] |
| 45 | 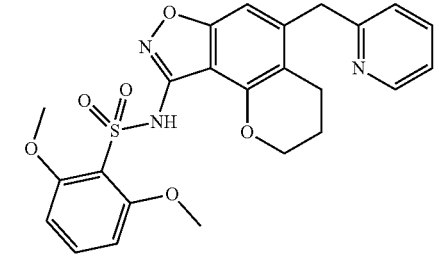 [SMILES: COc1cccc(OC)c1S(=O)(=O)Nc1noc2cc(Cc3ccccn3)c3c(c12)OCCC3] |
| 46 | |
| 47 | |
| 48 | |
| 49 | |

TABLE 1A-continued

Exemplary Compounds

| Compound | Structure |
|---|---|
| 50 | |
| 51 | |
| 52 | |
| 53 | |
| 54 | 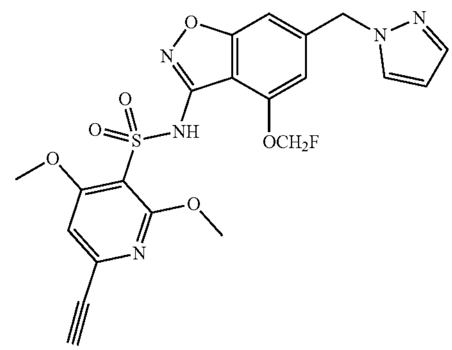 |
| 55 | 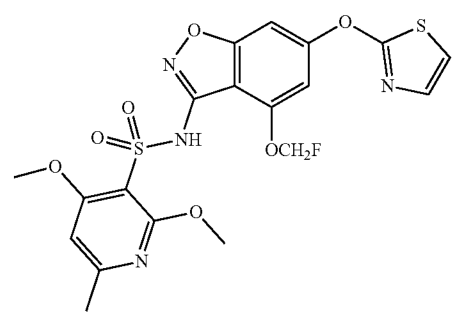 |
| 56 | 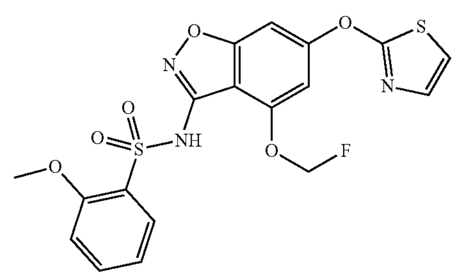 [SMILES: COc1ccccc1S(=O)(=O)Nc1noc2cc(Oc3nccs3)cc(OCF)c12] |
| 57 | 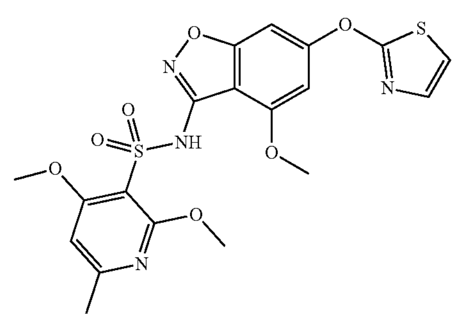 [SMILES: COc1cc(C)nc(OC)c1S(=O)(=O)Nc1noc2cc(Oc3nccs3)cc(OC)c12] |
| 58 | 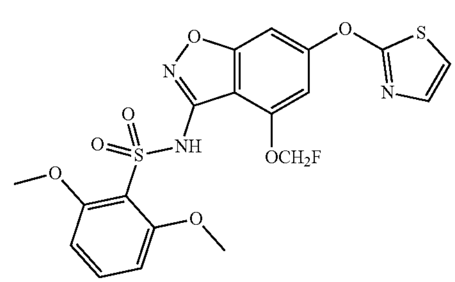 |

TABLE 1A-continued

Exemplary Compounds

| Compound | Structure |
|---|---|
| 59 | 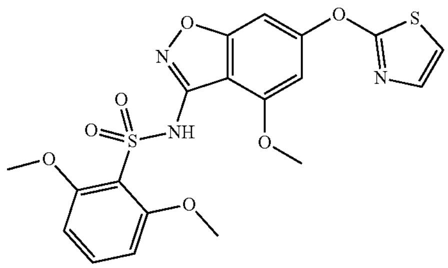 [SMILES: COc1cccc(OC)c1S(=O)(=O)Nc1noc2cc(Oc3nccs3)cc(OC)c12] |
| 60 | 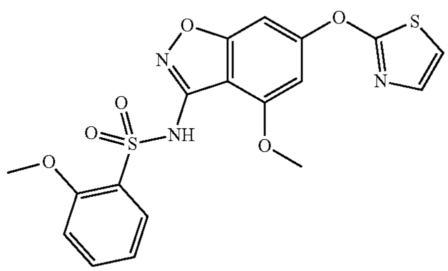 [SMILES: COc1ccccc1S(=O)(=O)Nc1noc2cc(Oc3nccs3)cc(OC)c12] |
| 61 | 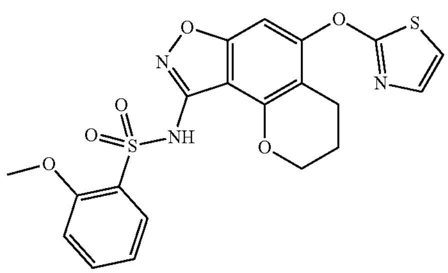 [SMILES: COc1ccccc1S(=O)(=O)Nc1noc2cc(Oc3nccs3)c3c(c12)OCCC3] |
| 62 | 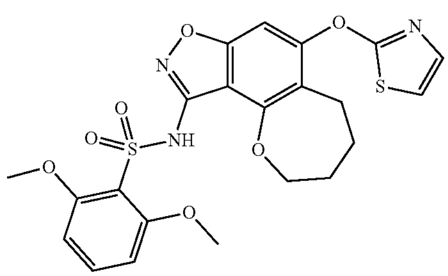 [SMILES: COc1cccc(OC)c1S(=O)(=O)Nc1noc2cc(Oc3nccs3)c3c(c12)OCCCC3] |
| 63 | 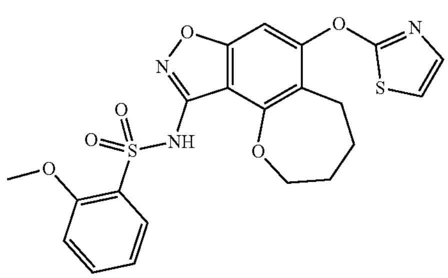 [SMILES: COc1ccccc1S(=O)(=O)Nc1noc2cc(Oc3nccs3)c3c(c12)OCCCC3] |
| 64 | |
| 65 | |
| 66 | |
| 67 | |
| 68 | |

In some embodiments disclosed herein is a compound of Formula (IV), or a pharmaceutically acceptable salt or solvate thereof:

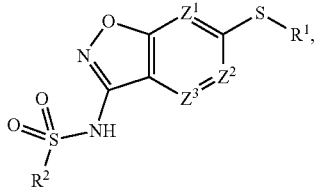

Formula (IV)

wherein:
R² is C₃₋₆ cycloalkyl, C₂₋₉ heterocycloalkyl, C₆₋₁₀ aryl, or C₁₋₉heteroaryl; each optionally substituted with one, two, three, or four groups selected from R¹⁵ᵉ;

Z¹ is CR¹ᵇ or N;
Z² is CR²ᵇ or N;
Z³ is CR³ᵇ or N;

R¹ is C₃₋₆cycloalkyl, C₂₋₉heterocycloalkyl, C₆₋₁₀aryl, or C₁₋₉heteroaryl; each optionally substituted with one, two, or three groups selected from R¹⁵ᵃ;

R¹ᵇ, R²ᵇ, and R³ᵇ are independently hydrogen, halogen, C₁₋₆alkyl, C₁₋₆haloalkyl, C₂₋₆alkenyl, C₂₋₆alkynyl, C₃₋₆cycloalkyl, C₂₋₉heterocycloalkyl, C₆₋₁₀aryl, C₁₋₉heteroaryl, —OR¹⁰, —SR¹⁰, —SF₅, —N(R¹⁰)(R¹¹), —C(O)OR¹⁰, —OC(O)N(R¹⁰)(R¹¹), —N(R¹²)C(O)N(R¹⁰)(R¹¹), —N(R¹²)C(O)OR¹³, —N(R¹²)S(O)₂R¹³, —C(O)R¹³, —S(O)R¹³, —OC(O)R¹³, —C(O)N(R¹⁰)(R¹¹), —C(O)C(O)N(R¹⁰)(R¹¹), —N(R¹²)C(O)R¹³, —S(O)₂R¹³, —S(O)₂N(R¹⁰)(R¹¹)—, S(O)(NH)N(R¹⁰)(R¹¹), —CH₂C(O)N(R¹⁰)(R¹¹), —CH₂N(R¹²)C(O)R¹³, —CH₂S(O)₂R¹³, and —CH₂S(O)₂N(R¹⁰)(R¹¹), wherein C₁₋₆alkyl, C₂₋₆alkenyl, C₂₋₆alkynyl, C₃₋₆cycloalkyl, C₂₋₉heterocycloalkyl, C₆₋₁₀aryl, and C₁₋₆heteroaryl are optionally substituted with one, two, or three groups selected from R¹⁵ᵇ;

or R²ᵇ and R³ᵇ are taken together to form a C₃₋₆cycloalkyl, C₂₋₉heterocycloalkyl, C₆₋₁₀aryl, or C₁₋₉heteroaryl; wherein C₃₋₆cycloalkyl, C₂₋₉heterocycloalkyl, C₆₋₁₀aryl, and C₁₋₉heteroaryl are optionally substituted with one, two, three, or four groups selected from R¹⁵ᵉ;

each R¹⁵ᵃ, each R¹⁵ᵇ, and each R¹⁵ᶜ are independently halogen, oxo, —CN, C₁₋₆alkyl, C₁₋₆haloalkyl, C₂₋₄alkenyl, C₂₋₆alkynyl, C₃₋₁₀cycloalkyl, —CH₂—C₃₋₆cycloalkyl, C₂₋₉heterocycloalkyl, —CH₂—C₂₋₉heterocycloalkyl, C₆₋₁₀aryl, —CH₂—C₆₋₁₀aryl, C₁₋₉heteroaryl, —CH₂—C₁₋₉heteroaryl, —OR¹⁰, —SR¹⁰, —N(R¹⁰)(R¹¹), —C(O)OR¹⁰, —OC(O)N(R¹⁰)(R¹¹), —N(R¹²)C(O)N(R¹⁰)(R¹¹), —N(R¹²)C(O)OR¹³, —N(R¹²)S(O)₂R¹³, —C(O)R¹³, —S(O)R¹³, —OC(O)R¹³, —C(O)N(R¹⁰)(R¹¹), —C(O)C(O)N(R¹⁰)(R¹¹), —N(R¹²)C(O)R¹³, —S(O)₂R¹³, —S(O)₂N(R¹⁰)(R¹¹)—, S(O)(NH)N(R¹⁰)(R¹¹), —CH₂C(O)N(R¹⁰)(R¹¹), —CH₂N(R¹²)C(O)R¹³, —CH₂S(O)₂R¹³, or —CH₂S(O)₂N(R¹⁰)(R¹¹), wherein C₁₋₆alkyl, C₂₋₆alkenyl, C₂₋₆alkynyl, C₃₋₆cycloalkyl, —CH₂—C₃₋₁₀cycloalkyl, C₂₋₉heterocycloalkyl, —CH₂—C₂₋₉heterocycloalkyl, C₆₋₁₀aryl, —CH₂—C₆₋₁₀aryl, —CH₂—C₁₋₉heteroaryl, and C₁₋₉heteroaryl are optionally substituted with one, two, or three groups independently selected from halogen, oxo, —CN, C₁₋₆alkyl, C₁₋₆haloalkyl, C₁₋₆alkoxy, C₁₋₆haloalkoxy, —OR¹⁰, —SR¹⁰, —N(R¹⁰)(R¹¹), —C(O)OR¹⁰, —OC(O)N(R¹⁰)(R¹¹), —N(R¹²)C(O)N(R¹⁰)(R¹¹), —N(R¹²)C(O)OR¹³, —N(R¹²)S(O)₂R¹³, —C(O)R¹³, —S(O)R¹³, —OC(O)R¹³, —C(O)N(R¹⁰)(R¹¹), —C(O)C(O)N(R¹⁰)(R¹¹), —N(R¹²)C(O)R¹³, —S(O)₂R¹³, —S(O)₂N(R¹⁰)(R¹¹)—, S(O)(NH)N(R¹⁰)(R¹¹), —CH₂C(O)N(R¹⁰)(R¹¹), —CH₂N(R¹²)C(O)R¹³, —CH₂S(O)₂R¹³, and —CH₂S(O)₂N(R¹⁰)(R¹¹);

each R¹⁵ᵉ are independently halogen, oxo, —CN, C₁₋₆alkyl, C₁₋₆haloalkyl, C₂₋₆alkenyl, C₂₋₆alkynyl, C₃₋₁₀cycloalkyl, —CH₂—C₃₋₆cycloalkyl, C₂₋₉heterocycloalkyl, —CH₂—C₂₋₉heterocycloalkyl, C₆₋₁₀aryl, —CH₂—C₆₋₁₀aryl, C₁₋₉heteroaryl, —CH₂—C₁₋₉heteroaryl, —OR¹⁰, —SR¹⁰, —N(R¹⁰)(R¹¹), —C(O)OR¹⁰, —OC(O)N(R¹⁰)(R¹¹), —N(R¹²)C(O)N(R¹⁰)(R¹¹), —N(R¹²)C(O)OR¹³, —N(R¹²)S(O)₂R¹³, —C(O)R¹³, —S(O)R¹³, —OC(O)R¹³, —C(O)N(R¹⁰)(R¹¹), —C(O)C(O)N(R¹⁰)(R¹¹), —N(R¹²)C(O)R¹³, —S(O)₂R¹³, —S(O)₂N(R¹⁰)(R¹¹)—, S(O)(NH)N(R¹⁰)(R¹¹), —CH₂C(O)N(R¹⁰)(R¹¹), —CH₂N(R¹²)C(O)R¹³, —CH₂S(O)₂R¹³, or —CH₂S(O)₂N(R¹⁰)(R¹¹), wherein C₁₋₆alkyl, C₂₋₆alkenyl, C₂₋₆alkynyl, C₃₋₆cycloalkyl, —CH₂—C₃₋₁₀cycloalkyl, C₂₋₉heterocycloalkyl, —CH₂—C₂₋₉heterocycloalkyl, C₆₋₁₀aryl, —CH₂—C₆₋₁₀aryl, —CH₂—C₁₋₉heteroaryl, and C₁₋₉heteroaryl are optionally substituted with one, two, or three groups independently selected from halogen, oxo, —CN, C₁₋₆alkyl, C₁₋₆haloalkyl, C₁₋₆alkoxy, C₁₋₆haloalkoxy, —OR¹⁰, —SR¹⁰, —N(R¹⁰)(R¹¹), —C(O)OR¹⁰, —OC(O)N(R¹⁰)(R¹¹), —N(R¹²)C(O)N(R¹⁰)(R¹¹), —N(R¹²)C(O)OR¹³, —N(R¹²)S(O)₂R¹³, —C(O)R¹³, —S(O)R¹³, —OC(O)R¹³, —C(O)N(R¹⁰)(R¹¹), —C(O)C(O)N(R¹⁰)(R¹¹), —N(R¹²)C(O)R¹³, —S(O)₂R¹³, —S(O)₂N(R¹⁰)(R¹¹)—, S(O)(NH)N(R¹⁰)(R¹¹), —CH₂C(O)N(R¹⁰)(R¹¹), —CH₂N(R¹²)C(O)R¹³, —CH₂S(O)₂R¹³, and —CH₂S(O)₂N(R¹⁰)(R¹¹);

or two R¹⁵ᵉ on the adjacent carbon are taken together to form a C₂₋₆alkenylene;

or two R¹⁵ᵉ on the same atom are taken together to form a C₃₋₆cycloalkyl or C₂₋₉heterocycloalkyl; each optionally substituted with one, two, or three groups independently selected from halogen, oxo, —CN, C₁₋₆alkyl, C₁₋₆haloalkyl, C₁₋₆alkoxy, C₁₋₆haloalkoxy, —OR¹⁰, —SR¹⁰, —N(R¹⁰)(R¹¹), —C(O)OR¹⁰, —OC(O)N(R¹⁰)(R¹¹), —N(R¹²)C(O)N(R¹⁰)(R¹¹), —N(R²)C(O)OR¹³, —N(R¹²)S(O)₂R¹³, —C(O)R¹³, —S(O)R¹³, —OC(O)R¹³, —C(O)N(R¹⁰)(R¹¹), —C(O)C(O)N(R¹⁰)(R¹¹), —N(R¹²)C(O)R¹³, —S(O)₂R¹³, —S(O)₂N(R¹⁰)(R¹¹)—, S(O)(NH)N(R¹⁰)(R¹¹), —CH₂C(O)N(R¹⁰)(R¹¹), —CH₂N(R¹²)C(O)R¹³, —CH₂S(O)₂R¹³, and —CH₂S(O)₂N(R¹⁰)(R¹¹);

or two R¹⁰ on the different atom are taken together to form a C₃₋₆cycloalkyl, C₂₋₉heterocycloalkyl, C₆₋₁₀aryl, or C₁₋₉heteroaryl; each optionally substituted with one, two, or three groups independently selected from halogen, oxo, —CN, C₁₋₆alkyl, C₁₋₆haloalkyl, C₁₋₆alkoxy, C₁₋₆haloalkoxy, —OR¹⁰, —SR¹⁰, —N(R¹⁰)(R¹¹), —C(O)OR¹⁰, —OC(O)N(R¹⁰)(R¹¹), —N(R¹²)C(O)N(R¹⁰)(R¹¹), —N(R¹²)C(O)OR¹³, —N(R¹²)S(O)₂R¹³, —C(O)R¹³, —S(O)R¹³, —OC(O)R¹³, —C(O)N(R¹⁰)(R¹¹), —C(O)C(O)N(R¹⁰)(R¹¹), —N(R¹²)C(O)R¹³, —S(O)₂R¹³, —S(O)₂N(R¹⁰)(R¹¹)—, S(O)(NH)N(R¹⁰)(R¹¹), —CH₂C(O)N(R¹⁰)(R¹¹), —CH₂N(R¹²)C(O)R¹³, —CH₂S(O)₂R¹³, and —CH₂S(O)₂N(R¹⁰)(R¹¹);

each R¹⁰ is independently hydrogen, C₁₋₆alkyl, C₁₋₆haloalkyl, C₂₋₆alkenyl, C₂₋₆alkynyl, C₃₋₆cycloalkyl, C₂₋₉heterocycloalkyl, C₆₋₁₀aryl, or C₁₋₉heteroaryl, wherein C₁₋₆alkyl, C₂₋₆alkenyl, C₂₋₆alkynyl, C₃₋₆cycloalkyl, C₂₋₉heterocycloalkyl, C₆₋₁₀aryl, and C₁₋₉heteroaryl are optionally substituted with one, two, or three groups selected from halogen, —CN, hydroxy, C₁₋₆alkyl, C₁₋₆haloalkyl, C₁₋₆alkoxy, C₃₋₆cycloalkyl, C₂₋₉heterocycloalkyl, C₆₋₁₀aryl, and C₁₋₉heteroaryl;

each $R^{11}$ is independently hydrogen, $C_{1-6}$alkyl, or $C_{1-6}$haloalkyl;

each $R^{12}$ is independently hydrogen, $C_{1-6}$alkyl, or $C_{1-6}$haloalkyl; and each $R^{13}$ is independently hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, or $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl.

In some embodiments of a compound of Formula (IV), $R^2$ is $C_{6-10}$aryl or $C_{1-9}$heteroaryl; each optionally substituted with one, two, three, or four groups selected from $R^{15c}$.

In some embodiments of a compound of Formula (IV), $R^2$ is $C_{1-9}$heteroaryl optionally substituted with one, two, three, or four groups selected from $R^{15c}$.

In some embodiments of a compound of Formula (IV), $R^2$ is 5- or 6-membered heteroaryl optionally substituted with one, two, three, or four groups selected from $R^{15c}$.

In some embodiments of a compound of Formula (IV), $R^2$ is 6-membered heteroaryl optionally substituted with one, two, three, or four groups selected from $R^{15c}$.

In some embodiments of a compound of Formula (IV), $R^2$ is pyridinyl optionally substituted with one, two, three, or four groups selected from $R^{15c}$.

In some embodiments of a compound of Formula (IV), $R^2$ is phenyl optionally substituted with one, two, three, or four groups selected from $R^{15c}$.

In some embodiments of a compound of Formula (IV), $R^2$ is

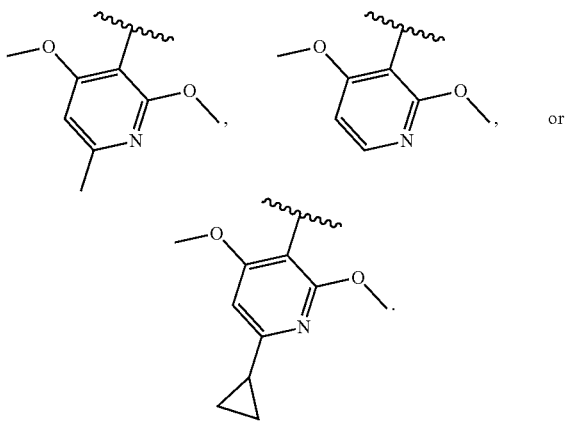

In some embodiments of a compound of Formula (IV),
$Z^1$ is $CR^{1b}$;
$Z^2$ is $CR^{2b}$; and
$Z^3$ is $CR^{3b}$.
In some embodiments of a compound of Formula (IV),
$Z^1$ is N;
$Z^2$ is $CR^{2b}$; and
$Z^3$ is $CR^{1b}$.
In some embodiments of a compound of Formula (IV),
$Z^1$ is $CR^{1b}$;
$Z^2$ is N; and
$Z^3$ is $CR^{3b}$.

In some embodiments of a compound of Formula (IV),
$Z^1$ is $CR^{1b}$;
$Z^2$ is $CR^{2b}$; and
$Z^3$ is N.

In some embodiments of a compound of Formula (IV), $R^{1b}$, $R^{2b}$, and $R^{3b}$ are independently hydrogen, halogen, $C_{1-6}$alkyl, $C_{1-6}$haloalkyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$C(O)R^{13}$, or —$C(O)N(R^{10})(R^{11})$, wherein $C_{1-6}$alkyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15b}$.

In some embodiments of a compound of Formula (IV), $R^{1b}$, $R^{2b}$, and $R^{3b}$ are independently hydrogen, halogen, $C_{1-6}$alkyl, $C_{1-6}$haloalkyl, $C_{3-6}$cycloalkyl, $C_{2-9}$heterocycloalkyl, —$OR^{10}$, —$SR^{10}$, or —$SF_5$, wherein $C_{1-6}$alkyl, $C_{3-6}$cycloalkyl, and $C_{2-9}$heterocycloalkyl are optionally substituted with one, two, or three groups selected from $R^{15b}$.

In some embodiments of a compound of Formula (IV), $R^{1b}$, $R^{2b}$, and $R^{3b}$ are independently hydrogen, halogen, $C_{3-6}$cycloalkyl, —$OR^{10}$, —$SR^{10}$, or —$SF_5$, wherein $C_{3-6}$cycloalkyl is optionally substituted with one, two, or three groups selected from $R^{15b}$.

In some embodiments of a compound of Formula (IV), $R^{1b}$, $R^{2b}$, and $R^{3b}$ are independently hydrogen, halogen, —$OR^{10}$, —$SR^{10}$, or —$SF_5$.

In some embodiments of a compound of Formula (IV), $R^{1b}$, $R^{2b}$, and $R^{3b}$ are independently hydrogen or —$OR^{10}$.

In some embodiments of a compound of Formula (IV), $R^{1b}$, $R^{2b}$, and $R^{3b}$ are hydrogen.

In some embodiments of a compound of Formula (IV), $R^{1b}$ is hydrogen.

In some embodiments of a compound of Formula (IV), $R^{2b}$ and $R^{3b}$ are taken together to form a $C_{3-6}$cycloalkyl, $C_{2-9}$heterocycloalkyl, $C_{6-10}$aryl, or $C_{1-9}$heteroaryl; wherein $C_{3-6}$cycloalkyl, $C_{2-9}$heterocycloalkyl, $C_{6-10}$aryl, and $C_{1-9}$heteroaryl are optionally substituted with one, two, three, or four groups selected from $R^{15e}$.

In some embodiments of a compound of Formula (IV), $R^{2b}$ and $R^{3b}$ are taken together to form $C_{3-6}$cycloalkyl or $C_{2-9}$heterocycloalkyl; wherein $C_{3-6}$cycloalkyl and $C_{2-9}$heterocycloalkyl are optionally substituted with one, two, three, or four groups selected from $R^{15e}$.

In some embodiments of a compound of Formula (IV), $R^{2b}$ and $R^{3b}$ are taken together to form $C_{2-9}$heterocycloalkyl optionally substituted with one, two, three, or four groups selected from $R^{15e}$.

In some embodiments of a compound of Formula (IV), $R^{2b}$ and $R^{3b}$ are taken together to form $C_{2-6}$heterocycloalkyl optionally substituted with one, two, three, or four groups selected from $R^{15e}$.

In some embodiments of a compound of Formula (IV), $R^{2b}$ and $R^{3b}$ are taken together to form $C_{6-9}$heterocycloalkyl optionally substituted with one, two, three, or four groups selected from $R^{15e}$.

In some embodiments of a compound of Formula (IV), $R^{2b}$ and $R^{3b}$ are taken together to form a 5- to 7-membered heterocycloalkyl containing one or two heteroatoms selected from O and N. In some embodiments of a compound of Formula (IV), $R^{2b}$ and $R^{3b}$ are taken together to form a 6-membered heterocycloalkyl containing one heteroatom that is O.

In some embodiments of a compound of Formula (IV), each $R^{15e}$ are independently halogen, oxo, —CN, $C_{1-6}$alkyl, $C_{1-6}$haloalkyl, $C_{3-10}$cycloalkyl, —$CH_2$—$C_{1-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$N(R^{10})(R^{11})$, —$C(O)OR^{10}$, —$C(O)R^{13}$, or —$C(O)N(R^{10})(R^{11})$.

In some embodiments of a compound of Formula (IV), each $R^{15e}$ are independently halogen, oxo, —CN, $C_{1-6}$alkyl, or $C_{1-6}$haloalkyl.

In some embodiments of a compound of Formula (IV), each $R^{15e}$ are independently halogen, oxo, $C_{1-6}$alkyl, or $C_{1-6}$haloalkyl.

In some embodiments of a compound of Formula (IV), two $R^{15e}$ on the adjacent carbon are taken together to form a $C_{2-6}$alkenylene.

In some embodiments of a compound of Formula (IV), two $R^{15e}$ on the same atom are taken together to form a $C_{3-6}$cycloalkyl or $C_{2-9}$heterocycloalkyl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{10}$, and —N(R$^{10}$)(R$^{11}$).

In some embodiments of a compound of Formula (IV), two $R^{15e}$ on the same atom are taken together to form a $C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{10}$, and —N(R$^{10}$)(R$^{11}$).

In some embodiments of a compound of Formula (IV), two $R^{15e}$ on the same atom are taken together to form a $C_{3-6}$cycloalkyl.

In some embodiments of a compound of Formula (IV), two $R^{15e}$ on the different atom are taken together to form a $C_{3-6}$cycloalkyl or $C_{2-9}$heterocycloalkyl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{10}$, and —N(R$^{10}$)(R$^{11}$).

In some embodiments of a compound of Formula (IV), two $R^{15e}$ on the different atom are taken together to form a $C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{10}$, and —N(R$^{10}$)(R$^{11}$).

In some embodiments of a compound of Formula (IV), two $R^{15e}$ on the different atom are taken together to form a $C_{3-6}$cycloalkyl.

In some embodiments of a compound of Formula (IV), $R^{2b}$ and $R^{3b}$ are taken together to form

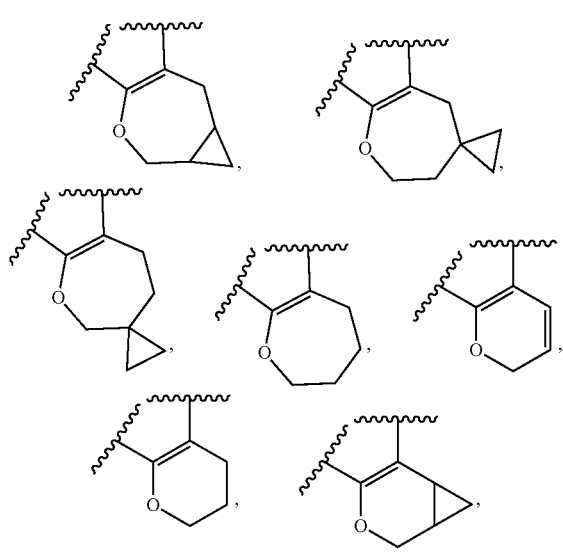

-continued

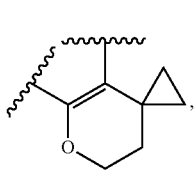 or 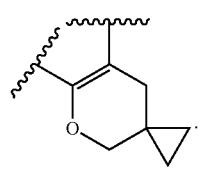

In some embodiments of a compound of Formula (IV), $R^1$ is $C_{6-10}$aryl or $C_{1-9}$heteroaryl; each optionally substituted with one, two, or three groups selected from $R^{15a}$.

In some embodiments of a compound of Formula (IV), $R^1$ is $C_{1-9}$heteroaryl optionally substituted with one, two, or three groups selected from $R^{15a}$.

In some embodiments of a compound of Formula (IV), $R^1$ is 5- or 6-membered heteroaryl optionally substituted with one, two, or three groups selected from $R^{15a}$.

In some embodiments of a compound of Formula (IV), $R^1$ is 5-membered heteroaryl optionally substituted with one, two, or three groups selected from $R^{15a}$.

In some embodiments of a compound of Formula (IV), or a pharmaceutically acceptable salt or solvate thereof, $R^1$ is optionally substituted $C_{1-9}$heteroaryl. In some embodiments of a compound of Formula (IV), or a pharmaceutically acceptable salt or solvate thereof, $R^1$ is optionally substituted 5 or 6 membered heteroaryl. In some embodiments of a compound of Formula (IV), or a pharmaceutically acceptable salt or solvate thereof, $R^1$ is optionally substituted 5 membered heteroaryl. In some embodiments of a compound of Formula (IV), or a pharmaceutically acceptable salt or solvate thereof, $R^1$ is optionally substituted 6 membered heteroaryl. In some embodiments of a compound of Formula (IV), or a pharmaceutically acceptable salt or solvate thereof, $R^1$ is monocyclic heteroaryl. In some embodiments of a compound of Formula (IV), or a pharmaceutically acceptable salt or solvate thereof, $R^1$ is bicyclic heteroaryl. In some embodiments, $R^1$ is optionally substituted with one, two, or three groups selected from $R^{15a}$. In some embodiments, $R^1$ is optionally substituted with one, two, or three groups selected from halogen, $C_{1-6}$alkyl, $C_{1-6}$haloalkyl, and $C_{1-6}$alkoxyl. In some embodiments, $R^1$ is optionally substituted with one, two, or three groups selected from oxo, —CN, amino, OH, halogen, $C_{1-6}$alkyl, $C_{1-6}$haloalkyl, $C_{1-6}$alkoxyl, and $C_{3-6}$cycloalkyl.

In some embodiments of a compound of Formula (IV), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are optionally substituted with one, two, or three groups selected from $R^{15a}$. In some embodiments of a compound of Formula (IV), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from $R^{15a}$. In some embodiments of a compound of Formula (IV), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from $R^{15a}$ and each $R^{15a}$ is independently selected from halogen, $C_{1-6}$alkyl, $C_{1-6}$haloalkyl, and —$OR^{10}$. In some embodiments of a compound of Formula (IV), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, pyrazolyl, imidazolyl, isoxazolyl, thiazolyl, oxazolyl, pyrimidinyl, pyridazinyl, and pyridinyl are substituted with one group selected from $R^{15a}$ and $R^{15a}$ is selected from halogen, $C_{1-6}$alkyl, $C_{1-6}$haloalkyl, and —$OR^{10}$.

In some embodiments of a compound of Formula (IV), $R^1$ is $C_{1-9}$heteroaryl selected from pyrazolyl and thiazolyl, wherein pyrazolyl and thiazolyl are optionally substituted with one, two, or three groups selected from $R^{15a}$.

In some embodiments of a compound of Formula (IV), $R^1$ is thiazolyl optionally substituted with one, two, or three groups selected from $R^{15a}$.

In some embodiments of a compound of Formula (IV), $R^1$ is pyrazolyl optionally substituted with one, two, or three groups selected from $R^{15a}$.

In some embodiments of a compound of Formula (IV), $R^1$ is

In some embodiments of a compound of Formula (IV), each $R^{15a}$, each $R^{15b}$, and each $R^{15c}$ are independently halogen, oxo, —CN, $C_{1-6}$alkyl, $C_{1-6}$haloalkyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$N(R^{10})(R^{11})$, —$C(O)OR^{10}$, —$C(O)R^{13}$, or —$C(O)N(R^{10})(R^{11})$. In some embodiments of a compound of Formula (IV), each $R^{15a}$, each $R^{15b}$, and each $R^{15c}$ are independently halogen, oxo, —CN, $C_{1-6}$alkyl, $C_{1-6}$haloalkyl, $C_{3-10}$cycloalkyl, —$OR^{10}$, or —$N(R^{10})(R^{11})$. In some embodiments of a compound of Formula (IV), each $R^{15a}$, each $R^{15b}$, and each $R^{15c}$ are independently halogen, oxo, —CN, $C_{1-6}$alkyl, $C_{1-6}$haloalkyl, —$OR^{10}$, or —$N(R^{10})(R^{11})$. In some embodiments of a compound of Formula (IV), each $R^{15a}$, each $R^{15b}$, and each $R^{15c}$ are independently halogen, $C_{1-6}$alkyl, $C_{1-6}$haloalkyl, $C_{3-10}$cycloalkyl, or —$OR^{10}$.

In some embodiments of a compound of Formula (IV), each $R^{15a}$, each $R^{15b}$, and each $R^{15c}$ are independently halogen, $C_{1-6}$alkyl, $C_{1-6}$haloalkyl, or —$OR^{10}$. In some embodiments of a compound of Formula (IV), each $R^{15a}$, each $R^{15b}$, and each $R^{15c}$ are independently halogen, $C_{1-6}$alkyl, $C_{3-10}$cycloalkyl, or —$OR^{10}$. In some embodiments of a compound of Formula (IV), each $R^{15a}$, each $R^{15b}$, and each $R^{15c}$ are independently halogen, $C_{1-6}$alkyl, or —$OR^{10}$. In some embodiments of a compound of Formula (IV), each $R^{15a}$, each $R^{15b}$, and each $R^{15c}$ are independently $C_{1-6}$alkyl, $C_{3-10}$cycloalkyl, or —$OR^{10}$. In some embodiments of a compound of Formula (IV), each $R^{15a}$, each $R^{15b}$, and each $R^{15c}$ are independently $C_{1-6}$alkyl or —$OR^{10}$. In some embodiments of a compound of Formula (IV), each $R^{15a}$, each $R^{15b}$, and each $R^{15c}$ are independently $C_{3-10}$cycloalkyl or —$OR^{10}$. In some embodiments of a compound of Formula (IV), each $R^{15a}$, each $R^{15b}$, and each $R^{15c}$ are independently —$OR^{10}$.

In some embodiments of a compound of Formula (IV), each $R^{15a}$ are independently halogen, oxo, —CN, $C_{1-6}$alkyl, $C_{1-6}$haloalkyl, $C_{3-10}$cycloalkyl, —$CH_2$—$C_{1-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$N(R^{10})(R^{11})$, —$C(O)OR^{10}$, —$C(O)R^{13}$, or —$C(O)N(R^{10})(R^{11})$. In some embodiments of a compound of Formula (IV), each $R^{15a}$ are independently halogen, oxo, —CN, $C_{1-6}$alkyl, $C_{1-6}$haloalkyl, $C_{3-10}$cycloalkyl, —$OR^{10}$, or —$N(R^{10})(R^{11})$. In some embodiments of a compound of Formula (IV), each $R^{15a}$ are independently halogen, oxo, —CN, $C_{1-6}$alkyl, $C_{1-6}$haloalkyl, —$OR^{10}$, or —$N(R^{10})(R^{11})$. In some embodiments of a compound of Formula (IV), each $R^{15a}$ are independently halogen, $C_{1-6}$alkyl, $C_{1-6}$haloalkyl, $C_{3-10}$cycloalkyl, or —$OR^{10}$. In some embodiments of a compound of Formula (IV), each $R^{15a}$ are independently halogen, $C_{1-6}$alkyl, $C_{1-6}$haloalkyl, or —$OR^{10}$. In some embodiments of a compound of Formula (IV), each $R^{15a}$ are independently halogen, $C_{1-6}$alkyl, $C_{3-10}$cycloalkyl, or —$OR^{10}$. In some embodiments of a compound of Formula (IV), each $R^{15a}$ are independently halogen, $C_{1-6}$alkyl, or —$OR^{10}$. In some embodiments of a compound of Formula (IV), each $R^{15a}$ are independently $C_{1-6}$alkyl, $C_{3-10}$cycloalkyl, or —$OR^{10}$. In some embodiments of a compound of Formula (IV), each $R^{15a}$ are independently $C_{1-6}$alkyl or —$OR^{10}$. In some embodiments of a compound of Formula (IV), each $R^{15a}$ are independently $C_{3-10}$cycloalkyl or —$OR^{10}$. In some embodiments of a compound of Formula (IV), each $R^{15a}$ are independently —$OR^{10}$.

In some embodiments of a compound of Formula (IV), each $R^{15a}$ are independently halogen, oxo, —CN, $C_{1-6}$alkyl, $C_{1-6}$haloalkyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$N(R^{10})(R^{11})$, —$C(O)OR^{10}$, —$C(O)R^{13}$, or —$C(O)N(R^{10})(R^{11})$. In some embodiments of a compound of Formula (IV), each $R^{15b}$ are independently halogen, oxo, —CN, $C_{1-6}$alkyl, $C_{1-6}$haloalkyl, $C_{3-10}$cycloalkyl, —$OR^{10}$, or —$N(R^{10})(R^{11})$. In some embodiments of a compound of Formula (IV), each $R^{15b}$ are independently halogen, oxo, —CN, $C_{1-6}$alkyl, $C_{1-6}$haloalkyl, —$OR^{10}$, or —$N(R^{10})(R^{11})$. In some embodiments of a compound of Formula (IV), each $R^{15b}$ are independently halogen, $C_{1-6}$alkyl, $C_{1-6}$haloalkyl, $C_{3-10}$cycloalkyl, or —$OR^{10}$.

In some embodiments of a compound of Formula (IV), each $R^{15b}$ are independently halogen, $C_{1-6}$alkyl, $C_{1-6}$haloalkyl, or —$OR^{10}$. In some embodiments of a compound of Formula (IV), each $R^{15b}$ are independently halogen, $C_{1-6}$alkyl, $C_{3-10}$cycloalkyl, or —$OR^{10}$. In some embodiments of a compound of Formula (IV), each $R^{15b}$ are independently halogen, $C_{1-6}$alkyl, or —$OR^{10}$. In some embodiments of a compound of Formula (IV), each $R^{15b}$ are independently $C_{1-6}$alkyl, $C_{3-10}$cycloalkyl, or —$OR^{10}$. In some embodiments of a compound of Formula (IV), each $R^{15b}$ are independently $C_{1-6}$alkyl or —$OR^{10}$. In some embodiments of a compound of Formula (IV), each $R^{15b}$ are independently $C_{3-10}$cycloalkyl or —$OR^{10}$. In some embodiments of a compound of Formula (IV), each $R^{15b}$ are independently —$OR^{10}$.

In some embodiments of a compound of Formula (IV), each $R^{15c}$ are independently halogen, oxo, —CN, $C_{1-6}$alkyl, $C_{1-6}$haloalkyl, $C_{3-10}$cycloalkyl, —$CH_2$—$C_{1-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$N(R^{10})(R^{11})$, —$C(O)OR^{10}$, —$C(O)R^{13}$, or —$C(O)N(R^{10})(R^{11})$. In some embodiments of a compound of Formula (IV), each $R^{15c}$ are independently halogen, oxo, —CN, C$_{1-6}$alkyl, C$_{1-6}$haloalkyl, C$_{3-10}$cycloalkyl, —OR$^{10}$, or —N(R$^{10}$)(R$^{11}$). In some embodiments of a compound of Formula (IV), each R$^{15c}$ are independently halogen, oxo, —CN, C$_{1-6}$alkyl, C$_{1-6}$haloalkyl, —OR$^{10}$, or —N(R$^{10}$)(R$^{11}$). In some embodiments of a compound of Formula (IV), each R$^{15c}$ are independently halogen, C$_{1-6}$alkyl, C$_{1-6}$haloalkyl, C$_{3-10}$cycloalkyl, or —OR$^{10}$.

In some embodiments of a compound of Formula (IV), each R$^{15c}$ are independently halogen, C$_{1-6}$alkyl, C$_{1-6}$haloalkyl, or —OR$^{10}$. In some embodiments of a compound of Formula (IV), each R$^{15c}$ are independently halogen, C$_{1-6}$alkyl, C$_{3-10}$cycloalkyl, or —OR$^{10}$. In some embodiments of a compound of Formula (IV), each R$^{15c}$ are independently halogen, C$_{1-6}$alkyl, or —OR$^{10}$. In some embodiments of a compound of Formula (IV), each R$^{15c}$ are independently C$_{1-6}$alkyl, C$_{3-10}$cycloalkyl, or —OR$^{10}$. In some embodiments of a compound of Formula (IV), each R$^{15c}$ are independently C$_{1-6}$alkyl or —OR$^{10}$. In some embodiments of a compound of Formula (IV), each R$^{15c}$ are independently C$_{3-10}$cycloalkyl or —OR$^{10}$. In some embodiments of a compound of Formula (IV), each R$^{15c}$ are independently —OR$^{10}$.

Also disclosed herein is a compound of Formula (V), or a pharmaceutically acceptable salt or solvate thereof:

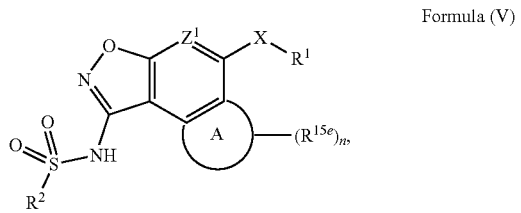

Formula (V)

wherein:
R$^2$ is C$_{1-9}$heteroaryl optionally substituted with one, two, three, or four groups selected from R$^{15c}$;
Z$^1$ is CR$^{1b}$ or N;
R$^1$ is C$_{3-6}$cycloalkyl, C$_{2-9}$heterocycloalkyl, C$_{6-10}$aryl, or C$_{1-9}$heteroaryl; each optionally substituted with one, two, or three groups selected from R$^{15a}$;
R$^{1b}$ is hydrogen, halogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^2$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$), S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, or —CH$_2$S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15b}$;
X is —C(R$^6$)(R$^{6a}$)—, —S—, —O—, or —N(R$^7$)—;
R$^6$ and R$^{6a}$ are independently hydrogen, halogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, or —CH$_2$S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;
or R$^6$ and R$^{6a}$ are taken together to form an oxo;
R$^7$ is hydrogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, or C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;
Ring A is C$_{3-6}$cycloalkyl, C$_{2-9}$heterocycloalkyl, C$_{6-10}$aryl, or C$_{1-9}$heteroaryl;
each R$^{15a}$, each R$^{15a}$, and each R$^{15c}$ are independently halogen, oxo, —CN, C$_{1-6}$alkyl, C$_{1-6}$haloalkyl, C$_{2-6}$alkenyl, C$_{2-6}$alkynyl, C$_{3-10}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, C$_{1-9}$heteroaryl, —CH$_2$—C$_{1-9}$heteroaryl, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, or —CH$_2$S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, —CH$_2$—C$_{3-10}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, —CH$_2$—C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);
each R$^{15e}$ are independently halogen, oxo, —CN, C$_{1-6}$alkyl, C$_{1-6}$haloalkyl, C$_{2-6}$alkenyl, C$_{2-6}$alkynyl, C$_{3-10}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, C$_{1-9}$heteroaryl, —CH$_2$—C$_{1-9}$heteroaryl, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, or —CH$_2$S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, —CH$_2$—C$_{3-10}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, —CH$_2$—C$_{1-9}$heteroaryl, and C$_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

or two R$^{15e}$ on the adjacent carbon are taken together to form a $C_{2-6}$alkenylene;

or two R$^{15e}$ on the same atom are taken together to form a $C_{3-6}$cycloalkyl or $C_{2-9}$heterocycloalkyl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

or two R$^{15e}$ on the different atom are taken together to form a $C_{3-6}$cycloalkyl, $C_{2-9}$heterocycloalkyl, $C_{6-10}$aryl, or $C_{1-9}$heteroaryl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

n is 0-6;

each R$^{10}$ is hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each R$^{11}$ is hydrogen, $C_{1-6}$alkyl, or $C_{1-6}$haloalkyl;

each R$^{12}$ is hydrogen, $C_{1-6}$alkyl, or $C_{1-6}$haloalkyl; and each R$^{13}$ is hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, or $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl.

In some embodiments of a compound of Formula (V), R$^2$ is 5- or 6-membered heteroaryl optionally substituted with one, two, three, or four groups selected from R$^{15c}$.

In some embodiments of a compound of Formula (V), R$^2$ is 6-membered heteroaryl optionally substituted with one, two, three, or four groups selected from R$^{15c}$.

In some embodiments of a compound of Formula (V), R$^2$ is pyridinyl optionally substituted with one, two, three, or four groups selected from R$^{15c}$.

In some embodiments of a compound of Formula (V), R$^2$ is or

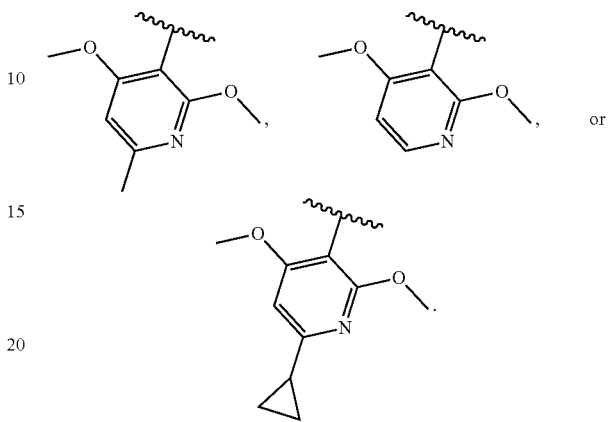

In some embodiments of a compound of Formula (V), Ring A is $C_{3-6}$cycloalkyl or $C_{2-9}$heterocycloalkyl.

In some embodiments of a compound of Formula (V), Ring A is $C_{2-9}$heterocycloalkyl.

In some embodiments of a compound of Formula (V), Ring A is $C_{2-6}$heterocycloalkyl.

In some embodiments of a compound of Formula (V), Ring A is $C_{6-9}$heterocycloalkyl. In some embodiments of a compound of Formula (V), Ring A is 6-membered heterocycloalkyl. In some embodiments of a compound of Formula (V), Ring A is 5- to 7-membered heterocycloalkyl containing one or two heteroatoms elected from O and N. In some embodiments of a compound of Formula (V), Ring A is 6-membered heterocycloalkyl containing one heteroatom that is O.

In some embodiments of a compound of Formula (V), each R$^{15e}$ are independently halogen, oxo, —CN, $C_{1-6}$alkyl, $C_{1-6}$haloalkyl, $C_{3-10}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-6}$heteroaryl, —CH$_2$—$C_{1-9}$heteroaryl, —OR$^{10}$, —N(R$^{10}$)(R$^{11}$), —C(O)OR$^{10}$, —C(O)R$^{13}$, or —C(O)N(R$^{10}$)(R$^{11}$).

In some embodiments of a compound of Formula (V), each R$^{15e}$ are independently halogen, oxo, —CN, $C_{1-6}$alkyl, or $C_{1-6}$haloalkyl.

In some embodiments of a compound of Formula (V), each R$^{15e}$ are independently halogen, oxo, $C_{1-6}$alkyl, or $C_{1-6}$haloalkyl.

In some embodiments of a compound of Formula (V), two R$^{15e}$ on the adjacent carbon are taken together to form a $C_{2-6}$alkenylene.

In some embodiments of a compound of Formula (V), two R$^{15e}$ on the same atom are taken together to form a $C_{3-6}$cycloalkyl or $C_{2-9}$heterocycloalkyl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{10}$, and —N(R$^{10}$)(R$^{11}$).

In some embodiments of a compound of Formula (V), two R$^{15e}$ on the same atom are taken together to form a $C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{10}$, and —N(R$^{10}$)(R$^{11}$).

In some embodiments of a compound of Formula (V), two $R^{15e}$ on the same atom are taken together to form a $C_{3-6}$cycloalkyl.

In some embodiments of a compound of Formula (V), two $R^{15e}$ on the different atom are taken together to form a $C_{3-6}$cycloalkyl or $C_{2-9}$heterocycloalkyl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, and —$N(R^{10})(R^{11})$.

In some embodiments of a compound of Formula (V), two $R^{15e}$ on the different atom are taken together to form a $C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, and —$N(R^{10})(R^{11})$.

In some embodiments of a compound of Formula (V), two $R^{15e}$ on the different atom are taken together to form a $C_{3-6}$cycloalkyl.

In some embodiments of a compound of Formula (V), n is 0-4. In some embodiments of a compound of Formula (V), n is 2-4. In some embodiments of a compound of Formula (V), n is 2. In some embodiments of a compound of Formula (V), n is 1 or 2. In some embodiments of a compound of Formula (V), n is 1. In some embodiments of a compound of Formula (V), n is 1-3.

In some embodiments of a compound of Formula (V),

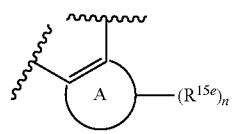

is

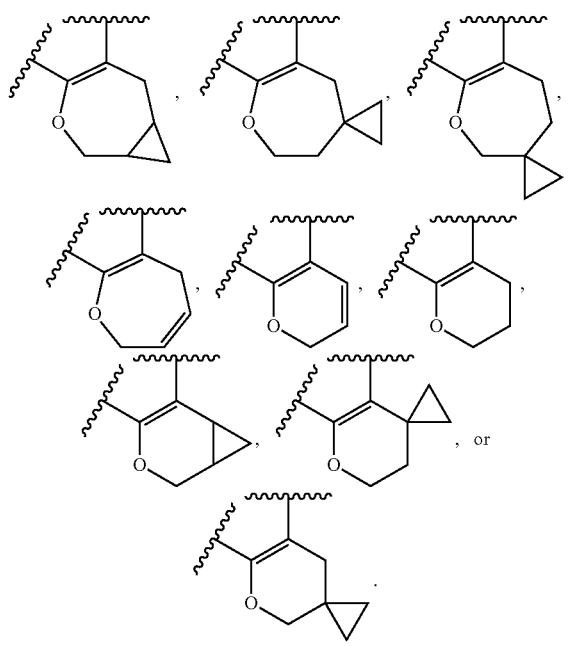

In some embodiments of a compound of Formula (V), $Z^1$ is N. In some embodiments of a compound of Formula (V), $Z^1$ is $CR^{1b}$.

In some embodiments of a compound of Formula (V), $R^{1b}$ is hydrogen or halogen. In some embodiments of a compound of Formula (V), $R^{1b}$ is hydrogen.

In some embodiments of a compound of Formula (V), X is —$C(R^6)(R^{6a})$—, —S—, or —O—. In some embodiments of a compound of Formula (V), X is —$C(R^6)(R^{6a})$— or —O—. In some embodiments of a compound of Formula (V), X is —$C(R^6)(R^{6a})$—. In some embodiments of a compound of Formula (V), X is —O—. In some embodiments of a compound of Formula (V), X is —S—. In some embodiments of a compound of Formula (V), X is —$N(R^7)$—. In some embodiments of a compound of Formula (V), X is —S—, —O—, or —$N(R^7)$—.

In some embodiments of a compound of Formula (V), $R^6$ and $R^{6a}$ are independently hydrogen, halogen, $C_{1-6}$alkyl, or $C_{1-6}$haloalkyl. In some embodiments of a compound of Formula (V), $R^6$ and $R^{6a}$ are independently hydrogen or $C_{1-6}$alkyl. In some embodiments of a compound of Formula (V), $R^6$ and $R^{6a}$ are hydrogen. In some embodiments of a compound of Formula (V), $R^6$ and $R^{6a}$ are taken together to form an oxo.

In some embodiments of a compound of Formula (V), $R^7$ is hydrogen, $C_{1-6}$alkyl, or $C_{1-6}$haloalkyl. In some embodiments of a compound of Formula (V), $R^7$ is hydrogen or $C_{1-6}$alkyl. In some embodiments of a compound of Formula (V), $R^7$ is hydrogen.

In some embodiments of a compound of Formula (V), $R^1$ is $C_{6-10}$aryl or $C_{1-9}$heteroaryl; each optionally substituted with one, two, or three groups selected from $R^{15a}$.

In some embodiments of a compound of Formula (V), $R^1$ is $C_{1-9}$heteroaryl optionally substituted with one, two, or three groups selected from $R^{15a}$.

In some embodiments of a compound of Formula (V), $R^1$ is 5- or 6-membered heteroaryl optionally substituted with one, two, or three groups selected from $R^{15a}$.

In some embodiments of a compound of Formula (V), $R^1$ is 5-membered heteroaryl optionally substituted with one, two, or three groups selected from $R^{15a}$.

In some embodiments of a compound of Formula (V), or a pharmaceutically acceptable salt or solvate thereof, $R^1$ is optionally substituted $C_{1-9}$heteroaryl. In some embodiments of a compound of Formula (V), or a pharmaceutically acceptable salt or solvate thereof, $R^1$ is optionally substituted 5 or 6 membered heteroaryl. In some embodiments of a compound of Formula (V), or a pharmaceutically acceptable salt or solvate thereof, $R^1$ is optionally substituted 5 membered heteroaryl. In some embodiments of a compound of Formula (V), or a pharmaceutically acceptable salt or solvate thereof, $R^1$ is optionally substituted 6 membered heteroaryl. In some embodiments of a compound of Formula (V), or a pharmaceutically acceptable salt or solvate thereof, $R^1$ is monocyclic heteroaryl. In some embodiments of a compound of Formula (V), or a pharmaceutically acceptable salt or solvate thereof, $R^1$ is bicyclic heteroaryl. In some embodiments, $R^1$ is optionally substituted with one, two, or three groups selected from $R^{15a}$. In some embodiments, $R^1$ is optionally substituted with one, two, or three groups selected from halogen, $C_{1-6}$alkyl, $C_{1-6}$haloalkyl, and $C_{1-6}$alkoxyl. In some embodiments, $R^1$ is optionally substituted with one, two, or three groups selected from oxo, —CN, amino, OH, halogen, $C_{1-6}$alkyl, $C_{1-6}$haloalkyl, $C_{1-6}$alkoxyl, and $C_{3-6}$cycloalkyl.

In some embodiments of a compound of Formula (V), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are optionally substituted with one, two, or three groups selected from $R^{15a}$. In some embodiments of a compound of Formula (IV), or a pharmaceutically acceptable salt or solvate thereof, $R^1$ is $C_{1\text{-}9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from $R^{15a}$. In some embodiments of a compound of Formula (V), or a pharmaceutically acceptable salt or solvate thereof, $R^1$ is $C_{1\text{-}9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from $R^{15a}$ and each $R^{15a}$ is independently selected from halogen, $C_{1\text{-}6}$alkyl, $C_{1\text{-}6}$haloalkyl, and —$OR^{10}$. In some embodiments of a compound of Formula (V), or a pharmaceutically acceptable salt or solvate thereof, $R^1$ is $C_{1\text{-}9}$heteroaryl selected from pyrazolyl, imidazolyl, isoxazolyl, thiazolyl, oxazolyl, pyrimidinyl, pyridazinyl, and pyridinyl, pyrazolyl, imidazolyl, isoxazolyl, thiazolyl, oxazolyl, pyrimidinyl, pyridazinyl, and pyridinyl are substituted with one group selected from $R^{15a}$ and $R^{15a}$ is selected from halogen, $C_{1\text{-}6}$alkyl, $C_{1\text{-}6}$haloalkyl, and —$OR^{10}$.

In some embodiments of a compound of Formula (V), $R^1$ is $C_{1\text{-}9}$heteroaryl selected from pyrazolyl and thiazolyl, wherein pyrazolyl and thiazolyl are optionally substituted with one, two, or three groups selected from $R^{15a}$.

In some embodiments of a compound of Formula (V), $R^1$ is thiazolyl optionally substituted with one, two, or three groups selected from $R^{15a}$.

In some embodiments of a compound of Formula (V), $R^1$ is pyrazolyl optionally substituted with one, two, or three groups selected from $R^{15a}$.

In some embodiments of a compound of Formula (V), $R^1$ is

In some embodiments of a compound of Formula (V), $R^1$ is

In some embodiments of a compound of Formula (V), each $R^{15a}$, each $R^{15b}$, and each $R^{15c}$ are independently halogen, oxo, —CN, $C_{1\text{-}6}$alkyl, $C_{1\text{-}6}$haloalkyl, $C_{3\text{-}10}$cycloalkyl, —$CH_2$—$C_{3\text{-}6}$cycloalkyl, $C_{2\text{-}9}$heterocycloalkyl, —$CH_2$—$C_{2\text{-}9}$heterocycloalkyl, $C_{6\text{-}10}$aryl, —$CH_2$—$C_{6\text{-}10}$aryl, $C_{1\text{-}9}$heteroaryl, —$CH_2$—$C_{1\text{-}9}$heteroaryl, —$OR^{10}$, —$N(R^{10})(R^{11})$, —$C(O)OR^{10}$, —$C(O)R^{13}$, or —$C(O)N(R^{10})(R^{11})$. In some embodiments of a compound of Formula (V), each $R^{15a}$, each $R^{15b}$, and each $R^{15c}$ are independently halogen, oxo, —CN, $C_{1\text{-}6}$alkyl, $C_{1\text{-}6}$haloalkyl, $C_{3\text{-}10}$cycloalkyl, —$OR^{10}$, or —$N(R^{10})(R^{11})$. In some embodiments of a compound of Formula (V), each $R^{15a}$, each $R^{15b}$, and each $R^{15c}$ are independently halogen, oxo, —CN, $C_{1\text{-}6}$alkyl, $C_{1\text{-}6}$haloalkyl, —$OR^{10}$, or —$N(R^{10})(R^{11})$. In some embodiments of a compound of Formula (V), each $R^{15a}$, each $R^{15b}$, and each $R^{15c}$ are independently halogen, $C_{1\text{-}6}$alkyl, $C_{1\text{-}6}$haloalkyl, $C_{3\text{-}10}$cycloalkyl, or —$OR^{10}$. In some embodiments of a compound of Formula (V), each $R^{15a}$, each $R^{15b}$, and each $R^{15c}$ are independently halogen, $C_{1\text{-}6}$alkyl, $C_{1\text{-}6}$haloalkyl, or —$OR^{10}$. In some embodiments of a compound of Formula (V), each $R^{15a}$, each $R^{15b}$, and each $R^{15c}$ are independently halogen, $C_{1\text{-}6}$alkyl, $C_{3\text{-}10}$cycloalkyl, or —$OR^{10}$. In some embodiments of a compound of Formula (V), each $R^{15a}$, each $R^{15b}$, and each $R^{15c}$ are independently halogen, $C_{1\text{-}6}$alkyl, or —$OR^{10}$. In some embodiments of a compound of Formula (V), each $R^{15a}$, each $R^{15b}$, and each $R^{15c}$ are independently $C_{1\text{-}6}$alkyl, $C_{3\text{-}10}$cycloalkyl, or —$OR^{10}$. In some embodiments of a compound of Formula (V), each $R^{15a}$, each $R^{15b}$, and each $R^{15c}$ are independently $C_{1\text{-}6}$alkyl or —$OR^{10}$. In some embodiments of a compound of Formula (V), each $R^{15a}$, each $R^{15b}$, and each $R^{15c}$ are independently $C_{3\text{-}10}$cycloalkyl or —$OR^{10}$. In some embodiments of a compound of Formula (V), each $R^{15a}$, each $R^{15b}$, and each $R^{15c}$ are independently —$OR^{10}$.

In some embodiments of a compound of Formula (V), each $R^{15a}$ are independently halogen, oxo, —CN, $C_{1\text{-}6}$alkyl, $C_{1\text{-}6}$haloalkyl, $C_{3\text{-}10}$cycloalkyl, —$CH_2$—$C_{3\text{-}6}$cycloalkyl, $C_{2\text{-}9}$heterocycloalkyl, —$CH_2$—$C_{2\text{-}9}$heterocycloalkyl, $C_{6\text{-}10}$aryl, —$CH_2$—$C_{6\text{-}10}$aryl, $C_{1\text{-}9}$heteroaryl, —$CH_2$—$C_{1\text{-}9}$heteroaryl, —$OR^{10}$, —$N(R^{10})(R^{11})$, —$C(O)OR^{10}$, —$C(O)R^{13}$, or —$C(O)N(R^{10})(R^{11})$. In some embodiments of a compound of Formula (V), each $R^{15a}$ are independently halogen, oxo, —CN, $C_{1\text{-}6}$alkyl, $C_{1\text{-}6}$haloalkyl, $C_{3\text{-}10}$cycloalkyl, —$OR^{10}$, or —$N(R^{10})(R^{11})$. In some embodiments of a compound of Formula (V), each $R^{15a}$ are independently halogen, oxo, —CN, $C_{1\text{-}6}$alkyl, $C_{1\text{-}6}$haloalkyl, —$OR^{10}$, or —$N(R^{10})(R^{11})$. In some embodiments of a compound of Formula (V), each $R^{15a}$ are independently halogen, $C_{1\text{-}6}$alkyl, $C_{1\text{-}6}$haloalkyl, $C_{3\text{-}10}$cycloalkyl, or —$OR^{10}$. In some embodiments of a compound of Formula (V), each $R^{15a}$ are independently halogen, $C_{1\text{-}6}$alkyl, $C_{1\text{-}6}$haloalkyl, or —$OR^{10}$. In some embodiments of a compound of Formula (V), each $R^{15a}$ are independently halogen, $C_{1\text{-}6}$alkyl, $C_{3\text{-}10}$cycloalkyl, or —$OR^{10}$. In some embodiments of a compound of Formula (V), each $R^{15a}$ are independently halogen, $C_{1\text{-}6}$alkyl, or —$OR^{10}$. In some embodiments of a compound of Formula (V), each $R^{15a}$ are independently $C_{1\text{-}6}$alkyl, $C_{3\text{-}10}$cycloalkyl, or —$OR^{10}$. In some embodiments of a compound of Formula (V), each $R^{15a}$ are independently $C_{1\text{-}6}$alkyl or —$OR^{10}$. In some embodiments of a compound of Formula (V), each $R^{15a}$ are independently $C_{3\text{-}10}$cycloalkyl or —$OR^{10}$. In some embodiments of a compound of Formula (V), each $R^{15a}$ are independently —$OR^{10}$.

In some embodiments of a compound of Formula (V), each $R^{15b}$ are independently halogen, oxo, —CN, $C_{1\text{-}6}$alkyl, $C_{1\text{-}6}$haloalkyl, $C_{3\text{-}10}$cycloalkyl, —$CH_2$—$C_{3\text{-}6}$cycloalkyl, $C_{2\text{-}9}$heterocycloalkyl, —$CH_2$—$C_{2\text{-}9}$heterocycloalkyl, $C_{6\text{-}10}$aryl, —$CH_2$—$C_{6\text{-}10}$aryl, $C_{1\text{-}9}$heteroaryl, —$CH_2$—$C_{1\text{-}9}$heteroaryl, —$OR^{10}$, —$N(R^{10})(R^{11})$, —$C(O)OR^{10}$, —$C(O)R^{13}$, or —$C(O)N(R^{10})(R^{11})$. In some embodiments of a compound of Formula (V), each $R^{15b}$ are independently halogen, oxo, —CN, $C_{1\text{-}6}$alkyl, $C_{1\text{-}6}$haloalkyl, $C_{3\text{-}10}$cycloalkyl, —$OR^{10}$, or —$N(R^{10})(R^{11})$. In some embodiments of a compound of Formula (V), each $R^{15b}$ are independently halogen, oxo, —CN, $C_{1\text{-}6}$alkyl, $C_{1\text{-}6}$haloalkyl, —$OR^{10}$, or —$N(R^{10})(R^{11})$. In some embodiments of a compound of Formula (V), each $R^{15b}$ are independently halogen, $C_{1\text{-}6}$alkyl, $C_{1\text{-}6}$haloalkyl, $C_{3\text{-}10}$cycloalkyl, or —$OR^{10}$.

In some embodiments of a compound of Formula (V), each $R^{15b}$ are independently halogen, $C_{1\text{-}6}$alkyl, $C_{1\text{-}6}$haloalkyl, or —$OR^{10}$. In some embodiments of a compound of Formula (V), each $R^{15b}$ are independently halogen, $C_{1-6}$alkyl, $C_{3-10}$cycloalkyl, or —$OR^{10}$. In some embodiments of a compound of Formula (V), each $R^{15b}$ are independently halogen, $C_{1-6}$alkyl, or —$OR^{10}$. In some embodiments of a compound of Formula (V), each $R^{15b}$ are independently $C_{1-6}$alkyl, $C_{3-10}$cycloalkyl, or —$OR^{10}$. In some embodiments of a compound of Formula (V), each $R^{15b}$ are independently $C_{1-6}$alkyl or —$OR^{10}$. In some embodiments of a compound of Formula (V), each $R^{15b}$ are independently $C_{3-10}$cycloalkyl or —$OR^{10}$. In some embodiments of a compound of Formula (V), each $R^{15b}$ are independently —$OR^{11}$.

In some embodiments of a compound of Formula (V), each $R^{15c}$ are independently halogen, oxo, —CN, $C_{1-6}$alkyl, $C_{1-6}$haloalkyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$N(R^{10})(R^{11})$, —$C(O)OR^{10}$, —$C(O)R^{13}$, or —$C(O)N(R^{10})(R^{11})$. In some embodiments of a compound of Formula (V), each $R^{15c}$ are independently halogen, oxo, —CN, $C_{1-6}$alkyl, $C_{1-6}$haloalkyl, $C_{3-10}$cycloalkyl, —$OR^{10}$, or —$N(R^{10})(R^{11})$. In some embodiments of a compound of Formula (V), each $R^{15c}$ are independently halogen, oxo, —CN, $C_{1-6}$alkyl, $C_{1-6}$haloalkyl, —$OR^{10}$, or —$N(R^{10})(R^{11})$. In some embodiments of a compound of Formula (V), each $R^{15c}$ are independently halogen, $C_{1-6}$alkyl, $C_{1-6}$haloalkyl, $C_{3-10}$cycloalkyl, or —$OR^{10}$.

In some embodiments of a compound of Formula (V), each $R^{15c}$ are independently halogen, $C_{1-6}$alkyl, $C_{1-6}$haloalkyl, or —$OR^{10}$. In some embodiments of a compound of Formula (V), each $R^{15c}$ are independently halogen, $C_{1-6}$alkyl, $C_{3-10}$cycloalkyl, or —$OR^{10}$. In some embodiments of a compound of Formula (V), each $R^{15c}$ are independently halogen, $C_{1-6}$alkyl, or —$OR^{10}$. In some embodiments of a compound of Formula (V), each $R^{15c}$ are independently $C_{1-6}$alkyl, $C_{3-10}$cycloalkyl, or —$OR^{10}$. In some embodiments of a compound of Formula (V), each $R^{15c}$ are independently $C_{1-6}$alkyl or —$OR^{10}$. In some embodiments of a compound of Formula (V), each $R^{15c}$ are independently $C_{3-10}$cycloalkyl or —$OR^{10}$. In some embodiments of a compound of Formula (V), each $R^{15c}$ are independently —$OR^{10}$.

Also disclosed herein is a compound of Formula (VI), or a pharmaceutically acceptable salt or solvate thereof:
wherein:

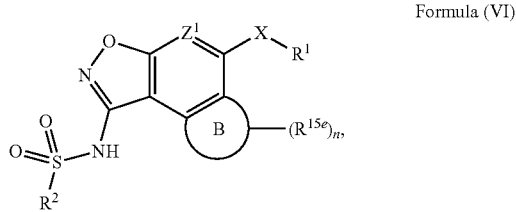

Formula (VI)

$R^2$ is $C_{3-6}$cycloalkyl, $C_{2-9}$heterocycloalkyl, $C_{6-10}$aryl, or $C_{1-9}$heteroaryl; each optionally substituted with one, two, three, or four groups selected from $R^{15c}$;

$Z^1$ is $CR^{1b}$ or N;

$R^1$ is $C_{3-6}$cycloalkyl, $C_{2-9}$heterocycloalkyl, $C_{6-10}$aryl, or $C_{1-9}$heteroaryl; each optionally substituted with one, two, or three groups selected from $R^{15c}$;

$R^{1b}$ is hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)N(R^{10})(R^{11})$, —$N(R^{12})C(O)R^{13}$, —$S(O)_2R^{13}$, —$S(O)_2N(R^{10})(R^{11})$—, S(O)(NH)N(R^{10})(R^{11})$, —$CH_2C(O)N(R^{10})(R^{11})$, —$CH_2N(R^{12})C(O)R^{13}$, —$CH_2S(O)_2R^{13}$, or —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15b}$;

X is —$C(R^6)(R^{6a})$—, —S—, —O—, or —$N(R^7)$—;

$R^6$ and $R^{6a}$ are independently hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, S(O)(NH)N(R^{10})(R^{11})$, —$CH_2C(O)N(R^{10})(R^{11})$, —$CH_2N(R^{12})C(O)R^{13}$, —$CH_2S(O)_2R^{13}$, or —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

or $R^6$ and $R^{6a}$ are taken together to form an oxo;

$R^7$ is selected from hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-4}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

Ring B is $C_{3-6}$cycloalkyl, $C_{6-9}$heterocycloalkyl, $C_{6-10}$aryl, or $C_{1-9}$heteroaryl;

each $R^{15a}$, each $R^{15b}$, and each $R^{15c}$ are independently halogen, oxo, —CN, $C_{1-6}$alkyl, $C_{1-6}$haloalkyl, $C_{2-4}$alkenyl, $C_{2-6}$alkynyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, S(O)(NH)N(R^{10})(R^{11})$, —$CH_2C(O)N(R^{10})(R^{11})$, —$CH_2N(R^{12})C(O)R^{13}$, —$CH_2S(O)_2R^{13}$, or —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, —$CH_2$—$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

each R$^{15e}$ are independently halogen, oxo, —CN, C$_{1-6}$alkyl, C$_{1-6}$haloalkyl, C$_{2-6}$alkenyl, C$_{2-6}$alkynyl, C$_{3-10}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, C$_{1-9}$heteroaryl, —CH$_2$—C$_{1-9}$heteroaryl, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, or —CH$_2$S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, —CH$_2$—C$_{3-10}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, —CH$_2$—C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

or two R$^{15e}$ on the adjacent carbon are taken together to form a C$_{2-6}$alkenylene;

or two R$^{15e}$ on the same atom are taken together to form a C$_{3-6}$cycloalkyl or C$_{2-9}$heterocycloalkyl; each optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{2}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

or two R$^{15e}$ on the different atom are taken together to form a C$_{3-6}$cycloalkyl, C$_{2-9}$heterocycloalkyl, C$_{6-10}$aryl, or C$_{1-9}$heteroaryl; each optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

n is 0-6;

each R$^{10}$ is hydrogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

each R$^{11}$ is hydrogen, C$_{1-6}$alkyl, or C$_{1-6}$haloalkyl;

each R$^{12}$ is hydrogen, C$_{1-6}$alkyl, or C$_{1-6}$haloalkyl; and each R$^{13}$ is hydrogen, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, or C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-4}$heterocycloalkyl, C$_{6-10}$aryl, and C$_{1-9}$heteroaryl.

In some embodiments of a compound of Formula (VI), R$^2$ is C$_{6-10}$aryl or C$_{1-9}$heteroaryl; each optionally substituted with one, two, three, or four groups selected from R$^{15c}$.

In some embodiments of a compound of Formula (VI), R$^2$ is C$_{1-9}$heteroaryl optionally substituted with one, two, three, or four groups selected from R$^{15c}$.

In some embodiments of a compound of Formula (VI), R$^2$ is 5- or 6-membered heteroaryl optionally substituted with one, two, three, or four groups selected from R$^{15c}$.

In some embodiments of a compound of Formula (VI), R$^2$ is 6-membered heteroaryl optionally substituted with one, two, three, or four groups selected from R$^{15c}$.

In some embodiments of a compound of Formula (VI), R$^2$ is pyridinyl optionally substituted with one, two, three, or four groups selected from R$^{15c}$.

In some embodiments of a compound of Formula (VI), R$^2$ is phenyl optionally substituted with one, two, three, or four groups selected from R$^{15c}$.

In some embodiments of a compound of Formula (VI), R$^2$ is

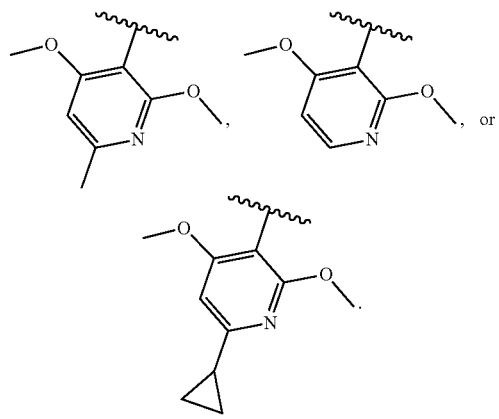

In some embodiments of a compound of Formula (VI), Ring B is C$_{6-9}$heterocycloalkyl.

In some embodiments of a compound of Formula (VI), each R$^{15e}$ are independently halogen, oxo, —CN, C$_{1-6}$alkyl, C$_{1-6}$haloalkyl, C$_{3-10}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, C$_{1-9}$heteroaryl, —CH$_2$—C$_{1-9}$heteroaryl, —OR$^{10}$, —N(R$^{10}$)(R$^{11}$), —C(O)OR$^{10}$, —C(O)R$^{13}$, or —C(O)N(R$^{10}$)(R$^{11}$).

In some embodiments of a compound of Formula (VI), each R$^{15e}$ are independently halogen, oxo, —CN, C$_{1-6}$alkyl, or C$_{1-6}$haloalkyl.

In some embodiments of a compound of Formula (VI), each R$^{15e}$ are independently halogen, oxo, C$_{1-6}$alkyl, or C$_{1-6}$haloalkyl.

In some embodiments of a compound of Formula (VI), two $R^{15e}$ on the adjacent carbon are taken together to form a $C_{2-6}$alkenylene.

In some embodiments of a compound of Formula (VI), two $R^{15e}$ on the same atom are taken together to form a $C_{3-6}$cycloalkyl or $C_{2-9}$heterocycloalkyl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, and —$N(R^{10})(R^{11})$.

In some embodiments of a compound of Formula (VI), two $R^{15e}$ on the same atom are taken together to form a $C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, and —$N(R^{10})(R^{11})$.

In some embodiments of a compound of Formula (VI), two $R^{15e}$ on the same atom are taken together to form a $C_{3-6}$cycloalkyl.

In some embodiments of a compound of Formula (VI), two $R^{15e}$ on the different atom are taken together to form a $C_{3-6}$cycloalkyl or $C_{2-9}$heterocycloalkyl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, and —$N(R^{10})(R^{11})$.

In some embodiments of a compound of Formula (VI), two $R^{15e}$ on the different atom are taken together to form a $C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, and —$N(R^{10})(R^{11})$.

In some embodiments of a compound of Formula (VI), two $R^{15e}$ on the different atom are taken together to form a $C_{3-6}$cycloalkyl.

In some embodiments of a compound of Formula (VI), n is 0-4. In some embodiments of a compound of Formula (VI), n is 2-4. In some embodiments of a compound of Formula (VI), n is 2. In some embodiments of a compound of Formula (VI), n is 1 or 2. In some embodiments of a compound of Formula (VI), n is 1. In some embodiments of a compound of Formula (VI), n is 1-3.

In some embodiments of a compound of Formula (VI),

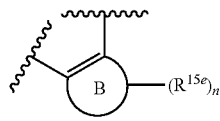

is

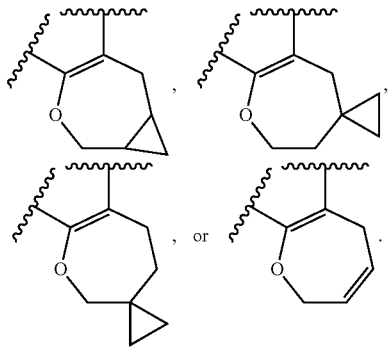

In some embodiments of a compound of Formula (VI), $Z^1$ is N. In some embodiments of a compound of Formula (VI), $Z^1$ is $CR^{1b}$.

In some embodiments of a compound of Formula (VI), $R^{1b}$ is hydrogen or halogen. In some embodiments of a compound of Formula (VI), $R^{1b}$ is hydrogen.

In some embodiments of a compound of Formula (VI), X is —$C(R^6)(R^{6a})$—, —S—, or —O—. In some embodiments of a compound of Formula (VI), X is —$C(R^6)(R^{6a})$— or —O—. In some embodiments of a compound of Formula (VI), X is —$C(R^6)(R^{6a})$—. In some embodiments of a compound of Formula (VI), X is —O—. In some embodiments of a compound of Formula (VI), X is —S—. In some embodiments of a compound of Formula (VI), X is —$N(R^7)$—. In some embodiments of a compound of Formula (VI), X is —S—, —O—, or —$N(R^7)$—.

In some embodiments of a compound of Formula (VI), $R^6$ and $R^{6a}$ are independently hydrogen, halogen, $C_{1-6}$alkyl, or $C_{1-6}$haloalkyl. In some embodiments of a compound of Formula (VI), $R^6$ and $R^{6a}$ are independently hydrogen or $C_{1-6}$alkyl. In some embodiments of a compound of Formula (VI), $R^6$ and $R^{6a}$ are hydrogen. In some embodiments of a compound of Formula (VI), $R^6$ and $R^{6a}$ are taken together to form an oxo.

In some embodiments of a compound of Formula (VI), $R^7$ is hydrogen, $C_{1-6}$alkyl, or $C_{1-6}$haloalkyl. In some embodiments of a compound of Formula (VI), $R^7$ is hydrogen or $C_{1-6}$alkyl. In some embodiments of a compound of Formula (VI), $R^7$ is hydrogen.

In some embodiments of a compound of Formula (VI), $R^1$ is $C_{6-10}$aryl or $C_{1-9}$heteroaryl; each optionally substituted with one, two, or three groups selected from $R^{15a}$.

In some embodiments of a compound of Formula (VI), $R^1$ is $C_{1-9}$heteroaryl optionally substituted with one, two, or three groups selected from $R^{15a}$.

In some embodiments of a compound of Formula (VI), $R^1$ is 5- or 6-membered heteroaryl optionally substituted with one, two, or three groups selected from $R^{15a}$.

In some embodiments of a compound of Formula (VI), $R^1$ is 5-membered heteroaryl optionally substituted with one, two, or three groups selected from $R^{15a}$.

In some embodiments of a compound of Formula (VI), or a pharmaceutically acceptable salt or solvate thereof, $R^1$ is optionally substituted $C_{1-9}$heteroaryl. In some embodiments of a compound of Formula (VI), or a pharmaceutically acceptable salt or solvate thereof, $R^1$ is optionally substituted 5 or 6 membered heteroaryl. In some embodiments of a compound of Formula (VI), or a pharmaceutically acceptable salt or solvate thereof, $R^1$ is optionally substituted 5 membered heteroaryl. In some embodiments of a compound of Formula (VI), or a pharmaceutically acceptable salt or solvate thereof, $R^1$ is optionally substituted 6 membered heteroaryl. In some embodiments of a compound of Formula (VI), or a pharmaceutically acceptable salt or solvate thereof, $R^1$ is monocyclic heteroaryl. In some embodiments of a compound of Formula (VI), or a pharmaceutically acceptable salt or solvate thereof, $R^1$ is bicyclic heteroaryl. In some embodiments, $R^1$ is optionally substituted with one, two, or three groups selected from $R^{15a}$. In some embodiments, $R^1$ is optionally substituted with one, two, or three groups selected from halogen, $C_{1-6}$alkyl, $C_{1-6}$haloalkyl, and $C_{1-6}$alkoxyl. In some embodiments, $R^1$ is optionally substituted with one, two, or three groups selected from oxo, —CN, amino, OH, halogen, $C_{1-6}$alkyl, $C_{1-6}$haloalkyl, $C_{1-6}$alkoxyl, and $C_{3-6}$cycloalkyl.

In some embodiments of a compound of Formula (VI), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are optionally substituted with one, two, or three groups selected from $R^{15a}$. In some embodiments of a compound of Formula (VI), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from $R^{15a}$. In some embodiments of a compound of Formula (VI), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, wherein pyrazolyl, imidazolyl, isoxazolyl, thiazolyl, oxazolyl, pyrimidinyl, pyridazinyl, and pyridinyl are substituted with one, two, or three groups selected from $R^{15a}$ and each $R^{15a}$ is independently selected from halogen, $C_{1-6}$alkyl, $C_{1-6}$haloalkyl, and —$OR^{10}$. In some embodiments of a compound of Formula (VI), or a pharmaceutically acceptable salt or solvate thereof, $R^1$ is $C_{1-9}$heteroaryl selected from pyrazolyl, imidazolyl, isoxazolyl, thiazolyl, oxazolyl, pyrimidinyl, pyridazinyl, and pyridinyl, pyrazolyl, imidazolyl, isoxazolyl, thiazolyl, oxazolyl, pyrimidinyl, pyridazinyl, and pyridinyl are substituted with one group selected from $R^{15a}$ and $R^{15a}$ is selected from halogen, $C_{1-6}$alkyl, $C_{1-6}$haloalkyl, and —$OR^{10}$.

In some embodiments of a compound of Formula (VI), $R^1$ is $C_{1-9}$heteroaryl selected from pyrazolyl and thiazolyl, wherein pyrazolyl and thiazolyl are optionally substituted with one, two, or three groups selected from $R^{15a}$.

In some embodiments of a compound of Formula (VI), $R^1$ is thiazolyl optionally substituted with one, two, or three groups selected from $R^{15a}$.

In some embodiments of a compound of Formula (VI), $R^1$ is pyrazolyl optionally substituted with one, two, or three groups selected from $R^{15a}$.

In some embodiments of a compound of Formula (VI), $R^1$ is

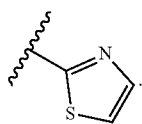

In some embodiments of a compound of Formula (VI), $R^1$ is

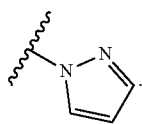

In some embodiments of a compound of Formula (VI), each $R^{15a}$, each $R^{15b}$, and each $R^{15c}$ are independently halogen, oxo, —CN, $C_{1-6}$alkyl, $C_{1-6}$haloalkyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$N(R^{10})(R^{11})$, —$C(O)OR^{10}$, —$C(O)R^{13}$, or —$C(O)N(R^{10})(R^{11})$. In some embodiments of a compound of Formula (VI), each $R^{15a}$, each $R^{15b}$, and each $R^{15c}$ are independently halogen, oxo, —CN, $C_{1-6}$alkyl, $C_{1-6}$haloalkyl, $C_{3-10}$cycloalkyl, —$OR^{10}$, or —$N(R^{10})(R^{11})$. In some embodiments of a compound of Formula (VI), each $R^{15a}$, each $R^{15b}$, and each $R^{15c}$ are independently halogen, oxo, —CN, $C_{1-6}$alkyl, $C_{1-6}$haloalkyl, —$OR^{10}$, or —$N(R^{10})(R^{11})$. In some embodiments of a compound of Formula (VI), each $R^{15a}$, each $R^{15b}$, and each $R^{15c}$ are independently halogen, $C_{1-6}$alkyl, $C_{1-6}$haloalkyl, $C_{3-10}$cycloalkyl, or —$OR^{10}$.

In some embodiments of a compound of Formula (VI), each $R^{15a}$, each $R^{15b}$, and each $R^{15c}$ are independently halogen, $C_{1-6}$alkyl, $C_{1-6}$haloalkyl, or —$OR^{10}$. In some embodiments of a compound of Formula (VI), each $R^{15a}$, each $R^{15b}$, and each $R^{15c}$ are independently halogen, $C_{1-6}$alkyl, $C_{3-10}$cycloalkyl, or —$OR^{10}$. In some embodiments of a compound of Formula (VI), each $R^{15a}$, each $R^{15b}$, and each $R^{15c}$ are independently halogen, $C_{1-6}$alkyl, or —$OR^{10}$. In some embodiments of a compound of Formula (VI), each $R^{15a}$, each $R^{15b}$, and each $R^{15c}$ are independently $C_{1-6}$alkyl, $C_{3-10}$cycloalkyl, or —$OR^{10}$. In some embodiments of a compound of Formula (VI), each $R^{15a}$, each $R^{15b}$, and each $R^{15c}$ are independently $C_{1-6}$alkyl or —$OR^{10}$. In some embodiments of a compound of Formula (VI), each $R^{15a}$, each $R^{15b}$, and each $R^{15c}$ are independently $C_{3-10}$cycloalkyl or —$OR^{10}$. In some embodiments of a compound of Formula (VI), each $R^{15a}$, each $R^{15b}$, and each $R^{15c}$ are independently —$OR^{10}$.

In some embodiments of a compound of Formula (VI), each $R^{15a}$ are independently halogen, oxo, —CN, $C_{1-6}$alkyl, $C_{1-6}$haloalkyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$N(R^{10})(R^{11})$, —$C(O)OR^{10}$, —$C(O)R^{13}$, or —$C(O)N(R^{10})(R^{11})$. In some embodiments of a compound of Formula (VI), each $R^{15a}$ are independently halogen, oxo, —CN, $C_{1-6}$alkyl, $C_{1-6}$haloalkyl, $C_{3-10}$cycloalkyl, —$OR^{10}$, or —$N(R^{10})(R^{11})$. In some embodiments of a compound of Formula (VI), each $R^{15a}$ are independently halogen, oxo, —CN, $C_{1-6}$alkyl, $C_{1-6}$haloalkyl, —$OR^{10}$, or —$N(R^{10})(R^{11})$. In some embodiments of a compound of Formula (VI), each $R^{15a}$ are independently halogen, $C_{1-6}$alkyl, $C_{1-6}$haloalkyl, $C_{3-10}$cycloalkyl, or —$OR^{10}$. In some embodiments of a compound of Formula (VI), each $R^{15a}$ are independently halogen, $C_{1-6}$alkyl, $C_{1-6}$haloalkyl, or —$OR^{10}$. In some embodiments of a compound of Formula (VI), each $R^{15a}$ are independently halogen, $C_{1-6}$alkyl, $C_{3-10}$cycloalkyl, or —$OR^{10}$. In some embodiments of a compound of Formula (VI), each $R^{15a}$ are independently halogen, $C_{1-6}$alkyl, or —$OR^{10}$. In some embodiments of a compound of Formula (VI), each $R^{15a}$ are independently $C_{1-6}$alkyl, $C_{3-10}$cycloalkyl, or —$OR^{10}$. In some embodiments of a compound of Formula (VI), each $R^{15a}$ are independently $C_{1-6}$alkyl or —$OR^{10}$. In some embodiments of a compound of Formula (VI), each $R^{15a}$ are independently $C_{3-10}$cycloalkyl or —$OR^{10}$. In some embodiments of a compound of Formula (VI), each $R^{15a}$ are independently —$OR^{10}$.

In some embodiments of a compound of Formula (VI), each $R^{15b}$ are independently halogen, oxo, —CN, $C_{1-6}$alkyl, $C_{1-6}$haloalkyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$N(R^{10})(R^{11})$, —$C(O)OR^{10}$, —$C(O)R^{13}$, or —$C(O)N(R^{10})(R^{11})$. In some embodiments of a compound of Formula (VI), each $R^{15b}$ are independently halogen, oxo, —CN, $C_{1-6}$alkyl, $C_{1-6}$haloalkyl, $C_{3-10}$cycloalkyl, —$OR^{10}$, or —$N(R^{10})(R^{11})$. In some embodiments of a compound of Formula (VI), each $R^{15b}$ are independently halogen, oxo, —CN, $C_{1-6}$alkyl, $C_{1-6}$haloalkyl, —OR$^{10}$, or —N(R$^{10}$)(R$^{11}$). In some embodiments of a compound of Formula (VI), each R$^{15b}$ are independently halogen, $C_{1-6}$alkyl, $C_{1-6}$haloalkyl, $C_{3-10}$cycloalkyl, or —OR$^{10}$.

In some embodiments of a compound of Formula (VI), each R$^{15b}$ are independently halogen, $C_{1-6}$alkyl, $C_{1-6}$haloalkyl, or —OR$^{10}$. In some embodiments of a compound of Formula (VI), each R$^{15b}$ are independently halogen, $C_{1-6}$alkyl, $C_{3-10}$cycloalkyl, or —OR$^{10}$. In some embodiments of a compound of Formula (VI), each R$^{15b}$ are independently halogen, $C_{1-6}$alkyl, or —OR$^{10}$. In some embodiments of a compound of Formula (VI), each R$^{15b}$ are independently $C_{1-6}$alkyl, $C_{3-10}$cycloalkyl, or —OR$^{10}$. In some embodiments of a compound of Formula (VI), each R$^{15b}$ are independently $C_{1-6}$alkyl or —OR$^{10}$. In some embodiments of a compound of Formula (VI), each R$^{15b}$ are independently $C_{3-10}$cycloalkyl or —OR$^{10}$. In some embodiments of a compound of Formula (VI), each R$^{15b}$ are independently —OR$^{10}$.

In some embodiments of a compound of Formula (VI), each R$^{15c}$ are independently halogen, oxo, —CN, $C_{1-6}$alkyl, $C_{1-6}$haloalkyl, $C_{3-10}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-9}$heteroaryl, —CH$_2$—$C_{1-9}$heteroaryl, —OR$^{10}$, —N(R$^{10}$)(R$^{11}$), —C(O)OR$^{10}$, —C(O)R$^{13}$, or —C(O)N(R$^{10}$)(R$^{11}$). In some embodiments of a compound of Formula (VI), each R$^{15c}$ are independently halogen, oxo, —CN, $C_{1-6}$alkyl, $C_{1-6}$haloalkyl, $C_{3-10}$cycloalkyl, —OR$^{10}$, or —N(R$^{10}$)(R$^{11}$). In some embodiments of a compound of Formula (VI), each R$^{15c}$ are independently halogen, oxo, —CN, $C_{1-6}$alkyl, $C_{1-6}$haloalkyl, —OR$^{10}$, or —N(R$^{10}$)(R$^{11}$). In some embodiments of a compound of Formula (VI), each R$^{15c}$ are independently halogen, $C_{1-6}$alkyl, $C_{1-6}$haloalkyl, $C_{3-10}$cycloalkyl, or —OR$^{10}$.

In some embodiments of a compound of Formula (VI), each R$^{15c}$ are independently halogen, $C_{1-6}$alkyl, $C_{1-6}$haloalkyl, or —OR$^{10}$. In some embodiments of a compound of Formula (VI), each R$^{15c}$ are independently halogen, $C_{1-6}$alkyl, $C_{3-10}$cycloalkyl, or —OR$^{10}$. In some embodiments of a compound of Formula (VI), each R$^{15c}$ are independently halogen, $C_{1-6}$alkyl, or —OR$^{10}$. In some embodiments of a compound of Formula (VI), each R$^{15c}$ are independently $C_{1-6}$alkyl, $C_{3-10}$cycloalkyl, or —OR$^{10}$. In some embodiments of a compound of Formula (VI), each R$^{15c}$ are independently $C_{1-6}$alkyl or —OR$^{10}$. In some embodiments of a compound of Formula (VI), each R$^{15c}$ are independently $C_{3-10}$cycloalkyl or —OR$^{10}$. In some embodiments of a compound of Formula (VI), each R$^{15c}$ are independently —OR$^{10}$.

In some embodiments of a compound of Formula (IV), (V), or (VI), each R$^{10}$ is independently hydrogen, $C_{1-6}$alkyl, $C_{1-6}$haloalkyl, $C_{3-6}$cycloalkyl, $C_{2-9}$heterocycloalkyl, $C_{6-10}$aryl, or $C_{1-9}$heteroaryl, wherein $C_{1-6}$alkyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-4}$haloalkyl, $C_{1-6}$alkoxy, $C_{3-6}$cycloalkyl, $C_{2-9}$heterocycloalkyl, $C_{6-10}$aryl, and $C_{1-6}$heteroaryl. In some embodiments of a compound of Formula (IV), (V), or (VI), each R$^{10}$ is independently hydrogen, $C_{1-6}$alkyl, $C_{1-6}$haloalkyl, $C_{3-6}$cycloalkyl, $C_{2-9}$heterocycloalkyl, wherein $C_{1-6}$alkyl, $C_{3-6}$cycloalkyl, and $C_{2-9}$heterocycloalkyl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-6}$heteroaryl. In some embodiments of a compound of Formula (IV), (V), or (VI), each R$^{10}$ is independently hydrogen, $C_{1-6}$alkyl, or $C_{1-6}$haloalkyl, wherein $C_{1-6}$alkyl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl. In some embodiments of a compound of Formula (IV), (V), or (VI), each R$^{10}$ is independently hydrogen, $C_{1-6}$alkyl, or $C_{1-6}$haloalkyl. In some embodiments of a compound of Formula (IV), (V), or (VI), each R$^{10}$ is independently $C_{1-6}$alkyl or $C_{1-6}$haloalkyl. In some embodiments of a compound of Formula (IV), (V), or (VI), each R$^{10}$ is independently $C_{1-6}$alkyl. In some embodiments of a compound of Formula (IV), (V), or (VI), each R$^{10}$ is methyl. In some embodiments of a compound of Formula (IV), (V), or (VI), each R$^{10}$ is independently $C_{1-6}$haloalkyl.

In some embodiments of a compound of Formula (IV), (V), or (VI), each R$^{11}$ is independently hydrogen or $C_{1-6}$alkyl. In some embodiments of a compound of Formula (IV), (V), or (VI), each R$^{11}$ is independently hydrogen. In some embodiments of a compound of Formula (IV), (V), or (VI), each R$^{11}$ is independently $C_{1-6}$alkyl. In some embodiments of a compound of Formula (IV), (V), or (VI), each R$^{12}$ is independently hydrogen, $C_{1-6}$alkyl, or $C_{1-6}$haloalkyl. In some embodiments of a compound of Formula (IV), (V), or (VI), each R$^{12}$ is independently hydrogen or $C_{1-6}$alkyl. In some embodiments of a compound of Formula (IV), (V), or (VI), each R$^{12}$ is independently hydrogen. In some embodiments of a compound of Formula (IV), (V), or (VI), each R$^{12}$ is independently $C_{1-6}$alkyl.

In some embodiments of a compound of Formula (IV), (V), or (VI), each R$^{13}$ is independently hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, or $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl. In some embodiments of a compound of Formula (IV), (V), or (VI), each R$^{13}$ is independently hydrogen, $C_{1-6}$alkyl, $C_{3-6}$cycloalkyl, $C_{2-9}$heterocycloalkyl, $C_{6-10}$aryl, or $C_{1-9}$heteroaryl, wherein $C_{1-6}$alkyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl. In some embodiments of a compound of Formula (IV), (V), or (VI), each R$^{13}$ is independently hydrogen, $C_{1-6}$alkyl, $C_{3-6}$cycloalkyl, or $C_{2-9}$heterocycloalkyl, wherein $C_{1-6}$alkyl, $C_{3-6}$cycloalkyl, and $C_{2-9}$heterocycloalkyl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl. In some embodiments of a compound of Formula (IV), (V), or (VI), each R$^{13}$ is independently hydrogen, $C_{1-6}$alkyl optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl. In some embodiments of a compound of Formula (IV), (V), or (VI), each R$^{13}$ is independently hydrogen or $C_{1-6}$alkyl. In some embodiments of a compound of Formula (IV), (V), or (VI), each R$^{13}$ is independently $C_{1-6}$alkyl.

Any combination of the groups described above for the various variables is contemplated herein. Throughout the specification, groups and substituents thereof are chosen by one skilled in the field to provide stable moieties and compounds.

In some embodiments, described herein is a compound, or a pharmaceutically acceptable salt or solvate thereof, wherein the compound is selected from a compound of Table 1B:
TABLE 1B
Exemplary Compounds
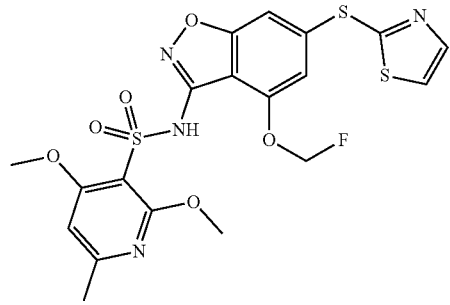 [SMILES: COc1cc(C)nc(OC)c1S(=O)(=O)Nc1noc2cc(Sc3nccs3)cc(OCF)c12]
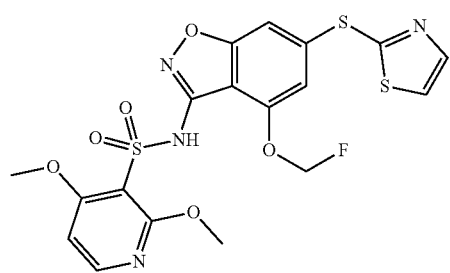 [SMILES: COc1ccnc(OC)c1S(=O)(=O)Nc1noc2cc(Sc3nccs3)cc(OCF)c12]
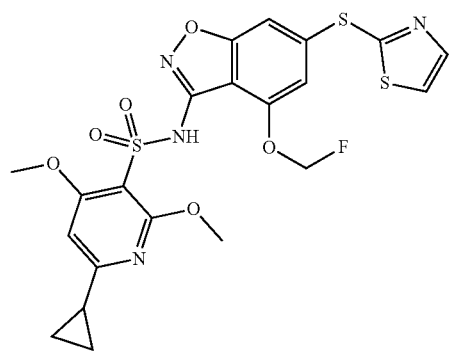 [SMILES: COc1cc(C2CC2)nc(OC)c1S(=O)(=O)Nc1noc2cc(Sc3nccs3)cc(OCF)c12]
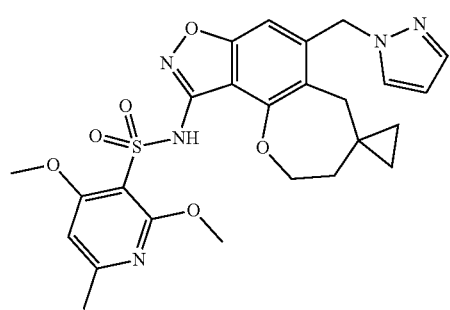 [SMILES: COc1cc(C)nc(OC)c1S(=O)(=O)Nc1noc2cc(Cn3cccn3)c3c(c12)OCCC1(CC1)C3]
TABLE 1B-continued
Exemplary Compounds
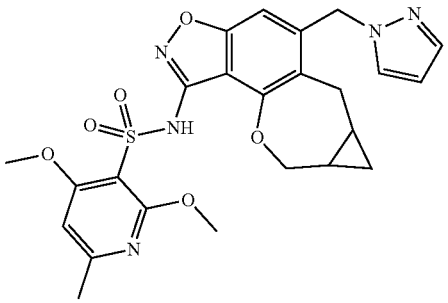 [SMILES: COc1cc(C)nc(OC)c1S(=O)(=O)Nc1noc2cc(Cn3cccn3)c3c(c12)OCC1CC1C3]
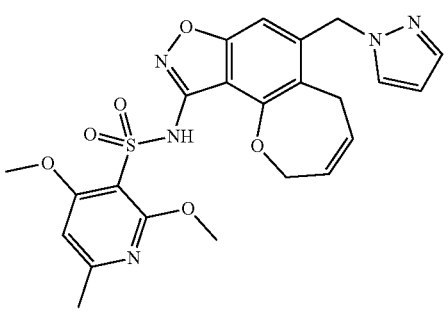 [SMILES: COc1cc(C)nc(OC)c1S(=O)(=O)Nc1noc2cc(Cn3cccn3)c3c(c12)OCC=CC3]
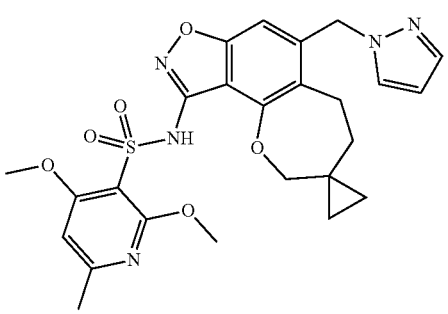 [SMILES: COc1cc(C)nc(OC)c1S(=O)(=O)Nc1noc2cc(Cn3cccn3)c3c(c12)OCC1(CC3)CC1]
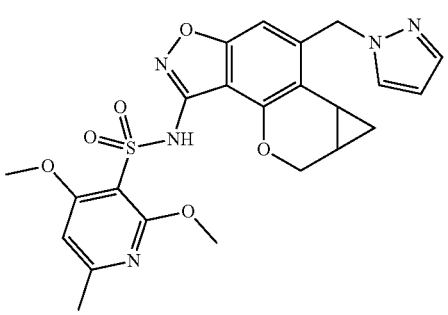 [SMILES: COc1cc(C)nc(OC)c1S(=O)(=O)Nc1noc2cc(Cn3cccn3)c3c(c12)OCC1CC31]
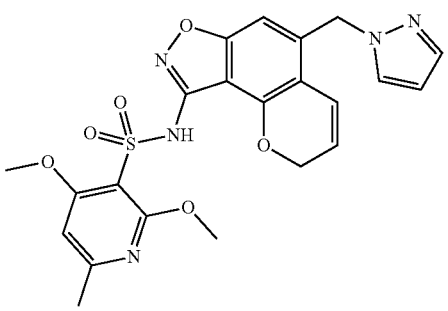 [SMILES: COc1cc(C)nc(OC)c1S(=O)(=O)Nc1noc2cc(Cn3cccn3)c3c(c12)OCC=C3]

TABLE 1B-continued

Exemplary Compounds

TABLE 1B-continued
Exemplary Compounds
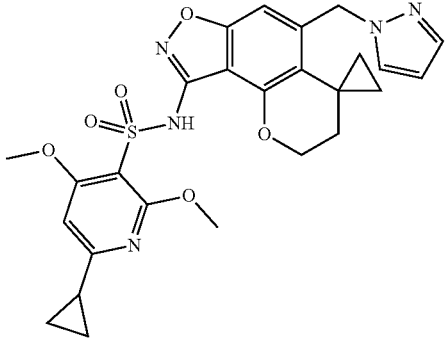 [SMILES: COc1cc(C2CC2)nc(OC)c1S(=O)(=O)Nc1noc2cc(Cn3cccn3)c3c(c12)OCCC31CC1]
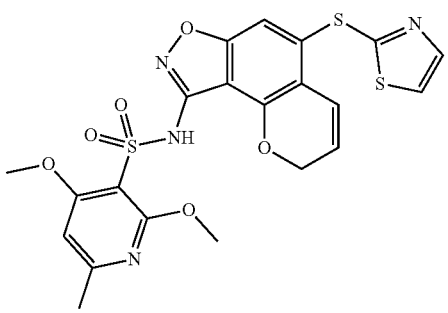 [SMILES: COc1cc(C)nc(OC)c1S(=O)(=O)Nc1noc2cc(Sc3nccs3)c3c(c12)OCC=C3]
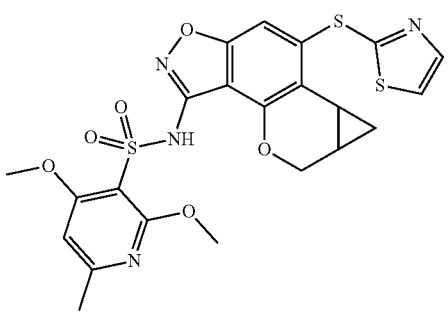 [SMILES: COc1cc(C)nc(OC)c1S(=O)(=O)Nc1noc2cc(Sc3nccs3)c3c(c12)OCC1CC31]
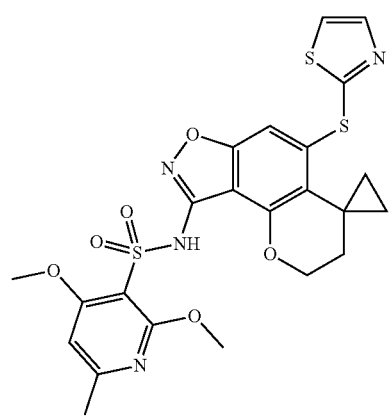 [SMILES: COc1cc(C)nc(OC)c1S(=O)(=O)Nc1noc2cc(Sc3nccs3)c3c(c12)OCCC31CC1]
TABLE 1B-continued
Exemplary Compounds
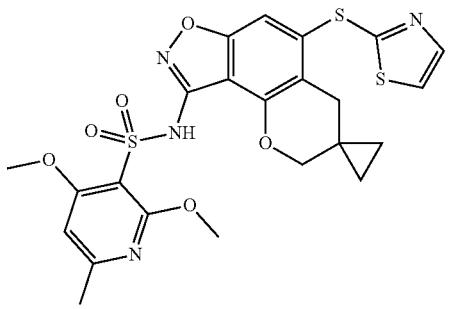 [SMILES: COc1cc(C)nc(OC)c1S(=O)(=O)Nc1noc2cc(Sc3nccs3)c3c(c12)OCC1(CC1)C3]
In some embodiments, described herein is a compound, or a pharmaceutically acceptable salt or solvate thereof, wherein the compound is selected from a compound of Table 1C:
TABLE 1C
Exemplary Compounds
| Compound # | Structure |
| --- | --- |
| 66 | 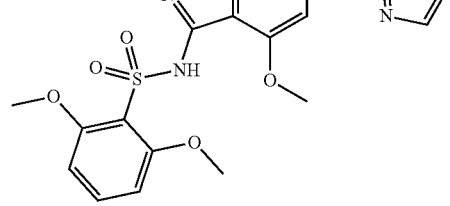 |
| 67 | 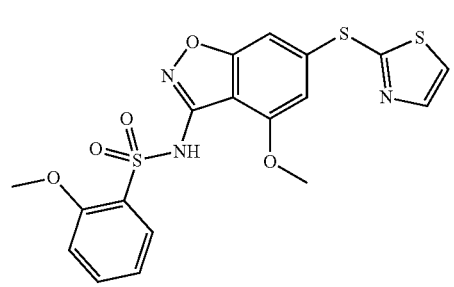 [SMILES: COc1ccccc1S(=O)(=O)Nc1noc2cc(Sc3nccs3)cc(OC)c12] |
| 68 | 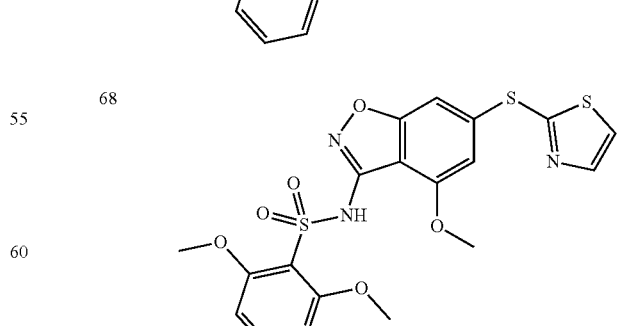 |

TABLE 1C-continued

Exemplary Compounds

| Compound # | Structure |
|---|---|
| 69 | 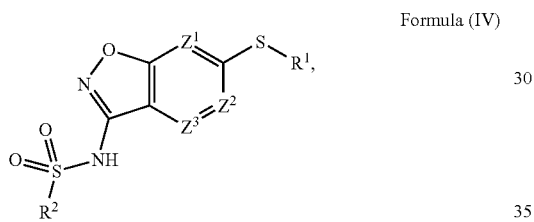 |

In some aspects, disclosure provided herein is further illustrated in numbered embodiments as the following.

NUMBERED EMBODIMENTS

Embodiment 1. A compound of Formula (IV), or a pharmaceutically acceptable salt thereof:

Formula (IV)

wherein:
$R^2$ is $C_{3-6}$cycloalkyl, $C_{2-9}$heterocycloalkyl, $C_{6-10}$aryl, or $C_{1-9}$heteroaryl; each optionally substituted with one, two, three, or four groups selected from $R^{15c}$;
$Z^1$ is $CR^{1b}$ or N;
$Z^2$ is $CR^{2b}$ or N;
$Z^3$ is $CR^{3b}$ or N;
$R^1$ is $C_{3-6}$cycloalkyl, $C_{2-9}$heterocycloalkyl, $C_{6-10}$aryl, or $C_{1-9}$heteroaryl; each optionally substituted with one, two, or three groups selected from $R^{15a}$;
$R^{1b}$, $R^{2b}$, and $R^{3b}$ are independently hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{10}$, —$SR^{10}$, —$SF_5$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(O)(NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15b}$;
or $R^{2b}$ and $R^{3b}$ are taken together to form a $C_{3-6}$cycloalkyl, $C_{2-9}$heterocycloalkyl, $C_{6-10}$aryl, or $C_{1-9}$heteroaryl; wherein $C_{3-6}$cycloalkyl, $C_{2-9}$heterocycloalkyl, $C_{6-10}$aryl, and $C_{1-9}$heteroaryl are optionally substituted with one, two, three, or four groups selected from $R^{15e}$;

each $R^{15a}$, each $R^{15b}$, and each $R^{15c}$ are independently halogen, oxo, —CN, $C_{1-6}$alkyl, $C_{1-6}$haloalkyl, $C_{2-6}$alkenyl, $C_{2-6}$alkynyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-6}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(O)(NH)N(R^{10})(R^{11})$, —$CH_2C(O)N(R^{10})(R^{11})$, —$CH_2N(R^{12})C(O)R^{13}$, —$CH_2S(O)_2R^{13}$, or —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, —$CH_2$—$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(O)(NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$;

each $R^{15e}$ are independently halogen, oxo, —CN, $C_{1-6}$alkyl, $C_{1-6}$haloalkyl, $C_{2-6}$alkenyl, $C_{2-6}$alkynyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(O)(NH)N(R^{10})(R^{11})$, —$CH_2C(O)N(R^{10})(R^{11})$, —$CH_2N(R^{12})C(O)R^{13}$, —$CH_2S(O)_2R^{13}$, or —$CH_2S(O)_2N(R^{10})(R^{11})$, wherein $C_{1-6}$alkyl, $C_{2-6}$alkenyl, $C_{2-6}$alkynyl, $C_{3-6}$cycloalkyl, —$CH_2$—$C_{3-10}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, —$CH_2$—$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N(R^{10})(R^{11})$, —$N(R^{12})C(O)R^{13}$, —$S(O)_2R^{13}$, —$S(O)_2N(R^{10})(R^{11})$—, $S(O)(NH)N(R^{10})(R^{11})$, —$CH_2C(O)N(R^{10})(R^{11})$, —$CH_2N(R^{12})C(O)R^{13}$, —$CH_2S(O)_2R^{13}$, and —$CH_2S(O)_2N(R^{10})(R^{11})$;

or two $R^{15e}$ on the adjacent carbon are taken together to form a $C_{2-6}$alkenylene;

or two $R^{15e}$ on the same atom are taken together to form a $C_{3-6}$cycloalkyl or $C_{2-9}$heterocycloalkyl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, —$SR^{10}$, —$N(R^{10})(R^{11})$, —$C(O)OR^{10}$, —$OC(O)N(R^{10})(R^{11})$, —$N(R^{12})C(O)N(R^{10})(R^{11})$, —$N(R^{12})C(O)OR^{13}$, —$N(R^{12})S(O)_2R^{13}$, —$C(O)R^{13}$, —$S(O)R^{13}$, —$OC(O)R^{13}$, —$C(O)N(R^{10})(R^{11})$, —$C(O)C(O)N( ($R^{10}$)($R^{11}$), —N($R^{12}$)C(O)$R^{13}$, —S(O)$_2$$R^{13}$, —S(O)$_2$N($R^{10}$)($R^{11}$)—, S(O)(NH)N($R^{10}$)($R^{11}$), —CH$_2$C(O)N($R^{10}$)($R^{11}$), —CH$_2$N($R^{12}$)C(O)$R^{13}$, —CH$_2$S(O)$_2$$R^{13}$, and —CH$_2$S(O)$_2$N($R^{10}$)($R^{11}$);

or two $R^{15e}$ on the different atom are taken together to form a $C_{3-6}$cycloalkyl, $C_{2-9}$heterocycloalkyl, $C_{6-10}$aryl, or $C_{1-9}$heteroaryl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{10}$, —SR$^{10}$, —N($R^{10}$)($R^{11}$), —C(O)OR$^{10}$, —OC(O)N($R^{10}$)($R^{11}$), —N($R^{12}$)C(O)N($R^{10}$)($R^{11}$), —N($R^{12}$)C(O)OR$^{13}$, —N($R^{12}$)S(O)$_2$$R^{13}$, —C(O)$R^{13}$, —S(O)$R^{13}$, —OC(O)$R^{13}$, —C(O)N($R^{10}$)($R^{11}$), —C(O)C(O)N($R^{10}$)($R^{11}$), —N($R^{12}$)C(O)$R^{13}$, —S(O)$_2$$R^{13}$, —S(O)$_2$N($R^{10}$)($R^{11}$)—, S(O)(NH)N($R^{10}$)($R^{11}$), —CH$_2$C(O)N($R^{10}$)($R^{11}$), —CH$_2$N($R^{12}$)C(O)$R^{13}$, —CH$_2$S(O)$_2$$R^{13}$, and —CH$_2$S(O)$_2$N($R^{10}$)($R^{11}$);

each $R^{10}$ is independently hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, or $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is independently hydrogen, $C_{1-6}$alkyl, or $C_{1-6}$haloalkyl;

each $R^{12}$ is independently hydrogen, $C_{1-6}$alkyl, or $C_{1-6}$haloalkyl; and each $R^{13}$ is independently hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, or $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl.

Embodiment 2. The compound of embodiment 1, or a pharmaceutically acceptable salt thereof, wherein $R^2$ is $C_{6-10}$aryl or $C_{1-9}$heteroaryl; each optionally substituted with one, two, three, or four groups selected from $R^{15c}$.

Embodiment 3. The compound of embodiment 1 or 2, or a pharmaceutically acceptable salt thereof, wherein $R^2$ is $C_{1-9}$heteroaryl optionally substituted with one, two, three, or four groups selected from $R^{15c}$.

Embodiment 4. The compound of embodiment 1 or 2, or a pharmaceutically acceptable salt thereof, wherein $R^2$ is 5- or 6-membered heteroaryl optionally substituted with one, two, three, or four groups selected from $R^{15c}$.

Embodiment 5. The compound of embodiment 1 or 2, or a pharmaceutically acceptable salt thereof, wherein $R^2$ is 6-membered heteroaryl optionally substituted with one, two, three, or four groups selected from $R^{15c}$.

Embodiment 6. The compound of embodiment 1 or 2, or a pharmaceutically acceptable salt thereof, wherein $R^2$ is pyridinyl optionally substituted with one, two, three, or four groups selected from $R^{15c}$.

Embodiment 7. The compound of embodiment 1 or 2, or a pharmaceutically acceptable salt thereof, wherein $R^2$ is phenyl optionally substituted with one, two, three, or four groups selected from $R^{15c}$.

Embodiment 8. The compound of any one of embodiments 1-7, or a pharmaceutically acceptable salt thereof, wherein:

$Z^3$ is N;
$Z^2$ is $CR^{2b}$; and
$Z^3$ is $CR^{3b}$.

Embodiment 9. The compound of any one of embodiments 1-7, or a pharmaceutically acceptable salt thereof, wherein:

$Z^1$ is $CR^{1b}$;
$Z^2$ is N; and
$Z^3$ is $CR^{3b}$.

Embodiment 10. The compound of any one of embodiments 1-7, or a pharmaceutically acceptable salt thereof, wherein:

$Z^1$ is $CR^{1b}$;
$Z^2$ is $CR^{2b}$; and
$Z^3$ is N.

Embodiment 11. The compound of any one of embodiments 1-10, or a pharmaceutically acceptable salt thereof, wherein $R^{1b}$, $R^{2b}$, and $R^{3b}$ are independently hydrogen, halogen, $C_{1-6}$alkyl, $C_{1-6}$haloalkyl, $C_{3-6}$cycloalkyl, $C_{2-9}$heterocycloalkyl, $C_{6-10}$aryl, $C_{1-9}$heteroaryl, —OR$^{10}$, —SR$^{10}$, —SF$_5$, —N($R^{10}$)($R^{11}$), —C(O)OR$^{10}$, —C(O)$R^{13}$, or —C(O)N($R^{10}$)($R^{11}$), wherein $C_{1-6}$alkyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15b}$.

Embodiment 12. The compound of any one of embodiments 1-10, or a pharmaceutically acceptable salt thereof, wherein $R^{1b}$, $R^{2b}$, and $R^{3b}$ are independently hydrogen, halogen, $C_{1-6}$alkyl, $C_{1-6}$haloalkyl, $C_{3-6}$cycloalkyl, $C_{2-9}$heterocycloalkyl, —OR$^{10}$, —SR$^{10}$, or —SF$_5$, wherein $C_{1-6}$alkyl, $C_{3-10}$cycloalkyl, and $C_{2-9}$heterocycloalkyl are optionally substituted with one, two, or three groups selected from $R^{15b}$.

Embodiment 13. The compound of any one of embodiments 1-10, or a pharmaceutically acceptable salt thereof, wherein $R^{1b}$, $R^{2b}$, and $R^{3b}$ are independently hydrogen, halogen, $C_{3-6}$cycloalkyl, —OR$^{10}$, —SR$^{10}$, or —SF$_5$, wherein $C_{3-6}$cycloalkyl is optionally substituted with one, two, or three groups selected from $R^{15b}$.

Embodiment 14. The compound of any one of embodiments 1-10, or a pharmaceutically acceptable salt thereof, wherein $R^{1b}$, $R^{2b}$, and $R^{3b}$ are independently hydrogen, halogen, —OR$^{10}$, —SR$^{10}$, or —SF$_5$.

Embodiment 15. The compound of any one of embodiments 1-10, or a pharmaceutically acceptable salt thereof, wherein $R^{1b}$, $R^{2b}$, and $R^{3b}$ are independently hydrogen or —OR$^{10}$.

Embodiment 16. The compound of any one of embodiments 1-10, or a pharmaceutically acceptable salt thereof, wherein $R^{1b}$, $R^{2b}$, and $R^{3b}$ are hydrogen.

Embodiment 17. A compound of Formula (V), or a pharmaceutically acceptable salt thereof:

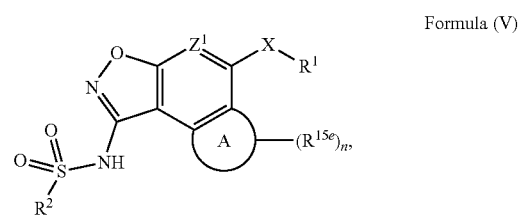

Formula (V)

wherein:

$R^2$ is $C_{1-9}$heteroaryl optionally substituted with one, two, three, or four groups selected from $R^{15c}$;

$Z^1$ is $CR^{1b}$ or N;

$R^1$ is $C_{3-6}$cycloalkyl, $C_{2-9}$heterocycloalkyl, $C_{6-10}$aryl, or $C_{1-9}$heteroaryl; each optionally substituted with one, two, or three groups selected from $R^{15a}$;

$R^{1b}$ is hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, $-OR^{10}$, $-SR^{10}$, $-SF_5$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $S(O)(NH)N(R^{10})(R^{11})$, $-CH_2C(O)N(R^{10})(R^{11})$, $-CH_2N(R^{12})C(O)R^{13}$, $-CH_2S(O)_2R^{13}$, or $-CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from $R^{15b}$;

X is $-C(R^6)(R^{6a})-$, $-S-$, $-O-$, or $-N(R^7)-$;

$R^6$ and $R^{6a}$ are independently hydrogen, halogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, $-OR^{10}$, $-SR^{10}$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $S(O)(NH)N(R^{10})(R^{11})$, $-CH_2C(O)N(R^{10})(R^{11})$, $-CH_2N(R^{12})C(O)R^{13}$, $-CH_2S(O)_2R^{13}$, or $-CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-6}$heteroaryl are optionally substituted with one, two, or three groups selected from halogen, $-CN$, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

or $R^6$ and $R^{6a}$ are taken together to form an oxo;

$R^7$ is hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, or $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, $-CN$, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

Ring A is $C_{3-6}$cycloalkyl, $C_{2-9}$heterocycloalkyl, $C_{6-10}$aryl, or $C_{1-9}$heteroaryl;

each $R^{15a}$, each $R^{15b}$, and each $R^{15c}$ are independently halogen, oxo, $-CN$, $C_{1-6}$alkyl, $C_{1-6}$haloalkyl, $C_{2-6}$alkenyl, $C_{2-6}$alkynyl, $C_{3-10}$cycloalkyl, $-CH_2-C_{3-6}$cycloalkyl, $C_{2-9}$heterocycloalkyl, $-CH_2-C_{2-9}$heterocycloalkyl, $C_{6-10}$aryl, $-CH_2-C_{6-10}$aryl, $C_{1-6}$heteroaryl, $-CH_2-C_{1-9}$heteroaryl, $-OR^{10}$, $-SR^{10}$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $S(O)(NH)N(R^{10})(R^{11})$, $-CH_2C(O)N(R^{10})(R^{11})$, $-CH_2N(R^{12})C(O)R^{13}$, $-CH_2S(O)_2R^{13}$, or $-CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, $-CH_2-C_{1-9}$heteroaryl, and $C_{1-9}$heteroaryl are optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{10}$, $-SR^{10}$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $S(O)(NH)N(R^{10})(R^{11})$, $-CH_2C(O)N(R^{10})(R^{11})$, $-CH_2N(R^{12})C(O)R^{13}$, $-CH_2S(O)_2R^{13}$, and $-CH_2S(O)_2N(R^{10})(R^{11})$;

each $R^{15e}$ are independently halogen, oxo, $-CN$, $C_{1-6}$alkyl, $C_{1-6}$haloalkyl, $C_{2-6}$alkenyl, $C_{2-6}$alkynyl, $C_{3-10}$cycloalkyl, $-CH_2-C_{3-6}$cycloalkyl, $C_{2-9}$heterocycloalkyl, $-CH_2-C_{2-9}$heterocycloalkyl, $C_{6-10}$aryl, $-CH_2-C_{6-10}$aryl, $C_{1-9}$heteroaryl, $-CH_2-C_{1-9}$heteroaryl, $-OR^{10}$, $-SR^{10}$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $S(O)(NH)N(R^{10})(R^{11})$, $-CH_2C(O)N(R^{10})(R^{11})$, $-CH_2N(R^{12})C(O)R^{13}$, $-CH_2S(O)_2R^{13}$, or $-CH_2S(O)_2N(R^{10})(R^{11})$, wherein $C_{1-6}$alkyl, $C_{2-6}$alkenyl, $C_{2-6}$alkynyl, $C_{3-6}$cycloalkyl, $-CH_2-C_{3-10}$cycloalkyl, $C_{2-9}$heterocycloalkyl, $-CH_2-C_{2-9}$heterocycloalkyl, $C_{6-10}$aryl, $-CH_2-C_{6-10}$aryl, $-CH_2-C_{1-9}$heteroaryl, and $C_{1-9}$heteroaryl are optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{10}$, $-SR^{10}$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $S(O)(NH)N(R^{10})(R^{11})$, $-CH_2C(O)N(R^{10})(R^{11})$, $-CH_2N(R^{12})C(O)R^{13}$, $-CH_2S(O)_2R^{13}$, and $-CH_2S(O)_2N(R^{10})(R^{11})$;

or two $R^{15e}$ on the adjacent carbon are taken together to form a $C_{2-6}$alkenylene;

or two $R^{15e}$ on the same atom are taken together to form a $C_{3-6}$cycloalkyl or $C_{2-9}$heterocycloalkyl; each optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{10}$, $-SR^{10}$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $S(O)(NH)N(R^{10})(R^{11})$, $-CH_2C(O)N(R^{10})(R^{11})$, $-CH_2N(R^{12})C(O)R^{13}$, $-CH_2S(O)_2R^{13}$, and $-CH_2S(O)_2N(R^{10})(R^{11})$;

or two $R^{15e}$ on the different atom are taken together to form a $C_{3-6}$cycloalkyl, $C_{2-9}$heterocycloalkyl, $C_{6-10}$aryl, or $C_{1-9}$heteroaryl; each optionally substituted with one, two, or three groups independently selected from halogen, oxo, $-CN$, $C_{1-6}$alkyl, $C_{1-6}$haloalkyl, $C_{1-6}$alkoxy, $C_{1-6}$haloalkoxy, $-OR^{10}$, $-SR^{10}$, $-N(R^{10})(R^{11})$, $-C(O)OR^{10}$, $-OC(O)N(R^{10})(R^{11})$, $-N(R^{12})C(O)N(R^{10})(R^{11})$, $-N(R^{12})C(O)OR^{13}$, $-N(R^{12})S(O)_2R^{13}$, $-C(O)R^{13}$, $-S(O)R^{13}$, $-OC(O)R^{13}$, $-C(O)N(R^{10})(R^{11})$, $-C(O)C(O)N(R^{10})(R^{11})$, $-N(R^{12})C(O)R^{13}$, $-S(O)_2R^{13}$, $-S(O)_2N(R^{10})(R^{11})-$, $S(O)(NH)N(R^{10})(R^{11})$, $-CH_2C(O)N(R^{10})(R^{11})$, $-CH_2N(R^{12})C(O)R^{13}$, $-CH_2S(O)_2R^{13}$, and $-CH_2S(O)_2N(R^{10})(R^{11})$;

n is 0-6;

each $R^{10}$ is hydrogen, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-6}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl;

each $R^{11}$ is hydrogen, $C_{1-6}$alkyl, or $C_{1-6}$haloalkyl;

each $R^{12}$ is hydrogen, $C_{1-6}$alkyl, or $C_{1-6}$haloalkyl; and each $R^{13}$ is $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, or $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl.

Embodiment 18. The compound of embodiment 17, or a pharmaceutically acceptable salt thereof, wherein $R^2$ is 5- or 6-membered heteroaryl optionally substituted with one, two, three, or four groups selected from $R^{15c}$.

Embodiment 19. The compound of embodiment 17, or a pharmaceutically acceptable salt thereof, wherein $R^2$ is 6-membered heteroaryl optionally substituted with one, two, three, or four groups selected from $R^{15c}$.

Embodiment 20. The compound of embodiment 17, or a pharmaceutically acceptable salt thereof, wherein $R^2$ is pyridinyl optionally substituted with one, two, three, or four groups selected from $R^{15c}$.

Embodiment 21. The compound of any one of embodiments 17-20, or a pharmaceutically acceptable salt thereof, wherein Ring A is $C_{3-6}$cycloalkyl or $C_{2-9}$heterocycloalkyl.

Embodiment 22. The compound of any one of embodiments 17-20, or a pharmaceutically acceptable salt thereof, wherein Ring A is $C_{2-9}$heterocycloalkyl.

Embodiment 23. The compound of any one of embodiments 17-20, or a pharmaceutically acceptable salt thereof, wherein Ring A is $C_{2-6}$heterocycloalkyl.

Embodiment 24. The compound of any one of embodiments 17-20, or a pharmaceutically acceptable salt thereof, wherein Ring A is $C_{6-9}$heterocycloalkyl.

Embodiment 25. The compound of any one of embodiments 17-24, or a pharmaceutically acceptable salt thereof, wherein each $R^{15e}$ are independently halogen, oxo, —CN, $C_{1-6}$alkyl, $C_{1-6}$haloalkyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$N(R^{10})(R^{11})$, —$C(O)OR^{10}$, —$C(O)R^{13}$, or —$C(O)N(R^{10})(R^{11})$.

Embodiment 26. The compound of any one of embodiments 17-24, or a pharmaceutically acceptable salt thereof, wherein each $R^{15e}$ are independently halogen, oxo, —CN, $C_{1-6}$alkyl, or $C_{1-6}$haloalkyl.

Embodiment 27. The compound of any one of embodiments 17-24, or a pharmaceutically acceptable salt thereof, wherein each $R^{15e}$ are independently halogen, oxo, $C_{1-6}$alkyl, or $C_{1-6}$haloalkyl.

Embodiment 28. The compound of any one of embodiments 17-24, or a pharmaceutically acceptable salt thereof, wherein two $R^{15e}$ on the adjacent carbon are taken together to form a $C_{2-6}$alkenylene.

Embodiment 29. The compound of any one of embodiments 17-24, or a pharmaceutically acceptable salt thereof, wherein two $R^{15e}$ on the same atom are taken together to form a $C_{3-6}$cycloalkyl or $C_{2-9}$heterocycloalkyl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, and —$N(R^{10})(R^{11})$.

Embodiment 30. The compound of any one of embodiments 17-24, or a pharmaceutically acceptable salt thereof, wherein two $R^{15e}$ on the same atom are taken together to form a $C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, and —$N(R^{10})(R^{11})$.

Embodiment 31. The compound of any one of embodiments 17-24, or a pharmaceutically acceptable salt thereof, wherein two $R^{15e}$ on the same atom are taken together to form a $C_{3-6}$cycloalkyl.

Embodiment 32. The compound of any one of embodiments 17-24, or a pharmaceutically acceptable salt thereof, wherein two $R^{15e}$ on the different atom are taken together to form a $C_{3-6}$cycloalkyl or $C_{2-9}$heterocycloalkyl; each optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, and —$N(R^{10})(R^{11})$.

Embodiment 33. The compound of any one of embodiments 17-24, or a pharmaceutically acceptable salt thereof, wherein two $R^{15e}$ on the different atom are taken together to form a $C_{3-6}$cycloalkyl optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{10}$, and —$N(R^{10})(R^{11})$.

Embodiment 34. The compound of any one of embodiments 17-24, or a pharmaceutically acceptable salt thereof, wherein two $R^{15e}$ on the different atom are taken together to form a $C_{3-6}$cycloalkyl.

Embodiment 35. The compound of any one of embodiments 17-34, or a pharmaceutically acceptable salt thereof, wherein n is 0-4.

Embodiment 36. The compound of any one of embodiments 17-35, or a pharmaceutically acceptable salt thereof, wherein n is 2-4.

Embodiment 37. The compound of any one of embodiments 17-36, or a pharmaceutically acceptable salt thereof, wherein n is 2.

Embodiment 38. The compound of any one of embodiments 17-20, or a pharmaceutically acceptable salt thereof, wherein

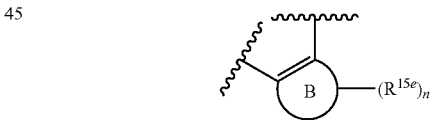

is

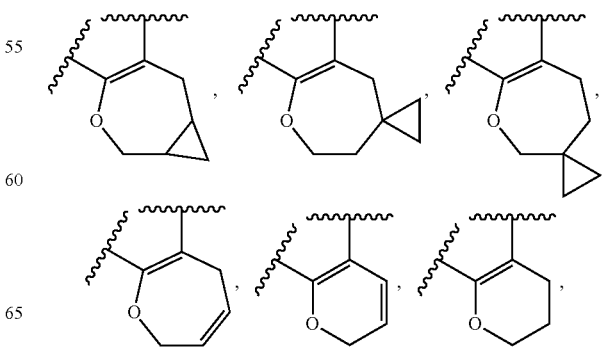

-continued

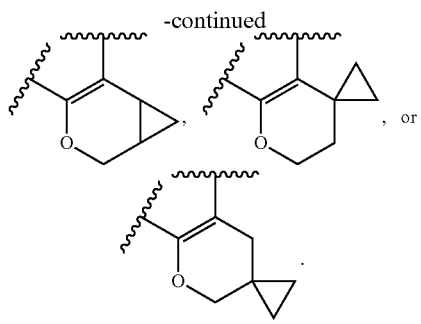

Embodiment 39. A compound of Formula (VI), or a pharmaceutically acceptable salt thereof:

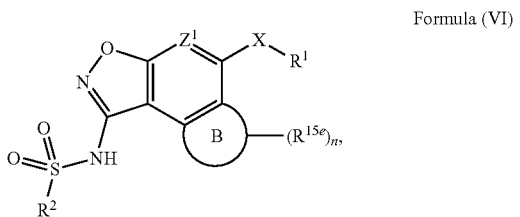

Formula (VI)

wherein:

R$^2$ is C$_{3-6}$cycloalkyl, C$_{2-9}$heterocycloalkyl, C$_{6-10}$aryl, or C$_{1-9}$heteroaryl; each optionally substituted with one, two, three, or four groups selected from R$^{15c}$;

Z$^1$ is CR$^{1b}$ or N;

R$^1$ is C$_{3-6}$cycloalkyl, C$_{2-9}$heterocycloalkyl, C$_{6-10}$aryl, or C$_{1-9}$heteroaryl; each optionally substituted with one, two, or three groups selected from R$^{15a}$;

R$^{1b}$ is hydrogen, halogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —SF$_5$, —N(R$^{10}$)(R$^{11}$), —C(O)OR$^{11}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, or —CH$_2$S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from R$^{15b}$;

X is —C(R$^6$)(R$^{6a}$)—, —S—, —O—, or —N(R$^7$)—;

R$^6$ and R$^{6a}$ are independently hydrogen, halogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, or —CH$_2$S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-4}$heterocycloalkyl, C$_{6-10}$aryl, and C$_{1-9}$heteroaryl;

or R$^6$ and R$^{6a}$ are taken together to form an oxo;

R$^7$ is selected from hydrogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-4}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

Ring B is C$_{3-6}$cycloalkyl, C$_{6-9}$heterocycloalkyl, C$_{6-10}$aryl, or C$_{1-6}$heteroaryl;

each R$^{15a}$, each R$^{15b}$, and each R$^{15c}$ are independently halogen, oxo, —CN, C$_{1-6}$alkyl, C$_{1-6}$haloalkyl, C$_{2-4}$alkenyl, C$_{2-6}$alkynyl, C$_{3-10}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, C$_{1-9}$heteroaryl, —CH$_2$—C$_{1-9}$heteroaryl, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, or —CH$_2$S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, —CH$_2$—C$_{3-10}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, —CH$_2$—C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

each R$^{15e}$ are independently halogen, oxo, —CN, C$_{1-6}$alkyl, C$_{1-6}$haloalkyl, C$_{2-6}$alkenyl, C$_{2-6}$alkynyl, C$_{3-10}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, C$_{1-9}$heteroaryl, —CH$_2$—C$_{1-9}$heteroaryl, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, or —CH$_2$S(O)$_2$N(R$^{10}$)(R$^{11}$), wherein C$_{1-6}$alkyl, C$_{2-6}$alkenyl, C$_{2-6}$alkynyl, C$_{3-6}$cycloalkyl, —CH$_2$—C$_{3-10}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, —CH$_2$—C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

or two R$^{15e}$ on the adjacent carbon are taken together to form a C$_{2-6}$alkenylene;

or two R$^{15e}$ on the same atom are taken together to form a C$_{3-6}$cycloalkyl or C$_{2-9}$heterocycloalkyl; each optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^2$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$); or two R$^{15e}$ on the different atom are taken together to form a C$_{3-6}$cycloalkyl, C$_{2-9}$heterocycloalkyl, C$_{6-10}$aryl, or C$_{1-9}$heteroaryl; each optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, —SR$^{10}$, —N(R$^{10}$)(R$^{11}$), —C(O)OR$^{10}$, —OC(O)N(R$^{10}$)(R$^{11}$), —N(R$^{12}$)C(O)N(R$^{10}$)(R$^{11}$), —N(R$^{12}$)C(O)OR$^{13}$, —N(R$^{12}$)S(O)$_2$R$^{13}$, —C(O)R$^{13}$, —S(O)R$^{13}$, —OC(O)R$^{13}$, —C(O)N(R$^{10}$)(R$^{11}$), —C(O)C(O)N(R$^{10}$)(R$^{11}$), —N(R$^{12}$)C(O)R$^{13}$, —S(O)$_2$R$^{13}$, —S(O)$_2$N(R$^{10}$)(R$^{11}$)—, S(O)(NH)N(R$^{10}$)(R$^{11}$), —CH$_2$C(O)N(R$^{10}$)(R$^{11}$), —CH$_2$N(R$^{12}$)C(O)R$^{13}$, —CH$_2$S(O)$_2$R$^{13}$, and —CH$_2$S(O)$_2$N(R$^{10}$)(R$^{11}$);

n is 0-6;

each R$^{15e}$ is hydrogen, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-6}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl;

each R$^{11}$ is hydrogen, C$_{1-6}$alkyl, or C$_{1-6}$haloalkyl;

each R$^{12}$ is hydrogen, C$_{1-6}$alkyl, or C$_{1-6}$haloalkyl; and each R$^{13}$ is C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, or C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three groups selected from halogen, —CN, hydroxy, C$_{1-6}$alkyl, C$_{1-6}$haloalkyl, C$_{1-6}$alkoxy, C$_{3-6}$cycloalkyl, C$_{2-9}$heterocycloalkyl, C$_{6-10}$aryl, and C$_{1-9}$heteroaryl.

Embodiment 40. The compound of embodiment 39, or a pharmaceutically acceptable salt thereof, wherein R$^2$ is C$_{6-10}$aryl or C$_{1-9}$heteroaryl; each optionally substituted with one, two, three, or four groups selected from R$^{15c}$.

Embodiment 41. The compound of embodiment 39, or a pharmaceutically acceptable salt thereof, wherein R$^2$ is C$_{1-9}$heteroaryl optionally substituted with one, two, three, or four groups selected from R$^{15c}$.

Embodiment 42. The compound of embodiment 39, or a pharmaceutically acceptable salt thereof, wherein R$^2$ is 5- or 6-membered heteroaryl optionally substituted with one, two, three, or four groups selected from R$^{15c}$.

Embodiment 43. The compound of embodiment 39, or a pharmaceutically acceptable salt thereof, wherein R$^2$ is 6-membered heteroaryl optionally substituted with one, two, three, or four groups selected from R$^{15c}$.

Embodiment 44. The compound of embodiment 39, or a pharmaceutically acceptable salt thereof, wherein R$^2$ is pyridinyl optionally substituted with one, two, three, or four groups selected from R$^{15c}$.

Embodiment 45. The compound of embodiment 39, or a pharmaceutically acceptable salt thereof, wherein R$^2$ is phenyl optionally substituted with one, two, three, or four groups selected from R$^{15c}$.

Embodiment 46. The compound of any one of embodiments 39-45, or a pharmaceutically acceptable salt thereof, wherein Ring B is C$_{6-9}$heterocycloalkyl.

Embodiment 47. The compound of any one of embodiments 39-46, or a pharmaceutically acceptable salt thereof, wherein each R$^{15e}$ are independently halogen, oxo, —CN, C$_{1-6}$alkyl, C$_{1-6}$haloalkyl, C$_{3-10}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, C$_{1-9}$heteroaryl, —CH$_2$—C$_{1-9}$heteroaryl, —OR$^{10}$, —N(R$^{10}$)(R$^{11}$), —C(O)OR$^{10}$, —C(O)R$^{13}$, or —C(O)N(R$^{10}$)(R$^{11}$).

Embodiment 48. The compound of any one of embodiments 39-46, or a pharmaceutically acceptable salt thereof, wherein each R$^{15e}$ are independently halogen, oxo, —CN, C$_{1-6}$alkyl, or C$_{1-6}$haloalkyl.

Embodiment 49. The compound of any one of embodiments 39-46, or a pharmaceutically acceptable salt thereof, wherein each R$^{15e}$ are independently halogen, oxo, C$_{1-6}$alkyl, or C$_{1-6}$haloalkyl.

Embodiment 50. The compound of any one of embodiments 39-46, or a pharmaceutically acceptable salt thereof, wherein two R$^{15e}$ on the adjacent carbon are taken together to form a C$_{2-6}$alkenylene.

Embodiment 51. The compound of any one of embodiments 39-46, or a pharmaceutically acceptable salt thereof, wherein two R$^{15e}$ on the same atom are taken together to form a C$_{3-6}$cycloalkyl or C$_{2-9}$heterocycloalkyl; each optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, and —N(R$^{10}$)(R$^{11}$).

Embodiment 52. The compound of any one of embodiments 39-46, or a pharmaceutically acceptable salt thereof, wherein two R$^{15e}$ on the same atom are taken together to form a C$_{3-6}$cycloalkyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, and —N(R$^{10}$)(R$^{11}$).

Embodiment 53. The compound of any one of embodiments 39-46, or a pharmaceutically acceptable salt thereof, wherein two R$^{15e}$ on the same atom are taken together to form a C$_{3-6}$cycloalkyl.

Embodiment 54. The compound of any one of embodiments 39-46, or a pharmaceutically acceptable salt thereof, wherein two R$^{15e}$ on the different atom are taken together to form a C$_{3-6}$cycloalkyl or C$_{2-9}$heterocycloalkyl; each optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, and —N(R$^{10}$)(R$^{11}$).

Embodiment 55. The compound of any one of embodiments 39-46, or a pharmaceutically acceptable salt thereof, wherein two R$^{15e}$ on the different atom are taken together to form a C$_{3-6}$cycloalkyl optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{10}$, and —N(R$^{10}$)(R$^{11}$).

Embodiment 56. The compound of any one of embodiments 39-46, or a pharmaceutically acceptable salt thereof, wherein two R$^{15e}$ on the different atom are taken together to form a C$_{3-6}$cycloalkyl.

Embodiment 57. The compound of any one of embodiments 39-56, or a pharmaceutically acceptable salt thereof, wherein n is 0-4.

Embodiment 58. The compound of any one of embodiments 39-57, or a pharmaceutically acceptable salt thereof, wherein n is 2-4.

Embodiment 59. The compound of any one of embodiments 39-58, or a pharmaceutically acceptable salt thereof, wherein n is 2.

Embodiment 60. The compound of any one of embodiments 39-45, or a pharmaceutically acceptable salt thereof, wherein

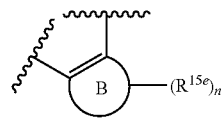

is

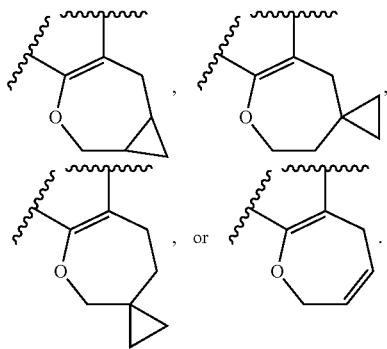

Embodiment 61. The compound of any one of embodiments 17-60, or a pharmaceutically acceptable salt thereof, wherein $Z^1$ is N.

Embodiment 62. The compound of any one of embodiments 17-60, or a pharmaceutically acceptable salt thereof, wherein $Z^1$ is $CR^{1b}$.

Embodiment 63. The compound of any one of embodiments 17-62, or a pharmaceutically acceptable salt thereof, wherein $R^{1b}$ is hydrogen or halogen.

Embodiment 64. The compound of any one of embodiments 17-62, or a pharmaceutically acceptable salt thereof, wherein $R^{1b}$ is hydrogen.

Embodiment 65. The compound of any one of embodiments 17-64, or a pharmaceutically acceptable salt thereof, wherein X is —C($R^6$)($R^{6a}$)—, —S—, or —O—.

Embodiment 66. The compound of any one of embodiments 17-64, or a pharmaceutically acceptable salt thereof, wherein X is —C($R^6$)($R^{6a}$)— or —O—.

Embodiment 67. The compound of any one of embodiments 17-64, or a pharmaceutically acceptable salt thereof, wherein X is —C($R^6$)($R^{6a}$)—.

Embodiment 68. The compound of any one of embodiments 17-64, or a pharmaceutically acceptable salt thereof, wherein X is —O—.

Embodiment 69. The compound of any one of embodiments 17-64, or a pharmaceutically acceptable salt thereof, wherein X is —S—.

Embodiment 70. The compound of any one of embodiments 17-69, or a pharmaceutically acceptable salt thereof, wherein $R^6$ and $R^{6a}$ are independently hydrogen, halogen, $C_{1-6}$alkyl, or $C_{1-6}$haloalkyl.

Embodiment 71. The compound of any one of embodiments 17-69, or a pharmaceutically acceptable salt thereof, wherein $R^6$ and $R^{6a}$ are independently hydrogen or $C_{1-6}$alkyl.

Embodiment 72. The compound of any one of embodiments 17-69, or a pharmaceutically acceptable salt thereof, wherein $R^6$ and $R^{6a}$ are hydrogen.

Embodiment 73. The compound of any one of embodiments 17-69, or a pharmaceutically acceptable salt thereof, wherein $R^6$ and $R^{6a}$ are taken together to form an oxo.

Embodiment 74. The compound of any one of embodiments 17-73, or a pharmaceutically acceptable salt thereof, wherein $R^7$ is hydrogen, $C_{1-6}$alkyl, or $C_{1-6}$haloalkyl.

Embodiment 75. The compound of any one of embodiments 17-73, or a pharmaceutically acceptable salt thereof, wherein $R^7$ is hydrogen or $C_{1-6}$alkyl.

Embodiment 76. The compound of any one of embodiments 17-73, or a pharmaceutically acceptable salt thereof, wherein $R^7$ is hydrogen.

Embodiment 77. The compound of any one of embodiments 1-76, or a pharmaceutically acceptable salt thereof, wherein $R^1$ is $C_{6-10}$aryl or $C_{1-9}$heteroaryl; each optionally substituted with one, two, or three groups selected from $R^{15a}$.

Embodiment 78. The compound of any one of embodiments 1-76, or a pharmaceutically acceptable salt thereof, wherein $R^1$ is $C_{1-9}$heteroaryl optionally substituted with one, two, or three groups selected from $R^{15a}$.

Embodiment 79. The compound of any one of embodiments 1-76, or a pharmaceutically acceptable salt thereof, wherein $R^1$ is 5- or 6-membered heteroaryl optionally substituted with one, two, or three groups selected from $R^{15a}$.

Embodiment 80. The compound of any one of embodiments 1-76, or a pharmaceutically acceptable salt thereof, wherein $R^1$ is 5-membered heteroaryl optionally substituted with one, two, or three groups selected from $R^{15a}$.

Embodiment 81. The compound of any one of embodiments 1-76, or a pharmaceutically acceptable salt thereof, wherein $R^1$ is $C_{1-9}$heteroaryl selected from pyrazolyl, imidazolyl, isoxazolyl, oxazolyl, thiazolyl, and pyridinyl, wherein pyrazolyl, imidazolyl, isoxazolyl, oxazolyl, thiazolyl, and pyridinyl are optionally substituted with one, two, or three groups selected from $R^{15a}$.

Embodiment 82. The compound of any one of embodiments 1-76, or a pharmaceutically acceptable salt thereof, wherein $R^1$ is $C_{1-9}$heteroaryl selected from pyrazolyl and thiazolyl, wherein pyrazolyl and thiazolyl are optionally substituted with one, two, or three groups selected from $R^{15a}$.

Embodiment 83. The compound of any one of embodiments 1-76, or a pharmaceutically acceptable salt thereof, wherein $R^1$ is thiazolyl optionally substituted with one, two, or three groups selected from $R^{15}$.

Embodiment 84. The compound of any one of embodiments 1-76, or a pharmaceutically acceptable salt thereof, wherein $R^1$ is pyrazolyl optionally substituted with one, two, or three groups selected from $R^{15}$.

Embodiment 85. The compound of any one of embodiments 1-84, or a pharmaceutically acceptable salt thereof, wherein each $R^{15a}$, each $R^{15b}$, and each $R^{15c}$ are independently halogen, oxo, —CN, $C_{1-6}$alkyl, $C_{1-6}$haloalkyl, $C_{3-10}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{10}$, —$N(R^{10})(R^{11})$, —$C(O)OR^{10}$, —$C(O)R^{13}$, or —$C(O)N(R^{10})(R^{11})$.

Embodiment 86. The compound of any one of embodiments 1-84, or a pharmaceutically acceptable salt thereof, wherein each $R^{15a}$, each $R^{15b}$, and each $R^{15c}$ are independently halogen, oxo, —CN, $C_{1-6}$alkyl, $C_{1-6}$haloalkyl, —OR$^{10}$, or —N(R$^{10}$)(R$^{11}$).

Embodiment 87. The compound of any one of embodiments 1-84, or a pharmaceutically acceptable salt thereof, wherein each $R^{15a}$, each $R^{15b}$, and each $R^{15c}$ are independently halogen, $C_{1-6}$alkyl, $C_{1-6}$haloalkyl, or —OR$^{10}$.

Embodiment 88. The compound of any one of embodiments 1-84, or a pharmaceutically acceptable salt thereof, wherein each $R^{15a}$, each $R^{15b}$, and each $R^{15c}$ are independently halogen, $C_{1-6}$alkyl, or —OR$^{10}$.

Embodiment 89. The compound of any one of embodiments 1-84, or a pharmaceutically acceptable salt thereof, wherein each $R^{15a}$, each $R^{15b}$, and each $R^{15c}$ are independently $C_{1-6}$alkyl or —OR$^{10}$.

Embodiment 90. The compound of any one of embodiments 1-89, or a pharmaceutically acceptable salt thereof, wherein each $R^{10}$ is independently hydrogen, $C_{1-6}$alkyl, $C_{1-6}$haloalkyl, $C_{3-6}$cycloalkyl, $C_{2-9}$heterocycloalkyl, $C_{6-10}$aryl, or $C_{1-9}$heteroaryl, wherein $C_{1-6}$alkyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl.

Embodiment 91. The compound of any one of embodiments 1-89, or a pharmaceutically acceptable salt thereof, wherein each $R^{10}$ is independently hydrogen, $C_{1-6}$alkyl, $C_{1-6}$haloalkyl, $C_{3-6}$cycloalkyl, $C_{2-9}$heterocycloalkyl, wherein $C_{1-6}$alkyl, $C_{3-6}$cycloalkyl, and $C_{2-9}$heterocycloalkyl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl.

Embodiment 92. The compound of any one of embodiments 1-89, or a pharmaceutically acceptable salt thereof, wherein each $R^{10}$ is independently hydrogen, $C_{1-6}$alkyl, or $C_{1-6}$haloalkyl, wherein $C_{1-6}$alkyl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl.

Embodiment 93. The compound of any one of embodiments 1-89, or a pharmaceutically acceptable salt thereof, wherein each $R^{10}$ is independently hydrogen, $C_{1-6}$alkyl, or $C_{1-6}$haloalkyl.

Embodiment 94. The compound of any one of embodiments 1-89, or a pharmaceutically acceptable salt thereof, wherein each $R^{10}$ is independently $C_{1-6}$alkyl or $C_{1-6}$haloalkyl.

Embodiment 95. The compound of any one of embodiments 1-89, or a pharmaceutically acceptable salt thereof, wherein each $R^{10}$ is independently $C_{1-6}$alkyl.

Embodiment 96. The compound of any one of embodiments 1-89, or a pharmaceutically acceptable salt thereof, wherein each $R^{10}$ is independently $C_{1-6}$haloalkyl.

Embodiment 97. The compound of any one of embodiments 1-96, or a pharmaceutically acceptable salt thereof, wherein each $R^{11}$ is independently hydrogen or $C_{1-6}$alkyl.

Embodiment 98. The compound of any one of embodiments 1-96, or a pharmaceutically acceptable salt thereof, wherein each $R^{11}$ is independently hydrogen.

Embodiment 99. The compound of any one of embodiments 1-96, or a pharmaceutically acceptable salt thereof, wherein each $R^{11}$ is independently $C_{1-6}$alkyl.

Embodiment 100. The compound of any one of embodiments 1-99, or a pharmaceutically acceptable salt thereof, wherein each $R^{12}$ is independently hydrogen, $C_{1-6}$alkyl, or $C_{1-6}$haloalkyl.

Embodiment 101. The compound of any one of embodiments 1-99, or a pharmaceutically acceptable salt thereof, wherein each $R^{12}$ is independently hydrogen or $C_{1-6}$alkyl.

Embodiment 102. The compound of any one of embodiments 1-99, or a pharmaceutically acceptable salt thereof, wherein each $R^{12}$ is independently hydrogen.

Embodiment 103. The compound of any one of embodiments 1-99, or a pharmaceutically acceptable salt thereof, wherein each $R^{12}$ is independently $C_{1-6}$alkyl.

Embodiment 104. The compound of any one of embodiments 1-103, or a pharmaceutically acceptable salt thereof, wherein each $R^{13}$ is independently hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, or $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl.

Embodiment 105. The compound of any one of embodiments 1-103, or a pharmaceutically acceptable salt thereof, wherein each $R^{13}$ is independently hydrogen, $C_{1-6}$alkyl, $C_{3-6}$cycloalkyl, $C_{2-9}$heterocycloalkyl, $C_{6-10}$aryl, or $C_{1-9}$heteroaryl, wherein $C_{1-6}$alkyl, $C_{3-6}$cycloalkyl, $C_{2-9}$heterocycloalkyl, $C_{6-10}$aryl, and $C_{1-9}$heteroaryl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl.

Embodiment 106. The compound of any one of embodiments 1-103, or a pharmaceutically acceptable salt thereof, wherein each $R^{13}$ is independently hydrogen, $C_{1-6}$alkyl, $C_{3-6}$cycloalkyl, or $C_{2-9}$heterocycloalkyl, wherein $C_{1-6}$alkyl, $C_{3-6}$cycloalkyl, and $C_{2-9}$heterocycloalkyl are optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl.

Embodiment 107. The compound of any one of embodiments 1-103, or a pharmaceutically acceptable salt thereof, wherein each $R^{13}$ is independently hydrogen, $C_{1-6}$alkyl optionally substituted with one, two, or three groups selected from halogen, —CN, hydroxy, $C_{1-6}$alkyl, $C_{1-6}$haloalkyl, $C_{1-6}$alkoxy, $C_{3-6}$cycloalkyl, $C_{2-9}$heterocycloalkyl, $C_{6-10}$aryl, and $C_{1-9}$heteroaryl.

Embodiment 108. The compound of any one of embodiments 1-103, or a pharmaceutically acceptable salt thereof, wherein each $R^{13}$ is independently hydrogen or $C_{1-6}$alkyl.

Embodiment 109. A compound selected from a compound found in Table 1B or Table 1C, or a pharmaceutically acceptable salt thereof.

Embodiment 110. A pharmaceutical composition comprising a compound of any one of embodiments 1-109, or a pharmaceutically acceptable salt thereof, and at least one pharmaceutically acceptable excipient.

Embodiment 111. A method of treating cancer in a mammal in need thereof, comprising administering to the mammal a compound of any one of embodiments 1-109, or a pharmaceutically acceptable salt thereof.

Embodiment 112. The method of embodiment 111, wherein the cancer is selected from lung cancer, mesothelioma, bone cancer, pancreatic cancer, skin cancer, cancer of the head or neck, cutaneous or intraocular melanoma, uterine cancer, ovarian cancer, rectal cancer, stomach cancer, hepatocellular carcinoma, colon cancer, breast cancer, carcinoma of the endometrium, carcinoma of the cervix, carcinoma of the vagina, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, hematology malignancy, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, glioblastoma, brain stem glioma, pituitary adenoma, or a combination of two or more of the foregoing cancers.

Embodiment 113. The method of embodiment 111, wherein the cancer is selected from ER-positive breast cancer, glioblastoma, non-small cell lung cancer (NSCLC), small cell lung cancer (SCLC), melanoma, ovarian cancer, prostate cancer, pancreatic cancer, colorectal cancer (CRC), hepatocellular carcinoma (HCC), renal cell carcinoma (RCC), leukemia, lymphoma or multiple myeloma, acute lymphocytic leukemia (ALL), acute myeloid leukemia (AML), chronic lymphocytic leukemia (CLL), chronic myeloid leukemia (CML), and non-Hodgkin's lymphoma.

Embodiment 114. The method of embodiment 111, wherein the cancer is ER-positive breast cancer.

Embodiment 115. The method of embodiment 111, wherein the cancer is a solid tumor with KAT6A/6B amplification or overexpression, or leukemia or solid tumor with KAT6A/6B fusion protein resulting from chromosomal translocation.

Further Forms of Compounds Disclosed Herein
Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine and chloride, such as $^2$H (D), $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and the pharmaceutically acceptable salts, solvates, or stereoisomers thereof which contain the aforementioned isotopes and/or other isotopes of other atoms are within the scope of this disclosure. Certain isotopically-labeled compounds, for example those into which radioactive isotopes such as $^3$H and $^{14}$C are incorporated, are useful in drug and/or substrate tissue distribution assays. Tritiated, i.e., $^3$H and carbon-14, i.e., $^{14}$C, isotopes are particularly preferred for their ease of preparation and detectability. In some embodiments, the compounds described herein may be artificially enriched in one or more isotopes that are not predominantly found in nature. In some embodiments, the compounds described herein may be artificially enriched in one or more isotopes selected from deuterium ($^2$H), tritium ($^3$H), iodine-125 ($^{125}$I) or carbon-14 ($^{14}$C). In some embodiments, the compounds described herein are artificially enriched in one or more isotopes selected from $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{131}$I, and $^{125}$I. In some embodiments, the abundance of the enriched isotopes is independently at least 1%, at least 10%, at least 20%, at least 30%, at least 40%, at least 50%, at least 60%, at least 70%, at least 80%, at least 90%, or 100% by molar.

In some embodiments, the abundance of deuterium in each of the substituents disclosed herein is independently at least 1%, at least 10%, at least 20%, at least 30%, at least 40%, at least 50%, at least 60%, at least 70%, at least 80%, at least 90%, or 100% by molar. In some embodiments, one or more of the substituents disclosed herein comprise deuterium at a percentage higher than the natural abundance of deuterium. In some embodiments, one or more $^1$H are replaced with one or more deuteriums in one or more of the substituents disclosed herein.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\text{ alkyl})_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Disclosed herein is a method of treating a disease in which inhibition of KAT6A is beneficial, the method comprising administering a compound of Formula (I), (I'), (Ia), (II), (III), (IV), (V), or (VI), disclosed herein, or a pharmaceutically acceptable salt or solvate thereof. In some embodiments, the method comprises administering a pharmaceutical composition comprising a compound of Formula (I), (I'), (Ia), (II), (III), (IV), (V), or (VI) disclosed herein, or a pharmaceutically acceptable salt or solvate thereof.

Disclosed herein is a method of treating a disease or disorder associated with KAT6A, the method comprising administering to the subject a compound of Formula (I), (I'), (Ia), (II), (III), (IV), (V), or (VI), disclosed herein, or a pharmaceutically acceptable salt or solvate thereof. In some embodiments, the method comprises administering a pharmaceutical composition comprising a compound of Formula (I), (Ia), (II), or (III) disclosed herein, or a pharmaceutically acceptable salt or solvate thereof.

In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof.

In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is selected from lung cancer, mesothelioma, bone cancer, pancreatic cancer, skin cancer, cancer of the head or neck, cutaneous or intraocular melanoma, uterine cancer, ovarian cancer, rectal cancer, stomach cancer, hepatocellular carcinoma, colon cancer, breast cancer, carcinoma of the endometrium, carcinoma of the cervix, carcinoma of the vagina, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, hematology malignancy, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, glioblastoma, brain stem glioma, pituitary adenoma, or a combination of two or more of the foregoing cancers.

In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is selected from ER-positive breast cancer, glioblastoma, non-small cell lung cancer (NSCLC), small cell lung cancer (SCLC), melanoma, ovarian cancer, prostate cancer, pancreatic cancer, colorectal cancer (CRC), hepatocellular carcinoma (HCC), renal cell carcinoma (RCC), leukemia, lymphoma or multiple myeloma, acute lymphocytic leukemia (ALL), acute myeloid leukemia (AML), chronic lymphocytic leukemia (CLL), chronic myeloid leukemia (CML), and non-Hodgkin's lymphoma. In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is ER-positive breast cancer. In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is glioblastoma. In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is non-small cell lung cancer (NSCLC). In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is small cell lung cancer (SCLC). In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is melanoma. In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is ovarian cancer. In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is prostate cancer. In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is pancreatic cancer. In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is colorectal cancer (CRC). In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is hepatocellular carcinoma (HCC). In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is renal cell carcinoma (RCC). In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is leukemia. In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is lymphoma. In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is multiple myeloma. In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is acute lymphocytic leukemia (ALL). In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is acute myeloid leukemia (AML). In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is chronic lymphocytic leukemia (CLL). In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is chronic myeloid leukemia (CML). In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is non-Hodgkin's lymphoma.

In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is a solid tumor with KAT6A/6B amplification or overexpression, or leukemia or solid tumor with KAT6A/6B fusion protein resulting from chromosomal translocation. In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is a solid tumor with KAT6A/6B amplification or overexpression. In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is a leukemia or solid tumor with KAT6A/6B fusion protein resulting from chromosomal translocation.

In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is a MYST overexpressing cancer. In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer overexpresses more than one KATs of the MYST family. In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer overexpresses more than one KATs of the MYST family selected from TIP60, KAT6A, KAT6B, HBO1, and MOF.

In some embodiments is a method of treating cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer is a bromodomain overexpressing cancer. In some embodiments is a method of treating a bromodomain overexpressing cancer in a mammal in need thereof, comprising administering to the mammal a compound of Formula (I), (I'), (Ia), (II), (III), (IV), (V), or (VI), or a pharmaceutically acceptable salt or solvate thereof, wherein the cancer overexpresses one or more bromodomain proteins selected from BRD2, BRD3, BRD4, BRD7, BRD8, BRD9, BRDT, TAF1/TAF1L, TFIID, SMARC2, and SMARC4.

Dosing

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of or risk factor for the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent or daily treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{10}$ and the $ED_{90}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the subject every 12 hours; (v) the compound is administered to the subject every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

The compounds described herein are administered to a subject in need thereof, either alone or in combination with pharmaceutically acceptable carriers, excipients or diluents, in a pharmaceutical composition, according to standard pharmaceutical practice. In one embodiment, the compounds of this disclosure may be administered to animals. The compounds can be administered orally or parenterally, including the intravenous, intramuscular, intraperitoneal, subcutaneous, rectal and topical routes of administration.

In another aspect, provided herein are pharmaceutical compositions comprising a compound of Formula (I), (I'), (Ia), (II), (III), (IV), (V), or (VI), described herein, or a pharmaceutically acceptable salt or solvate thereof, and at least one pharmaceutically acceptable excipient. In some embodiments is a pharmaceutical compositions comprising a compound of Formula (I) described herein, or a pharmaceutically acceptable salt or solvate thereof, and at least one pharmaceutically acceptable excipient. In some embodiments is a pharmaceutical compositions comprising a compound of Formula (I') described herein, or a pharmaceutically acceptable salt or solvate thereof, and at least one pharmaceutically acceptable excipient. In some embodiments is a pharmaceutical compositions comprising a compound of Formula (Ia) described herein, or a pharmaceutically acceptable salt or solvate thereof, and at least one pharmaceutically acceptable excipient. In some embodiments is a pharmaceutical compositions comprising a compound of Formula (II) described herein, or a pharmaceutically acceptable salt or solvate thereof, and at least one pharmaceutically acceptable excipient. In some embodiments is a pharmaceutical compositions comprising a compound of Formula (III) described herein, or a pharmaceutically acceptable salt or solvate thereof, and at least one pharmaceutically acceptable excipient. In some embodiments is a pharmaceutical compositions comprising a compound of Formula (IV) described herein, or a pharmaceutically acceptable salt or solvate thereof, and at least one pharmaceutically acceptable excipient. In some embodiments is a pharmaceutical compositions comprising a compound of Formula (V) described herein, or a pharmaceutically acceptable salt or solvate thereof, and at least one pharmaceutically acceptable excipient. In some embodiments is a pharmaceutical compositions comprising a compound of Formula (VI) described herein, or a pharmaceutically acceptable salt or solvate thereof, and at least one pharmaceutically acceptable excipient.

Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical compositions described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds described herein, or a pharmaceutically acceptable salt or solvate thereof are manufactured in a conventional manner, such as, by way of example only, by means of conventional mixing, dissolving, granulating, dragee-making, levigating, emulsifying, encapsulating, entrapping, or compression processes.

Pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical compositions that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

Pharmaceutical compositions for parental use are formulated as infusions or injections. In some embodiments, the pharmaceutical composition suitable for injection or infusion includes sterile aqueous solutions, or dispersions, or sterile powders comprising a compound described herein, or a pharmaceutically acceptable salt or solvate thereof. In some embodiments, the pharmaceutical composition comprises a liquid carrier. In some embodiments, the liquid carrier is a solvent or liquid dispersion medium comprising, for example, water, saline, ethanol, a polyol (for example, glycerol, propylene glycol, liquid polyethylene glycols, and the like), vegetable oils, nontoxic glyceryl esters, and any combinations thereof. In some embodiments, the pharmaceutical compositions further comprise a preservative to prevent growth of microorganisms.

EXAMPLES

The following examples are provided for illustrative purposes only and not to limit the scope of the claims provided herein.

As used above, and throughout the description of the disclosure, the following abbreviations, unless otherwise indicated, shall be understood to have the following meanings:

| | |
|---|---|
| ACN or MeCN | acetonitrile |
| AcOH | acetic acid |
| Ac | acetyl |
| Bn | benzyl |
| BOC or Boc | tert-butyl carbamate |
| i-Bu | iso-butyl |
| t-Bu | tert-butyl |
| CDI | 1,1-carbonyldiimidazole |
| DBU | 1,8-diazabicyclo[5.4.0]undec-7-ene |
| DCE | dichloroethane (ClCH$_2$CH$_2$Cl) |
| DCM | dichloromethane (CH$_2$Cl$_2$) |
| DIBAL-H | diisobutylaluminum hydride |
| DIPEA or DIEA | diisopropylethylamine |
| DMAP | 4-(N,N-dimethylamino)pyridine |
| DME | 1,2-dimethoxyethane |
| DMF | N,N-dimethylformamide |
| DMA | N,N-dimethylacetamide |
| DMPU | N,N'-dimethylpropyleneurea |
| DMSO | dimethylsulfoxide |
| DPPA | diphenyl phosphoryl azide |
| Dppf or dppf | 1,1'-bis(diphenylphosphino)ferrocene |
| EDC or EDCI | N-(3-dimethylaminopropyl)-N'-ethylcarbodiimide hydrochloride |
| eq | equivalent(s) |
| Et | ethyl |
| Et$_2$O | diethyl ether |
| EtOH | ethanol |
| EtOAc | ethyl acetate |
| HATU | 1-[bis(dimethylamino)methylene]-1H-1,2,3-triazolo[4,5-b]pyridinium 3-oxid hexafluorophosphate |
| HOBt | 1-hydroxybenzotriazole |
| HPLC | high performance liquid chromatography |
| KOAc | potassium acetate |
| KOtBu | potassium tert-butoxide |
| KHMDS | potassium bis(trimethylsilyl)amide |
| NaHMDS | sodium bis(trimethylsilyl)amide |

| | |
|---|---|
| LiHMDS | lithium bis(trimethylsilyl)amide |
| LAH/LiAlH₄ | lithium aluminum anhydride |
| LCMS | liquid chromatography mass spectrometry |
| Me | methyl |
| MeOH | methanol |
| MS | mass spectroscopy |
| MTBE | methyl tert-butyl ether |
| NBS | N-bromosuccinimide |
| NMP | N-methyl-pyrrolidin-2-one |
| NMR | nuclear magnetic resonance |
| PE | petroleum ether |
| Ph | phenyl |
| iPr/i-Pr | iso-propyl |
| PyAOP | 7-Azabenzotriazol-1-yloxy)tripyrrolidinophosphonium hexafluorophosphate |
| RP-HPLC | reverse-phase high-pressure liquid chromatography |
| rt | room temperature |
| SEM | 2-(trimethylsilyl)ethoxymethyl |
| TBS | tert-butyldimethylsilyl |
| TEA | triethylamine |
| TFA | trifluoroacetic acid |
| THF | tetrahydrofuran |
| TLC | thin layer chromatography |
| TMS | trimethylsilyl |

Example 1: Synthesis of N-(6-((1H-pyrazol-1-yl)methyl)isoxazolo[4,5-b]pyridin-3-yl)-2,6-dimethoxybenzenesulfonamide (Compound 1)

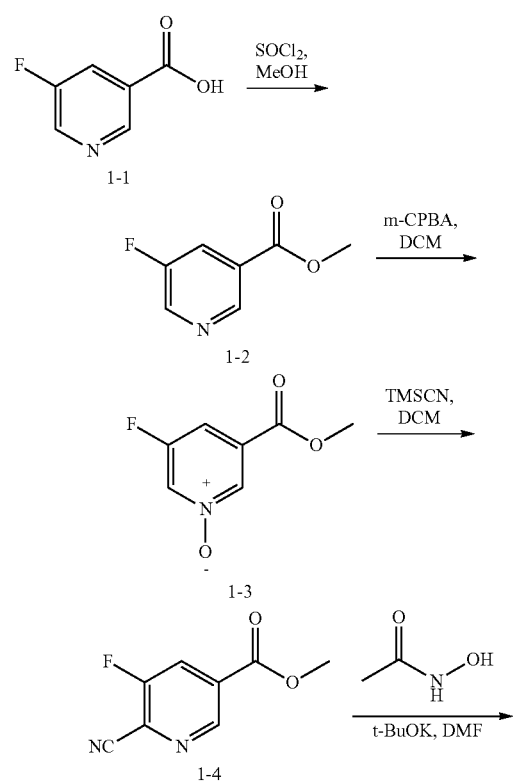

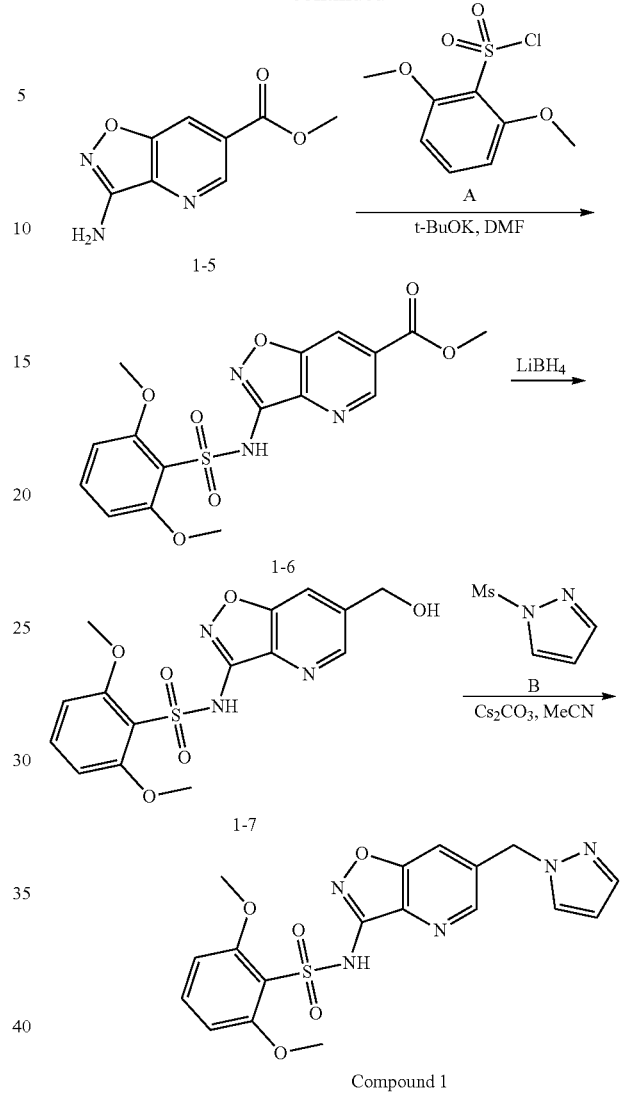

Step 1: To a solution of 1-1 (4.0 g, 28.3 mmol) in methanol (20 mL) was added thionyl chloride (3.1 mL, 42.5 mmol). The mixture was stirred at 90° C. for 18 h and concentrated under reduced pressure. The residue was diluted with ethyl acetate (40 mL) and washed with saturated aqueous sodium bicarbonate (20 mL), brine (30 mL), dried over sodium sulfate and concentrated under reduced pressure to afford 1-2 (3.2 g, 73% yield) as a pale brown solid.

Step 2: To a solution of 1-2 (3.2 g, 20.63 mmol) in dichloromethane (20 mL) was added 3-chloroperoxybenzoic acid (7.12 g, 41.26 mmol) at one portion under an ice bath. The mixture was stirred under room temperature for 10 h. A saturated sodium bicarbonate solution (30 mL) was then added to the solution. Following extraction with ethyl acetate (50 mL×3), the organic phases were combined, washed with brine, dried over anhydrous Na₂SO₄ and filtered. The filtrate was concentrated under reduced pressure and then purified by flash silica gel chromatography to provide the corresponding 1-3 (2.5 g, 71% yield) as a white solid.

Step 3: To a solution of 1-3 (2.5 g, 14.6 mmol) in dichloromethane (20 mL) was added triethylamine (6.9 mL, 51.2 mmol) and TMSCN (6.2 mL, 51.2 mmol) under an ice bath. The mixture was stirred at room temperature for 20 h and then concentrated under reduced pressure and purified by flash silica gel chromatography to provide 1-4 (2.0 g, 76% yield) as a yellow solid.

Step 4: To a solution of 1-4 (1.0 g, 5.55 mmol) in DMF (10 mL) was added t-BuOK (1.24 g, 11.10 mmol) and N-hydroxyacetamide (833 mg, 11.1 mmol). This reaction mixture was stirred at 60° C. for 12 hours. The reaction mixture was filtered and concentrated in vacuum to give a residue which was purified by flash silica gel chromatography to afford 1-5 (500 mg, 47% yield) as a yellow solid. LCMS: 194.0 [M+H]⁺.

Step 5: To a solution of 1-5 (500 mg, 2.59 mmol) in DMF (10 mL) was added t-BuOK (580 mg, 5.18 mmol) and then Compound A (918.92 mg, 3.88 mmol) in DMF (1 mL) at 0° C. This reaction mixture was stirred at 25° C. for 1 hour. This reaction mixture was concentrated in vacuum to crude product which was further purified by Prep-HPLC to afford 1-6 (200 mg, 20% yield) as a white solid. LCMS: 394.0 [M+H]⁺.

Step 6: To a solution of 1-6 (200 mg, 0.51 mmol) in THF (5 mL) was added LiBH₄ (22.15 mg, 1.02 mmol) at 0° C. This reaction mixture was stirred at 70° C. for 2 h. The reaction mixture was quenched with water (10 mL). The aqueous phase was extracted with DCM (20 mL×2). The combined organic phase was washed with brine (20 mL), dried with anhydrous sodium sulfate, filtered, and concentrated in vacuum to afford 1-7 (60 mg, 0.16 mmol, 32% yield) as a white solid. LCMS: 365.9 [M+H]⁺.

Step 7: To a solution of 1-7 (60 mg, 0.16 mmol) in acetonitrile (3 mL) were added Compound B (26.4 mg, 0.18 mmol) and Cs₂CO₃ (104 mg, 0.32 mmol). The reaction was stirred at 70° C. for 2 h. The reaction mixture was concentrated. The residue was purified by Prep-HPLC to afford Compound 1 (5 mg, 7% yield) as a white solid. LCMS: 416.1 [M+H]⁺. ¹H NMR (400 MHz, DMSO-d₆) δ 11.67 (s, 1H), 8.54 (s, 1H), 7.92 (d, J=2.1 Hz, 1H), 7.88-7.69 (m, 1H), 7.50 (d, J=1.4 Hz, 1H), 7.40 (s, 1H), 6.69 (s, 2H), 6.30 (t, J=2.0 Hz, 1H), 5.55 (s, 2H), 3.65 (s, 6H).

Example 2: Synthesis of N-(6-((1H-pyrazol-1-yl)methyl)-4-methoxybenzo[d]isoxazol-3-yl)-2,4-dimethoxypyridine-3-sulfonamide (Compound 2)

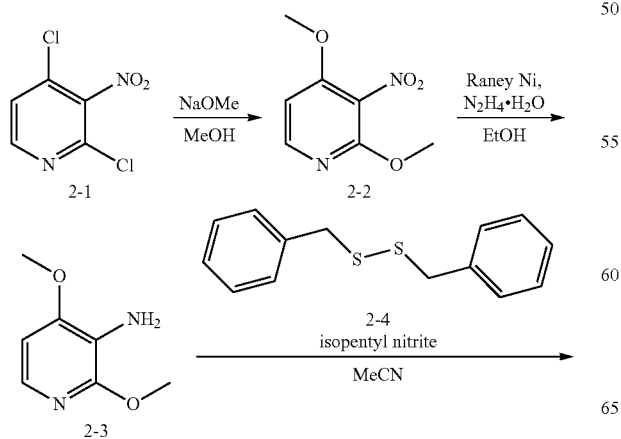

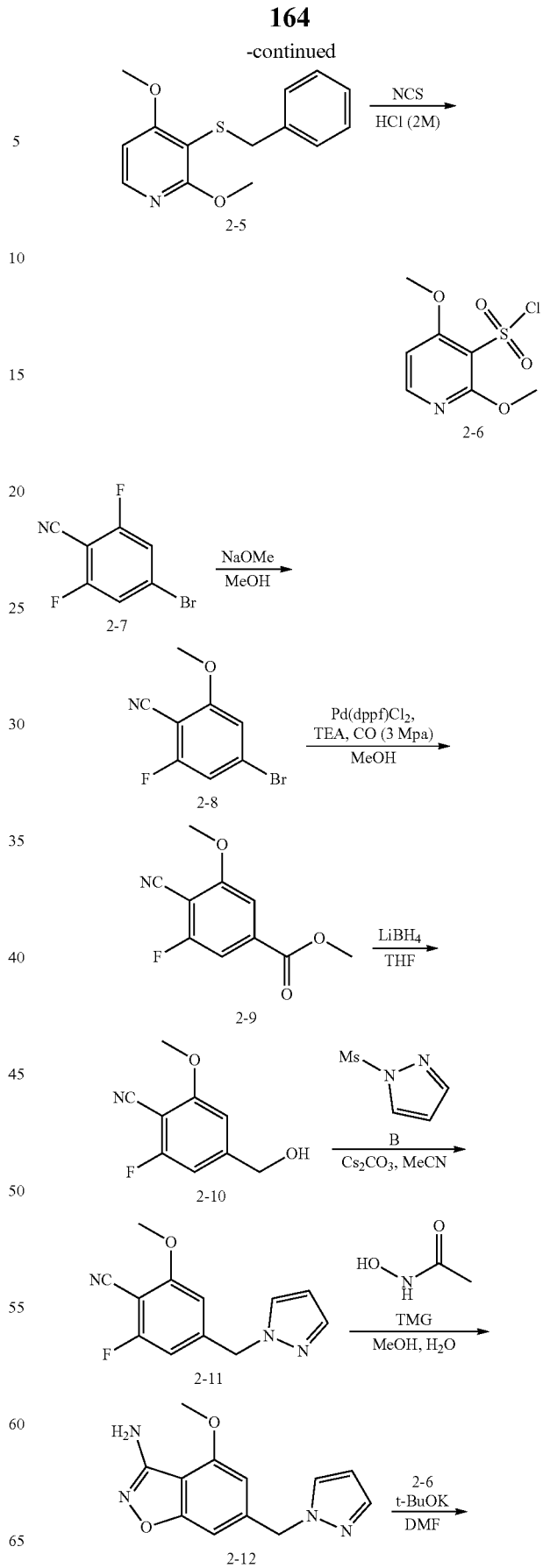

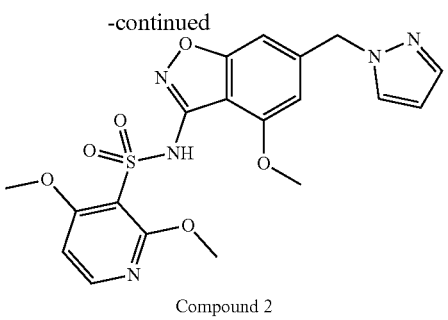

Compound 2

Step 1: To a solution of 2-1 (50.0 g, 260 mmol) in MeOH (500 mL) was added NaOMe (42.2 g, 781 mmol). The mixture was stirred at 60° C. for 2 h. The reaction mixture was concentrated to remove MeOH. Then the residue was diluted with DCM (500 mL) and washed with H₂O (500 mL). The organic layer was washed with aqueous brine (200 mL), dried over Na₂SO₄, filtered and concentrated under reduced pressure to give a residue. The residue was purified by flash silica gel chromatography to give 2-2 (40.0 g, 83% yield) as a white solid.

Step 2: To a solution of 2-2 (10.0 g, 54.3 mmol) in EtOH (200 mL) was added N₂H₄·H₂O solution (14.8 mL, 272 mmol) and Raney Ni (2.00 g, 9.15 mmol) at 0° C. The reaction mixture was stirred at 25° C. for 20 min. The reaction mixture was filtered and concentrated in vacuum to give a residue which was purified by flash silica gel chromatography to afford 2-3 (8.00 g, 95% yield) as a white solid. LCMS: 155.0 [M+H]⁺.

Step 3: To a solution of 2-3 (650 mg, 4.22 mmol) in acetonitrile (10 mL) was added 2-4 (1.25 g, 5.06 mmol) and isopentyl nitrite (1.39 mL, 9.28 mmol) at 80° C. This reaction mixture was stirred at 80° C. for 2 h. The reaction mixture was concentrated in vacuum to give a residue which was purified by flash silica gel chromatography to afford 2-5 (300 mg, 27% yield) as a brown oil. LCMS: 262.3 [M+H]⁺.

Step 4: To a solution of 2-5 (300 mg, 1.15 mmol) in MeCN (6 mL) was added HCl (0.630 mL, 1.26 mmol, 2 M) and NCS (920 mg, 6.89 mmol) at 0° C. This reaction mixture was stirred at 25° C. for 0.5 h. The reaction mixture was purified by flash silica gel chromatography to afford 2-6 as a white solid. LCMS: 238.1 [M+H]⁺.

Step 5: To a solution of 2-7 (30 g, 138 mmol) in THF (250 mL) and MeOH (50 mL) was added NaOMe (8.92 g, 165 mmol) at 0° C. The mixture was stirred at room temperature for 12 h. The reaction mixture was diluted with water (300 mL). The aqueous phase was extracted with ethyl acetate (300 mL×2). The combined organic phase was washed by brine (300 mL), dried with anhydrous sodium sulfate, filtered, and concentrated in vacuum to give a residue. The residue was purified by flash silica gel chromatography to afford 2-8 (22 g, 70% yield) as a white solid.

Step 6: To a solution of 2-8 (11.55 g, 50.2 mmol) in MeOH (250 mL) was added TEA (21.0 mL, 151 mmol) and Pd(dppf)Cl₂ (3.67 g, 5.02 mmol). This reaction mixture was stirred at 80° C. for 12 h under CO (3 Mpa) atmosphere. This reaction mixture was concentrated in vacuum to give a residue which was purified by flash silica gel chromatography to afford 2-9 (7.39 g, 70% yield) as a white solid.

Step 7: To a solution of 2-9 (4.20 g, 20.1 mmol) in THF (45 mL) was added LiBH₄ (0.870 g, 40.2 mmol) at 0° C. This reaction mixture was stirred at 70° C. for 2 h. The reaction mixture was quenched with water (40 mL). The aqueous phase was extracted with DCM (50 mL×2). The combined organic phase was washed by brine (50 mL), dried with anhydrous sodium sulfate, filtered, and concentrated in vacuum to afford 2-10 (3.63 g) as a white solid. LCMS: 182.0 [M+H]⁺.

Step 8: To a solution of 2-10 (650 mg, 3.59 mmol) and Compound B (629 mg, 4.30 mmol) in ACN (12 mL) was added Cs₂CO₃ (1.40 g, 4.30 mmol). The mixture was stirred at 70° C. for 1 h. The reaction mixture was concentrated under reduced pressure to give a residue. The residue was purified by flash silica gel chromatography to afford 2-11 (500 mg, 60% yield) as a yellow solid. LCMS: 232.0 [M+H]⁺.

Step 9: To a solution of 2-11 (500 mg, 2.16 mmol) in acetonitrile (9 mL) and H₂O (1 mL) was added 1,1,3,3-tetramethylguanidine (1.49 g, 13.0 mmol) and N-hydroxyacetamide (487 mg, 6.49 mmol). This reaction mixture was stirred at 60° C. for 12 h. The reaction mixture was filtered and concentrated in vacuum to give a residue which was purified by flash silica gel chromatography to afford 2-12 (300 mg, 57% yield) as a yellow solid. LCMS: 245.1 [M+H]⁺.

Step 10: To a solution of 2-12 (100 mg, 0.410 mmol) in DMF (2 mL) was added t-BuOK (138 mg, 1.23 mmol) and 2-6 (107.03 mg, 0.45 mmol) in THF (1 mL) at 0° C. This reaction mixture was stirred at 25° C. for 1 h. This reaction mixture was concentrated in vacuum to give a residue which was further purified by Prep-HPLC to afford Compound 2 (5.88 mg, 22% yield) as a white solid. LCMS: 446.1 [M+H]⁺. ¹H NMR (400 MHz, CDCl₃) δ 8.17 (s, 1H), 8.12 (d, J=6.0 Hz, 1H), 7.59 (s, 1H), 7.45 (s, 1H), 6.81 (s, 1H), 6.59 (d, J=6.0 Hz, 1H), 6.50 (s, 1H), 6.34 (s, 1H), 5.41 (s, 2H), 3.97 (s, 9H).

Example 3: Synthesis of N-(6-((1H-pyrazol-1-yl)methyl)-4-(difluoromethoxy)benzo[d]isoxazol-3-yl)-2,6-dimethoxybenzenesulfonamide (Compound 3)

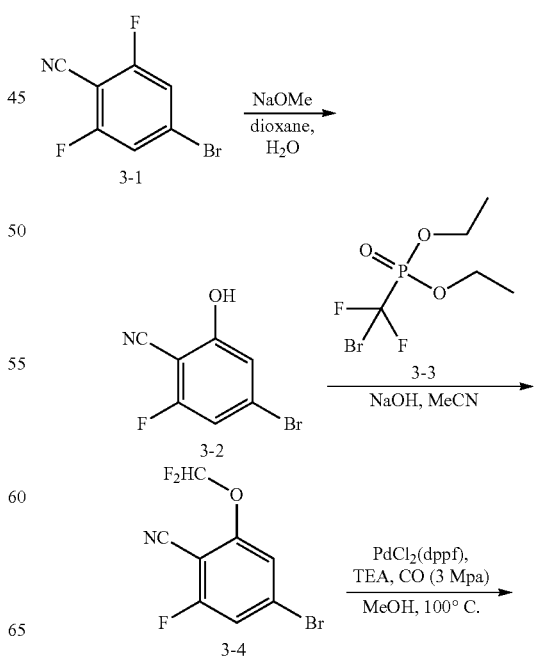

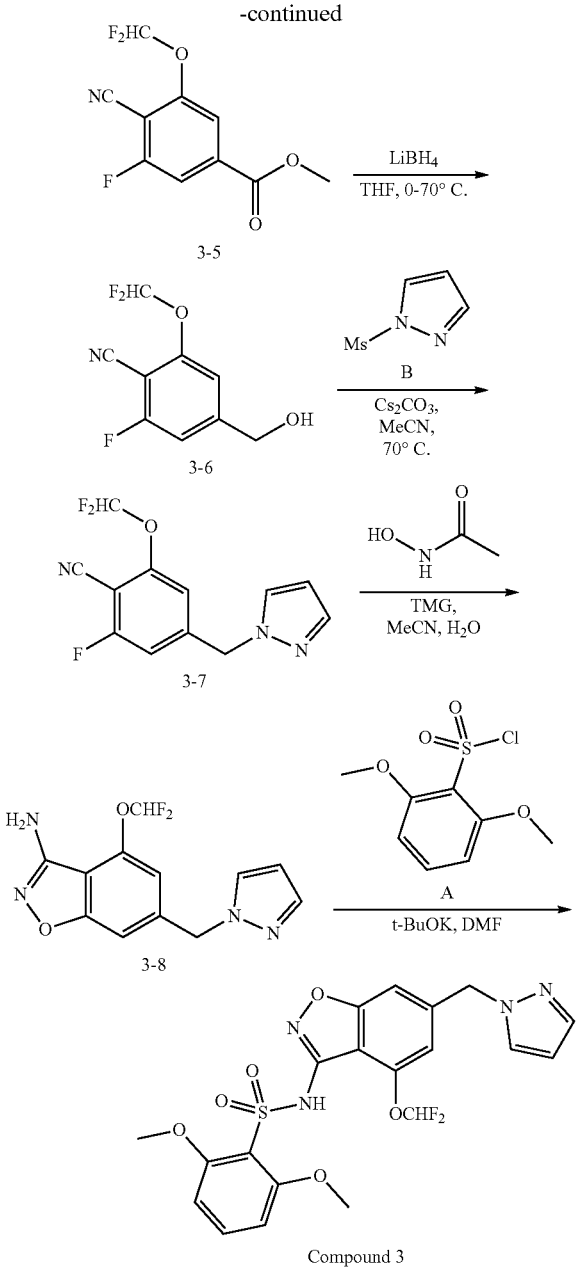

Na₂SO₄, filtered, and concentrated. The residue was purified by flash silica gel chromatography to give 3-4 (1.02 g, 39% yield) as a colorless oil.

Step 3: To a solution of 3-4 (1.02 g, 3.59 mmol) in MeOH (20 mL) were added Pd(dppf)Cl$_2$ (526 mg, 0.72 mmol) and TEA (1.49 mL, 10.77 mmol). The reaction mixture was stirred at 100° C. for 18 h under CO (3 MPa) atmosphere. Then the reaction mixture was filtered through a pad of celite. The filtrate was concentrated. The residue was purified by flash silica gel chromatography to give 3-5 (630 mg, 72% yield) as a colorless oil.

Step 4: To a solution of 3-5 (630 mg, 2.58 mmol) in THF (10 mL) were added LiBH$_4$ (170 mg, 7.74 mmol) at 0° C. The reaction mixture was stirred at 70° C. for 2 h. The reaction mixture was quenched by Na$_2$SO$_4$·10H$_2$O and filtered. The filtrate was concentrated. The residue was purified by flash silica gel chromatography to give 3-6 (380 mg, 68% yield) as a green oil.

Step 5: To a solution of 3-6 (380 mg, 1.76 mmol) in acetonitrile (5 mL) were added Compound B (308 mg, 2.11 mmol) and Cs$_2$CO$_3$ (688 mg, 2.11 mmol). The reaction mixture was stirred at 70° C. for 2 h. Then the reaction mixture was concentrated. The residue was purified by flash silica gel chromatography to give 3-7 (220 mg, 47% yield) as an orange oil. LCMS: 268.0 [M+H]⁺.

Step 6: To a solution of 3-7 (220 mg, 0.82 mmol) in acetonitrile (5 mL) and water (0.5 mL) were added N-hydroxyacetamide (185 mg, 2.46 mmol) and 1,1,3,3-tetramethylguanidine (566 mg, 0.56 mL, 4.92 mmol). The reaction was stirred at 60° C. for 3 h. Then the reaction mixture was concentrated. The residue was purified by flash silica gel chromatography to afford 3-8 (150 mg, 47% yield) as a green solid. LCMS: 281.0 [M+H]⁺.

Step 7: To a solution of 3-8 (150 mg, 0.54 mmol) in THF (3 mL) were added t-BuOK (182 mg, 1.62 mmol) at 0° C. and the mixture was stirred for 10 min. Then Compound A (255 mg, 1.08 mmol) was added, and the reaction mixture was stirred at room temperature for 1 h. The reaction mixture was concentrated in vacuo. The residue was purified by Prep-HPLC to give Compound 3 (22 mg, 9% yield) as a white solid. LCMS: 481.1 [M+H]⁺. ¹H NMR (400 MHz, DMSO-d₆) δ 10.24 (s, 1H), 7.89 (d, J=2.0 Hz, 1H), 7.54-7.46 (m, 2H), 7.29 (t, J=72 Hz, 1H), 7.22 (s, 1H), 7.00 (s, 1H), 6.77 (d, J=8.8 Hz, 2H), 6.31 (t, J=2.0 Hz, 1H), 5.51 (s, 2H), 3.75 (s, 6H). ¹⁹F NMR (376 MHz, DMSO-d₆) δ −83.46 (s).

Example 4: Synthesis of N-(6-((1H-pyrazol-1-yl)methyl)-4-(2,2,2-trifluoroethoxy)benzo[d]isoxazol-3-yl)-2,6-dimethoxybenzenesulfonamide (Compound 4)

Step 1: To a solution of 3-1 (10.00 g, 45.87 mmol) in dioxane (100 mL) and H$_2$O (100 mL) was added NaOH (11.00 g, 275.22 mmol). The mixture was stirred at 60° C. for 6 h. The reaction mixture was adjusted to pH=5-6 by aqueous HCl (1 M). The aqueous layer was back extracted with DCM (50 mL×3). The DCM layer was dried with Na$_2$SO$_4$, filtered, and concentrated under reduced pressure. The residue was purified by flash silica gel chromatography to give 3-2 (7.8 g, 79% yield) as a white solid.

Step 2: To a solution of 3-2 (2.0 g, 9.26 mmol) in acetonitrile (20 mL) and H$_2$O (20 mL) was added NaOH (14.84 g, 370 mmol) at −20° C. 3-3 (4.94 g, 18.52 mmol, 3.18 mL) was then added and the reaction mixture was stirred at 0° C. for 4 h. The reaction mixture was quenched with water (50 mL). The aqueous layer was back extracted with DCM (50 mL×3). The combined DCM layer was washed with saturated NaCl solution (25 mL×2), dried over

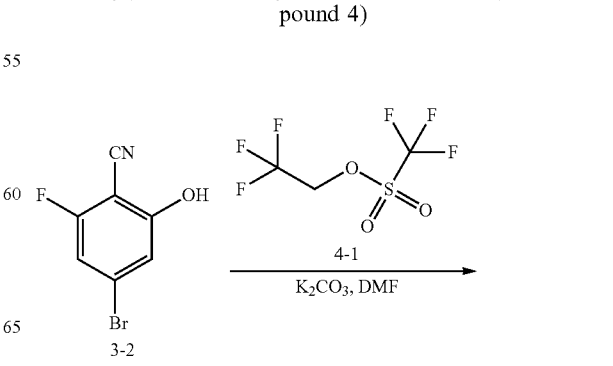

-continued

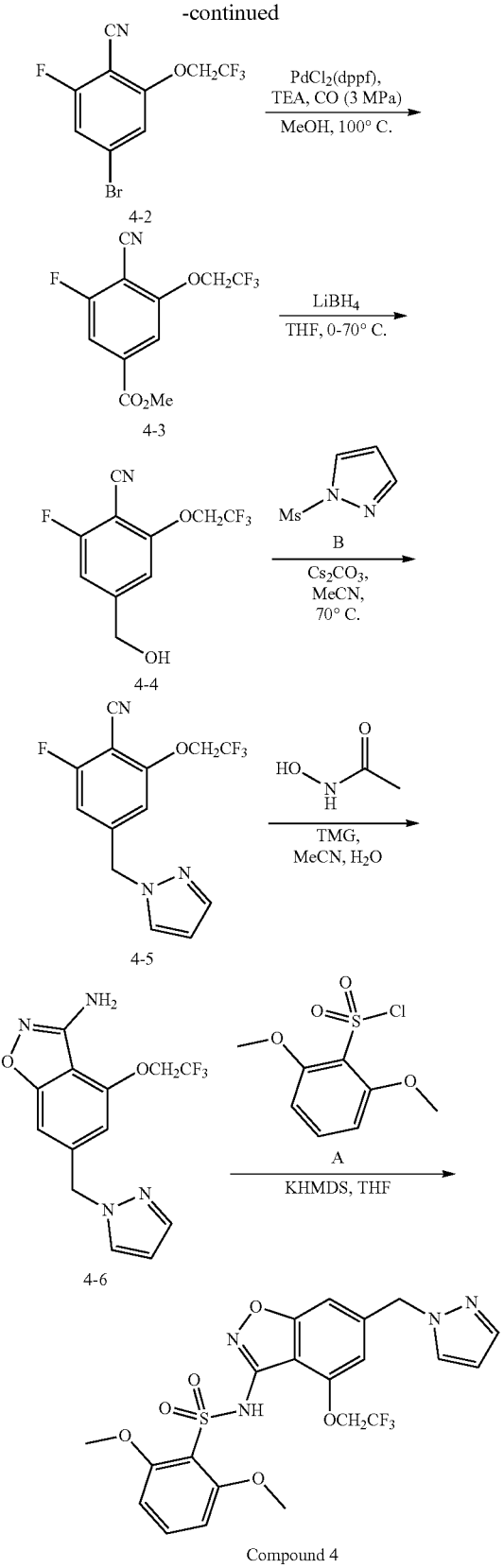

stirred at 25° C. for 1 h. The reaction mixture was quenched with water (60 mL), diluted with ethyl acetate (20 mL×3), washed with saturated NaCl (20 mL×3), dried over $Na_2SO_4$, filtered, and concentrated under reduced pressure. The residue was purified by flash silica gel chromatography to give 4-2 (3.8 g, 92% yield) as a white solid.

Step 2: To a solution of 4-2 (3.8 g, 12.79 mmol) in MeOH (40 mL) were added TEA (3.88 g, 38.38 mmol, 5.3 mL) and $Pd(dppf)Cl_2$ (936.02 mg, 1.28 mmol). The mixture was stirred at 100° C. for 16 h under CO (3 MPa) atmosphere. The reaction mixture was concentrated under reduced pressure. The residue was purified by flash silica gel chromatography to give 4-3 (2.9 g, 83% yield) as a white solid.

Step 3: To a solution of 4-3 (2.9 g, 10.58 mmol) in THF (50 mL) was added $LiBH_4$ (691.03 mg, 31.73 mmol) at 0° C. The mixture was stirred at 70° C. for 2 h. The reaction mixture was concentrated under reduced pressure. The residue was purified by flash silica gel chromatography to afford 4-4 (1.6 g, 61% yield) as a white solid.

Step 4: To a solution of 4-4 (1.6 g, 6.45 mmol) in ACN (20 mL) was added Compound B (1.13 g, 7.74 mmol) and $Cs_2CO_3$ (2.52 g, 7.74 mmol). The mixture was stirred at 70° C. for 1 h and then concentrated under reduced pressure to give a residue. The residue was purified by flash silica gel chromatography as a yellow solid. LCMS: 300.2 $[M+H]^+$.

Step 5: To a solution of 4-5 (1.2 g, 4.02 mmol) in $ACN/H_2O$ (18 mL/2 mL) were added N-hydroxyacetamide (0.739 mL, 12.07 mmol) and 1,1,3,3-tetramethylguanidine (2.77 g, 24.12 mmol) was added. The mixture was stirred at 60° C. for 3 h and then concentrated under reduced pressure to give a residue. The residue was purified by flash silica gel chromatography to give 4-6 (600 mg, 48% yield) as a white solid. LCMS: 313.0 $[M+H]^+$.

Step 6: To a solution of 4-6 (100 mg, 0.32 mmol) in THF (5 mL) were added potassium bis(trimethylsilyl)amide (1.28 mL, 1.28 mmol, 1 M) at −78° C. The reaction was stirred at −78° C. for 1 h. Then Compound A (113 mg, 0.481 mmol) was added, and the reaction mixture was stirred at −78° C. for 0.5 h. The reaction mixture was concentrated in vacuo. The residue was purified by Prep-HPLC to give Compound 4 (50 mg, 30% yield) as a white solid. LCMS: 513.2 $[M+H]^+$. $^1H$ NMR (400 MHz, DMSO-$d_6$) δ 9.29 (s, 1H), 7.88 (d, J=2.0 Hz, 1H), 7.65-7.43 (m, 2H), 7.02 (s, 1H), 6.95 (s, 1H), 6.78 (d, J=8.4 Hz, 2H), 6.31 (t, J=2.0 Hz, 1H), 5.45 (s, 2H), 4.99 (q, J=8.6 Hz, 2H), 3.76 (s, 6H).

Example 5: Synthesis of N-(6-((1H-pyrazol-1-yl)methyl)-4-(difluoromethoxy)benzo[d]isoxazol-3-yl)-2,4-dimethoxypyridine-3-sulfonamide (Compound 5)

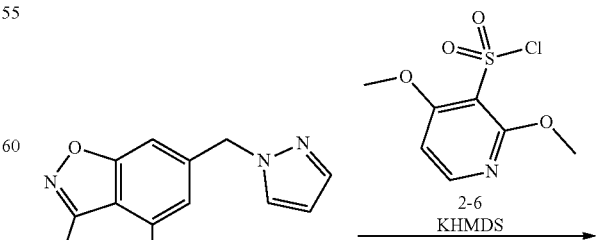

Step 1: To a solution of 3-2 (3.00 g, 13.95 mmol) in anhydrous DMF (25 mL) were added $K_2CO_3$ (5.78 g, 41.85 mmol) and 4-1 (3.017 mL, 20.93 mmol). The mixture was -continued

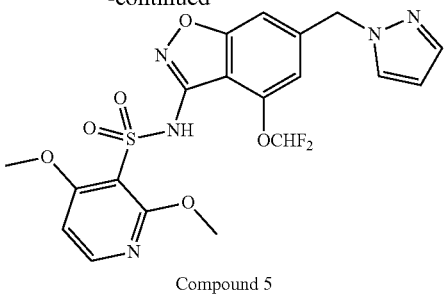

Compound 5

To a solution of 3-8 (90 mg, 0.32 mmol) in THF (10 mL) was added KHMDS (0.184 mL, 1.28 mmol) at −78° C. This reaction mixture was stirred at −78° C. for 1 h. 2-6 (114.49 mg, 0.48 mmol) in THF (1 mL) was added to the mixture and this reaction mixture was stirred at −78° C. for 0.5 h. The reaction mixture was quenched with $Na_2SO_4 \cdot 10H_2O$ and concentrated in vacuum to give a residue which was purified by Prep-HPLC to afford Compound 5 (2.68 mg, 2% yield) as a white solid. LCMS: Rt: 1.057 min; MS m/z (ESI): 482.2 [M+H]$^+$. $^1$H NMR (400 MHz, DMSO-$d_6$) δ 10.74 (s, 1H), 8.19 (s, 1H), 7.89 (d, J=2.0 Hz, 1H), 7.51 (d, J=2.0 Hz, 1H), 7.40-6.70 (m, 4H), 6.31 (s, 1H), 5.49 (s, 2H), 3.79 (s, 6H).

Example 6: Synthesis of N-(6-((1H-pyrazol-1-yl)methyl)-4-(difluoromethoxy)benzo[d]isoxazol-3-yl)-2-methoxybenzenesulfonamide (Compound 6)

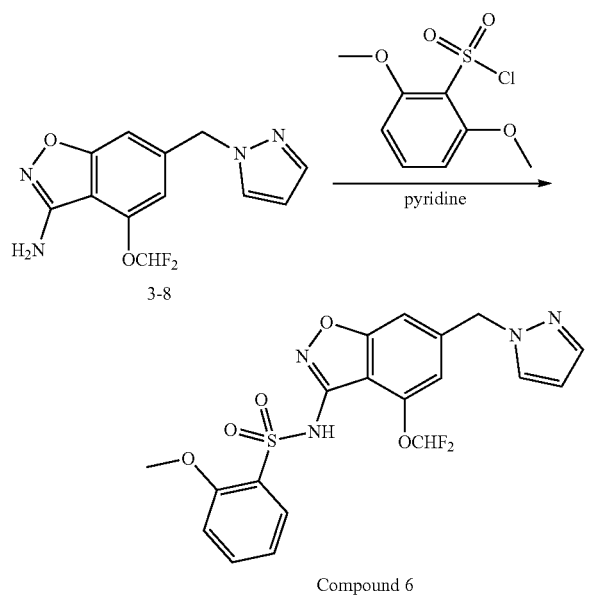

Compound 6

To a solution of 3-8 (100 mg, 0.35 mmol) in pyridine (10 mL) was added 2-methoxybenzenesulfonyl chloride (147 mg, 0.71 mmol). The mixture was stirred at 120° C. for 2 h under $N_2$. The reaction mixture was concentrated in vacuum to give a residue. The residue was purified by Prep-HPLC to afford Compound 6 (38 mg, 8% yield) as a white solid. LCMS: 451.1 [M+H]$^+$. $^1$H NMR (400 MHz, DMSO-$d_6$) δ 10.70 (s, 1H), 7.87 (d, J=2.0 Hz, 1H), 7.79 (dd, J=7.6, 1.6 Hz, 1H), 7.63-7.42 (m, 2H), 7.29-6.74 (m, 5H), 6.30 (t, J=2.0 Hz, 1H), 5.46 (s, 2H), 3.73 (s, 3H).

Example 7: Synthesis of N-(6-((1H-pyrazol-1-yl)methyl)-4-(difluoromethoxy)benzo[d]isoxazol-3-yl)-2-(trifluoromethoxy)benzenesulfonamide (Compound 7)

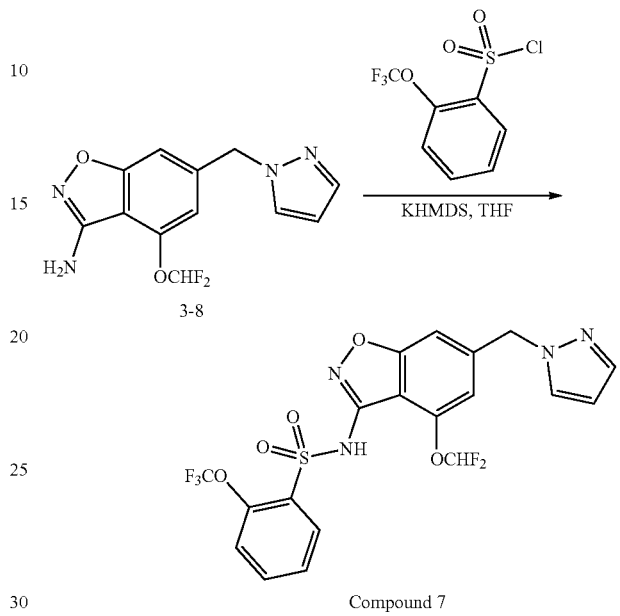

Compound 7

To a solution of 3-8 (120 mg, 0.43 mmol) in tetrahydrofuran (5 mL) was added potassium bis(trimethylsilyl)amide (0.39 mL, 1.71 mmol) at −78° C. for 30 min. 2-(Trifluoromethoxy) benzenesulfonyl chloride (168 mg, 0.64 mmol) was then added, and the reaction mixture was stirred at −78° C. for 20 min. The reaction mixture was diluted with water (15 mL). The aqueous phase was extracted with ethyl acetate (10 mL×2). The combined organic phase was washed by brine (10 mL), dried with anhydrous sodium sulfate, filtered, and concentrated in vacuum to give a residue. The residue was purified by Prep-HPLC to afford Compound 7 (23.0 mg, 11% yield) as a white solid. LCMS: 505.1 [M+H]$^+$. $^1$H NMR (400 MHz, DMSO-$d_6$) δ 8.24 (bs, 1H), 8.07 (t, J=77.6 Hz, 1H), 7.99 (dd, J=8.0, 2.0 Hz, 1H), 7.86 (d, J=2.0 Hz, 1H), 7.53-7.47 (m, 2H), 7.42-7.36 (m, 1H), 7.28 (d, J=8.4 Hz, 1H), 6.94 (s, 1H), 6.70 (s, 1H), 6.29 (t, J=2.0 Hz, 1H), 5.40 (s, 2H).

Example 8: Synthesis of N-(6-((1H-pyrazol-1-yl)methyl)-4-(trifluoromethoxy)benzo[d]isoxazol-3-yl)-2,6-dimethoxybenzenesulfonamide (Compound 8)

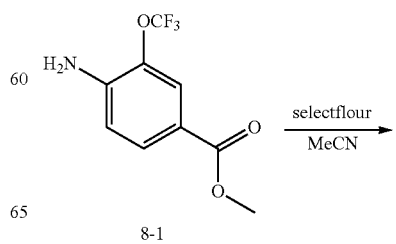

8-1

-continued

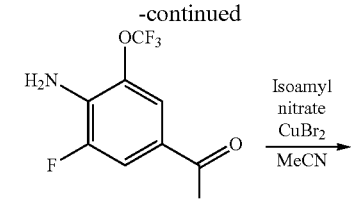

8-2

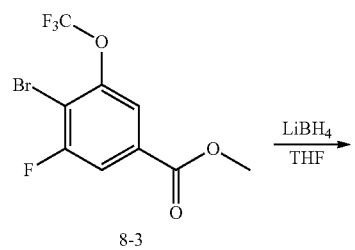

8-3

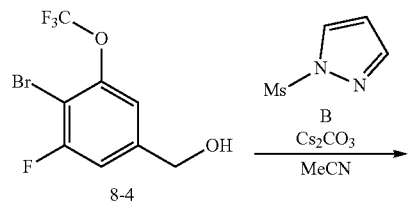

8-4

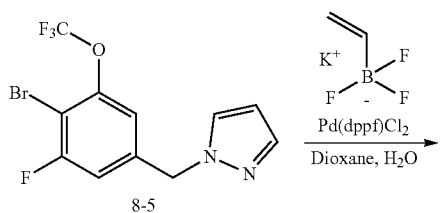

8-5

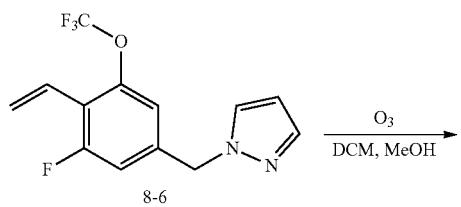

8-6

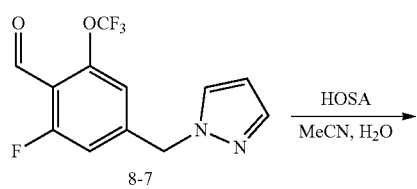

8-7

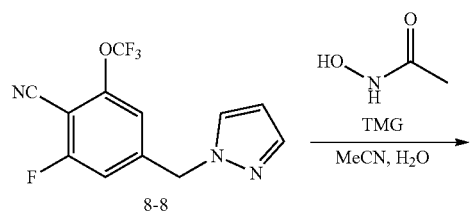

8-8

-continued

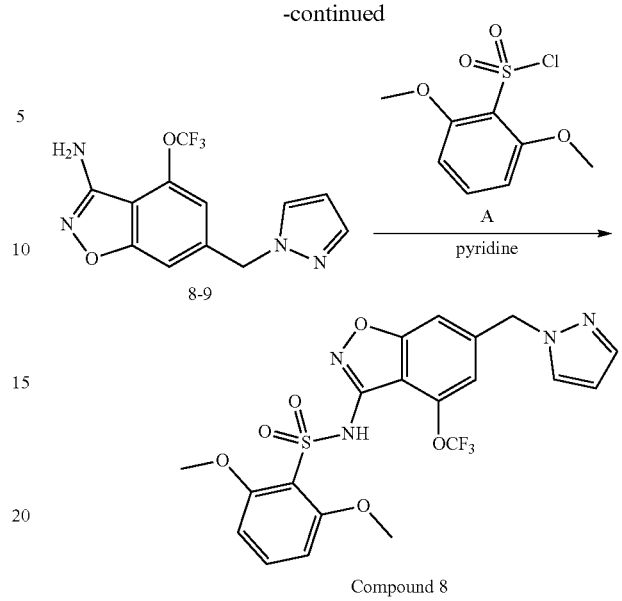

Compound 8

Step 1: To a solution of 8-1 (25 g, 106 mmol) in MeCN (500 mL) was added selectfluor (75.3 g, 213 mmol) at 0° C. The reaction mixture was stirred at 25° C. for 4 h. The reaction mixture was diluted with water (100 mL). The aqueous phase was extracted with ethyl acetate (500 mL×3). The combined organic phase was washed with brine (500 mL), dried over anhydrous sodium sulfate, filtered, and concentrated in vacuum to give crude product which was purified by flash silica gel chromatography to afford 8-2 (4.20 g, 16% yield) as an orange solid.

Step 2: To a solution of 8-2 (1.50 g, 5.93 mmol) in acetonitrile (20 mL) were added $CuBr_2$ (1.59 g, 7.11 mmol) and isopentyl nitrite (1.04 mL, 7.70 mmol). The mixture was stirred at room temperature for 2 h. A saturated sodium bicarbonate solution (30 mL) was then added to the solution. Following extraction with ethyl acetate (50 mL×3), the organic phases were combined, washed with brine, and dried over anhydrous $Na_2SO_4$. The filtrate was concentrated under reduced pressure to give a residue which was purified by flash silica gel chromatography to provide the corresponding 8-3 (800 mg, 46% yield) as a colorless oil.

Step 3: To a solution of 8-3 (2.40 g, 7.57 mmol) in tetrahydrofuran (24 mL) was added $LiBH_4$ (0.49 g, 22.71 mmol) at 0° C. The mixture was stirred at room temperature for 1 h. The reaction mixture was filtered and concentrated in vacuum to give a residue. The residue was purified by flash silica gel chromatography to give 8-4 (1.3 g, 59% yield) as a colorless oil.

Step 4: To a solution of 8-4 (1.3 g, 4.50 mmol) in acetonitrile (13 mL) were added Compound B (0.79 g, 5.40 mmol) and $Cs_2CO_3$ (1.76 g, 5.40 mmol). The mixture was stirred at 70° C. for 2 h. Then the mixture was concentrated under reduced pressure to give a residue. The residue was purified by flash silica gel chromatography to give 8-5 (600 mg, 39% yield) as a white solid. LCMS: 339.1 [M+H]$^+$.

Step 5: To a solution of 8-5 (300 mg, 0.95 mmol) in dioxane (20 mL) and $H_2O$ (3 mL) were added potassium vinyltrifluoroborate (380 mg, 2.84 mmol), $Cs_2CO_3$ (924 mg, 2.84 mmol), and Pd(dppf)Cl$_2$ (70 mg, 0.10 mmol). The reaction mixture was stirred at 100° C. overnight. The reaction mixture was filtered and concentrated in vacuum to give a residue which was purified by flash silica gel chromatography to afford 8-6 (200 mg, 80% yield) as a yellow solid. LCMS: 287.0 [M+H]$^+$.

Step 6: A solution of 8-6 (200 mg, 0.76 mmol) in dichloromethane (5 mL) and methanol (1 mL) at −78° C. under O$_3$ atmosphere for 10 min. Dimethyl sulfide (5 mL) was then added to the solution. The reaction mixture was concentrated in vacuum to give a residue which was purified by flash silica gel chromatography to afford 8-7 (150 mg, 74% yield) as a colorless oil. LCMS: 289.0 [M+H]$^+$.

Step 7: To a solution of 8-7 (150 mg, 0.56 mmol) in acetonitrile (5 mL) and H$_2$O (10 mL) was added hydroxylamine-O-sulfonic acid (191 mg, 1.68 mmol). This reaction mixture was stirred at 80° C. for 24 h. The aqueous phase was extracted with dichloromethane (20 mL×2). The combined organic phase was washed by brine (20 mL), dried with anhydrous sodium sulfate, and filtered. The filtrate was concentrated under reduced pressure and then purified by flash silica gel chromatography to provide the corresponding 8-8 (30 mg, 20% yield) as a colorless oil. LCMS: 286.0 [M+H]$^+$.

Step 8: To a solution of 8-8 (30 mg, 0.11 mmol) in acetonitrile (5 mL) and H$_2$O (1 mL) were added N-hydroxyacetamide (24 mg, 0.32 mmol) and 1,1,3,3-tetramethylguanidine (73 mg, 0.63 mmol). The mixture was stirred at 70° C. for 2 h. Then the reaction mixture was concentrated in vacuum to give a residue which was purified by flash silica gel chromatography to afford 8-9 (20 mg, 64% yield) as a colorless oil. LCMS: 299.0 [M+H]$^+$.

Step 9: To a solution of 8-9 (20 mg, 0.07 mmol) in pyridine (5 mL) were added 2,6-dimethoxybenzenesulfonyl chloride (32 mg, 0.13 mmol). The reaction was stirred at 120° C. for 2 h. The reaction mixture was concentrated. The residue was purified by Prep-HPLC to afford Compound 8 (1.5 mg, 4% yield) as a white solid. LCMS: 499.1 [M+H]$^+$. $^1$H NMR (400 MHz, DMSO-d$_6$) δ 7.88 (s, 1H), 7.50 (s, 1H), 7.18 (t, J=8.0 Hz, 1H), 7.02 (s, 1H), 6.81 (s, 1H), 6.56 (d, J=8.0 Hz, 2H), 6.30 (s, 1H), 5.45 (s, 2H), 3.54 (s, 6H).

Example 9: Synthesis of 2,6-dimethoxy-N-(4-methoxy-6-(pyridin-2-yloxy)benzo[d]isoxazol-3-yl)benzenesulfonamide (Compound 9)

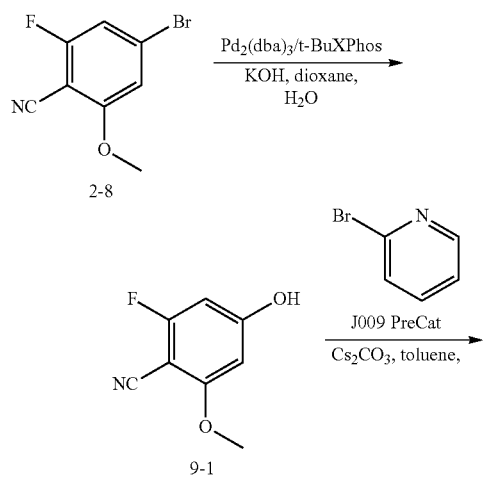

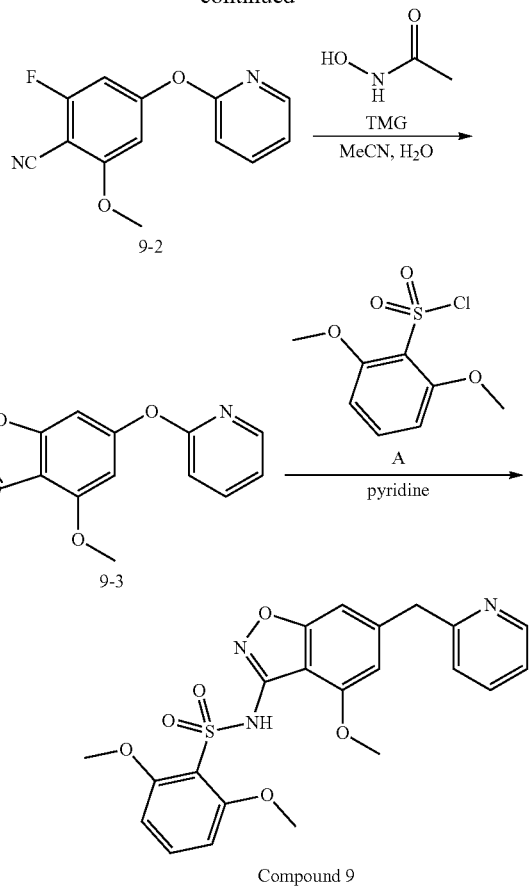

Compound 9

Step 1: To a solution of 2-8 (2.00 g, 8.69 mmol) were added t-BuXPhos (1.11 g, 2.61 mmol), KOH (1.46 g, 26.08 mmol), and Pd$_2$(dba)$_3$ (1.46 g, 26.08 mmol) in dioxane (15 mL) and H$_2$O (15 mL). The reaction mixture stirred at 100° C. for 5 h under N$_2$. Water (30 mL) was added and the mixture was extracted with ethyl acetate (50 mL×3). The combined organic phase was washed by brine (15 mL), dried with anhydrous sodium sulfate, filtered, and concentrated in vacuum to give a residue. The residue was purified by flash silica gel chromatography to give the 9-1 (1.3 g, 89% yield) as a yellow oil. LCMS: 168.1 [M+H]$^+$.

Step 2: To a mixture of 9-1 (200 mg, 1.20 mmol) and 2-bromopyridine (0.344 mL, 3.59 mmol) in toluene (5 mL) were added Cs$_2$CO$_3$ (390 mg, 1.20 mmol) and Josiphos SL-J009-1 Pd G3 (2 mg, 0.12 mmol). The mixture was stirred at 100° C. for 24 h. Water (10 mL) was then added to the mixture. Following extraction with ethyl acetate (20 mL×3), the organic phases were combined, washed with brine, dried over anhydrous Na$_2$SO$_4$, and filtered. The filtrate was concentrated under reduced pressure to give a residue which was purified by flash silica gel chromatography to afford 9-2 (230 mg, 79% yield) as a white solid. LCMS: 245.0 [M+H]$^+$.

Step 3: To a mixture of 9-2 (230 mg, 0.94 mmol), N-hydroxyacetamide (141 mg, 1.88 mmol), and water (0.5 mL) in MeCN (5 mL) was added 1,1,3,3-tetramethylguanidine (0.24 mL, 1.88 mmol). The mixture was stirred at 70° C. for 2 h. Water (10 mL) was added to the mixture. Following extraction with ethyl acetate (20 mL×3), the organic phases were combined, washed with brine, dried over anhydrous Na$_2$SO$_4$, and filtered. The filtrate was concentrated under reduced pressure and then purified by flash silica gel chromatography to afford 9-3 (180 mg, 74% yield) as a brown solid. LCMS: 258.0 [M+H]+.

Step 4: To a mixture of 9-3 (30 mg, 0.12 mmol) in pyridine (2 mL) was added 2,6-dimethoxybenzenesulfonyl chloride (27.60 mg, 0.12 mmol). The mixture was stirred at 120° C. for 1.5 h. The mixture was concentrated to give the crude product which was further purified by Prep-HPLC to afford Compound 9 (14 mg, 26% yield) as a white solid. LCMS: 458.1 [M+H]+. $^1$H NMR (400 MHz, DMSO-$d_6$) δ 9.08 (s, 1H), 8.20 (d, J=3.2 Hz, 1H), 7.92-7.88 (m, 1H), 7.48 (t, J=8.4 Hz, 1H), 7.21-7.18 (m, 1H), 7.11 (d, J=8.4 Hz, 1H), 6.90 (s, 1H), 6.78 (d, J=8.4 Hz, 2H), 6.65 (s, 1H), 3.87 (s, 3H), 3.78 (s, 6H).

Example 10: Synthesis of 7-chloro-1-(2-chlorophenyl)-4-(prop-2-yn-1-ylamino)quinazolin-2(1H)-one (Compound 10)

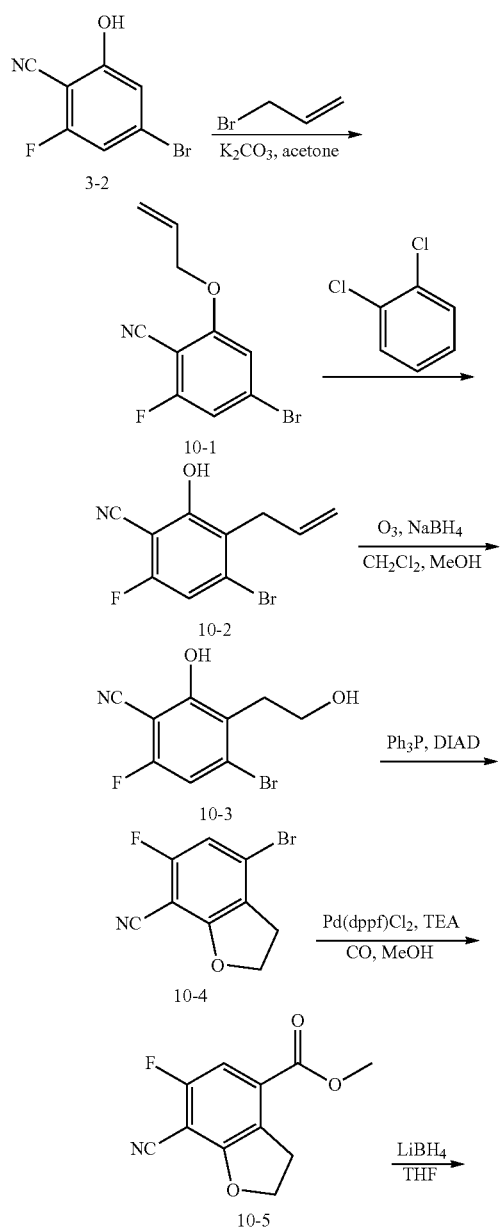

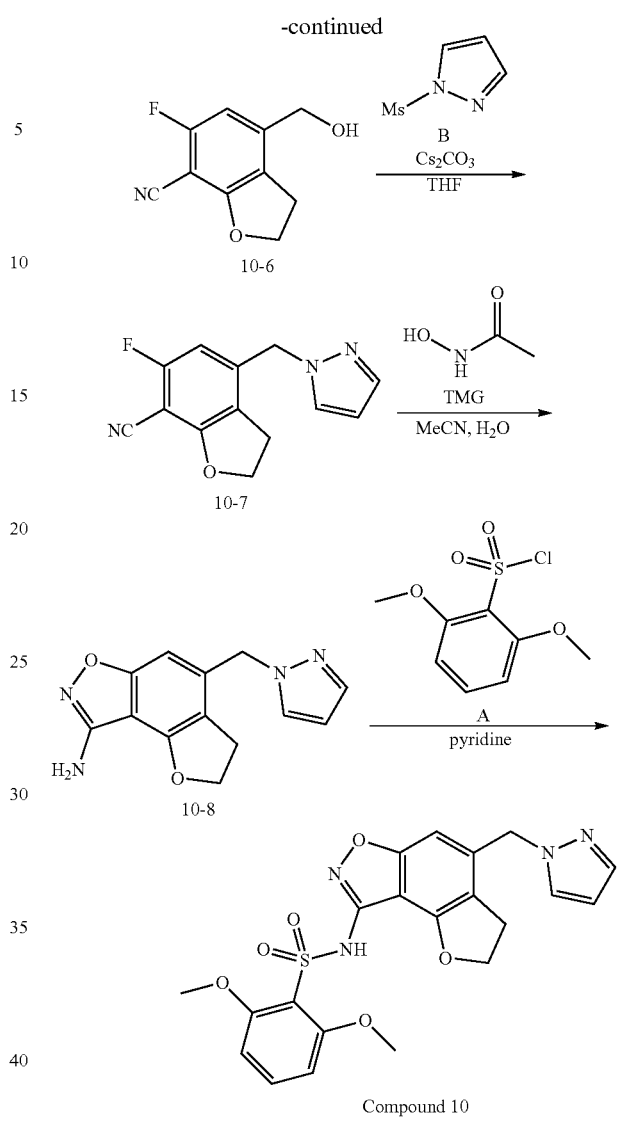

Step 1: To a mixture of 3-2 (2.0 g, 9.26 mmol) and 3-bromoprop-1-ene (1.21 mL, 13.89 mmol) in acetone (30 mL) was added potassium carbonate (3.8 g, 27.78 mmol). The mixture was stirred at 25° C. for 16 h. Water (30 mL) was then added. Following extraction with ethyl acetate (50 mL×3), the organic phases were combined, washed with brine and dried over anhydrous Na$_2$SO$_4$, and filtered. The filtrate was concentrated under reduced pressure to give a residue which was purified by flash silica gel chromatography to afford the 10-1 (1.2 g, 51% yield) as a white solid.

Step 2: A reaction mixture of 10-1 (1.2 g, 4.69 mmol) in 1,2-dichlorobenzene (12 mL) was stirred at 180° C. for 16 h under N$_2$. Water (30 mL) was then added. Following extraction with ethyl acetate (50 mL×3), the organic phases were combined, washed with brine, and dried over anhydrous Na$_2$SO$_4$, and filtered. The filtrate was concentrated under reduced pressure to give a residue which was purified by flash silica gel chromatography to provide the 10-2 (0.6 g, 50%) as a white solid.

Step 3: 10-2 (3.1 g, 12.11 mmol) was dissolved in DCM (30 mL) and MeOH (30 mL). The solution was cooled to −78° C. and treated with O$_3$ until a pale blue color persists. O$_2$ was bubbled through the mixture for 5 min, then NaBH$_4$ (920 mg, 24.22 mmol) was added slowly. The mixture was warmed to room temperature slowly over 15 min. The mixture was diluted with ethyl acetate (30 mL), and washed with 1N HCl (50 mL), sat. NaHCO$_3$ (50 mL), and brine. The organic solution was dried over Na$_2$SO$_4$ and filtered. The filtrate was concentrated to give 10-3 (1.78 g, 57% yield) as a brown oil. LCMS: 258.2 [M+H]$^+$.

Step 4: To a mixture of 10-3 (1.78 g, 6.86 mmol) and PPh$_3$ (2.70 g, 10.28 mmol) in THF (20 mL) was added DIAD (2.04 mL, 10.28 mmol). The mixture was stirred at 0° C. for 0.5 h. Water (30 mL) was then added. Following extraction with ethyl acetate (50 mL×3), the organic phases were combined, washed with brine, dried over anhydrous Na$_2$SO$_4$, and filtered. The filtrate was concentrated under reduced pressure and then purified by flash silica gel chromatography to afford 10-4 (1.2 g, 72% yield) as a white solid.

Step 5: To a mixture of 10-4 (0.06 g, 0.25 mmol) and TEA (0.052 mL, 0.37 mmol) in MeOH (10 mL) was added Pd(dppf)Cl$_2$ (0.02 g, 0.02 mmol). The mixture was stirred at 70° C. under CO (3 MPa) atmosphere for 16 h. Water (5 mL) was then added. Following extraction with ethyl acetate (10 mL×3), the organic phases were combined, washed with brine, dried over anhydrous Na$_2$SO$_4$, and filtered. The filtrate was concentrated under reduced pressure to give a residue which was purified by flash silica gel chromatography to afford 10-5 (30 mg, 54% yield) as a white solid.

Step 6: To a mixture of 10-5 (0.42 g, 1.90 mmol) in THF (8 mL) was added LiBH$_4$ (0.08 g, 3.80 mmol) at 0° C. The reaction mixture was stirred at 70° C. for 2 h. Water (10 mL) was added, and the mixture was extracted with ethyl acetate (10 mL×3), washed with brine, dried over anhydrous Na$_2$SO$_4$, and concentrated to give 10-6 (360 mg, 98% yield) as a colorless oil. LCMS: 194.0 [M+H]$^+$.

Step 7: To a mixture of 10-6 (0.18 g, 0.93 mmol), Compound B (0.16 g, 1.12 mmol) in acetonitrile (4 mL) was added Cs$_2$CO$_3$ (0.36 g, 1.12 mmol). The reaction mixture was stirred at 70° C. for 2 h. Water (30 mL) was then added. Following extraction with ethyl acetate (50 mL×3), the organic phases were combined, washed with brine, dried over anhydrous Na$_2$SO$_4$, and filtered. The filtrate was concentrated under reduced pressure to give a residue which was purified by flash silica gel chromatography to provide the 10-7 (110 mg, 36% yield) as a white solid. LCMS: 243.9 [M+H]$^+$.

Step 8: To a mixture of 10-7 (55 mg, 0.23 mmol), N-hydroxyacetamide (51 mg, 0.68 mmol), and water (0.1 mL) in MeCN (0.9 mL) was added 1,1,3,3-tetramethylguanidine (0.18 mL, 1.36 mmol). The reaction mixture was stirred at 60° C. for 16 h. Water (10 mL) was then added. Following extraction with ethyl acetate (20 mL×3), the organic phases were combined, washed with brine, dried over anhydrous Na$_2$SO$_4$, and filtered. The filtrate was concentrated under reduced pressure to give a residue which was purified by flash silica gel chromatography to afford 10-8 (20 mg, 33% yield) as a brown solid. LCMS: 257.1 [M+H]$^+$.

Step 9: To a mixture of 10-8 (20 mg, 0.078 mmol) in pyridine (2 mL) was added Compound A (37 mg, 0.156 mmol). The reaction mixture was stirred at 120° C. for 1.5 h and then concentrated. The residue obtained was purified by Prep-HPLC to afford Compound 10 (1.0 mg, 3% yield) as a white solid. LCMS: 457.1 [M+H]$^+$. $^1$H NMR (400 MHz, DMSO-d$_6$) δ 8.26 (s, 1H), 7.79 (d, J=2.4 Hz, 1H), 7.48 (d, J=1.2 Hz, 1H), 7.26 (t, J=7.4 Hz, 1H), 6.62 (d, J=8.4 Hz, 2H), 6.41 (s, 1H), 6.28 (t, J=2.0 Hz, 1H), 5.34 (s, 2H), 4.66 (t, J=8.8 Hz, 2H), 3.61 (s, 6H), 3.06 (t, J=8.8 Hz, 2H).

Example 11: Synthesis of N-(6-((1H-pyrazol-1-yl)methyl)-4-methoxybenzo[d]isoxazol-3-yl)-2,4-dimethoxy-6-methylpyridine-3-sulfonamide (Compound 11)

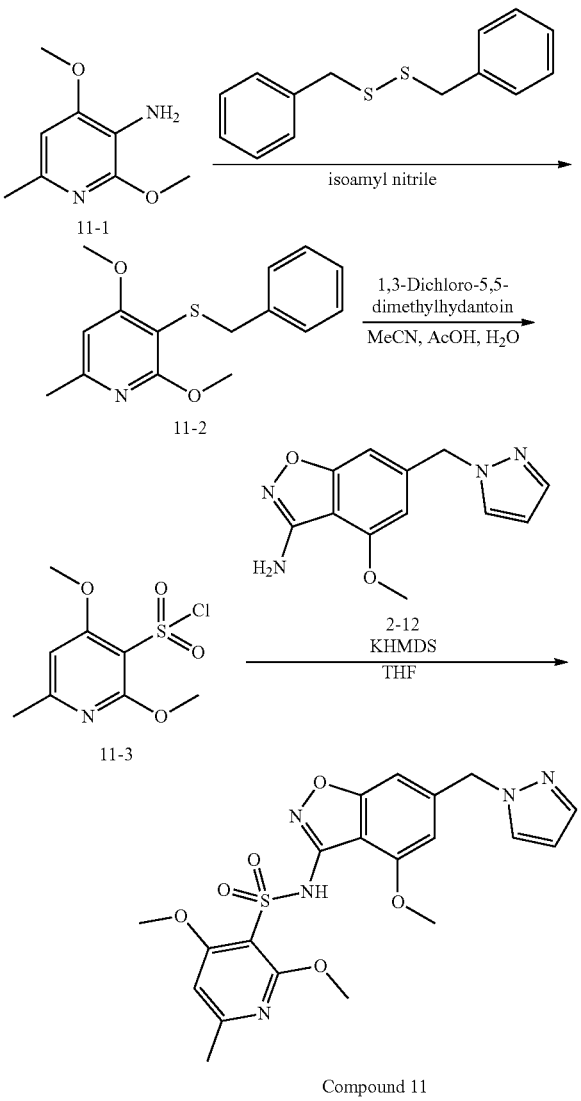

Compound 11

Step 1: To a mixture of 11-1 (10.0 g, 59.5 mmol) in MeCN (100 mL) were added dibenzyl disulfide (29.3 g, 119 mmol) and L(+)-Ascorbic acid (5.24 g, 29.8 mmol). Then isoamyl nitrite (25.8 g, 220 mmol) was added to this reaction mixture at 0° C. and the reaction mixture was stirred at 25° C. for 12 h. This reaction mixture was concentrated under reduced pressure and the obtained residue was purified by flash silica gel chromatography to afford 11-2 (4.4 g, 27% yield) as a yellow oil. LCMS: 276.1 [M+H]$^+$.

Step 2: To a mixture of 11-2 (1.00 g, 3.63 mmol) in MeCN (20 mL), AcOH (2.5 mL) and water (5 mL) was added 1,3-Dichloro-5,5-dimethylhydantoin (858 mg, 4.36 mmol) at −15° C. This reaction mixture was warmed to 25° C. with stirring for 1 h. Water (10 mL) was added to the mixture. Following extraction with DCM (20 mL×3), the organic phases were combined, washed with brine, dried over anhydrous Na$_2$SO$_4$, and filtered. The filtrate was concentrated under reduced pressure. The residue was purified by flash silica gel chromatography to afford 11-3 (660 mg, 72% yield) as a white solid. LCMS: 251.9 [M+H]⁺.

Step 3: To a mixture of 2-12 (18 mg, 0.08 mmol) in THF (5 mL) was added KHMDS (0.15 mL, 0.15 mmol) at −78° C. The mixture was stirred at −78° C. for 0.5 h. 11-3 (29 mg, 0.11 mmol) in THF (1 mL) was added to this mixture and this reaction mixture was stirred at −78° C. for 1.5 h. The mixture was concentrated to give the crude product which was further purified by Prep-HPLC to afford Compound 11 (5 mg, 15% yield). LCMS: 460.3 [M+H]⁺. ¹H NMR (400 MHz, DMSO-$d_6$) δ 7.84 (d, J=2.0 Hz, 1H), 7.46 (d, J=2.0 Hz, 1H), 6.73-6.60 (m, 3H), 6.27 (t, J=2.0 Hz, 1H), 5.39 (s, 2H), 3.81 (s, 3H), 3.71 (s, 6H), 2.31 (s, 3H).

Example 12: Synthesis of N-(6-((1H-pyrazol-1-yl)methyl)-4-(trifluoromethoxy)benzo[d]isoxazol-3-yl)-2-methoxybenzenesulfonamide (Compound 12)

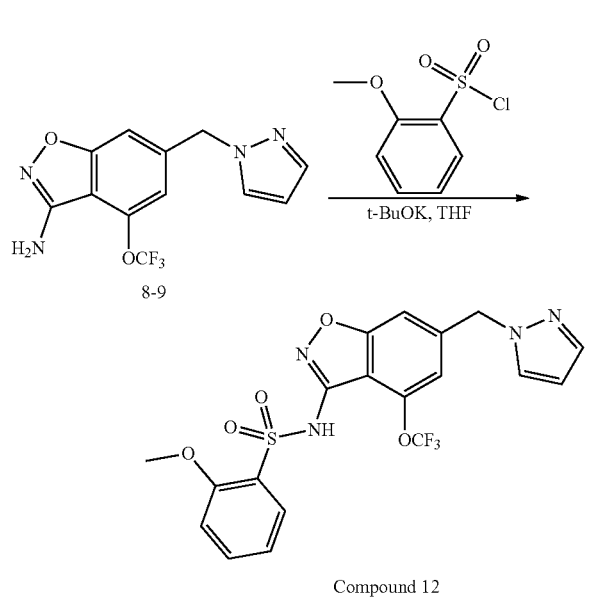

Compound 12

Step 1: To a mixture of 8-9 (20 mg, 0.07 mmol) in THF (3 mL) was added t-BuOK (21 mg, 0.20 mmol) at 0° C. and the mixture was stirred at this temperature for 0.5 h. Then 2-methoxybenzenesulfonyl chloride (21 mg, 0.10 mmol) was added and this reaction mixture was stirred at room temperature for 2 h. The mixture was concentrated to give the crude product which was further purified by Prep-HPLC to afford Compound 12 (2 mg, 6% yield). LCMS: 469.1 [M+H]⁺.

Example 13: Synthesis of N-(6-((1H-pyrazol-1-yl)methyl)-4-methoxyisoxazolo[5,4-b]pyridin-3-yl)-2,6-dimethoxybenzenesulfonamide (Compound 13)

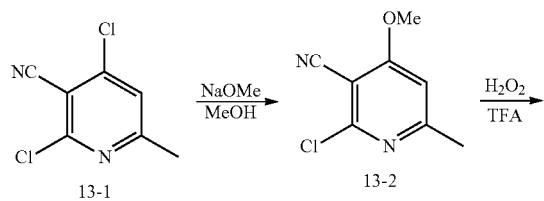

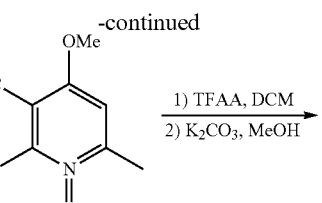

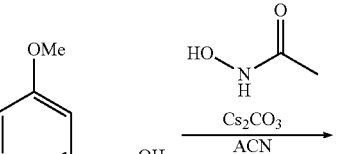

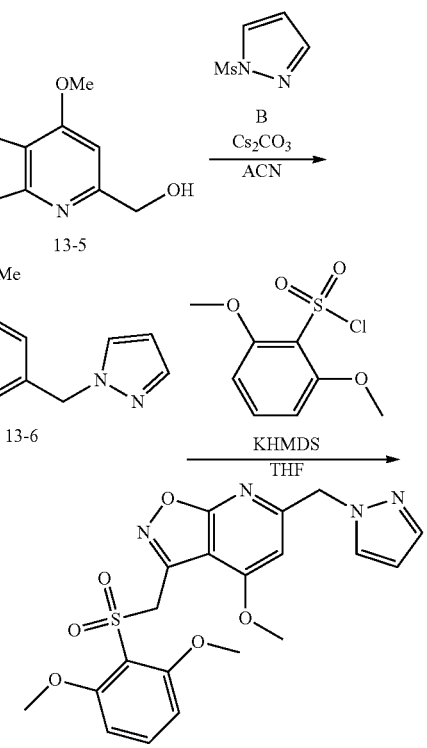

Compound 13

Step 1: To a solution of 13-1 (10.0 g, 53.5 mmol) in MeOH (100 mL) was added NaOMe (5.78 g, 107 mmol) at 0° C. The reaction mixture was stirred at 40° C. for 5 h under $N_2$. Water (100 mL) was added and the mixture was extracted with DCM (200 mL×3). The combined organic phase was washed with brine, dried over anhydrous $Na_2SO_4$, filtered, and concentrated in vacuum to afford 13-2 (5.0 g, 51%) as a white solid. LCMS: 183.1 [M+H]⁺.

Step 2: To a solution of 13-2 (2.1 g, 11.5 mmol) in TFA (25 mL) were added $H_2O_2$ (3.91 g, 34.5 mmol, 30%). The reaction mixture was stirred at 70° C. for 1 h. Water (50 mL) was added and the mixture was extracted with DCM (50 mL×3). The combined organic phase was washed with brine, dried over anhydrous $Na_2SO_4$, filtered, and concentrated in vacuum. The residue was purified by flash silica gel chromatography to afford 13-3 (1.6 g, 70%) as a white solid. LCMS: 199.0 [M+H]⁺.

Step 3: To a solution of 13-3 (900 mg, 4.5 mmol) in DCM (10 mL) were added TFAA (2.86 g, 22.7 mmol) at 0° C. The reaction mixture was stirred at 25° C. for 3 h. This reaction mixture was concentrated in vacuum to give a residue. To this residue were added MeOH (10 mL) and $K_2CO_3$ (3.13 g, 22.7 mmol). The reaction mixture was stirred at 25° C. for 1 h. Water (20 mL) was added and the mixture was extracted with DCM (20 mL×3). The combined organic phase was washed with brine, dried over anhydrous $Na_2SO_4$, filtered, and concentrated in vacuum. The residue was purified by flash silica gel chromatography to afford 13-4 (280 mg, 31%) as a white solid. LCMS: 199.3 $[M+H]^+$.

Step 4: To a solution of 13-4 (280 mg, 1.41 mmol) in MeCN (4 mL) were added N-hydroxyacetamide (318 mg, 4.23 mmol) and $Cs_2CO_3$ (1.38 g, 4.23 mmol). The reaction mixture was stirred at 25° C. for 3 h. This reaction mixture was concentrated. The residue was purified by flash silica gel chromatography to afford 13-5 (150 mg, 54%) as a white solid. LCMS: 196.2 $[M+H]^+$.

Step 5: To a solution of 13-5 (150 mg, 0.77 mmol) in MeCN (4 mL) were added B (135 mg, 0.923 mmol) and $Cs_2CO_3$ (301 mg, 0.923 mmol). The reaction mixture was stirred at 70° C. for 1 h. This reaction mixture was filtered and concentrated in vacuum. The residue was purified by flash silica gel chromatography to afford 13-6 (28 mg, 8%) as a white solid. LCMS: 246.1 $[M+H]^+$.

Step 6: To a mixture of 13-6 (20 mg, 0.08 mmol) in THF (5 mL) was added KHMDS (0.12 mL, 0.12 mmol) at −78° C. The mixture was stirred at −78° C. for 0.5 h. A (28.9 mg, 0.12 mmol) in THF (1 mL) was added to this mixture and this reaction mixture was stirred at −78° C. for 1.5 h. The mixture was concentrated to give the crude product which was further purified by Prep-HPLC to afford Compound 13 (5 mg, 13% yield). LCMS: 446.2 $[M+H]^+$. $^1$H NMR (400 MHz, DMSO-$d_6$) δ 8.29 (s, 1H), 7.87 (s, 1H), 7.49 (s, 1H), 7.23 (t, J=8.0 Hz, 1H), 6.60 (d, J=8.4 Hz, 2H), 6.49 (s, 1H), 6.30 (s, 1H), 5.40 (s, 2H), 3.87 (s, 3H), 3.58 (s, 6H).

Example 14: Synthesis of N-(5-((1H-pyrazol-1-yl)methyl)-3,4-dihydro-2H-chromeno [8,7-d]isoxazol-9-yl)-2,6-dimethoxybenzenesulfonamide (Compound 14)

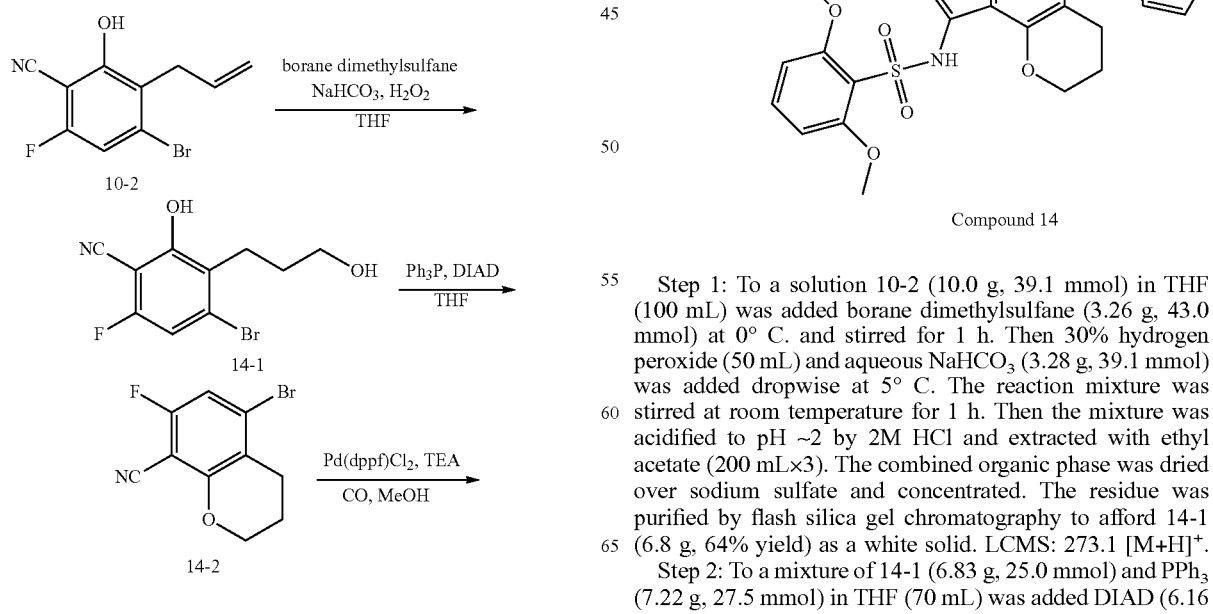

Compound 14

Step 1: To a solution 10-2 (10.0 g, 39.1 mmol) in THF (100 mL) was added borane dimethylsulfane (3.26 g, 43.0 mmol) at 0° C. and stirred for 1 h. Then 30% hydrogen peroxide (50 mL) and aqueous $NaHCO_3$ (3.28 g, 39.1 mmol) was added dropwise at 5° C. The reaction mixture was stirred at room temperature for 1 h. Then the mixture was acidified to pH ~2 by 2M HCl and extracted with ethyl acetate (200 mL×3). The combined organic phase was dried over sodium sulfate and concentrated. The residue was purified by flash silica gel chromatography to afford 14-1 (6.8 g, 64% yield) as a white solid. LCMS: 273.1 $[M+H]^+$.

Step 2: To a mixture of 14-1 (6.83 g, 25.0 mmol) and $PPh_3$ (7.22 g, 27.5 mmol) in THF (70 mL) was added DIAD (6.16 mL, 35.0 mmol) at 0° C. The mixture was stirred at room temperature overnight. Water (60 mL) was added. Following extraction with ethyl acetate (50 mL×3), the organic phases were combined, washed with brine, dried over anhydrous Na$_2$SO$_4$, and filtered. The filtrate was concentrated in vacuum to give the crude product which was purified by flash silica gel chromatography to afford 14-2 (4.0 g, 64% yield) as a white solid.

Step 3: To a mixture of 14-2 (4.0 g, 15.8 mmol) and TEA (6.5 mL, 47.3 mmol) in MeOH (40 mL) was added Pd(dppf)Cl$_2$ (1.2 g, 1.6 mmol). The mixture was stirred at 100° C. under CO (3 MPa) atmosphere for 16 h. The mixture was concentrated under reduced pressure to give a residue which was purified by flash silica gel chromatography to afford 14-3 (2.1 g, 55% yield) as a white solid.

Step 4: To a mixture of 14-3 (2.05 g, 8.72 mmol) in THF (20 mL) was added LiBH$_4$ (576 mg, 26.2 mmol) at 0° C. The reaction mixture was stirred at 70° C. for 2 h. Water (30 mL) was added and the mixture was extracted with ethyl acetate (50 mL×3). The combined organic phase was washed with brine, dried over anhydrous Na$_2$SO$_4$, and concentrated in vacuum to give the crude product which was purified by flash silica gel chromatography to afford 14-4 (1.52 g, 84% yield) as a colorless oil. LCMS: 208.2 [M+H]$^+$.

Step 5: To a mixture of 14-4 (1.52 g, 7.34 mmol), Compound B (1.28 g, 8.81 mmol) in MeCN (15 mL) was added Cs$_2$CO$_3$ (2.87 g, 8.81 mmol). The reaction mixture was stirred at 70° C. for 2 h. Water (50 mL) was added and the mixture was extracted with ethyl acetate (50 mL×3). The combined organic phase was washed with brine, dried over anhydrous Na$_2$SO$_4$, and concentrated to give the crude product which was purified by flash silica gel chromatography to afford 14-5 (1.56 g, 82% yield) as a white solid. LCMS: 258.2 [M+H]$^+$.

Step 6: To a mixture of 14-5 (1.56 g, 6.07 mmol), N-hydroxyacetamide (1.36 g, 18.21 mmol), and water (1.5 mL) in MeCN (15 mL) was added 1,1,3,3-tetramethylguanidine (4.2 mL, 36.42 mmol). The reaction mixture was stirred at 60° C. for 16 h. Water (20 mL) was added and the mixture was extracted with ethyl acetate (50 mL×3). The combined organic phase was washed with brine, dried over anhydrous Na$_2$SO$_4$, and concentrated to give the crude product which was purified by flash silica gel chromatography to provide 14-6 (1.22 g, 75% yield) as a brown solid. LCMS: 271.3 [M+H]$^+$.

Step 7: To a mixture of 14-6 (50 mg, 0.19 mmol) in pyridine (3 mL) was added A (109 mg, 0.46 mmol). The reaction mixture was stirred at 120° C. for 1.5 h. The reaction mixture was concentrated. The residue was purified by Prep-HPLC to afford Compound 14 (5.1 mg, 2% yield). LCMS: 471.2 [M+H]$^+$. $^1$H NMR (400 MHz, DMSO-d$_6$) δ 9.42 (s, 1H), 7.78 (d, J=2.0 Hz, 1H), 7.53-7.44 (m, 2H), 6.77 (d, J=8.4 Hz, 2H), 6.43 (s, 1H), 6.31 (t, J=2.0 Hz, 1H), 5.41 (s, 2H), 4.26 (t, J=4.8 Hz, 2H), 3.78 (s, 6H), 2.69 (t, J=6.4 Hz, 2H), 2.05-1.96 (m, 2H).

Example 15: Synthesis of N-(5-((1H-pyrazol-1-yl)methyl)-3,4-dihydro-2H-chromeno [8,7-d]isoxazol-9-yl)-2-methoxybenzenesulfonamide (Compound 15)

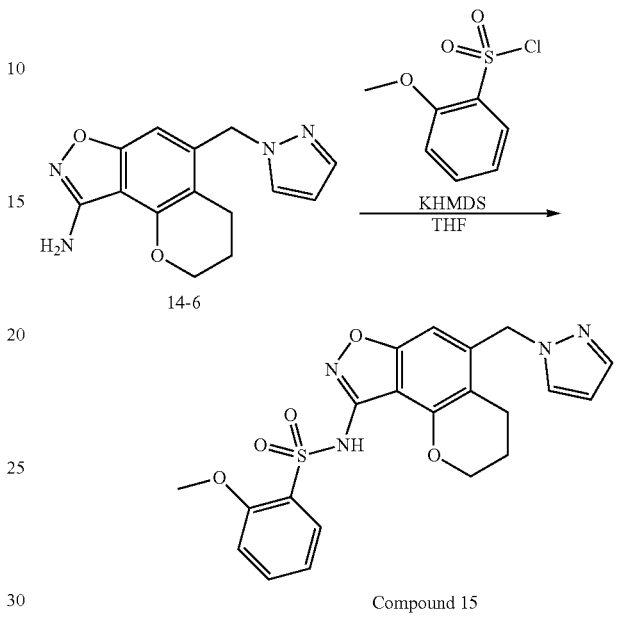

Compound 15

Step 1: To a mixture of 14-6 (30 mg, 0.11 mmol) in THF (5 mL) were added KHMDS (0.17 mL, 0.17 mmol) at −78° C. and the mixture was stirred at this temperature for 30 min. Then 2-methoxybenzenesulfonyl chloride (46 mg, 0.22 mmol) was added. The reaction mixture was stirred at −78° C. for 2 h. The mixture was concentrated to give the crude product which was further purified by Prep-HPLC to afford Compound 15 (13 mg, 27% yield). LCMS: 441.1 [M+H]$^+$. $^1$H NMR (400 MHz, DMSO-d$_6$) δ 9.96 (s, 1H), 7.85-7.73 (m, 2H), 7.69-7.58 (m, 1H), 7.51 (d, J=1.6 Hz, 1H), 7.21 (d, J=8.4 Hz, 1H), 7.10 (t, J=7.6 Hz, 1H), 6.45 (s, 1H), 6.31 (t, J=2.0 Hz, 1H), 5.41 (s, 2H), 4.19 (t, J=5.0 Hz, 2H), 3.81 (s, 3H), 2.69 (t, J=6.2 Hz, 2H), 2.03-1.93 (m, 2H).

Example 16: Synthesis of N-(5-((1H-pyrazol-1-yl)methyl)-3,4-dihydro-2H-chromeno [8,7-d]isoxazol-9-yl)-2-methoxypyridine-3-sulfonamide (Compound 16)

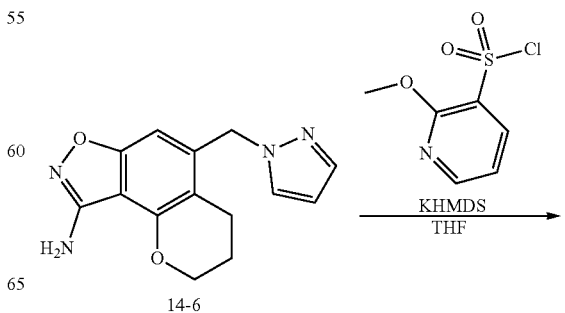

14-6

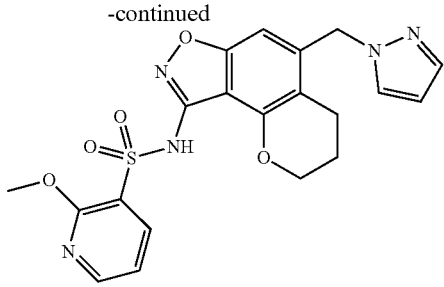

Compound 16

To a mixture of 14-6 (30 mg, 0.11 mmol) in THF (5 mL) were added KHMDS (0.22 mL, 0.22 mmol) at −78° C. and the mixture was stirred at this temperature for 30 min. Then 2-methoxypyridine-3-sulfonyl chloride (39 mg, 0.19 mmol) was added. The mixture was stirred at −78° C. for 2 h. The mixture was concentrated to give the crude product which was further purified by Prep-HPLC to afford Compound 16 (17 mg, 35% yield). LCMS: 442.1 [M+H]$^+$. $^1$H NMR (400 MHz, DMSO-d$_6$) δ 10.67 (s, 1H), 8.44-8.32 (m, 1H), 8.19-8.11 (m, 1H), 7.77 (d, J=2.0 Hz, 1H), 7.51 (d, J=1.6 Hz, 1H), 7.20-7.09 (m, 1H), 6.44 (s, 1H), 6.31 (t, J=2.0 Hz, 1H), 5.40 (s, 2H), 4.10 (t, J=5.0 Hz, 2H), 3.86 (s, 3H), 2.67 (t, J=6.4 Hz, 2H), 1.99-1.90 (m, 2H).

Example 17: Synthesis of N-(5-((1H-pyrazol-1-yl)methyl)-3,4-dihydro-2H-chromeno [8,7-d]isoxazol-9-yl)-2,4-dimethoxypyridine-3-sulfonamide (Compound 17

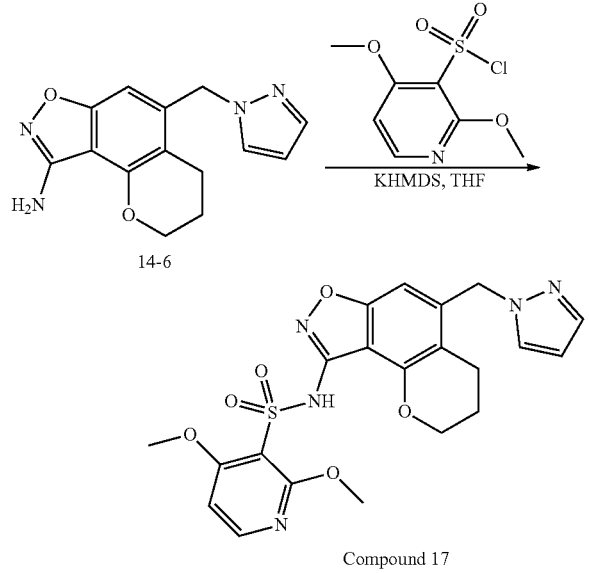

Compound 17

To a mixture of 14-6 (30 mg, 0.11 mmol) in THF (5 mL) was added KHMDS (0.2 mL, 0.20 mmol) at −78° C. The mixture was stirred at −78° C. for 0.5 h. 2,4-dimethoxypyridine-3-sulfonyl chloride (31 mg, 0.13 mmol) in THF (1 mL) was added to this mixture and this reaction mixture was stirred at −78° C. for 0.5 h. The mixture was concentrated to give the crude product which was further purified by Prep-HPLC to afford Compound 17 (7 mg, 4% yield). LCMS: 472.2 [M+H]$^+$. $^1$H NMR (400 MHz, DMSO-d$_6$) δ 10.12 (brs, 1H), 8.20 (d, J=6.0 Hz, 1H), 7.79 (d, J=2.4 Hz, 1H), 7.52 (d, J=1.6 Hz, 1H), 6.90 (d, J=5.6 Hz, 1H), 6.43 (s, 1H), 6.32 (t, J=2.0 Hz, 1H), 5.41 (s, 2H), 4.18 (t, J=5.0 Hz, 2H), 3.84 (s, 3H), 3.82 (s, 3H), 2.69 (t, J=6.4 Hz, 2H), 2.06-1.95 (m, 2H).

Example 18: Synthesis of N-(5-((1H-pyrazol-1-yl)methyl)-3,4-dihydro-2H-chromeno [8,7-d]isoxazol-9-yl)-2,4-dimethoxy-6-methylpyridine-3-sulfonamide (Compound 18)

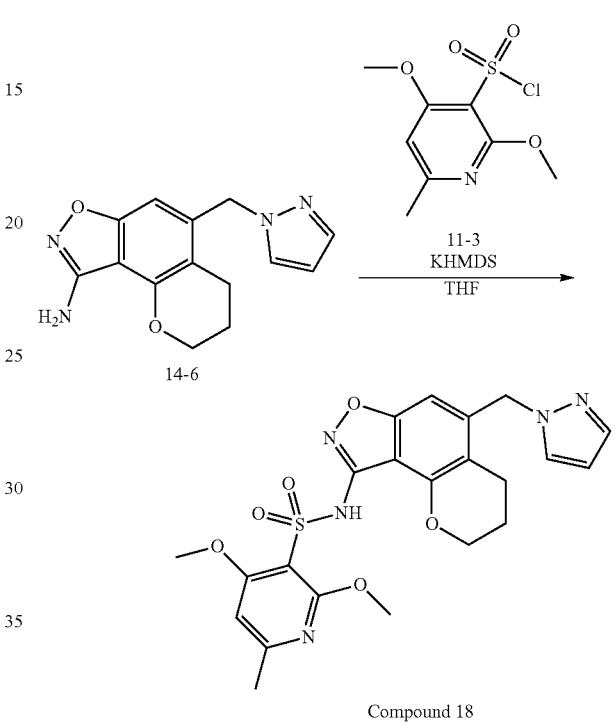

Compound 18

To a mixture of 14-6 (20 mg, 0.07 mmol) in THF (3 mL) were added KHMDS (0.11 mL, 0.11 mmol) at −78° C. and the mixture was stirred at this temperature for 30 min. Then 11-3 (22 mg, 0.09 mmol) was added. The mixture was stirred at −78° C. for 2 h. The mixture was concentrated to give the crude product which was further purified by Prep-HPLC to afford Compound 18 (5 mg, 15% yield). LCMS: 486.1 [M+H]$^+$. $^1$H NMR (400 MHz, DMSO-d$_6$) δ 9.80 (s, 1H), 7.78 (d, J=2.0 Hz, 1H), 7.51 (d, J=1.6 Hz, 1H), 6.77 (s, 1H), 6.42 (s, 1H), 6.31 (t, J=2.0 Hz, 1H), 5.41 (s, 2H), 4.21 (t, J=4.8 Hz, 2H), 3.81 (s, 3H), 3.80 (s, 3H), 2.69 (t, J=6.4 Hz, 2H), 2.37 (s, 3H), 2.04-1.94 (m, 2H).

Example 19: Synthesis of N-(6-((1H-pyrazol-1-yl)methyl)-2,3,4,5,9,10-hexahydrooxepino [3',2':5,6]benzo[1,2-d]isoxazol-10-yl)-2,6-dimethoxybenzenesulfonamide (Compound 19)

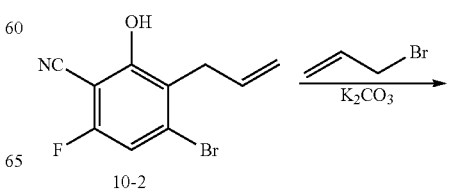

10-2

-continued

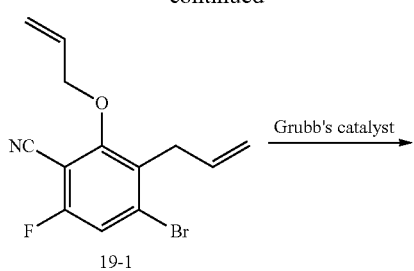
19-1

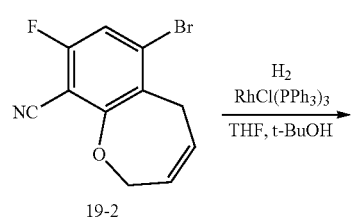
19-2

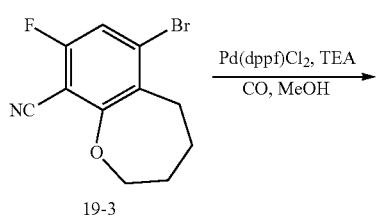
19-3

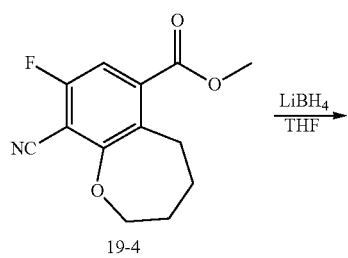
19-4

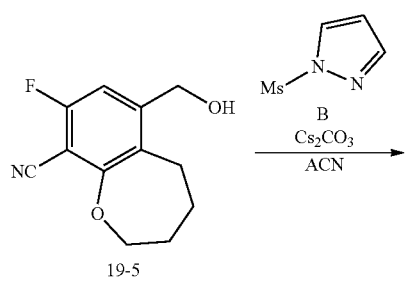
19-5

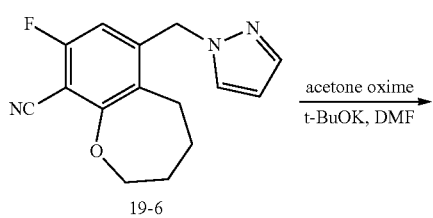
19-6

-continued

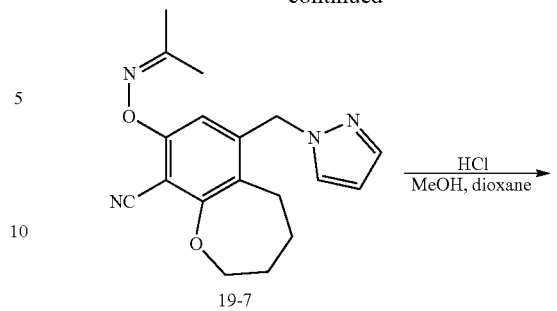
19-7

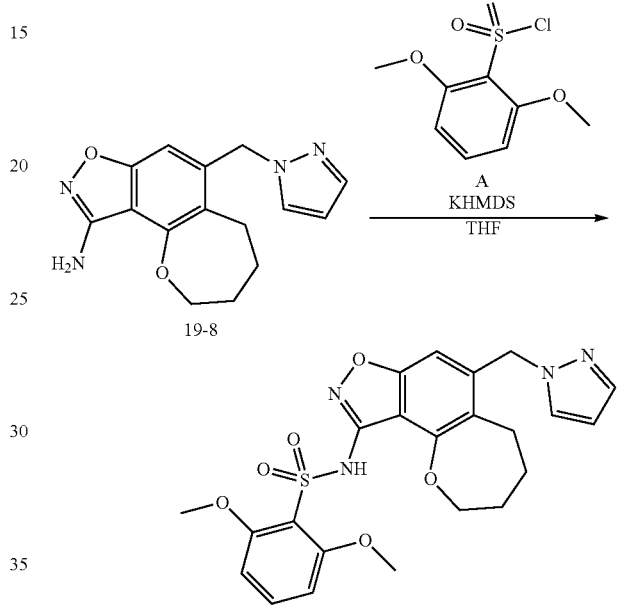

Compound 19

Step 1: To a mixture of 10-2 (2.5 g, 10 mmol) and 3-bromoprop-1-ene (1.8 g, 15 mmol) in MeCN (50 mL) was added potassium carbonate (4.1 g, 30 mmol). The mixture was stirred at 70° C. for 1 h. Water (30 mL) was added and the mixture was extracted with ethyl acetate (50 mL×3). The combined organic phase was washed with brine, dried over anhydrous $Na_2SO_4$, and concentrated. The residue was purified by flash silica gel chromatography to afford 19-1 (1.6 g, 54% yield) as a white solid.

Step 2: To a solution of 19-1 (1.6 g, 5.4 mmol) in DCM (50 mL) was added Grubbs Catalyst 2nd Generation (45.8 mg, 0.054 mmol). The mixture was stirred at 25° C. for 1 h. The reaction mixture was concentrated in vacuum to give a residue which was purified by flash silica gel chromatography to afford 19-2 (1.2 g, 83% yield) as a white solid.

Step 3: To a solution of 19-2 (1.2 g, 4.47 mmol) in THF (6 mL) and t-BuOH (6 mL) was added chlorotris(triphenylphosphine)rhodium(I) (240 mg, 0.26 mmol). The mixture was stirred at 25° C. for 2 h under $H_2$. Water (20 mL) was added and the mixture was extracted with ethyl acetate (50 mL×3). The combined organic phase was washed with brine, dried over anhydrous $Na_2SO_4$, and concentrated. The residue was purified by flash silica gel chromatography to afford 19-3 (700 mg, 58% yield) as a white solid.

Step 4: To a solution of 19-3 (700 mg, 2.59 mmol) in MeOH (10 mL) were added $Pd(dppf)Cl_2$ (189 mg, 0.26 mmol) and TEA (785 mg, 7.77 mmol). The mixture was stirred at 100° C. for 18 h under CO. The reaction mixture was concentrated in vacuum to give a residue which was purified by flash silica gel chromatography to afford 19-4 (300 mg, 46% yield) as a yellow solid.

Step 5: To a solution of 19-4 (300 mg, 1.2 mmol) in THF (10 mL) was added LiBH$_4$ (79 mg, 3.6 mmol) at 0° C. This reaction mixture was stirred at 40° C. for 1 h. Water (20 mL) was then added and the mixture was extracted with ethyl acetate (50 mL×3). The combined organic phase was washed with brine, dried over anhydrous Na$_2$SO$_4$, and concentrated. The residue was purified by flash silica gel chromatography to afford 19-5 (150 mg, 56% yield) as a yellow solid.

Step 6: To a solution of 19-5 (150 mg, 0.56 mmol) in MeCN (10 mL) was added Cs$_2$CO$_3$ (218 mg, 0.67 mmol) and compound B (90 mg, 0.61 mmol). This reaction mixture was stirred at 70° C. for 1 h. Water (20 mL) was then added and the mixture was extracted with ethyl acetate (30 mL×3). The combined organic phase was washed with brine, dried over anhydrous Na$_2$SO$_4$, and concentrated. The residue was purified by flash silica gel chromatography to afford 19-6 (80 mg, 52% yield) as a yellow solid. LCMS: 272.3 [M+H]$^+$.

Step 7: To a solution of 19-6 (80 mg, 0.29 mmol) in DMF (5 mL) was added t-BuOK (38 mg, 0.34 mmol). The mixture was stirred at room temperature for 0.5 h. Then acetone oxime (25 mg, 0.34 mmol) was added. This reaction mixture was stirred at room temperature for 1 h. Water (20 mL) was then added and the mixture was extracted with ethyl acetate (30 mL×3). The combined organic phase was washed with brine, dried over anhydrous Na$_2$SO$_4$, and concentrated. The residue was purified by flash silica gel chromatography to afford 19-7 (60 mg, 63% yield) as a white solid. LCMS: 325.4 [M+H]$^+$.

Step 8: To a solution of 19-7 (60 mg, 0.18 mmol) in MeOH (5 mL) was added 4M HCl in dioxane (5 mL). This reaction mixture was stirred at 25° C. for 18 h. The reaction mixture was concentrated in vacuum to give a residue which was purified by flash silica gel chromatography to afford 19-8 (40 mg, 78% yield) as a white solid. LCMS: 285.2 [M+H]$^+$. 1005101 Step 9: To a solution of 19-8 (40 mg, 0.14 mmol) in THF (5 mL) were added KHMDS (0.2 mL 0.2 mmol) at −78° C. The mixture was stirred at this temperature for 30 min. Then A (66 mg, 0.28 mmol) was added. The mixture was stirred at −78° C. for 1 h. The reaction mixture was concentrated. The residue was purified by Prep-HPLC to afford Compound 19 (11 mg, 16% yield). LCMS: 485.1 [M+H]$^+$. $^1$H NMR (400 MHz, DMSO-d$_6$) δ 9.63 (s, 1H), 7.74 (s, 1H), 7.57-7.41 (m, 2H), 6.84-6.77 (m, 2H), 6.77 (s, 1H), 6.30 (s, 1H), 5.50 (s, 2H), 4.21-4.03 (m, 2H), 3.78 (s, 6H), 2.90-2.79 (m, 2H), 1.94-1.84 (m, 2H), 1.62-1.50 (m, 2H).

Example 20: Synthesis of N-(6-((1H-pyrazol-1-yl)methyl)-2,3,4,5-tetrahydrooxepino [3',2':5,6]benzo[1,2-d]isoxazol-10-yl)-2,4-dimethoxypyridine-3-sulfonamide (Compound 20)

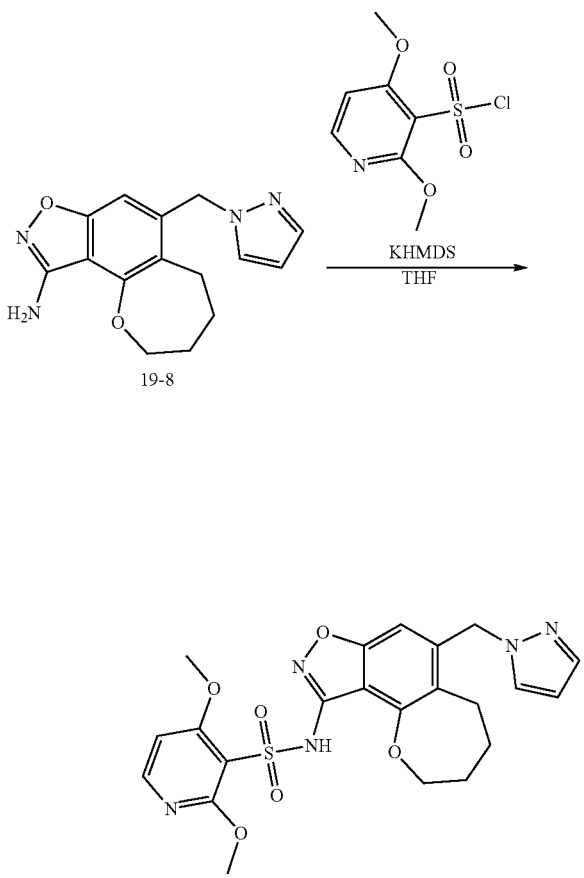

Compound 20

To a solution of 19-8 (40 mg, 0.14 mmol) in THF (5 mL) was added KHMDS (0.2 mL, 0.2 mmol) at −78° C. and the mixture was stirred at this temperature for 30 min. Then 2,4-dimethoxypyridine-3-sulfonyl chloride (66 mg, 0.28 mmol) was added. The mixture was stirred at −78° C. for 1 h. The reaction mixture was concentrated. The residue was purified by Prep-HPLC to afford Compound 20 (2 mg, 3% yield). LCMS: 486.1 [M+H]$^+$. $^1$H NMR (400 MHz, DMSO-d$_6$) δ 10.13 (s, 1H), 8.23 (d, J=6.0 Hz, 1H), 7.74 (d, J=2.0 Hz, 1H), 7.49 (d, J=1.6 Hz, 1H), 6.93 (d, J=6.0 Hz, 1H), 6.82 (s, 1H), 6.31 (t, J=2.0 Hz, 1H), 5.50 (s, 2H), 4.14-4.07 (m, 2H), 3.86 (s, 3H), 3.84 (s, 3H), 2.85-2.82 (m, 2H), 1.94-1.84 (m, 2H), 1.60-1.48 (m, 2H).

Example 21: Synthesis of N-(6-((1H-pyrazol-1-yl)methyl)-2,3,4,5-tetrahydrooxepino [3',2':5,6]benzo[1,2-d]isoxazol-10-yl)-2,4-dimethoxy-6-methylpyridine-3-sulfonamide (Compound 21)

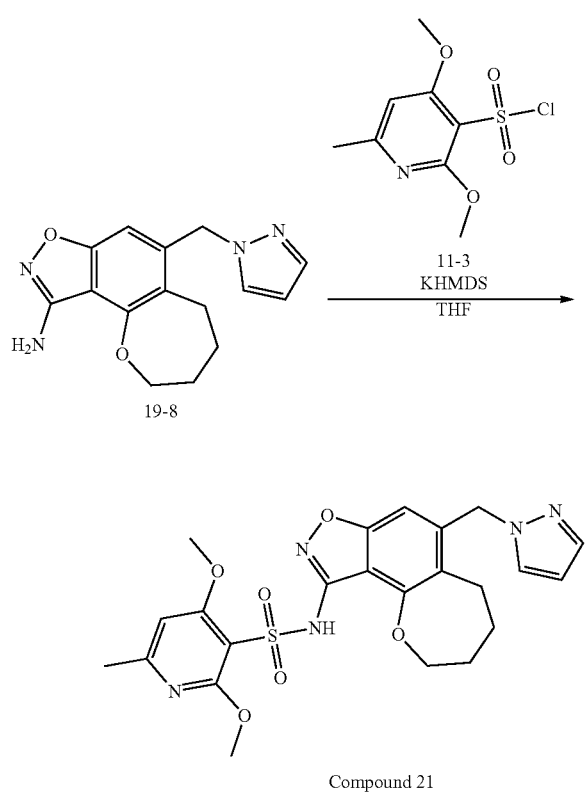

Compound 21

To a solution of 19-8 (60 mg, 0.21 mmol) in THF (5 mL) was added KHMDS (0.30 mL 0.30 mmol) at −78° C. and the mixture was stirred at this temperature for 30 min. Then 11-3 (106 mg, 0.42 mmol) was added. The mixture was stirred at −78° C. for 1 h. The reaction mixture was concentrated. The residue was purified by Prep-HPLC to afford Compound 21 (2 mg, 2% yield). LCMS: 500.2 [M+H]$^+$. $^1$H NMR (400 MHz, DMSO-$d_6$) δ 8.25 (s, 1H), 7.68 (d, J=2.0 Hz, 1H), 7.48 (d, J=1.6 Hz, 1H), 6.63 (s, 1H), 6.62 (s, 1H), 6.27 (t, J=2.0 Hz, 1H), 5.43 (s, 2H), 4.06-3.97 (m, 2H), 3.69 (s, 6H), 2.84-2.76 (m, 2H), 2.32 (s, 3H), 1.94-1.81 (m, 2H), 1.54-1.43 (m, 2H).

Example 22: Synthesis of N-(4-(difluoromethoxy)-6-(pyridin-2-yloxy)benzo[d]isoxazol-3-yl)-2,6-dimethoxybenzenesulfonamide (Compound 22)

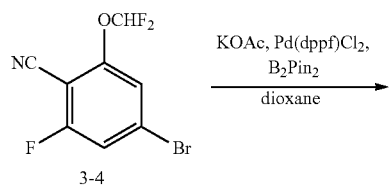

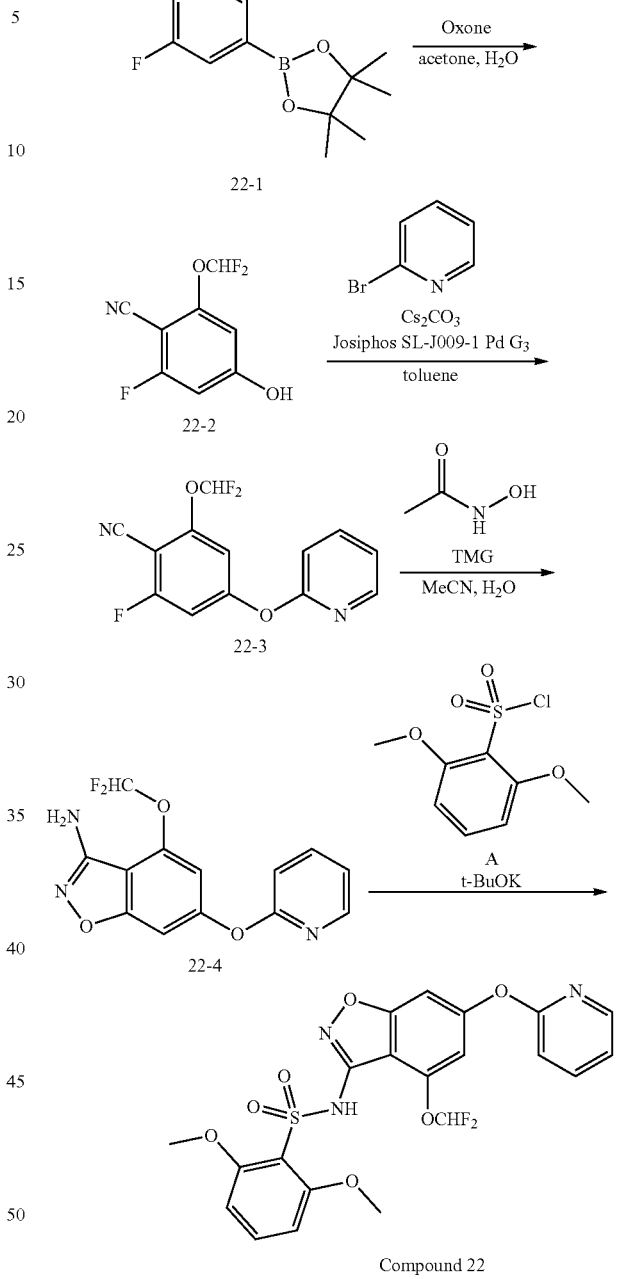

Compound 22

Step 1: To a solution of 3-4 (10.0 g, 37.59 mmol) in dioxane (100 mL) were added bis(pinacolato)diboron (11.5 g, 45.11 mmol), KOAc (7.37 g, 75.19 mmol), and Pd(dppf)Cl$_2$ (2.76 g, 3.76 mmol). The reaction mixture was stirred at 85° C. for 12 h under N$_2$. This reaction mixture was filtered and concentrated in vacuum to give the crude product 22-1 (11.8 g) as a brown oil which was used in the next step without further purification.

Step 2: To a solution of 22-1 (11.77 g, 37.6 mmol) in acetone (100 mL) was added oxone (27.8 g, 45.1 mmol) in H$_2$O (90 mL) at 0° C. The reaction mixture was stirred at 0° C. for 2 h. Water (50 mL) was added and the mixture was extracted with ethyl acetate (200 mL×3). The combined organic phase was washed with brine, dried over anhydrous Na$_2$SO$_4$, filtered, and concentrated in vacuum to give a residue. The residue was purified by flash silica gel chromatography to give 22-2 (3.8 g, 49.8% yield for two steps) as a white solid. LCMS: 202.0 [M−H]$^−$.

Step 3: To a mixture of 22-2 (3.80 g, 18.7 mmol) and 2-bromopyridine (8.87 g, 56.2 mmol) in toluene (80 mL) were added Cs$_2$CO$_3$ (18.31 g, 56.2 mmol) and Josiphos SL-J009-1 Pd G3 (347 mg, 0.38 mmol). The mixture was stirred at 100° C. for 12 h. This reaction mixture was filtered and concentrated under reduced pressure to give a residue which was purified by flash silica gel chromatography to afford 22-3 (3.1 g, 59% yield) as a white solid. LCMS: 281.0 [M+H]$^+$.

Step 4: To a mixture of 22-3 (500 mg, 1.78 mmol), N-hydroxyacetamide (402 mg, 5.35 mmol) in water (1 mL) and MeCN (9 mL) was added 1,1,3,3-tetramethylguanidine (1.17 mL, 10.7 mmol). The mixture was stirred at 60° C. for 2 h. Water (20 mL) was added to the mixture. Following extraction with ethyl acetate (20 mL×3), the organic phases were combined, washed with brine, dried over anhydrous Na$_2$SO$_4$, and filtered. The filtrate was concentrated under reduced pressure and the obtained residue was purified by flash silica gel chromatography to afford 22-4 (350 mg, 67% yield) as a yellow solid. LCMS: 294.0 [M+H]$^+$.

Step 5: To a mixture of 22-4 (80 mg, 0.27 mmol) in THF (2 mL) was added t-BuOK (76.5 mg, 0.68 mmol) and A (96.7 mg, 0.41 mmol) at 0° C. The mixture was stirred at 25° C. for 1.5 h. The mixture was concentrated to give the crude product which was further purified by Prep-HPLC to afford Compound 22 (16 mg, 12% yield). LCMS: 494.1 [M+H]$^+$. $^1$H NMR (400 MHz, DMSO-d$_6$) δ 10.23 (s, 1H), 8.25-8.17 (m, 1H), 8.01-7.88 (m, 1H), 7.52 (t, J=8.4 Hz, 1H), 7.39 (t, J=72.4 Hz, 1H), 7.35 (s, 1H), 7.26-7.19 (m, 1H), 7.17 (d, J=8.0 Hz, 1H), 6.96 (s, 1H), 6.79 (d, J=8.4 Hz, 2H), 3.78 (s, 6H).

Example 23: Synthesis of 2,6-dimethoxy-N-(4-(pyridin-2-yloxy)-2,3-dihydrobenzofuro [7,6-d] isoxazol-8-yl)benzenesulfonamide (Compound 23)

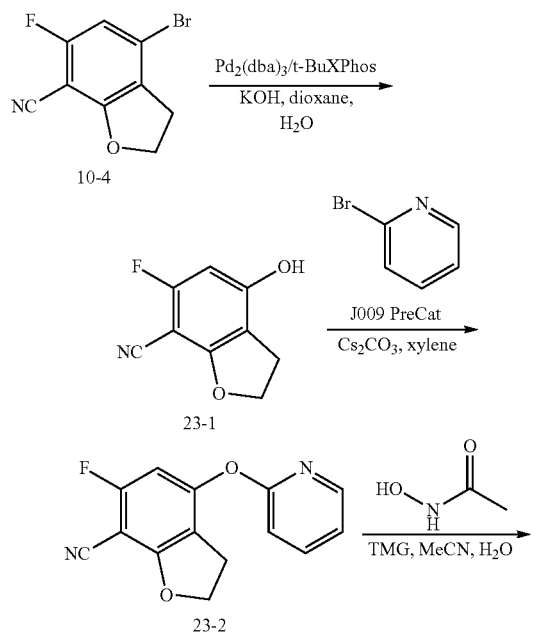

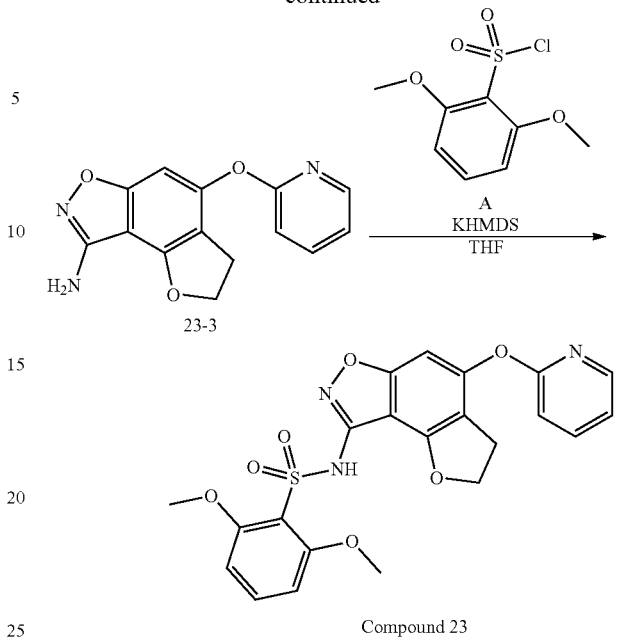

Compound 23

Step 1: To a solution of 10-4 (4.0 g, 15.6 mmol) in dioxane (40 mL) and H$_2$O (40 mL) were added t-BuXPhos (2.0 g, 4.7 mmol), KOH (2.6 g, 46.9 mmol), and Pd$_2$(dba)$_3$ (4.3 g, 4.7 mmol). The reaction mixture was stirred at 100° C. for 3 h under N$_2$. The reaction mixture was adjusted to pH ~5-6 by aqueous HCl (1 M). Water (30 mL) was added and the mixture was extracted with ethyl acetate (100 mL×3). The combined organic phase was washed with brine, dried over anhydrous Na$_2$SO$_4$ and concentrated in vacuum to give a residue. The residue was purified by flash silica gel chromatography to give the 23-1 (2.2 g, 79% yield) as a white solid. LCMS: 178.2 [M−H]$^−$.

Step 2: To a mixture of 23-1 (200 mg, 1.12 mmol) and 2-bromopyridine (0.28 mL, 3.11 mmol) in xylene (5 mL) were added Cs$_2$CO$_3$ (1.01 mg, 3.11 mmol) and Josiphos SL-J009-1 Pd G3 (2 mg, 0.12 mmol). The mixture was stirred at 149° C. for 12 h. This reaction mixture was filtered and concentrated to give a residue which was purified by flash silica gel chromatography to afford 23-2 (50 mg, 19% yield) as a yellow solid. LCMS: 257.1 [M+H]$^+$.

Step 3: To a mixture of 23-2 (50 mg, 0.19 mmol), N-hydroxyacetamide (43 mg, 0.57 mmol) and water (0.3 mL) in MeCN (3 mL) was added 1,1,3,3-tetramethylguanidine (0.14 mL, 1.14 mmol). The mixture was stirred at 60° C. for 12 h. Water (10 mL) was added to the mixture. Following extraction with ethyl acetate (20 mL×3), the organic phases were combined, washed with brine, dried over anhydrous Na$_2$SO$_4$, and filtered. The filtrate was concentrated under reduced pressure and then purified by flash silica gel chromatography to afford 23-3 (20 mg, 38% yield) as a yellow solid. LCMS: 270.1 [M+H]$^+$.

Step 4: To a mixture of 23-3 (60 mg, 0.22 mmol) in THF (5 mL) was added KHMDS (0.67 mL, 0.67 mmol) at −78° C. The mixture was stirred at −78° C. for 0.5 h. Compound A (79 mg, 0.33 mmol) in THF (1 mL) was added. The reaction mixture was stirred at −78° C. for 1 h. The mixture was concentrated to give the crude product which was further purified by Prep-HPLC to afford Compound 23 (15 mg, 14% yield). LCMS: 470.1 [M+H]$^+$. $^1$H NMR (400 MHz, DMSO-d$_6$) δ 10.42 (s, 1H), 8.20-8.16 (m, 1H), 7.93-7.87 (m, 1H), 7.53-7.49 (m, 1H), 7.20-7.12 (m, 2H), 6.89 (s, 1H), 6.78 (d, J=8.8 Hz, 2H), 4.71 (t, J=8.8 Hz, 2H), 3.79 (s, 6H), 2.94 (t, J=9.0 Hz, 2H).

Example 24: Synthesis of 2,6-dimethoxy-N-(5-(pyridin-2-yloxy)-3,4-dihydro-2H-chromeno[8,7-d]isoxazol-9-yl)benzenesulfonamide (Compound 24)

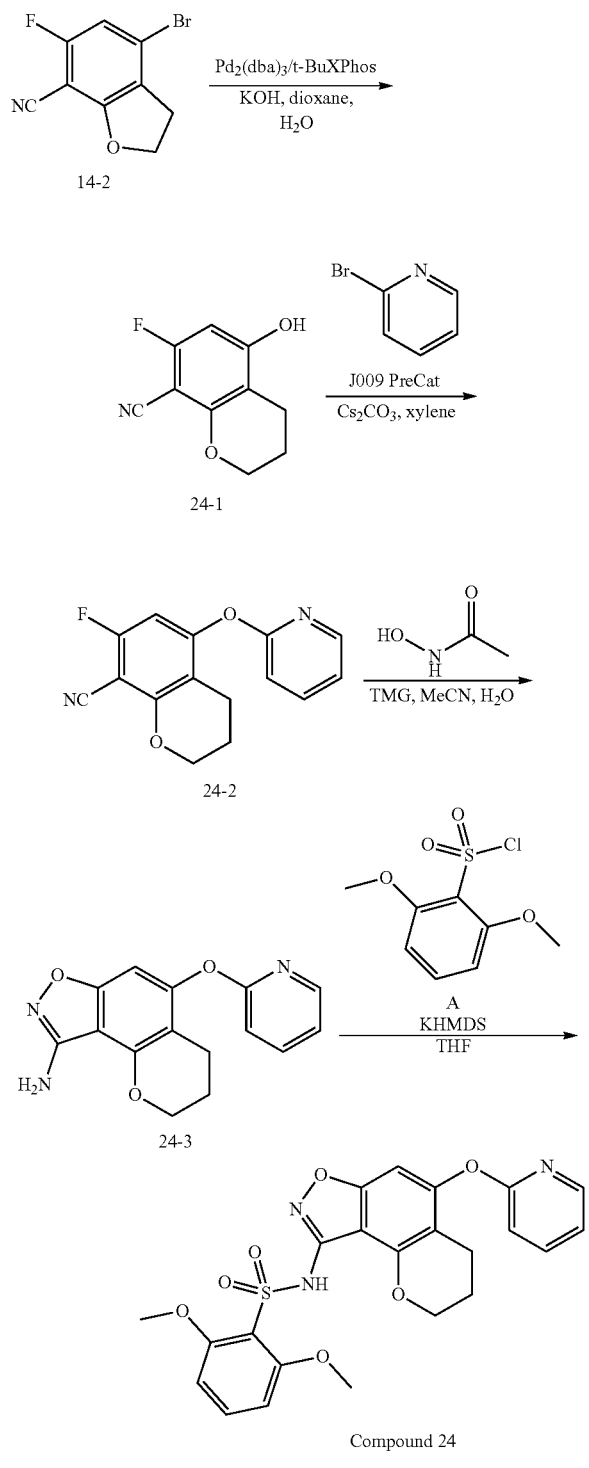

Step 1: To a solution of 14-2 (4.0 g, 15.62 mmol) in dioxane (40 mL) and H$_2$O (40 mL) were added t-BuXPhos (1.99 g, 4.69 mmol), KOH (2.63 g, 46.86 mmol), and Pd$_2$(dba)$_3$ (4.29 g, 4.69 mmol). The reaction mixture was stirred at 100° C. for 3 h under N$_2$. The reaction mixture was adjusted to pH ~5-6 by aqueous HCl (1 M). Water (30 mL) was added and the mixture was extracted with ethyl acetate (100 mL×3). The combined organic phase was washed with brine, dried over anhydrous Na$_2$SO$_4$ and concentrated in vacuum to give a residue. The residue was purified by flash silica gel chromatography to give the 24-1 (2.6 g, 86% yield) as a white solid. LCMS: 192.2 [M−H]$^-$.

Step 2: To a mixture of 24-1 (200 mg, 1.03 mmol) and 2-bromopyridine (0.28 mL, 3.11 mmol) in xylene (5 mL) were added Cs$_2$CO$_3$ (1.01 mg, 3.11 mmol) and Josiphos SL-J009-1 Pd G3 (2 mg, 0.12 mmol). The mixture was stirred at 149° C. for 12 h. This reaction mixture was filtered and concentrated under reduced pressure to give a residue which was purified by flash silica gel chromatography to afford 24-2 (100 mg, 35% yield) as a yellow solid. LCMS: 271.1 [M+H]$^+$.

Step 3: To a mixture of 24-2 (100 mg, 0.37 mmol), N-hydroxyacetamide (83 mg, 1.11 mmol), and water (0.3 mL) in MeCN (3 mL) was added 1,1,3,3-tetramethylguanidine (0.3 mL, 2.22 mmol). The mixture was stirred at 60° C. for 12 h. Water (10 mL) was added to the mixture. Following extraction with ethyl acetate (20 mL×3), the organic phases were combined, washed with brine, dried over anhydrous Na$_2$SO$_4$ and concentrated under reduced pressure and then purified by flash silica gel chromatography to afford 24-3 (50 mg, 48% yield) as a yellow solid. LCMS: 284.1 [M+H]$^+$.

Step 4: To a mixture of 24-3 (30 mg, 0.11 mmol) in THF (5 mL) was added KHMDS (0.27 mL, 0.27 mmol) at −78° C. The mixture was stirred at −78° C. for 0.5 h. A (38 mg, 0.16 mmol) in THF (1 mL) was added. The reaction mixture was stirred at −78° C. for 1 h. The mixture was concentrated to give the crude product which was further purified by Prep-HPLC to afford Compound 24 (5 mg, 10% yield). LCMS: 484.2 [M+H]$^+$. $^1$H NMR (400 MHz, DMSO-d$_6$) δ 9.52 (s, 1H), 8.16-8.14 (m, 1H), 7.91-7.86 (m, 1H), 7.54-7.49 (m, 1H), 7.18-7.15 (m, 1H), 7.10 (d, J=8.4 Hz, 1H), 6.88 (s, 1H), 6.80 (d, J=8.8 Hz, 2H), 4.28-4.21 (m, 2H), 3.81 (s, 6H), 2.51-2.46 (m, 2H), 1.96-1.90 (m, 2H).

Example 25: Synthesis of 2-methoxy-N-(5-(pyridin-2-yloxy)-3,4-dihydro-2H-chromeno[8,7-d]isoxazol-9-yl)benzenesulfonamide (Compound 25)

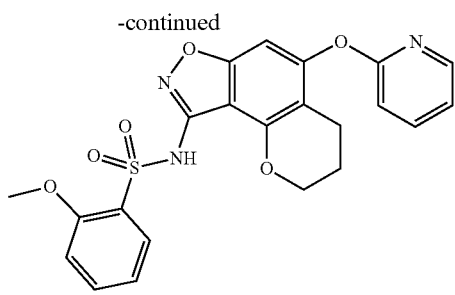

Compound 25

To a mixture of 24-3 (60 mg, 0.21 mmol) in THF (5 mL) was added KHMDS (0.42 mL, 0.42 mmol) at −78° C. The mixture was stirred at −78° C. for 0.5 h. 2-methoxybenzenesulfonyl chloride (65 mg, 0.31 mmol) in THF (1 mL) was added to this mixture and this reaction mixture was stirred at −78° C. for 0.5 h. The mixture was concentrated to give the crude product which was further purified by Prep-HPLC to afford Compound 25 (19 mg, 20% yield). LCMS: 454.1 [M+H]+. 1H NMR (400 MHz, DMSO-d6) δ 10.06 (s, 1H), 8.16-8.12 (m, 1H), 7.91-7.86 (m, 1H), 7.82 (dd, J=8.0, 1.6 Hz, 1H), 7.67-7.61 (m, 1H), 7.26-7.20 (m, 1H), 7.18-7.07 (m, 3H), 6.88 (s, 1H), 4.23-4.14 (m, 2H), 3.84 (s, 3H), 2.51-2.45 (m, 2H), 1.95-1.86 (m, 2H).

Example 26: Synthesis of 2-methoxy-N-(4-(pyridin-2-yloxy)-2,3-dihydrobenzofuro[7,6-d]isoxazol-8-yl)benzenesulfonamide (Compound 26)

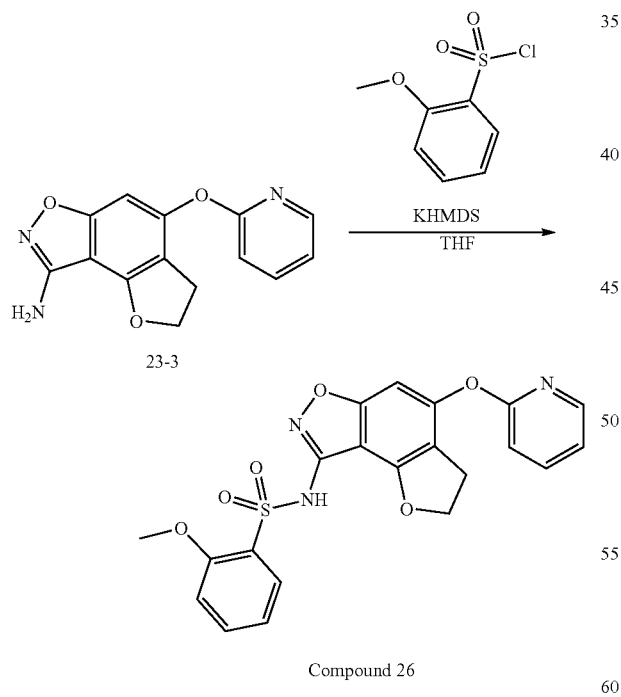

Compound 26

To a mixture of 23-3 (60 mg, 0.22 mmol) in THF (6 mL) were added KHMDS (0.45 mL, 0.45 mmol) at −78° C. and stirred at this temperature for 30 min. Then 2-methoxybenzenesulfonyl chloride (78 mg, 0.38 mmol) was added. The reaction was stirred at −78° C. for 2 h. The mixture was concentrated to give the crude product which was further purified by Prep-HPLC to afford Compound 26 (12.7 mg, 13% yield). LCMS: 440.0 [M+H]+. 1H NMR (400 MHz, DMSO-d6) δ 10.87 (s, 1H), 8.20-8.14 (m, 1H), 7.93-7.85 (m, 1H), 7.79-7.73 (m, 1H), 7.70-7.53 (m, 1H), 7.27-7.15 (m, 2H), 7.14-7.02 (m, 2H), 6.95-6.79 (m, 1H), 4.70 (t, J=8.8 Hz, 2H), 3.81 (s, 3H), 2.93 (t, J=8.8 Hz, 2H).

Example 27: Synthesis of N-(4-(difluoromethoxy)-6-(pyridin-2-yloxy)benzo[d]isoxazol-3-yl)-2-methoxybenzenesulfonamide (Compound 27)

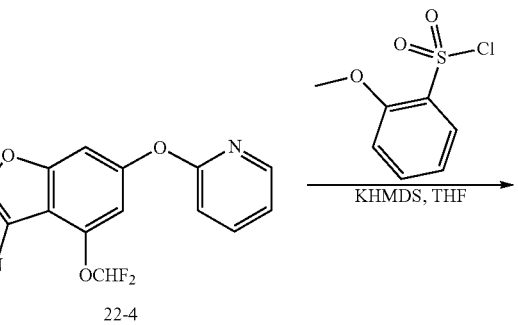

Compound 27

To a mixture of 22-4 (70 mg, 0.24 mmol) in THF (5 mL) was added KHMDS (0.48 mL, 0.48 mmol) at −78° C. The mixture was stirred at −78° C. for 0.5 h. 2-methoxybenzenesulfonyl chloride (84 mg, 0.48 mmol) in THF (1 mL) was added. The reaction mixture was stirred at −78° C. for 1.5 h. The mixture was concentrated to give the crude product which was further purified by Prep-HPLC to afford Compound 27 (20 mg, 18% yield). LCMS: 464.1 [M+H]+. 1H NMR (400 MHz, DMSO-d6) δ 10.72 (s, 1H), 8.22-8.18 (m, 1H), 7.96-7.90 (m, 1H), 7.84-7.79 (m, 1H), 7.66-7.60 (m, 1H), 7.39-7.14 (m, 5H), 7.14-7.06 (m, 1H), 6.96-6.91 (m, 1H), 3.79 (s, 3H).

Example 28: Synthesis of 2,4-dimethoxy-N-(5-(pyridin-2-yloxy)-3,4-dihydro-2H-chromeno[8,7-d]isoxazol-9-yl)pyridine-3-sulfonamide (Compound 28)

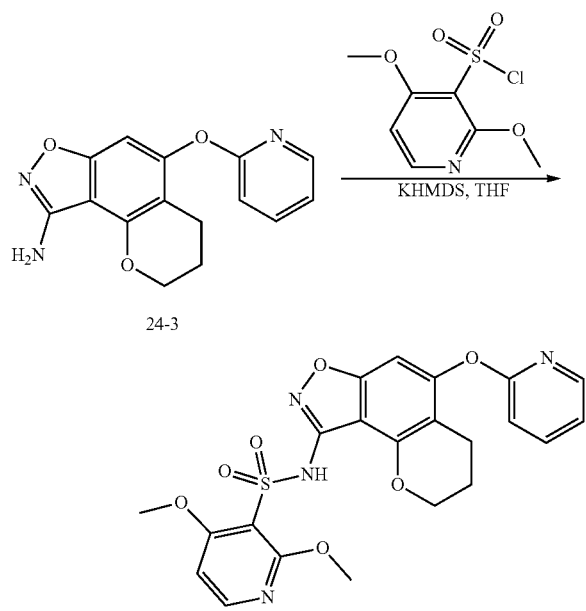

Compound 28

To a mixture of 24-3 (30 mg, 0.11 mmol) in THF (5 mL) was added KHMDS (0.21 mL, 0.21 mmol) at −78° C. The mixture was stirred at −78° C. for 0.5 h. 2,4-dimethoxypyridine-3-sulfonyl chloride (30 mg, 0.13 mmol) in THF (1 mL) was added to this mixture and this reaction mixture was stirred at −78° C. for 0.5 h. The mixture was concentrated to give the crude product which was further purified by Prep-HPLC to afford Compound 28 (19 mg, 37% yield). LCMS: 485.1 [M+H]$^+$. $^1$H NMR (400 MHz, DMSO-d$_6$) δ 10.15 (s, 1H), 8.24 (d, J=6.0 Hz, 1H), 8.18-8.14 (m, 1H), 7.91-7.87 (m, 1H), 7.18-7.15 (m, 1H), 7.10 (d, J=8.4 Hz, 1H), 6.95 (d, J=6.0 Hz, 1H), 6.90 (s, 1H), 4.21-4.14 (m, 2H), 3.89 (s, 3H), 3.87 (s, 3H), 2.51-2.46 (m, 2H), 1.94-1.88 (m, 2H).

Example 29: Synthesis of N-(4-(difluoromethoxy)-6-(pyridazin-3-yloxy)benzo[d]isoxazol-3-yl)-2,6-dimethoxybenzenesulfonamide (Compound 29)

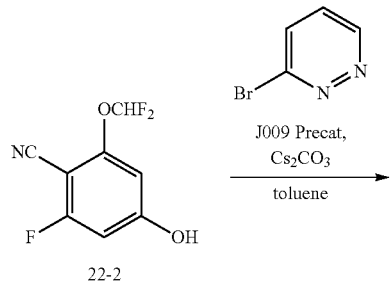

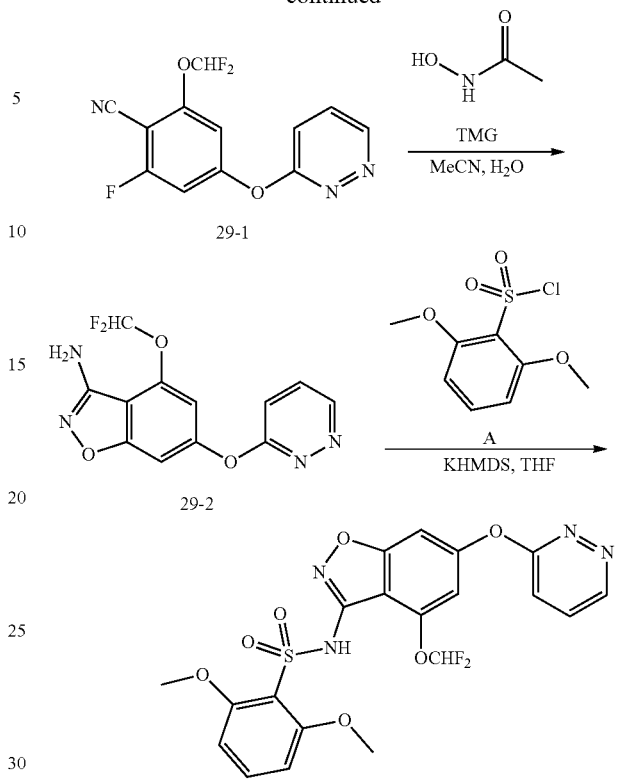

Compound 29

Step 1: To a solution of 22-2 (140 mg, 0.69 mmol) in toluene (5 mL) were added 3-bromo-1,2-diazine (329 mg, 2.07 mmol), Cs$_2$CO$_3$ (675 mg, 2.07 mmol) and Josiphos SL-J009-1 Pd G3 (13 mg, 0.014 mmol). The mixture was stirred at 100° C. for 18 h. The reaction mixture was concentrated in vacuum to give a residue which was purified by flash silica gel chromatography to afford 29-1 (70 mg, 36% yield) as a white solid. LCMS: 282.1 [M+H]$^+$ Step 2: To a solution of 29-1 (70 mg, 0.25 mmol) in MeCN (5 mL) and H$_2$O (0.5 mL) was added N-hydroxyacetamide (56 mg, 0.75 mmol) and 1,1,3,3-tetramethylguanidine (172 mg, 1.5 mmol). This reaction mixture was stirred at 60° C. for 1 h. The reaction mixture was quenched with water (10 mL). The aqueous phase was extracted with ethyl acetate (20 mL×3). The combined organic phase was washed with brine, dried with anhydrous sodium sulfate and concentrated under reduced pressure. The residue was purified by flash silica gel chromatography to afford 29-2 (35 mg, 48% yield) as a white solid. LCMS: 295.3 [M+H]$^+$.

Step 3: To a solution of 29-2 (35 mg, 0.12 mmol) in THF (5 mL) were added KHMDS (0.24 mL 0.24 mmol) at −78° C. and stirred at this temperature for 0.5 h. Then A (42 mg, 0.18 mmol) was added. The reaction was stirred at −78° C. for 1 h. The reaction mixture was concentrated. The residue was purified by Prep-HPLC to afford Compound 29 (11 mg, 18% yield). LCMS: 495.1 [M+H]$^+$. $^1$H NMR (400 MHz, DMSO-d$_6$) δ 10.29 (s, 1H), 9.10-9.07 (m, 1H), 7.89-7.80 (m, 1H), 7.62-7.50 (m, 3H), 7.40 (t, J=72 Hz, 1H), 7.09 (s, 1H), 6.80 (d, J=8.8 Hz, 2H), 3.78 (s, 6H).

Example 30: Synthesis of 2,6-dimethoxy-N-(5-(pyridazin-3-yloxy)-3,4-dihydro-2H-chromeno[8,7-d]isoxazol-9-yl)benzenesulfonamide (Compound 30)

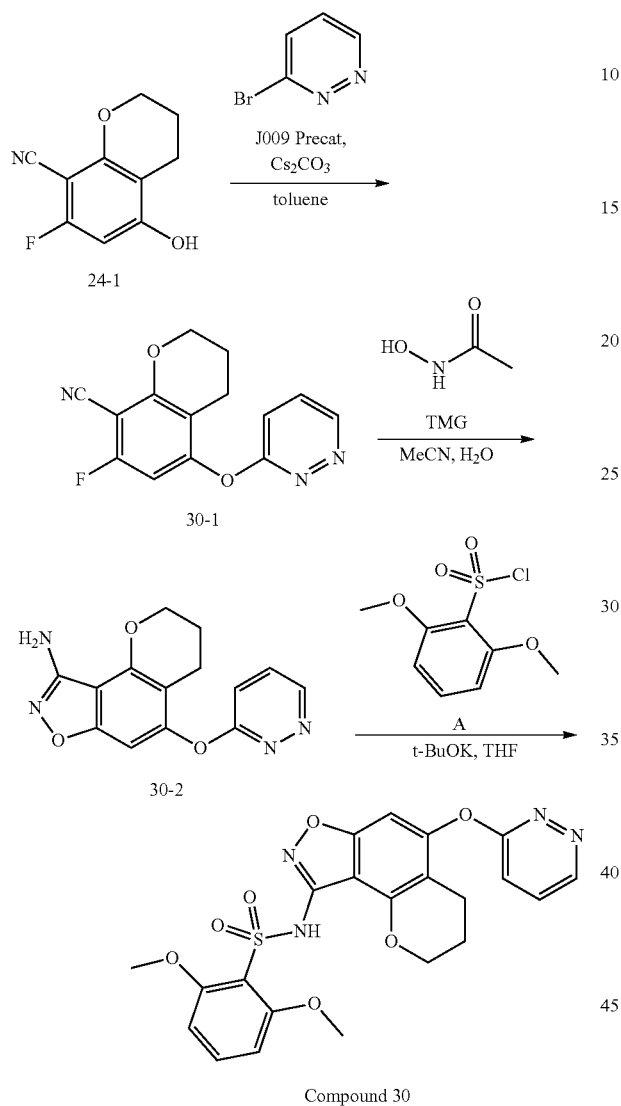

Compound 30

Step 1: To a solution of 24-1 (200 mg, 0.99 mmol) in toluene (5 mL) were added 3-bromo-1,2-diazine (173 mg, 0.99 mmol), $Cs_2CO_3$ (962 mg, 2.95 mmol) and Josiphos SL-J009-1 Pd G3 (18 mg, 0.02 mmol). The mixture was stirred at 95° C. for 18 h. The reaction mixture was concentrated to give a residue which was purified by flash silica gel chromatography to afford 30-1 (100 mg, 34% yield) as a white solid. LCMS: 272.1 [M+H]+

Step 2: To a solution of 30-1 (100 mg, 0.37 mmol) in MeCN (5 mL) and $H_2O$ (0.5 mL) was added N-hydroxyacetamide (83 mg, 1.11 mmol) and 1,1,3,3-tetramethylguanidine (255 mg, 2.21 mmol). This reaction mixture was stirred at 60° C. for 18 h. The reaction mixture was quenched with water (10 mL). The aqueous phase was extracted with ethyl acetate (20 mL×3). The combined organic phase was washed with brine, dried with anhydrous sodium sulfate and concentrated under reduced pressure. The residue was purified by flash silica gel chromatography to afford 30-2 (30 mg, 27% yield) as a white solid. LCMS: 285.3 [M+H]+.

Step 3: To a solution of 30-2 (20 mg, 0.07 mmol) in THF (5 mL) were added t-BuOK (16 mg, 0.14 mmol) and stirred at 0° C. for 0.5 h. Then A (17 mg, 0.07 mmol) was added. The reaction was stirred at room temperature for 1 h. The reaction mixture was concentrated. The residue was purified by Prep-HPLC to afford Compound 30 (6.0 mg, 18% yield). LCMS: 485.1 [M+H]+. $^1$H NMR (400 MHz, DMSO-$d_6$) δ 9.58 (brs, 1H), 9.03 (dd, J=4.8 Hz, 1.2 Hz 1H), 7.82-7.79 (m, 1H), 7.55-7.48 (m, 2H), 7.01 (s, 1H), 6.79 (d, J=8.4 Hz, 2H), 4.29-4.26 (m, 2H), 3.81 (s, 6H), 2.51-2.46 (m, 2H), 1.97-1.91 (m, 2H).

Example 31: Synthesis of N-(6-((1H-pyrazol-1-yl)methyl)-4-(fluoromethoxy)benzo[d]isoxazol-3-yl)-2,6-dimethoxybenzenesulfonamide (Compound 31)

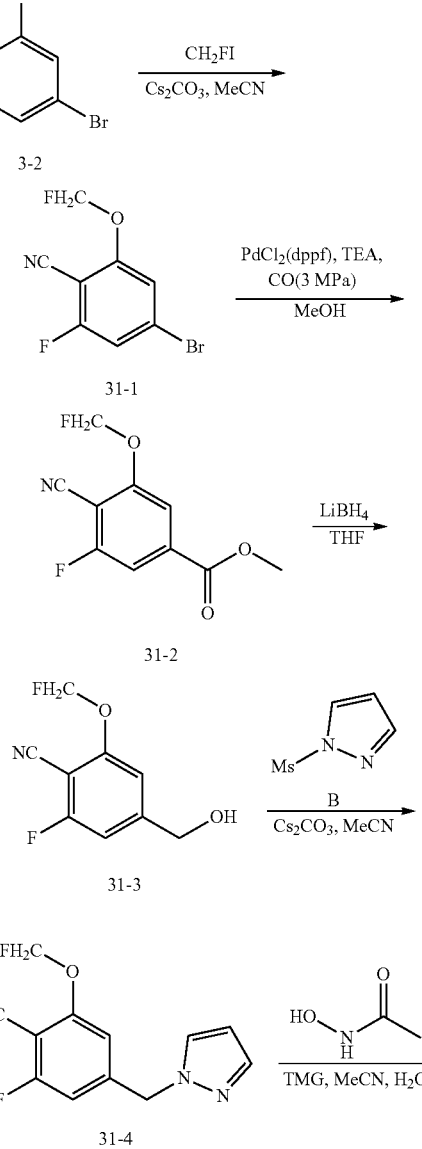

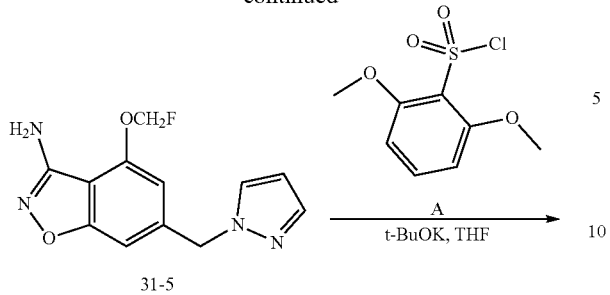

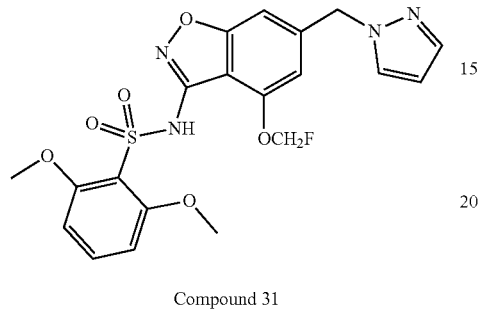

Compound 31

Step 1: To a solution of 3-2 (5.0 g, 23.15 mmol) in acetonitrile (50 mL) were added $Cs_2CO_3$ (11.3 g, 34.72 mmol) and $CH_2FI$ (5.5 g, 34.72 mmol). This reaction mixture was stirred at 25° C. for 6 h. The reaction mixture was quenched with water (50 mL). The aqueous layer was back extracted with ethyl acetate (100 mL×3). The combined organic layer was washed with brine, dried over anhydrous $Na_2SO_4$, and concentrated. The residue was purified by flash silica gel chromatography to give 31-1 (4.7 g, 82% yield) as a light-green solid.

Step 2: To a solution of 31-1 (5.18 g, 21.0 mmol) in MeOH (60 mL) was added Pd(dppf)Cl$_2$ (1.53 g, 2.01 mmol) and TEA (8.75 mL, 62.9 mmol). The reaction mixture was stirred at 100° C. for 18 h under CO (3 MPa) atmosphere. Then the reaction mixture was filtered. The filtrate was concentrated. The residue was purified by flash silica gel chromatography to give 31-2 (4.47 g, 94% yield) as a white solid.

Step 3: To a solution of 31-2 (800 mg, 7.05 mmol) in THF (15 mL) was added LiBH$_4$ (155 mg, 14.1 mmol) at 0° C. The reaction mixture was stirred at 25° C. for 2 h. The reaction mixture was quenched by $Na_2SO_4 \cdot 10H_2O$ and filtered. The filtrate was concentrated. The residue was purified by flash silica gel chromatography to give 31-3 (600 mg, 85% yield) as a white solid. LCMS: 198.2 [M−H]$^-$.

Step 4: To a solution of 31-3 (600 mg, 3.02 mmol) in acetonitrile (12 mL) were added Compound B (542 mg, 3.62 mmol) and $Cs_2CO_3$ (1.18 g, 3.62 mmol). The reaction mixture was stirred at 70° C. for 1 h. Then the reaction mixture was concentrated. The residue was purified by flash silica gel chromatography to give 31-4 (550 mg, 73% yield) as a yellow solid. LCMS: 250.2 [M+H]$^+$.

Step 5: To a solution of 31-4 (500 mg, 2.01 mmol) in acetonitrile (9 mL) and H$_2$O (1 mL) were added N-hydroxyacetamide (452 mg, 6.03 mmol) and 1,1,3,3-tetramethylguanidine (1.39 g, 6.03 mmol). The reaction was stirred at 60° C. for 2 h. Then the reaction mixture was concentrated. The residue was purified by flash silica gel chromatography to give 31-5 (280 mg, 53% yield) as a white solid. LCMS: 263.0 [M+H]$^+$.

Step 6: To a solution of 31-5 (50 mg, 0.19 mmol) in pyridine (2 mL) was added A (90.0 mg, 0.38 mmol). The reaction mixture was stirred at 120° C. for 1.5 h. The mixture was concentrated in vacuo. The residue was purified by Prep-HPLC to give Compound 31 (12 mg, 13% yield). LCMS: 463.1 [M+H]$^+$. $^1$H NMR (400 MHz, DMSO-d$_6$) δ 10.05 (s, 1H), 7.89 (s, 1H), 7.64-7.42 (m, 2H), 7.03 (s, 1H), 6.92 (s, 1H), 6.76 (d, J=8.4 Hz, 2H), 6.31 (s, 1H), 5.90 (d, J=53.6 Hz, 2H), 5.48 (s, 2H), 3.74 (s, 6H).

Example 32: Synthesis of N-(4-((1H-pyrazol-1-yl)methyl)-2,3-dihydrobenzofuro[7,6-d]isoxazol-8-yl)-2,4-dimethoxypyridine-3-sulfonamide (Compound 32)

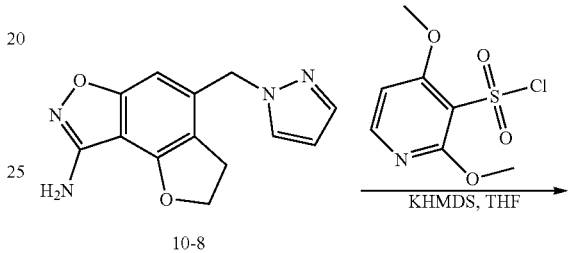

Compound 32

To a mixture of 10-8 (30 mg, 0.12 mmol) in THF (5 mL) was added KHMDS (0.24 mL, 0.24 mmol) at −78° C. The mixture was stirred at −78° C. for 0.5 h. 2,4-dimethoxypyridine-3-sulfonyl chloride (47 mg, 0.24 mmol) in THF (1 mL) was added to this mixture and this reaction mixture was stirred at −78° C. for 1.5 h. The mixture was concentrated to give the crude product which was further purified by Prep-HPLC to afford Compound 32 (2 mg, 4% yield). LCMS: 458.1 [M+H]$^+$. $^1$H NMR (400 MHz, DMSO-d$_6$) δ 10.82 (s, 1H), 8.28-8.07 (m, 1H), 7.82 (d, J=1.6 Hz, 1H), 7.49 (d, J=1.6 Hz, 1H), 6.95-6.82 (m, 1H), 6.67 (s, 1H), 6.30 (t, J=1.8 Hz, 1H), 5.40 (s, 2H), 4.68 (t, J=8.8 Hz, 2H), 3.81 (s, 6H), 3.09 (t, J=8.8 Hz, 2H).

Example 33: Synthesis of 2,6-dimethoxy-N-(5-(pyrimidin-2-yloxy)-3,4-dihydro-2H-chromeno[8,7-d]isoxazol-9-yl)benzenesulfonamide (Compound 33)

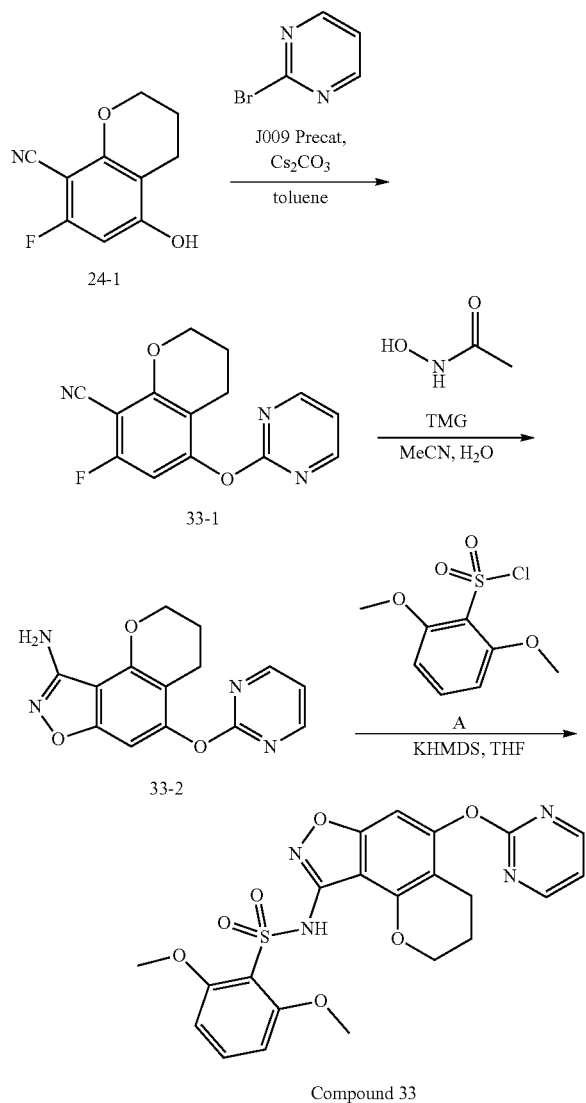

Step 1: To a solution of 24-1 (200 mg, 0.99 mmol) in toluene (5 mL) were added 2-bromopyrimidine (173 mg, 0.99 mmol), $Cs_2CO_3$ (962 mg, 2.95 mmol) and Josiphos SL-J009-1 Pd G3 (18 mg, 0.02 mmol). The mixture was stirred at 95° C. for 18 h. The reaction mixture was concentrated to give a residue which was purified by flash silica gel chromatography to afford 33-1 (50 mg, 17% yield) as a white solid. LCMS: 272.1 [M+H]+

Step 2: To a solution of 33-1 (30 mg, 0.11 mmol) in MeCN (5 mL) and $H_2O$ (0.5 mL) was added N-hydroxyacetamide (24 mg, 0.33 mmol) and 1,1,3,3-tetramethylguanidine (76 mg, 0.66 mmol). This reaction mixture was stirred at 60° C. for 18 h. The reaction mixture was quenched with water (10 mL). The aqueous phase was extracted with ethyl acetate (20 mL×3). The combined organic phase was washed with brine, dried with anhydrous sodium sulfate and concentrated. The residue was purified by flash silica gel chromatography to afford 33-2 (10 mg, 31% yield) as a white solid. LCMS: 285.3 [M+H]+.

Step 3: To a solution of 33-2 (10 mg, 0.04 mmol) in THF (5 mL) was added KHMDS (0.11 mL, 0.11 mmol) and stirred at −78° C. for 30 min. Then A (8 mg, 0.04 mmol) was added. The reaction was stirred at −78° C. for 1 h. The reaction mixture was concentrated. The residue was purified by Prep-HPLC to afford Compound 33 (1 mg, 18% yield). LCMS: 485.1 [M+H]+. 1HNMR (400 MHz, DMSO-$d_6$) δ 8.65 (d, J=4.8 Hz, 2H), 8.33 (s, 1H), 7.31-7.27 (m, 2H), 6.73 (s, 1H), 6.65 (d, J=8.4 Hz, 2H), 4.23-4.17 (m, 2H), 3.67 (s, 6H), 2.43-2.38 (m, 2H), 1.93-1.86 (m, 2H).

Example 34: Synthesis of 2,6-dimethoxy-N-(5-(oxazol-2-yloxy)-3,4-dihydro-2H-chromeno[8,7-d]isoxazol-9-yl)benzenesulfonamide (Compound 34)

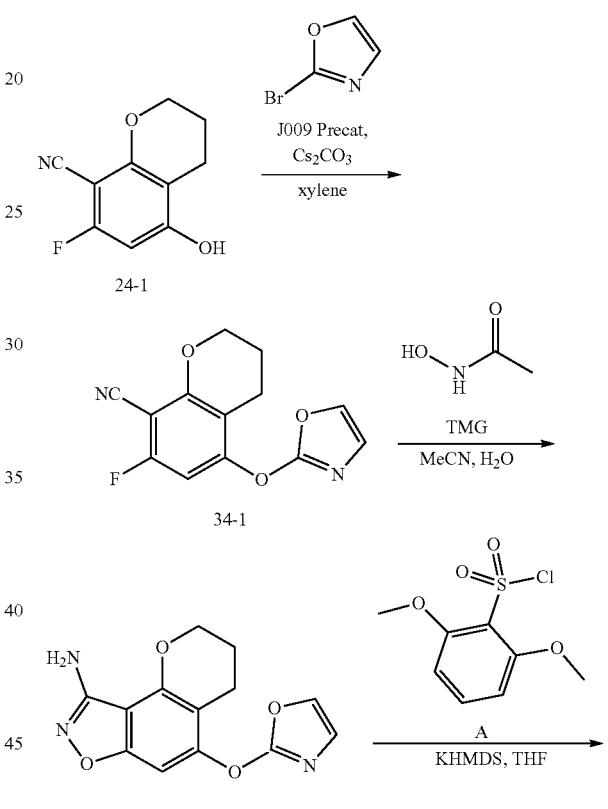

Step 1: To a solution of 24-1 (200 mg, 1.03 mmol) in xylene (10 mL) were added 2-bromooxazole (460 mg, 3.10 mmol), $Cs_2CO_3$ (1.01 g, 3.10 mmol) and Josiphos SL-J009-1 Pd G3 (96 mg, 0.10 mmol). The mixture was stirred at 145° C. for 18 h. The reaction mixture was concentrated to give a residue which was purified by flash silica gel chromatography to afford 34-1 (130 mg, 48% yield) as a white solid. LCMS: 261.1 [M+H]+

Step 2: To a solution of 34-1 (100 mg, 0.39 mmol) in MeCN (5 mL) and H₂O (0.5 mL) was added N-hydroxyacetamide (52 mg, 0.69 mmol) and 1,1,3,3-tetramethylguanidine (165 mg, 1.38 mmol). This reaction mixture was stirred at 60° C. for 18 h. The reaction mixture was quenched with water (10 mL). The aqueous phase was extracted with ethyl acetate (20 mL×3). The combined organic phase was washed with brine, dried with anhydrous Na₂SO₄ and concentrated under reduced pressure. The residue was purified by flash silica gel chromatography to afford 34-2 (30 mg, 28% yield) as a white solid. LCMS: 274.3 [M+H]+.

Step 3: To a solution of 34-2 (10 mg, 0.04 mmol) in THF (5 mL) was added KHMDS (0.11 Ml, 0.11 mmol) and stirred at −78° C. for 30 min. Then 2,6-dimethoxy benzenesulfonyl chloride (9 mg, 0.04 mmol) was added. The reaction mixture was stirred at −78° C. for 1 h. The reaction mixture was concentrated. The residue was purified by Prep-HPLC to afford Compound 34 (2 mg, 12% yield). LCMS: 474.1 [M+H]+. ¹H NMR (400 MHz, DMSO-d₆) δ 9.71 (s, 1H), 7.86 (d, J=0.8 Hz, 1H), 7.48 (t, J=8.4 Hz, 1H), 7.25 (s, 1H), 7.05 (d, J=0.8 Hz, 1H), 6.77 (d, J=8.4 Hz, 2H), 4.28 (t, J=5.0 Hz, 2H), 3.78 (s, 6H), 2.61 (t, J=6.4 Hz, 2H), 2.03-1.92 (m, 2H).

Example 35: Synthesis of 2,6-dimethoxy-N-(5-(thiazol-2-yloxy)-3,4-dihydro-2H-chromeno[8,7-d]isoxazol-9-yl)benzenesulfonamide (Compound 35)

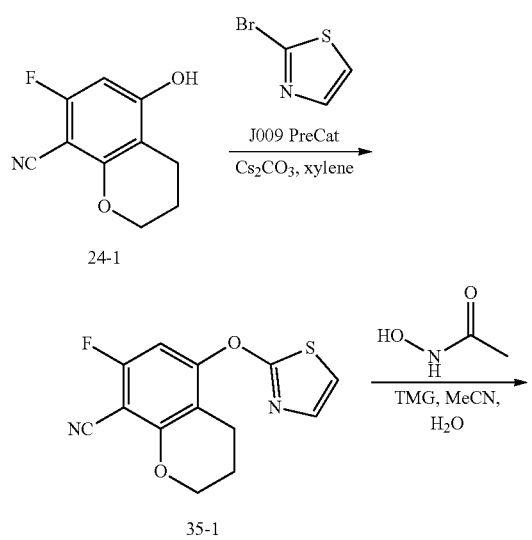

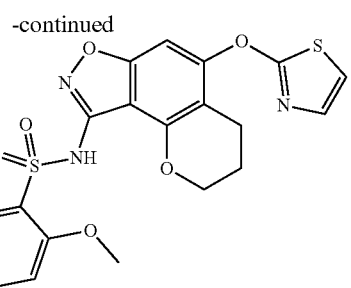

Compound 35

Step 1: To a mixture of 24-1 (200 mg, 1.04 mmol) and 2-bromo-1,3-thiazole (0.28 mL, 3.11 mmol) in xylene (5 mL) were added Cs₂CO₃ (1.01 mg, 3.11 mmol) and Josiphos SL-J009-1 Pd G3 (2 mg, 0.12 mmol). The mixture was stirred at 149° C. for 12 h. This reaction mixture was filtered and concentrated under reduced pressure to give a residue which was purified by flash silica gel chromatography to afford 35-1 (60 mg, 21% yield) as a yellow solid. LCMS: 277.1 [M+H]+.

Step 2: To a mixture of 35-1 (50 mg, 0.18 mmol), N-hydroxyacetamide (41 mg, 0.54 mmol) and water (0.3 mL) in MeCN (3 mL) was added 1,1,3,3-tetramethylguanidine (0.12 mL, 1.09 mmol). The mixture was stirred at 60° C. for 12 h. Water (10 mL) was added to the mixture. Following extraction with ethyl acetate (20 mL×3), the organic phases was combined, washed with brine, dried over anhydrous Na₂SO₄, and filtered. The filtrate was concentrated and then purified by flash silica gel chromatography to afford 35-2 (20 mg, 38% yield) as a yellow solid. LCMS: 290.1 [M+H]+.

Step 3: To a mixture of 35-2 (10 mg, 0.04 mmol) in THF (5 mL) was added KHMDS (0.07 mL, 0.07 mmol) at −78° C. The mixture was stirred at −78° C. for 0.5 h. A (13 mg, 0.05 mmol) in THF (1 mL) was added to this mixture and this reaction mixture was stirred at −78° C. for 1 h. The mixture was concentrated to give the crude product which was further purified by Prep-HPLC to afford Compound 35 (1 mg, 6% yield). LCMS: 490.1 [M+H]+. ¹H NMR (400 MHz, DMSO-d₆) δ 9.63 (s, 1H), 7.51 (t, J=8.0 Hz, 1H), 7.33-7.27 (m, 2H), 7.18 (s, 1H), 6.79 (d, J=8.4 Hz, 2H), 4.32-4.24 (m, 2H), 3.80 (s, 6H), 2.65-2.56 (m, 2H), 2.01-1.91 (m, 2H).

Example 36: Synthesis of 2,6-dimethoxy-N-(5-((3-methylpyridin-2-yl)oxy)-3,4-dihydro-2H-chromeno[8,7-d]isoxazol-9-yl)benzenesulfonamide (Compound 36)

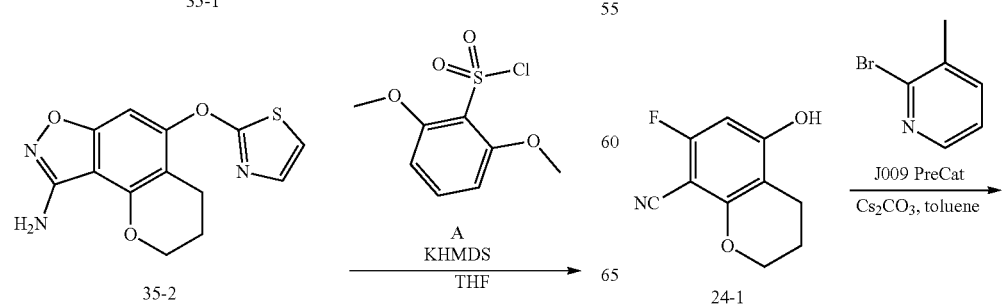

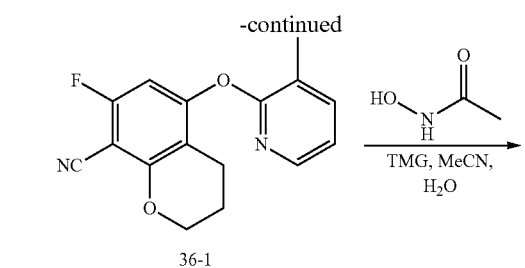

1H), 6.93-6.73 (m, 3H), 4.30-4.19 (m, 2H), 3.81 (s, 6H), 2.51-2.41 (m, 2H), 2.31 (s, 3H), 2.00-1.87 (m, 2H).

Example 37: Synthesis of N-(4-(fluoromethoxy)-6-(pyridin-2-ylmethyl)benzo[d]isoxazol-3-yl)-2,6-dimethoxybenzenesulfonamide (Compound 37)

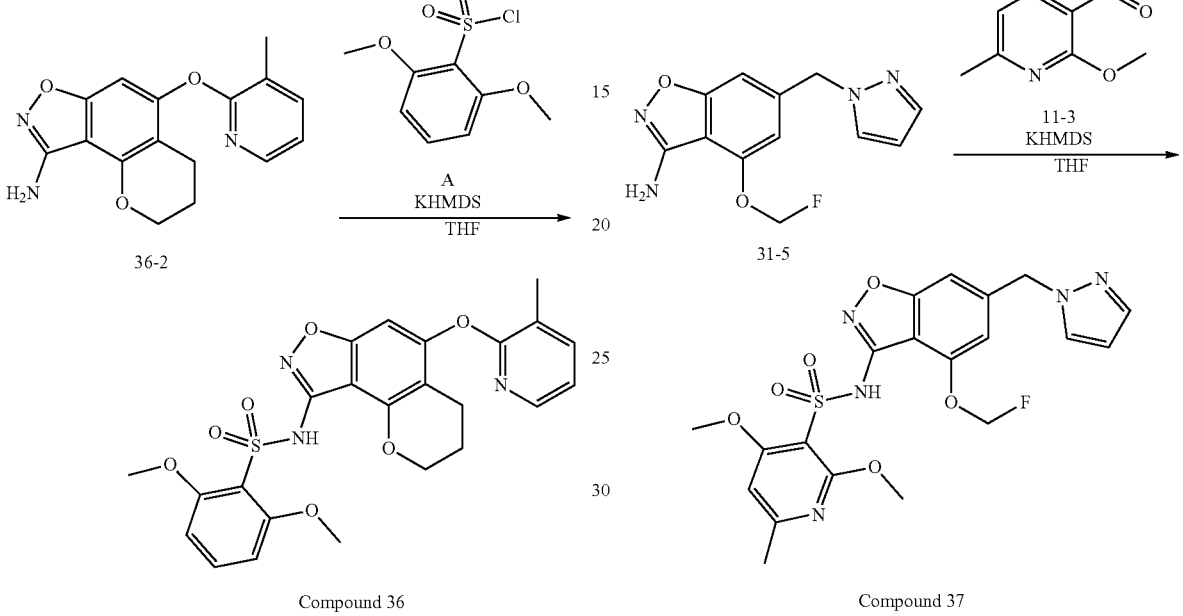

Step 1: To a mixture of 24-1 (200 mg, 1.04 mmol) and 2-bromo-3-methylpyridine (535 mg, 3.11 mmol) in toluene (5 mL) were added Cs$_2$CO$_3$ (1.01 g, 3.11 mmol) and Josiphos SL-J009-1 Pd G3 (19 mg, 0.02 mmol). The mixture was stirred at 100° C. for 12 h. This reaction mixture was filtered and concentrated under reduced pressure to give a residue which was purified by flash silica gel chromatography to afford 36-1 (150 mg, 51% yield) as a white solid. LCMS: 285.2 [M+H]$^+$.

Step 2: To a mixture of 36-1 (150 mg, 0.53 mmol), N-hydroxyacetamide (119 mg, 1.56 mmol) and water (0.5 mL) in MeCN (5 mL) was added 1,1,3,3-tetramethylguanidine (365 mg, 3.12 mmol). The mixture was stirred at 60° C. for 12 h. Water (10 mL) was added to the mixture. Following extraction with ethyl acetate (20 mL×3), the organic phases were combined, washed with brine, dried over anhydrous Na$_2$SO$_4$ and filtered. The filtrate was concentrated under reduced pressure and then purified by flash silica gel chromatography to afford 36-2 (60 mg, 38% yield) as a brown solid. LCMS: 298.1 [M+H]$^+$.

Step 3: To a mixture of 36-2 (10 mg, 0.03 mmol) in THF (5 mL) was added KHMDS (0.07 mL, 0.07 mL) at −78° C. The mixture was stirred at −78° C. for 0.5 h. A (12.0 mg, 0.05 mmol) in THF (1 mL) was added to this mixture and this reaction mixture was stirred at −78° C. for 1 h. The mixture was concentrated to give the crude product which was further purified by Prep-HPLC to afford Compound 36 (1 mg, 5% yield). LCMS: 498.1 [M+H]$^+$. $^1$H NMR (400 MHz, DMSO-d$_6$) δ 9.51 (s, 1H), 7.94 (d, J=4.4 Hz, 1H), 7.74 (d, J=7.2 Hz, 1H), 7.50 (t, J=8.0 Hz, 1H), 7.08 (t, J=5.6 Hz, To a mixture of 31-5 (20 mg, 0.08 mmol) in THF (5 mL) was added KHMDS (0.15 mL, 0.15 mmol) at −78° C. The mixture was stirred at −78° C. for 0.5 h. Then, 11-3 (29 mg, 0.11 mmol) in THF (1 mL) was added to this mixture and this reaction mixture was stirred at −78° C. for 1.5 h. The mixture was concentrated to give the crude product which was further purified by Prep-HPLC to afford Compound 37 (10 mg, 29% yield). LCMS: 478.1 [M+H]$^+$. $^1$H NMR (400 MHz, DMSO-d$_6$) δ 10.37 (brs, 1H), 7.89 (d, J=2.0 Hz, 1H), 7.51 (s, 1H), 7.03 (s, 1H), 6.91 (s, 1H), 6.78 (s, 1H), 6.31 (s, 1H), 5.93 (d, J=53.6 Hz, 2H), 5.48 (s, 2H), 3.80 (s, 3H), 3.78 (s, 3H), 2.37 (s, 3H).

Example 38: Synthesis of N-(6-((1H-pyrazol-1-yl)methyl)-4-methoxybenzo[d]isoxazol-3-yl)-4-methoxy-6-methylpyridine-3-sulfonamide (Compound 38)

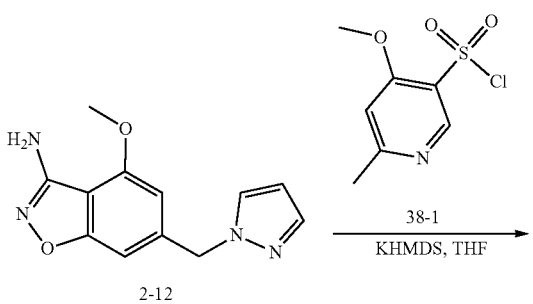

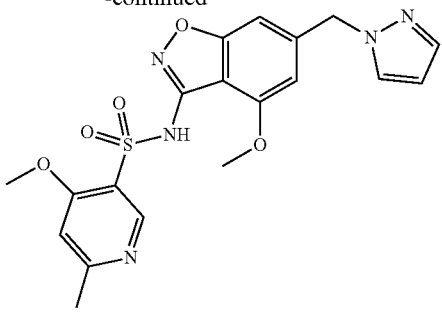

Compound 38

To a mixture of 2-12 (30 mg, 0.11 mmol) in THF (5 mL) was added KHMDS (0.17 mL, 0.17 mmol) at −78° C. The mixture was stirred at −78° C. for 0.5 h. Then 38-1 (30.0 mg, 0.11 mmol) in THF (1 mL) was added. The reaction mixture was stirred at −78° C. for 1.5 h. The mixture was concentrated to give the crude product which was further purified by Prep-HPLC to afford Compound 38 (2.3 mg, 4% yield). LCMS: 430.2 [M+H]⁺.

Example 39: Synthesis of N-(6-((1H-pyrazol-1-yl)methyl)-4-methoxybenzo[d]isoxazol-3-yl)-6-cyclopropyl-2,4-dimethoxypyridine-3-sulfonamide (Compound 39)

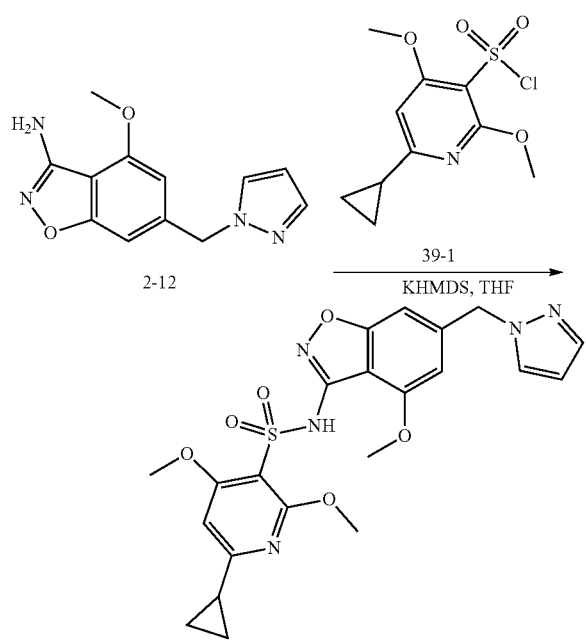

Compound 39

To a mixture of 2-12 (30 mg, 0.11 mmol) in THF (5 mL) was added KHMDS (0.17 mL, 1M) at −78° C. The mixture was stirred at −78° C. for 0.5 h. 39-1 (30.0 mg, 0.11 mmol) in THF (1 mL) was added. The reaction mixture was stirred at −78° C. for 1.5 h. The mixture was concentrated to give the crude product which was further purified by Prep-HPLC to afford Compound 39 (2.2 mg, 4% yield). LCMS: 486.3 [M+H]⁺.

Example 40: Synthesis of N-(6-((1H-pyrazol-1-yl)methyl)-4-methoxybenzo[d]isoxazol-3-yl)-6-(difluoromethyl)-2,4-dimethoxypyridine-3-sulfonamide (Compound 40)

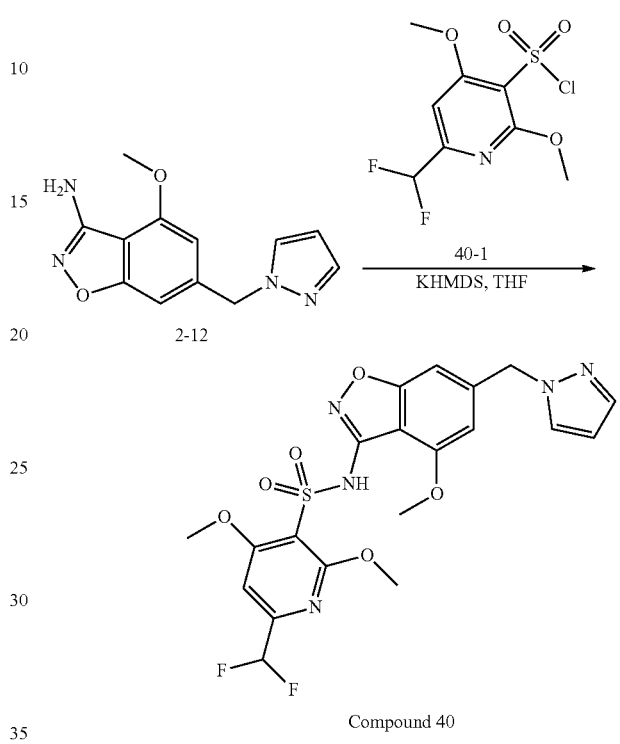

Compound 40

To a mixture of 2-12 (30 mg, 0.11 mmol) in THF (5 mL) was added KHMDS (0.17 mL, 0.17 mmol) at −78° C. The mixture was stirred at −78° C. for 0.5 h. Then 40-1 (30.0 mg, 0.11 mmol) in THF (1 mL) was added. The reaction mixture was stirred at −78° C. for 1.5 h. The mixture was concentrated to give the crude product which was further purified by Prep-HPLC to afford Compound 40 (1.8 mg, 3% yield). LCMS: 496.3 [M+H]⁺.

Example 41: Synthesis of N-(6-((1H-pyrazol-1-yl)methyl)-4-methoxybenzo[d]isoxazol-3-yl)-2,4-dimethoxy-6-(trifluoromethyl)pyridine-3-sulfonamide (Compound 41)

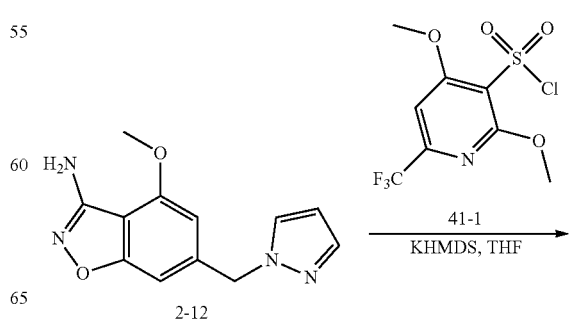

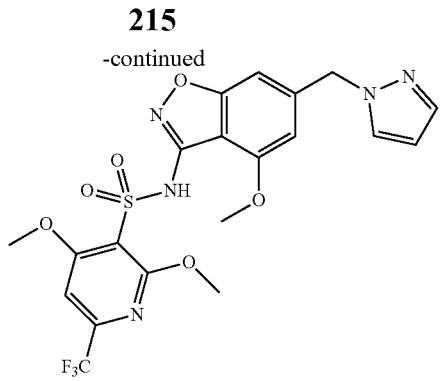

Compound 41

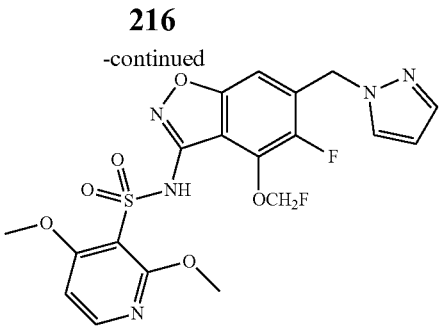

Compound 42

To a mixture of 2-12 (30 mg, 0.11 mmol) in THF (5 mL) was added KHMDS (0.17 mL, 0.17 mmol) at −78° C. The mixture was stirred at −78° C. for 0.5 h. Then 41-1 (30.0 mg, 0.11 mmol) in THF (1 mL) was added. The reaction mixture was stirred at −78° C. for 1.5 h. The mixture was concentrated to give the crude product which was further purified by Prep-HPLC to afford Compound 41 (1.6 mg, 3% yield). LCMS: 514.3 [M+H]$^+$.

Example 42: Synthesis of N-(6-((1H-pyrazol-1-yl)methyl)-5-fluoro-4-(fluoromethoxy) benzo[d]isoxazol-3-yl)-2,4-dimethoxypyridine-3-sulfonamide (Compound 42)

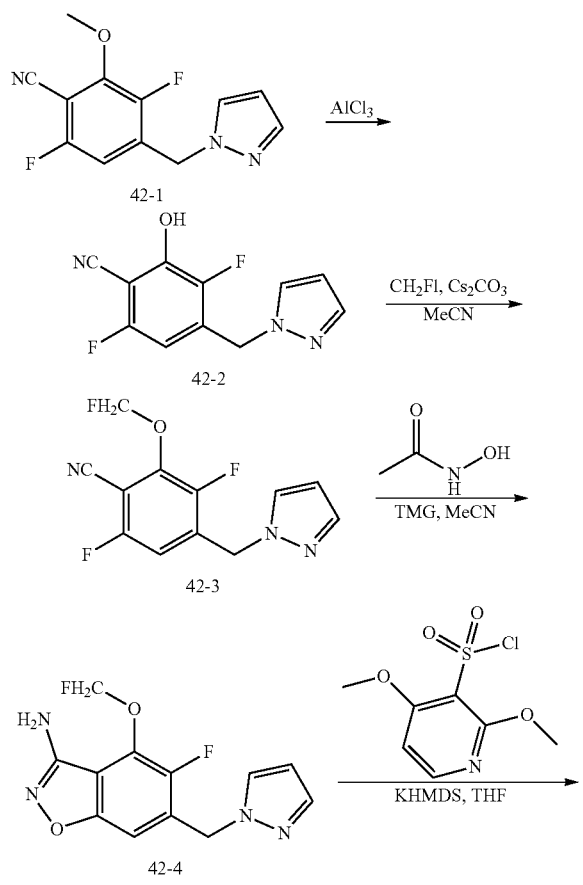

Step 1: To a solution of 42-1 (800 mg, 3.21 mmol) in MeCN (10 mL) was added AlCl$_3$ (2.18 g, 16.05 mmol), NaI (2.41 g, 16.05 mmol) at 0° C. The reaction was stirred at 80° C. for 18 h. Water (20 mL) was added and the mixture was extracted with ethyl acetate (15 mL×3). The combined organic phase was washed with brine and concentrated. The residue was purified by flash silica gel chromatography to give 42-2 (430 mg, 57%) as white solid. LCMS: 236.2 [M+H]$^+$.

Step 2: To a solution of 42-2 (60 mg, 0.26 mmol) in acetonitrile (3 mL) were added Cs$_2$CO$_3$ (125 mg, 0.38 mmol) and CH$_2$FI (61 mg, 0.38 mmol). The reaction mixture was stirred at room temperature for 5 h. Then the reaction mixture was concentrated. The residue was purified by flash silica gel chromatography to give 42-3 (60 mg, 88% yield) as a yellow solid. LCMS: 268.2 [M+H]$^+$.

Step 3: To a mixture of 42-3 (50 mg, 0.19 mmol), N-hydroxyacetamide (42 mg, 0.56 mmol), and water (0.2 mL) in MeCN (2.0 mL) was added 1,1,3,3-tetramethylguanidine (129 mg, 1.12 mmol). The reaction mixture was stirred at 60° C. for 16 h. Water (5 mL) was added and the mixture was extracted with ethyl acetate (5 mL×3). The combined organic phase was washed with brine, dried over anhydrous Na$_2$SO$_4$, and concentrated to give a residue which was purified by flash silica gel chromatography to afford 42-4 (42 mg, 80% yield) as a brown solid. LCMS: 281.3 [M+H]$^+$.

Step 4: To a solution of 42-4 (30 mg, 0.11 mmol) in THF (3 mL) was added KHMDS (0.18 mL, 0.18 mmol) at −78° C. This reaction mixture was stirred at −78° C. for 30 min. Then 2,4-dimethoxypyridine-3-sulfonyl chloride (30 mg, 0.13 mmol) in THF (1 mL) was added and the reaction mixture was stirred at −78° C. for 1 h. The mixture was concentrated to give the crude product which was purified by Prep-HPLC to afford Compound 42 (1.29 mg, 3% yield). LCMS: 482.1 [M+H]$^+$. $^1$H NMR (400 MHz, DMSO-d$_6$) δ 8.30 (s, 1H), 7.97 (d, J=6.0 Hz, 1H), 7.85 (d, J=2.0 Hz, 1H), 7.49 (d, J=1.2 Hz, 1H), 6.70 (d, J=5.6 Hz, 1H), 6.68 (s, 1H), 6.30 (t, J=2.0 Hz, 1H), 6.22 (d, J=55.6 Hz, 2H), 5.46 (s, 2H), 3.66 (s, 6H).

Example 43: Synthesis of N-(6-((1H-pyrazol-1-yl)methyl)-5-fluoro-4-(fluoromethoxy) benzo[d]isoxazol-3-yl)-2,4-dimethoxy-6-methylpyridine-3-sulfonamide (Compound 43)

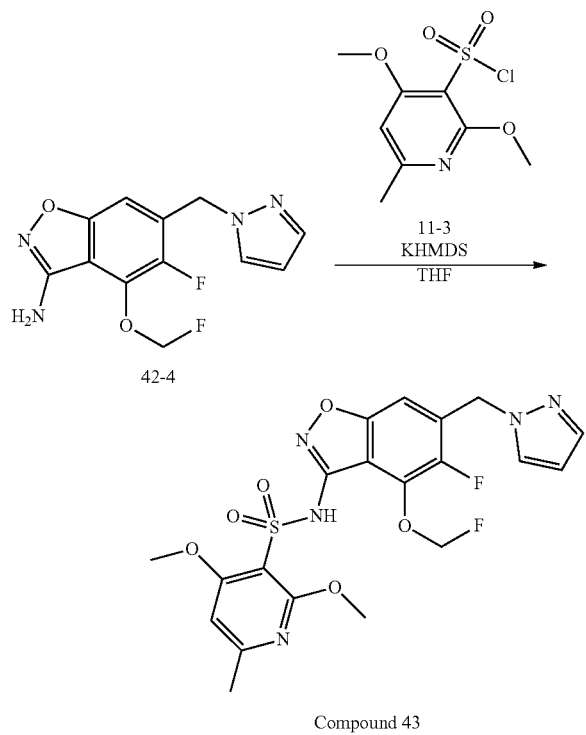

To a mixture of 42-4 (60 mg, 0.21 mmol) in THF (5 mL) was added KHMDS (0.32 mL, 0.32 mmol) at −78° C. and stirred at this temperature for 30 min. Then 11-3 (64 mg, 0.32 mmol) was added. The reaction was stirred at −78° C. for 2 h The mixture was concentrated to give the crude product which was further purified by Prep-HPLC to afford Compound 43 (4 mg, 4% yield). LCMS: 496.2 [M+H]+. $^1$H NMR (400 MHz, DMSO-$d_6$) δ 10.57 (s, 1H), 7.88 (d, J=2.0 Hz, 1H), 7.51 (d, J=1.2 Hz, 1H), 7.12 (s, 1H), 6.81 (s, 1H), 6.32 (t, J=2.0 Hz, 1H), 5.88 (d, J=53.6 Hz, 2H), 5.55 (s, 2H), 3.83 (s, 3H), 3.81 (s, 3H), 2.39 (s, 3H).

Example 44: Synthesis of N-(6-((1H-pyrazol-1-yl)methyl)-4-(difluoromethoxy)-5-fluorobenzo[d]isoxazol-3-yl)-2,4-dimethoxy-6-methylpyridine-3-sulfonamide (Compound 44)

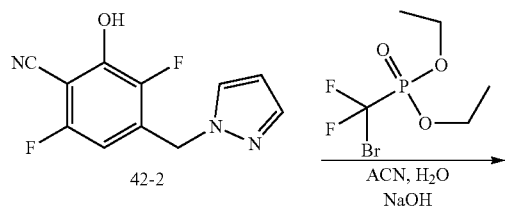

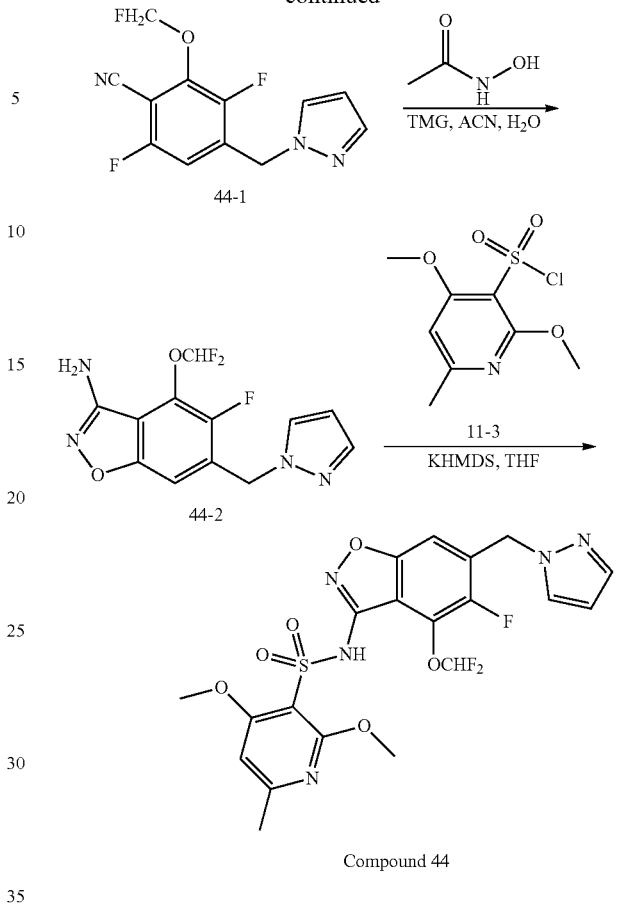

Step 1: To a mixture of 42-2 (50 mg, 0.21 mmol) in MeCN (2 mL) were added NaOH (340 mg, 8.51 mmol) in H$_2$O (2 mL) and diethyl bromodifluoromethyl phosphonate (114 mg, 0.43 mmol) at −20° C. The mixture was stirred at 0° C. for 4 h. Water (5 mL) was added. Following extraction with ethyl acetate (10 mL×3), the organic phase was combined, washed with brine, dried over anhydrous Na$_2$SO$_4$, and filtered. The filtrate was concentrated under reduced pressure and then purified by flash silica gel chromatography to afford 44-1 (50 mg, 82% yield) as a white solid. LCMS: 286.0 [M+H]+.

Step 2: To a mixture of 44-1 (40 mg, 0.14 mmol), N-hydroxyacetamide (32 mg, 0.42 mmol), and water (0.3 mL) in MeCN (3 mL) was added 1,1,3,3-tetramethylguanidine (96 mg, 0.84 mmol). The mixture was stirred at 60° C. for 2 h. This reaction mixture was concentrated under reduced pressure and then purified by flash silica gel chromatography to afford 44-2 (30 mg, 72% yield) as a brown solid. LCMS: 299.0 [M+H]+.

Step 3: To a mixture of 44-2 (20 mg, 0.07 mmol) in THF (5 mL) was added KHMDS (0.13 mL, 0.13 mmol) at −78° C. The mixture was stirred at −78° C. for 0.5 h. 11-3 (21.0 mg, 0.08 mmol) in THF (1 mL) was added to this mixture and this reaction mixture was stirred at −78° C. for 0.5 h. The mixture was concentrated to give the crude product which was further purified by Prep-HPLC to afford Compound 44 (2 mg, 6% yield). LCMS: 514.2 [M+H]+. $^1$H NMR (400 MHz, DMSO-$d_6$) δ 10.71 (brs, 1H), 7.89 (s, 1H), 7.52 (s, 1H), 7.46-7.09 (m, 2H), 6.81 (s, 1H), 6.32 (s, 1H), 5.57 (s, 2H), 3.83 (s, 3H), 3.81 (s, 3H), 2.40 (s, 3H).

Example 45: Synthesis of N-(4-(fluoromethoxy)-6-(pyridin-2-ylmethyl)benzo[d]isoxazol-3-yl)-2,6-dimethoxybenzenesulfonamide (Compound 45)

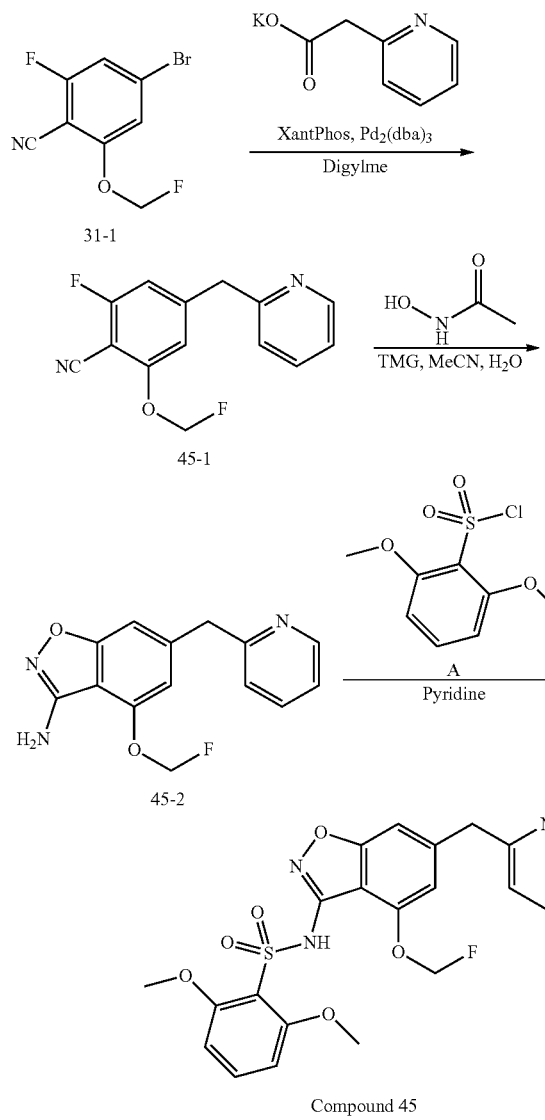

Compound 45

Step 1: To a mixture of 31-1 (200 mg, 0.81 mmol) in diglyme (5 mL) were added 2-(pyridin-2-yl)acetate (171 mg, 0.97 mmol), xantphos (280 mg, 0.48 mmol) and Pd$_2$(dba)$_3$ (74 mg, 0.08 mmol). The reaction mixture was stirred at 149° C. for 12 h. Water (10 mL) was added to the mixture. Following extraction with ethyl acetate (20 mL×3), the organic phase was combined, washed with brine, dried over anhydrous Na$_2$SO$_4$, and filtered. The filtrate was concentrated under reduced pressure and then purified by flash silica gel chromatography to afford 45-1 (150 mg, 71% yield) as a white solid. LCMS: 261.3 [M+H]$^+$.

Step 2: To a mixture of 45-1 (150 mg, 0.58 mmol), N-hydroxyacetamide (130 mg, 1.73 mmol), and water (0.5 mL) in MeCN (4.5 mL) was added 1,1,3,3-tetramethylguanidine (398 mg, 3.46 mmol). The mixture was stirred at 60° C. for 6 h. Water (10 mL) was added to the mixture. Following extraction with ethyl acetate (20 mL×3), the organic phase was combined, washed with brine, dried over anhydrous Na$_2$SO$_4$ and filtered. The filtrate was concentrated under reduced pressure and then purified by flash silica gel chromatography to afford 45-2 (50 mg, 32% yield) as a brown solid. LCMS: 274.2 [M+H]$^+$.

Step 3: To a mixture of 45-2 (150 mg, 0.55 mmol) in pyridine (5 mL) was added A (195 mg, 0.82 mmol). The reaction mixture was stirred at 120° C. for 5 h. The reaction mixture was concentrated in vacuo. The residue was purified by Prep-HPLC to give Compound 45 (13 mg, 5% yield). LCMS: 474.1 [M+H]$^+$. $^1$H NMR (400 MHz, DMSO-d$_6$) δ 9.96 (s, 1H), 8.51-8.47 (m, 1H), 7.75-7.70 (m, 1H), 7.52-7.42 (m, 1H), 7.34 (d, J=7.6 Hz, 1H), 7.27-7.19 (m, 2H), 6.98 (s, 1H), 6.75 (d, J=8.4 Hz, 2H), 5.92 (d, J=54 Hz, 2H), 4.21 (s, 2H), 3.74 (s, 6H).

Example 46: Synthesis of 2,6-dimethoxy-N-(5-(pyridin-2-ylmethyl)-3,4-dihydro-2H-chromeno[8,7-d]isoxazol-9-yl)benzenesulfonamide (Compound 46)

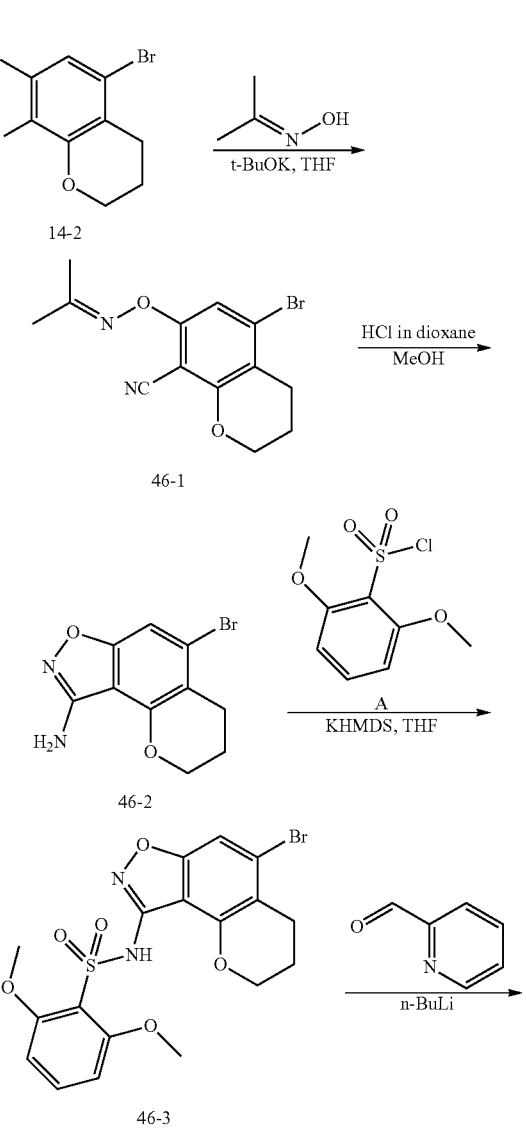

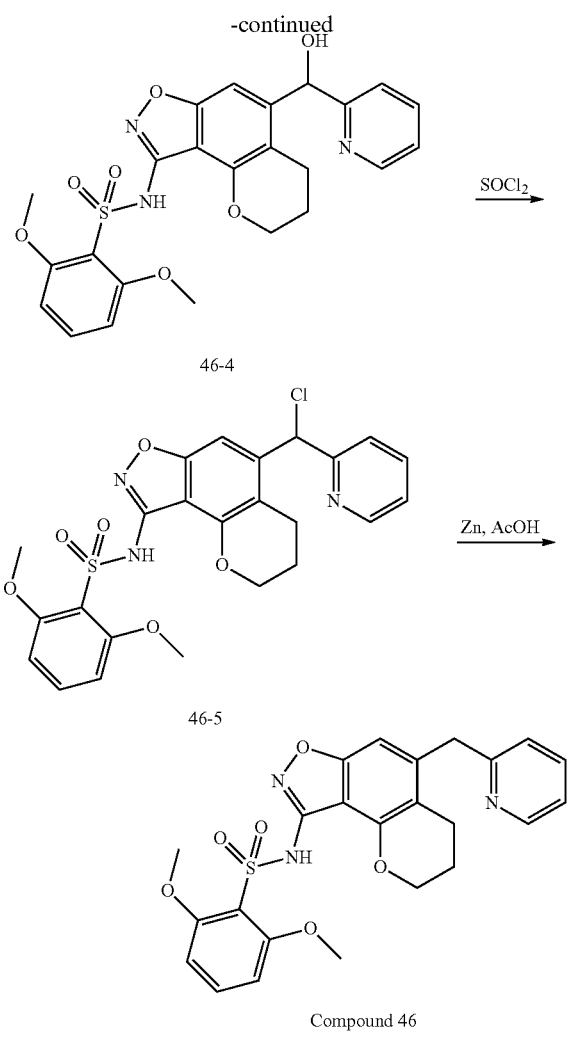

46-4

46-5

Compound 46

Step 1: To a solution of 14-2 (2 g, 7.8 mmol) in DMF (20 mL) was added t-BuOK (1.04 g, 9.3 mmol) at 25° C. and stirred for 1 h. Then acetone oxime (679 mg, 9.3 mmol) was added. This reaction mixture was stirred at 25° C. for 1 h. The reaction mixture was quenched with water (20 mL). The aqueous phase was extracted with ethyl acetate (20 mL×3). The combined organic phase was washed with brine, dried over anhydrous sodium sulfate and concentrated under reduced pressure. The residue was purified by flash silica gel chromatography to afford 46-1 (1.5 g, 62% yield) as a white solid. LCMS: 309.2 [M+H]⁺.

Step 2: To a solution of 46-1 (1.5 g, 4.87 mmol) in MeOH (15 mL) was added 4M HCl in dioxane (15 mL). This reaction mixture was stirred at 25° C. for 18 h. The reaction mixture was concentrated in vacuum to give a residue which was purified by flash silica gel chromatography to afford 46-2 (1 g, 77% yield) as a white solid. LCMS: 269.2 [M+H]⁺.

Step 3: To a solution of 46-2 (1 g, 3.72 mmol) in tetrahydrofuran (40 mL) was added potassium bis(trimethylsilyl)amide (11.15 mL, 11.15 mmol) at −78° C. for 30 min. A (1.76 g, 7.43 mmol) was added and the reaction mixture was stirred at −78° C. for 1.5 h. The reaction mixture was concentrated in vacuum to give a residue. The residue was purified by flash silica gel chromatography to afford 46-3 (500 mg, 29% yield) as a yellow solid. LCMS: 469.0 [M+H]⁺.

Step 4: To a solution of 46-3 (200 mg, 0.43 mmol) in tetrahydrofuran (15 mL) was added n-BuLi (0.8 mL, 1.28 mmol, 1.6 M) at −78° C. for 20 min. Then pyridine-2-carbaldehyde (91 mg, 0.85 mmol) was added and the reaction mixture was stirred at −78° C. for 3 h. The reaction mixture was quenched with saturated NH₄Cl (1 mL). The reaction mixture was concentrated. The residue was purified by flash silica gel chromatography to afford 46-4 (100 mg, 47% yield) as a yellow solid. LCMS: 498.0 [M+H]⁺.

Step 5: To a solution of 46-4 (100 mg, 0.20 mmol) in DCM (3 mL) was added SOCl₂ (267 mg, 2.25 mmol). This reaction mixture was stirred at room temperature for 3 h. This reaction mixture was concentrated to afford the crude product 46-5 (100 mg) as a white solid which was used in the next step without further purification. LCMS: 516.1 [M+H]⁺.

Step 6: To a solution of 46-5 (100 mg, 0.19 mmol) in AcOH (5 mL) was added Zn (89 mg, 1.36 mmol). This reaction mixture was stirred at 60° C. for 3 h. The reaction mixture was quenched with saturated NaHCO₃ (10 mL). The aqueous phase was extracted with ethyl acetate (20 mL×3). The combined organic phase was washed with brine, dried over anhydrous sodium sulfate and concentrated. The residue was purified by Prep-HPLC to afford Compound 46 (5 mg, 5% yield). LCMS: 482.1 [M+H]⁺. ¹H NMR (400 MHz, DMSO-d₆) δ 9.35 (s, 1H), 8.48 (d, J=4.4 Hz, 1H), 7.75-7.64 (m, 1H), 7.56-7.44 (m, 1H), 7.28-7.16 (m, 2H), 6.95 (s, 1H), 6.78 (d, J=8.8 Hz, 2H), 4.26-4.19 (m, 2H), 4.16 (s, 2H), 3.80 (s, 6H), 2.69-2.60 (m, 2H), 2.03-1.91 (m, 2H).

Example 47: Synthesis of 2,6-dimethoxy-N-(5-(pyridin-2-ylmethyl)-3,4-dihydro-2H-chromeno[8,7-d]isoxazol-9-yl)benzenesulfonamide (Compound 47)

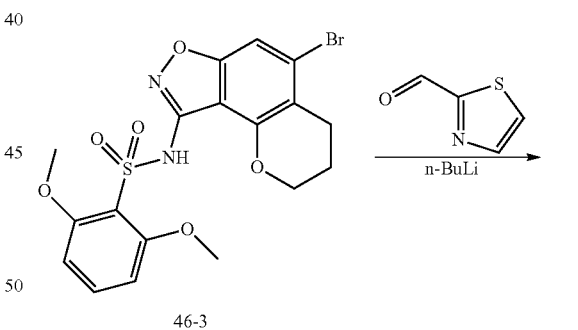

46-3

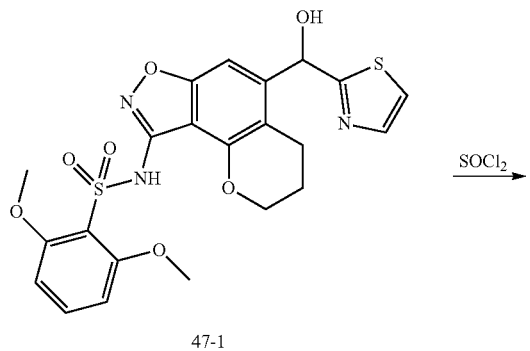

47-1

-continued

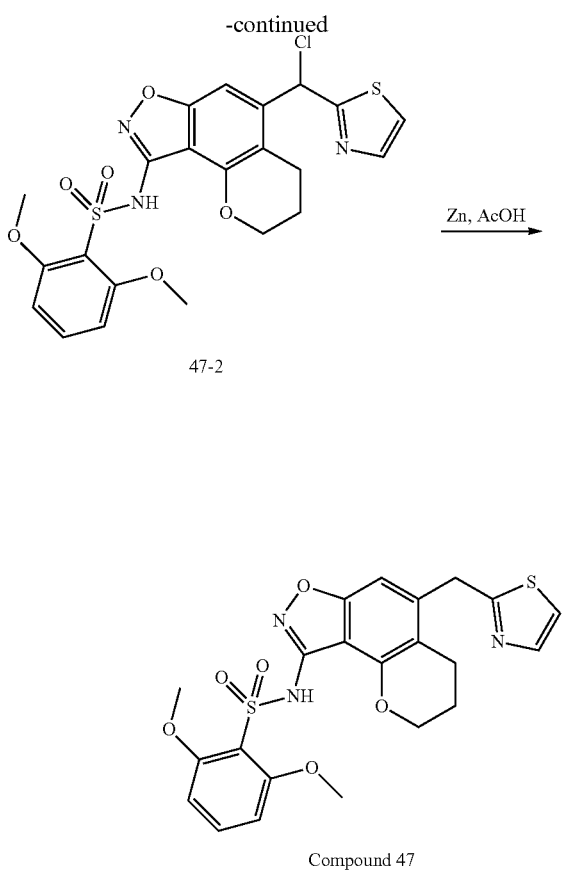

47-2

Compound 47

Step 1: To a solution of 46-3 (50 mg, 0.11 mmol) in tetrahydrofuran (15 mL) was added n-BuLi (0.2 mL, 0.32 mmol, 1.6 M) at −78° C. for 20 min. Then 1,3-thiazole-2-carbaldehyde (12 mg, 0.11 mmol) was added and the reaction mixture was stirred at −78° C. for 3 h. The reaction was quenched with saturated NH$_4$Cl (20 mL). The aqueous phase was extracted with DCM (20 mL×3). The combined organic phase was washed with brine, dried over anhydrous sodium sulfate, filtered and concentrated under reduced pressure to give a residue. The residue was purified by flash silica gel chromatography to afford 47-1 (20 mg, 37% yield) as a yellow oil. LCMS: 503.9 [M+H]$^+$.

Step 2: To a solution of 47-1 (20 mg, 0.04 mmol) in DCM (3 mL) was added SOCl$_2$ (54 mg, 0.46 mmol). This reaction mixture was stirred at room temperature for 3 h. This reaction mixture was concentrated to afford 47-2 (20 mg) as a white solid which was used in the next step without further purification. LCMS: 522.2 [M+H]$^+$.

Step 3: To a solution of 47-2 (20 mg, 0.04 mmol) in AcOH (3 mL) was added Zn (19 mg, 0.29 mmol). This reaction mixture was stirred at 60° C. for 3 h. The reaction mixture was quenched with NaHCO$_3$ (10 mL). The aqueous phase was extracted with DCM (20 mL×3). The combined organic phase was washed with brine, dried over anhydrous sodium sulfate and concentrated. The residue was purified by Prep-HPLC to afford Compound 47 (3 mg, 13% yield). LCMS: 488.1 [M+H]$^+$. $^1$H NMR (400 MHz, DMSO-d$_6$) δ 9.53 (s, 1H), 7.75-7.67 (m, 1H), 7.62-7.57 (m, 1H), 7.52-7.44 (m, 1H), 7.07 (s, 1H), 6.77 (d, J=8.4 Hz, 2H), 4.41 (s, 2H), 4.25-4.17 (m, 2H), 3.78 (s, 6H), 2.68-2.62 (m, 2H), 1.98-1.93 (m, 2H).

Example 48: Synthesis of N-(6-((1H-pyrazol-1-yl)methyl)-4-(fluoromethoxy) benzo[d]isoxazol-3-yl)-2,4-dimethoxypyridine-3-sulfonamide (Compound 48)

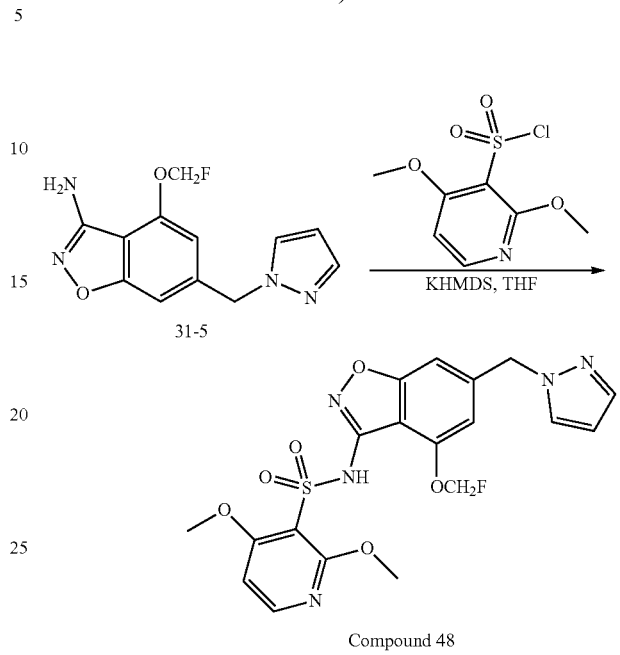

Compound 48

Step 1: To a mixture of 31-5 (30 mg, 0.11 mmol) in THF (5 mL) was added KHMDS (0.17 mL, 0.17 mmol) at −78° C. The mixture was stirred at −78° C. for 0.5 h. 2,4-dimethoxypyridine-3-sulfonyl chloride (41 mg, 0.17 mmol) in THF (1 mL) was added to this mixture and this reaction mixture was stirred at −78° C. for 1.5 h. The mixture was concentrated to give the crude product which was further purified by Prep-HPLC to afford Compound 48 (2.7 mg, 5% yield). LCMS: 464.1 [M+H]$^+$. $^1$H NMR (400 MHz, DMSO-d$_6$) δ 10.53 (s, 1H), 8.22 (d, J=6.0 Hz, 1H), 7.88 (d, J=2.0 Hz, 1H), 7.51 (d, J=1.2 Hz, 1H), 7.06 (s, 1H), 6.97-6.80 (m, 2H), 6.31 (t, J=2.0 Hz, 1H), 5.89 (d, J=53.2 Hz, 2H), 5.48 (s, 2H), 3.85 (s, 3H), 3.83 (s, 3H).

Example 49: Synthesis of N-(6-((1H-pyrazol-1-yl)methyl)-4-(fluoromethoxy)benzo [d]isoxazol-3-yl)-6-cyclopropyl-2,4-dimethoxypyridine-3-sulfonamide (Compound 49)

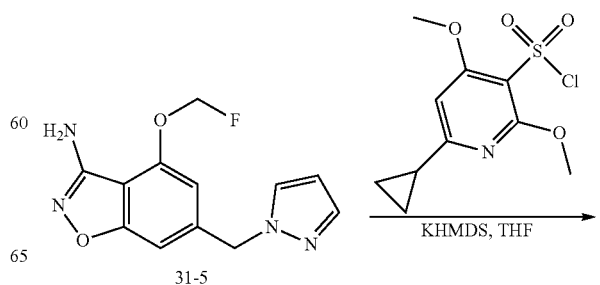

31-5

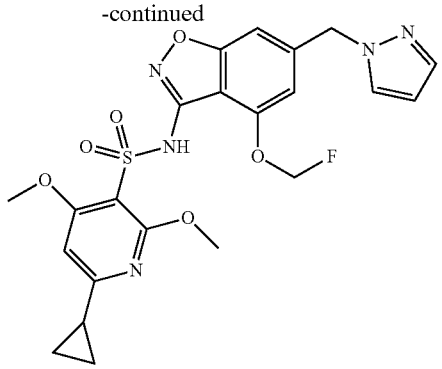

Compound 49

To a mixture of 31-5 (30 mg, 0.11 mmol) in THF (5 mL) was added KHMDS (0.17 mL, 0.17 mmol) at −78° C. The mixture was stirred at −78° C. for 0.5 h. 6-cyclopropyl-2,4-dimethoxypyridine-3-sulfonyl chloride (30.0 mg, 0.11 mmol) in THF (1 mL) was added. The reaction mixture was stirred at −78° C. for 1.5 h. The mixture was concentrated to give the crude product which was further purified by Prep-HPLC to afford Compound 49 (4.4 mg, 8% yield). LCMS: 504.2 [M+H]$^+$. $^1$H NMR (400 MHz, DMSO-d$_6$) δ 10.33 (brs, 1H), 7.88 (d, J=2.4 Hz, 1H), 7.51 (d, J=1.6 Hz, 1H), 7.02 (s, 1H), 6.89 (s, 1H), 6.31 (t, J=2.0 Hz, 1H), 6.25 (s, 1H), 5.94 (d, J=53.6 Hz, 2H), 5.47 (s, 2H), 3.79 (s, 3H), 3.76 (s, 3H), 3.40-3.30 (m, 1H), 1.12-1.01 (m, 2H), 0.94-0.83 (m, 2H).

Example 50: Synthesis of N-(6-((1H-pyrazol-1-yl)methyl)-4-(fluoromethoxy)benzo[d] isoxazol-3-yl)-6-(difluoromethyl)-2,4-dimethoxypyridine-3-sulfonamide (Compound 50)

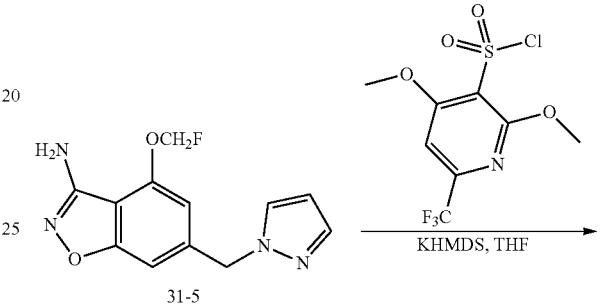

Compound 50

To a mixture of 31-5 (30 mg, 0.11 mmol) in THF (5 mL) was added KHMDS (0.17 mL, 0.17 mmol) at −78° C. The mixture was stirred at −78° C. for 0.5 h. Then 6-(difluoromethyl)-2,4-dimethoxypyridine-3-sulfonyl chloride (32 mg, 0.11 mmol) in THF (1 mL) was added. The reaction mixture was stirred at −78° C. for 1.5 h. The mixture was concentrated to give the crude product which was further purified by Prep-HPLC to afford Compound 50 (3.6 mg, 6% yield). LCMS: 514.2 [M+H]$^+$.

Example 51: Synthesis of N-(6-((1H-pyrazol-1-yl)methyl)-4-(fluoromethoxy)benzo[d] isoxazol-3-yl)-2,4-dimethoxy-6-(trifluoromethyl)pyridine-3-sulfonamide (Compound 51)

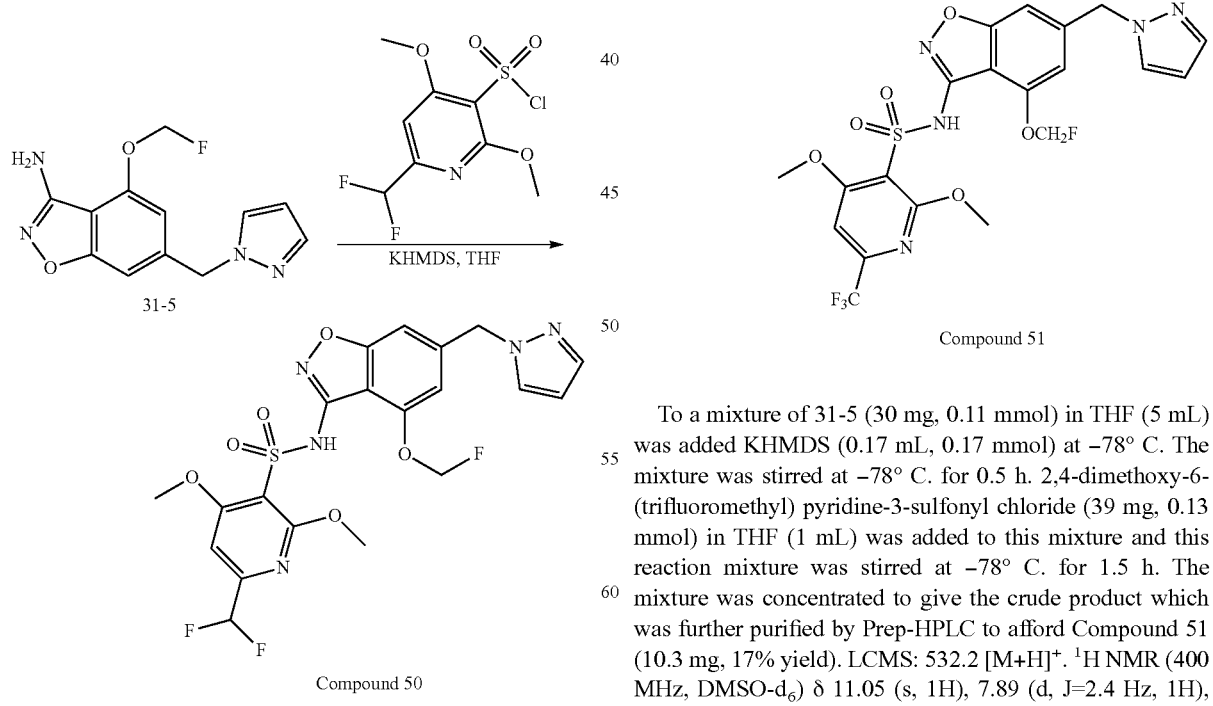

Compound 51

To a mixture of 31-5 (30 mg, 0.11 mmol) in THF (5 mL) was added KHMDS (0.17 mL, 0.17 mmol) at −78° C. The mixture was stirred at −78° C. for 0.5 h. 2,4-dimethoxy-6-(trifluoromethyl) pyridine-3-sulfonyl chloride (39 mg, 0.13 mmol) in THF (1 mL) was added to this mixture and this reaction mixture was stirred at −78° C. for 1.5 h. The mixture was concentrated to give the crude product which was further purified by Prep-HPLC to afford Compound 51 (10.3 mg, 17% yield). LCMS: 532.2 [M+H]$^+$. $^1$H NMR (400 MHz, DMSO-d$_6$) δ 11.05 (s, 1H), 7.89 (d, J=2.4 Hz, 1H), 7.52-7.50 (m, 1H), 7.40 (s, 1H), 7.07 (s, 1H), 6.95 (s, 1H), 6.31 (t, J=2.0 Hz, 1H), 5.88 (d, J=53.6 Hz, 2H), 5.49 (s, 2H), 3.97 (s, 3H), 3.87 (s, 3H).

Example 52: Synthesis of N-(6-((1H-pyrazol-1-yl)methyl)-4-(fluoromethoxy)benzo[d] isoxazol-3-yl)-6-ethyl-2,4-dimethoxypyridine-3-sulfonamide (Compound 50)

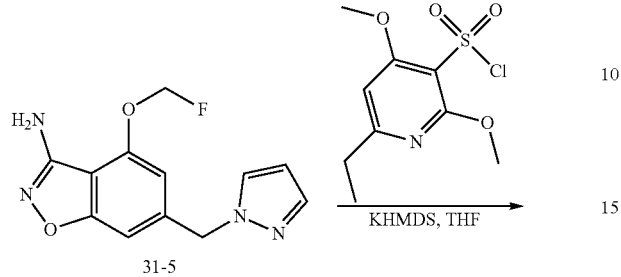

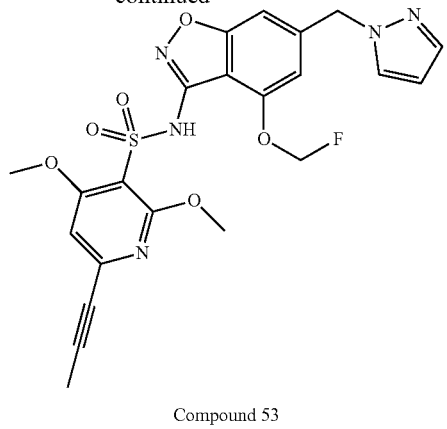

Compound 53

To a mixture of 31-5 (30 mg, 0.11 mmol) in THF (5 mL) was added KHMDS (0.17 mL, 0.17 mmol) at −78° C. The mixture was stirred at −78° C. for 0.5 h. Then, 2,4-dimethoxy-6-(prop-1-yn-1-yl) pyridine-3-sulfonyl chloride (30 mg, 0.11 mmol) in THF (1 mL) was added. The reaction mixture was stirred at −78° C. for 1.5 h. The mixture was concentrated to give the crude product which was further purified by Prep-HPLC to afford Compound 53 (2 mg, 3% yield). LCMS: 502.2 [M+H]$^+$.

Example 54: Synthesis of N-(6-((1H-pyrazol-1-yl)methyl)-4-(fluoromethoxy)benzo[d] isoxazol-3-yl)-6-ethynyl-2,4-dimethoxypyridine-3-sulfonamide (Compound 54)

Compound 52

To a mixture of 31-5 (30 mg, 0.11 mmol) in THF (5 mL) was added KHMDS (0.17 mL, 0.17 mmol) at −78° C. The mixture was stirred at −78° C. for 0.5 h. Then, 6-ethyl-2,4-dimethoxypyridine-3-sulfonyl chloride (29 mg, 0.11 mmol) in THF (1 mL) was added. The reaction mixture was stirred at −78° C. for 1.5 h. The mixture was concentrated to give the crude product which was further purified by Prep-HPLC to afford Compound 52 (4 mg, 6% yield). LCMS: 492.2 [M+H]$^+$. $^1$H NMR (400 MHz, CD$_3$OD) δ 7.77 (d, J=2.4 Hz, 1H), 7.56 (d, J=1.6 Hz, 1H), 6.94 (s, 1H), 6.86 (s, 1H), 6.37 (t, J=2.0 Hz, 1H), 6.26 (s, 1H), 5.91 (d, J=53.2 Hz, 2H), 5.48 (s, 2H), 3.93 (s, 3H), 3.84 (s, 3H), 3.21 (q, J=7.4 Hz, 2H), 1.27 (t, J=7.4 Hz, 3H).

Example 53: Synthesis of N-(6-((1H-pyrazol-1-yl)methyl)-4-(fluoromethoxy)benzo[d] isoxazol-3-yl)-2,4-dimethoxy-6-(prop-1-yn-1-yl)pyridine-3-sulfonamide (Compound 53)

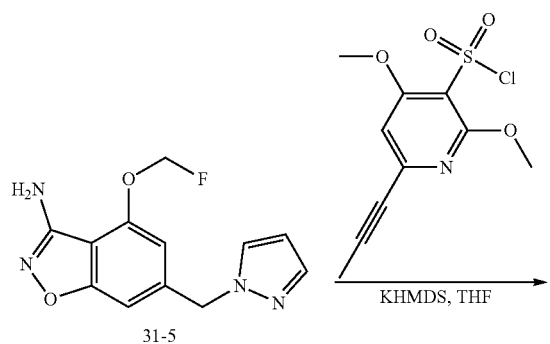

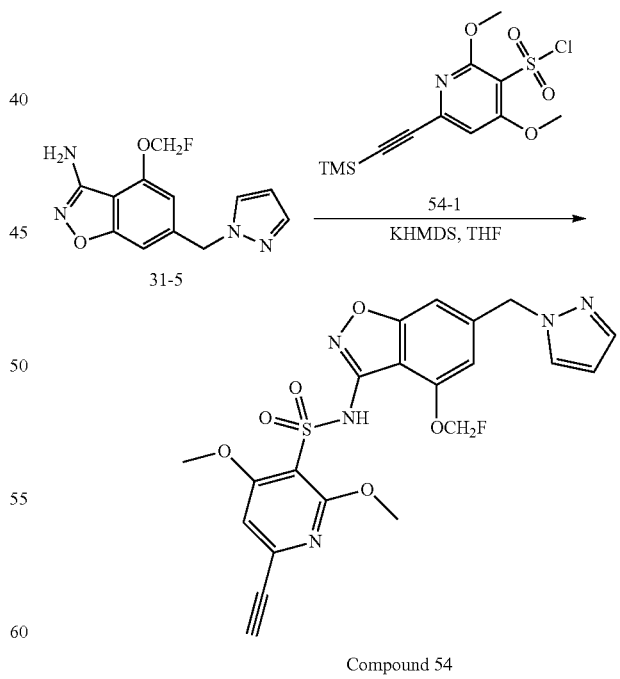

Compound 54

To a mixture of 31-5 (60 mg, 0.23 mmol) in THF (5 mL) was added KHMDS (0.34 mL, 0.34 mmol) at −78° C. The mixture was stirred at −78° C. for 0.5 h. 54-1 (84 mg, 0.25 mmol) in THF (1 mL) was added to this mixture and this reaction mixture was stirred at −78° C. for 1.5 h. The mixture was concentrated to give the crude product which was further purified by Prep-HPLC to afford Compound 54 (4.5 mg, 4% yield). LCMS: 488.2 [M+H]$^+$. $^1$H NMR (400 MHz, DMSO-d$_6$) δ 10.74 (s, 1H), 7.90-7.87 (m, 1H), 7.52-7.49 (m, 1H), 7.12 (s, 1H), 7.06 (s, 1H), 6.94 (s, 1H), 6.32-6.29 (m, 1H), 5.89 (d, J=53.2 Hz, 2H), 5.48 (s, 2H), 4.59 (s, 1H), 3.86 (s, 3H), 3.80 (s, 3H).

Example 55: Synthesis of N-(4-(fluoromethoxy)-6-(thiazol-2-yloxy)benzo[d]isoxazol-3-yl)-2,4-dimethoxy-6-methylpyridine-3-sulfonamide (Compound 55)

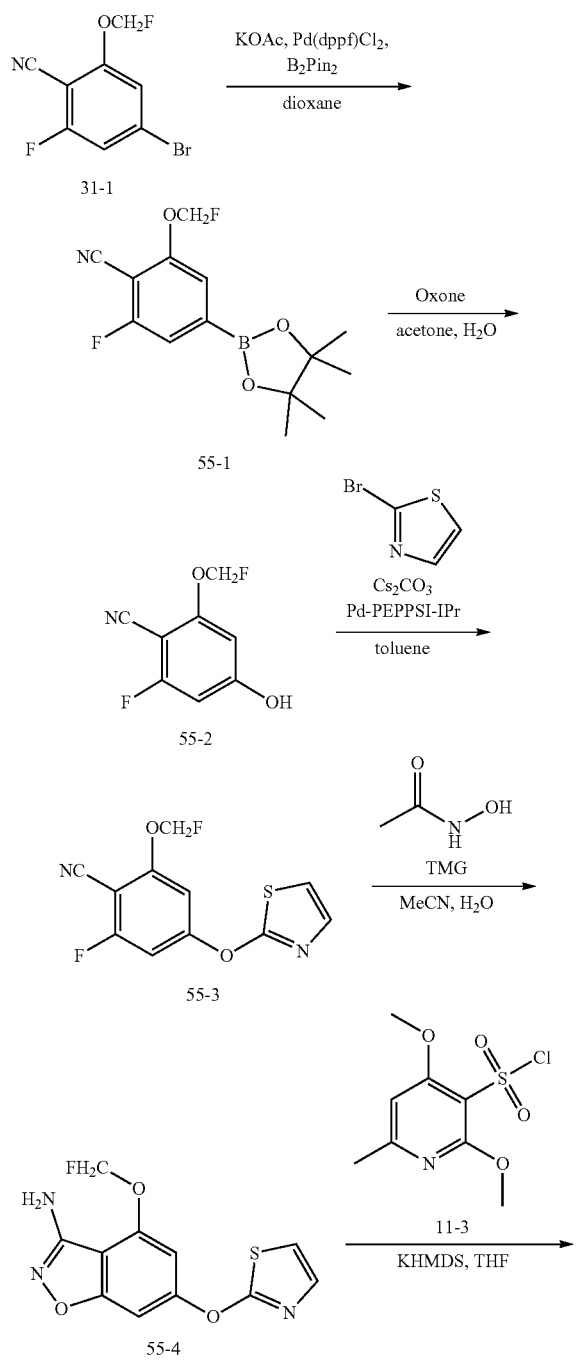

Compound 55

Step 1: To a solution of 31-1 (500 mg, 2.02 mmol) in dioxane (10 mL) were added Bis(pinacolato) diboron (768 mg, 3.02 mmol), KOAc (396 mg, 4.03 mmol) and Pd(dppf)Cl$_2$ (148 mg, 0.20 mmol). The reaction mixture was stirred at 85° C. for 12 h under N$_2$. This reaction mixture was filtered and concentrated in vacuum to give the 55-1 (600 mg, crude) as a brown oil.

Step 2: To a solution of 55-1 (600 mg, 2.02 mmol) in acetone (15 mL) was added oxone (1.50 g, 2.42 mmol) in H$_2$O (10 mL) at 0° C. The reaction mixture was stirred at 0° C. for 2 h. Water (10 mL) was added and the mixture was extracted with ethyl acetate (20 mL×3). The combined organic phase was washed with brine, dried over anhydrous Na$_2$SO$_4$, filtered and concentrated in vacuum to give a residue. The residue was purified by flash silica gel chromatography to give the 55-2 (200 mg, 53% yield for two steps) as a white solid. LCMS: 184.4 [M−H]$^−$.

Step 3: To a mixture of 55-2 (500 mg, 2.99 mmol) and 2-bromothiazole (1.47 g, 8.98 mmol) in toluene (10 mL) were added Cs$_2$CO$_3$ (2.92 g, 8.98 mmol) and Pd-PEPPSI-IPr catalyst (408 mg, 0.60 mmol). The mixture was stirred at 100° C. for 12 h. This reaction mixture was filtered and concentrated under reduced pressure to give a residue which was purified by flash silica gel chromatography to afford 55-3 (65 mg, 9% yield) as a yellow solid. LCMS: 269.2 [M+H]$^+$.

Step 4: To a mixture of 55-3 (65 mg, 0.25 mmol), N-hydroxyacetamide (55 mg, 0.73 mmol) in water (0.5 mL) and MeCN (4.5 mL) was added 1,1,3,3-tetramethylguanidine (0.16 mL, 1.45 mmol). The mixture was stirred at 60° C. for 2 h. Water (10 mL) was added to the mixture. Following extraction with ethyl acetate (20 mL×3), the organic phase was combined, washed with brine, dried over anhydrous Na$_2$SO$_4$, and filtered. The filtrate was concentrated under reduced pressure and then purified by flash silica gel chromatography to afford 55-4 (35 mg, 51% yield) as a yellow solid. LCMS: 282.3 [M+H]$^+$.

Step 5: To a solution of 55-4 (50 mg, 0.18 mmol) in THF (3 mL) was added KHMDS (0.36 mL, 0.36 mmol) at −78° C. under N$_2$ and stirred for 30 min. Then 11-3 (67 mg, 0.27 mmol) was added and the reaction mixture was stirred at −78° C. for 2 h. The mixture was concentrated. The residue was purified by flash silica gel chromatography to afford compound 55 (6 mg, 7% yield). LCMS: 497.2 [M+H]$^+$. $^1$H NMR (400 MHz, DMSO-d$_6$) δ 10.46 (s, 1H), 7.47 (s, 1H), 7.36 (s, 2H), 7.08 (s, 1H), 6.81 (s, 1H), 5.98 (d, J=52.8 Hz, 2H), 3.83 (s, 3H), 3.81 (s, 3H), 2.39 (s, 3H).

Example 56: Synthesis of N-(4-(fluoromethoxy)-6-(thiazol-2-yloxy)benzo[d]isoxazol-3-yl)-2-methoxy-benzenesulfonamide (Compound 56)

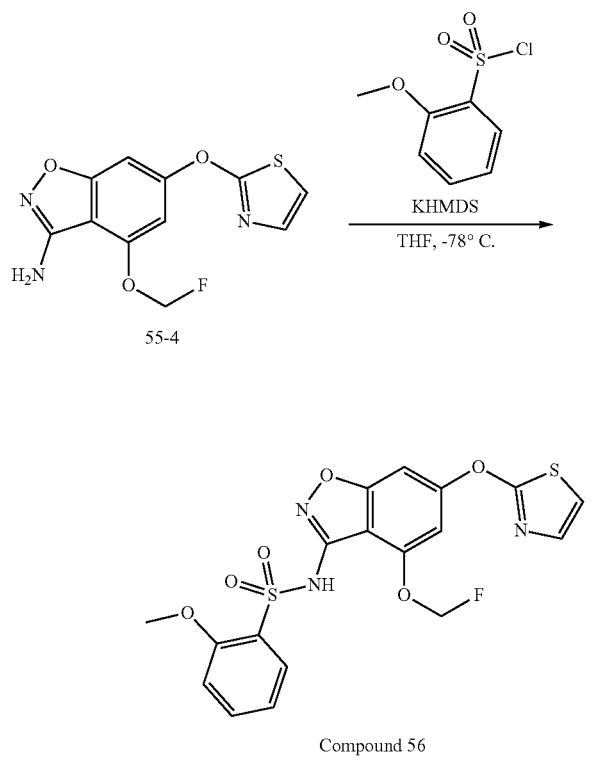

To a solution of 55-4 (50 mg, 0.18 mmol) in THF (3 mL) was added KHMDS (0.36 mL, 0.36 mmol) at −78° C. under $N_2$ and stirred for 30 min. Then 2-methoxybenzenesulfonyl chloride (55 mg, 0.27 mmol) was added and the reaction mixture was stirred at −78° C. for 2 h. The mixture was concentrated. The residue was purified by flash silica gel chromatography to afford compound 56 (7 mg, 8% yield). LCMS: 452.1 [M+H]$^+$. $^1$H NMR (400 MHz, DMSO-$d_6$) δ 10.62 (s, 1H), 7.88-7.81 (m, 1H), 7.64 (t, J=7.6 Hz, 1H), 7.46 (s, 1H), 7.35 (s, 2H), 7.21 (d, J=8.4 Hz, 1H), 7.15-7.03 (m, 2H), 5.94 (d, J=52.8 Hz, 2H), 3.79 (s, 3H).

Example 57: Synthesis of 2,4-dimethoxy-N-(4-methoxy-6-(thiazol-2-yloxy)benzo[d] isoxazol-3-yl)-6-methylpyridine-3-sulfonamide (Compound 57)

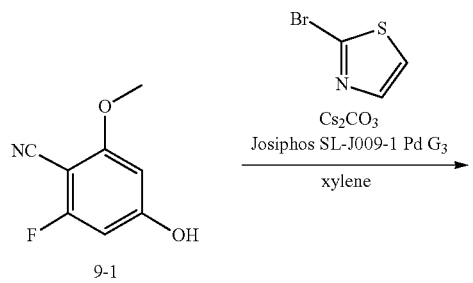

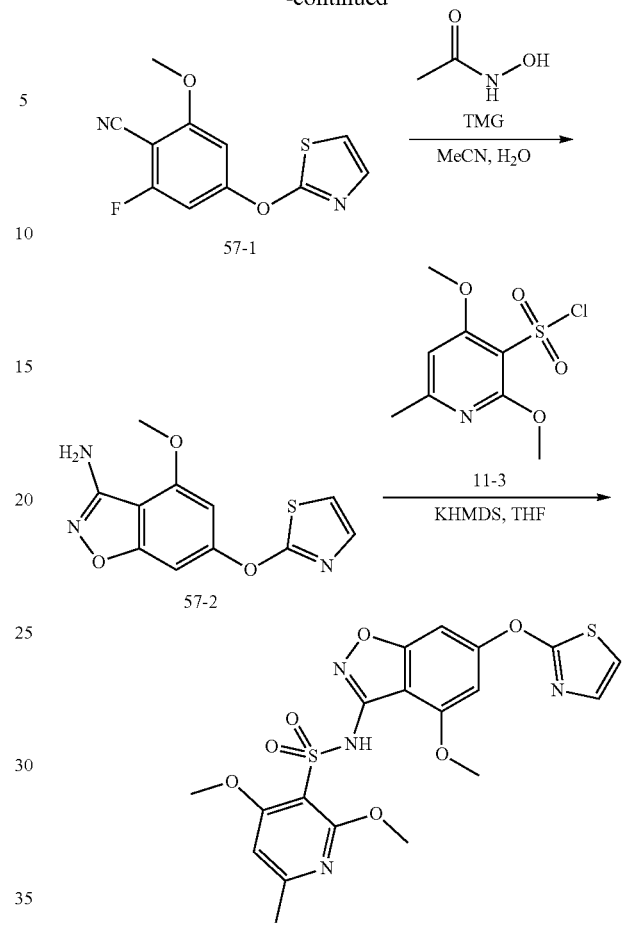

Step 1: To a mixture of 9-1 (800 mg, 4.79 mmol) and 2-bromothiazole (2.36 g, 14.36 mmol) in xylene (30 mL) were added $Cs_2CO_3$ (4.68 g, 14.36 mmol) and Josiphos SL-J009-1 Pd G3 (442 mg, 0.48 mmol). The mixture was stirred at 149° C. for 18 h. This reaction mixture was filtered and concentrated under reduced pressure to give a residue which was purified by flash silica gel chromatography to afford 57-1 (280 mg, 23% yield) as a yellow solid. LCMS: 251.4 [M+H]$^+$.

Step 2: To a solution of 57-1 (280 mg, 1.12 mmol) in MeCN (9 mL) and $H_2O$ (1 mL) were added 1,1,3,3-tetramethylguanidine (1.16 g, 10.07 mmol) and N-hydroxyacetamide (252 mg, 3.36 mmol). The reaction mixture was stirred at 70° C. under $N_2$ for 4 h. The mixture was concentrated. The residue was purified by flash silica gel chromatography to afford the 57-2 (100 mg, 34%) as a white solid. LCMS: 264.1 [M+H]$^+$.

Step 3: To a solution of 57-2 (50 mg, 0.19 mmol) in THF (3 mL) was added KHMDS (0.38 mL, 0.38 mmol) at −78° C. under $N_2$ and stirred for 30 min. Then 11-3 (72 mg, 0.29 mmol) was added and the reaction mixture was stirred at −78° C. for 2 h. The mixture was concentrated. The residue was purified by Prep-HPLC to afford compound 57 (3 mg, 3% yield). LCMS: 479.3 [M+H]$^+$. $^1$H NMR (400 MHz, DMSO-$d_6$) δ 10.12 (s, 1H), 7.37-7.31 (m, 2H), 7.26 (s, 1H), 6.89 (s, 1H), 6.81 (s, 1H), 3.89 (s, 3H), 3.84 (s, 3H), 3.82 (s, 3H), 2.39 (s, 3H).

Example 58: Synthesis of N-(6-((1H-pyrazol-1-yl)methyl)-4-(fluoromethoxy)benzo[d]isoxazol-3-yl)-2,4-dimethoxypyridine-3-sulfonamide (Compound 58)

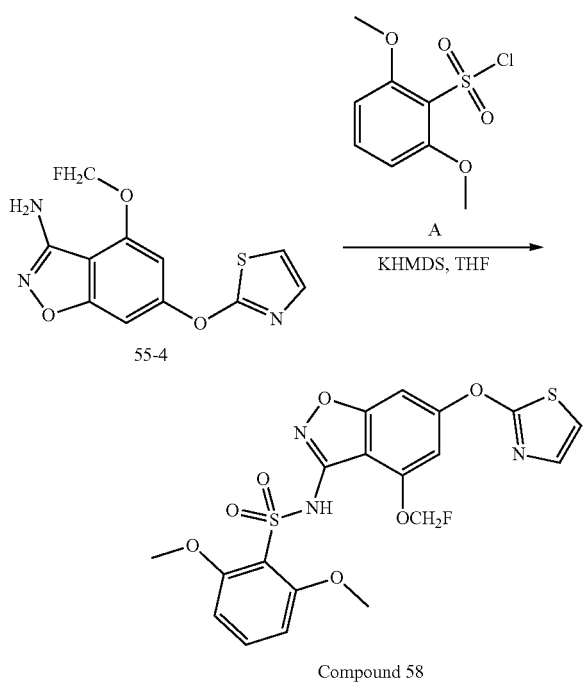

Compound 58

To a mixture of 55-4 (50 mg, 0.18 mmol) in THF (5 mL) was added KHMDS (0.36 mL, 0.36 mmol) at −78° C. and stirred for 0.5 h. Then A (63 mg, 0.27 mmol) in THF (1 mL) was added. The reaction mixture was stirred at −78° C. for 1.5 h. The mixture was concentrated to give the crude product which was further purified by Prep-HPLC to afford Compound 58 (4.5 mg, 5% yield). LCMS: 482.2 [M+H]⁺. ¹H NMR (400 MHz, DMSO-d₆) δ 10.14 (s, 1H), 7.54-7.45 (m, 2H), 7.35 (s, 2H), 7.08 (s, 1H), 6.78 (d, J=8.4 Hz, 2H), 5.97 (d, J=52.4 Hz, 2H), 3.76 (s, 6H).

Example 59: Synthesis of 2,6-dimethoxy-N-(4-methoxy-6-(thiazol-2-yloxy)benzo[d]isoxazol-3-yl)benzenesulfonamide (Compound 59)

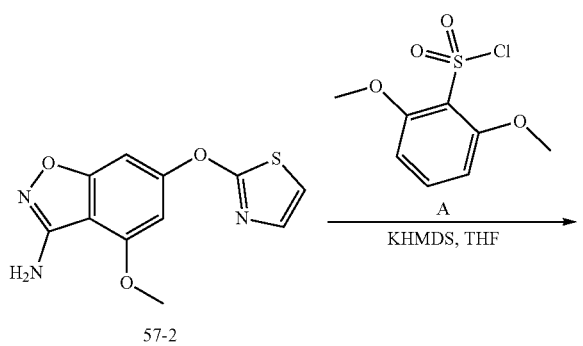

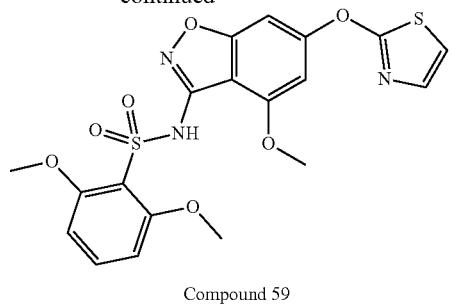

Compound 59

To a mixture of 57-2 (20 mg, 0.07 mmol) in THF (5 mL) was added KHMDS (0.14 mL, 0.14 mmol) at −78° C. and stirred for 0.5 h. Then A (18 mg, 0.07 mmol) in THF (1 mL) was added. The reaction mixture was stirred at −78° C. for 1.5 h. The mixture was concentrated to give the crude product which was further purified by Prep-HPLC to afford Compound 59 (3.5 mg, 10% yield). LCMS: 464.1 [M+H]⁺. ¹H NMR (400 MHz, DMSO-d₆) δ 9.75 (s, 1H), 7.50 (t, J=8.4 Hz, 1H), 7.35-7.32 (m, 2H), 7.24 (s, 1H), 6.89 (s, 1H), 6.78 (d, J=8.8 Hz, 2H), 3.90 (s, 3H), 3.78 (s, 6H).

Example 60: Synthesis of 2-methoxy-N-(4-methoxy-6-(thiazol-2-yloxy)benzo[d]isoxazol-3-yl)benzenesulfonamide (Compound 60)

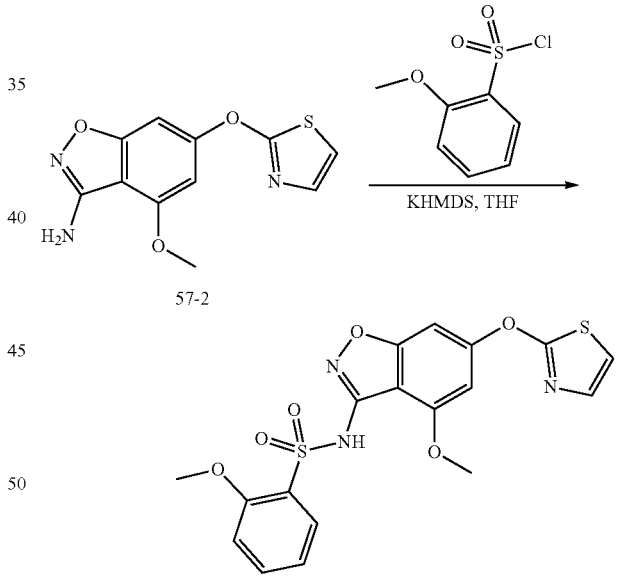

Compound 60

To a solution of 57-2 (35 mg, 0.12 mmol) in THF (5 mL) was added KHMDS (0.24 mL 0.24 mmol) at −78° C. and stirred for 0.5 h. Then 2-methoxybenzenesulfonyl chloride (42 mg, 0.18 mmol) was added. The reaction was stirred at −78° C. for 1 h. The reaction mixture was concentrated. The residue was purified by Prep-HPLC to afford Compound 60 (11 mg, 18% yield). LCMS: 434.2 [M+H]⁺. ¹H NMR (400 MHz, DMSO-d₆) δ 10.29 (s, 1H), 7.85-7.80 (m, 1H), 7.64 (t, J=7.4 Hz, 1H), 7.36-7.31 (m, 2H), 7.25 (s, 1H), 7.21 (d, J=8.0 Hz, 1H), 7.11 (t, J=7.4 Hz, 1H), 6.88 (s, 1H), 3.85 (s, 3H), 3.79 (s, 3H).

Example 61: Synthesis of 2-methoxy-N-(5-(thiazol-2-yloxy)-3,4-dihydro-2H-chromeno[8,7-d]isoxazol-9-yl)benzenesulfonamide (Compound 61)

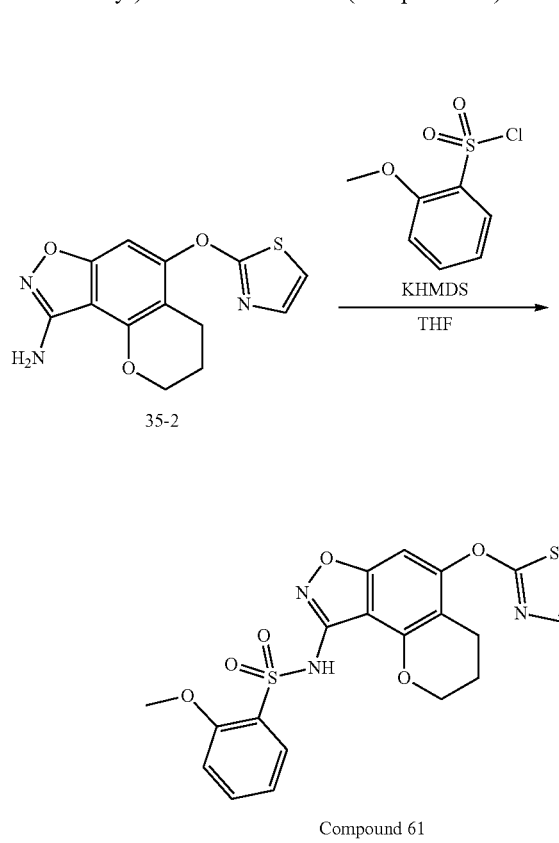

To a mixture of 35-2 (30 mg, 0.10 mmol) in THF (5 mL) was added KHMDS (0.2 mL, 0.20 mmol) at −78° C. and stirred for 0.5 h. Then 2-methoxybenzenesulfonyl chloride (26 mg, 0.12 mmol) in THF (1 mL) was added. The reaction mixture was stirred at −78° C. for 1 h. The mixture was concentrated to give the crude product which was further purified by Prep-HPLC to afford Compound 61 (7 mg, 15% yield). LCMS: 460.1 [M+H]$^+$. $^1$H NMR (400 MHz, DMSO-$d_6$) δ 10.21 (s, 1H), 7.82 (dd, J=8.0 Hz, 1.6 Hz, 1H), 7.68-7.59 (m, 1H), 7.34-7.26 (m, 2H), 7.22 (d, J=8.0 Hz, 1H), 7.19 (s, 1H), 7.10 (t, J=7.6 Hz, 1H), 4.21 (t, J=5.0 Hz, 2H), 3.81 (s, 3H), 2.59 (t, J=6.4 Hz, 2H), 1.99-1.90 (m, 2H).

Example 62: Synthesis of 2,6-dimethoxy-N-(6-(thiazol-2-yloxy)-2,3,4,5,9,10-hexahydrooxepino[3',2':5,6]benzo[1,2-d]isoxazol-10-yl)benzenesulfonamide (Compound 62)

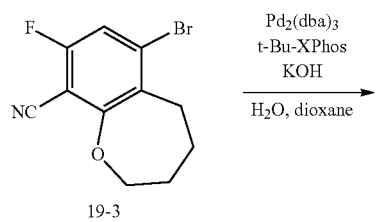

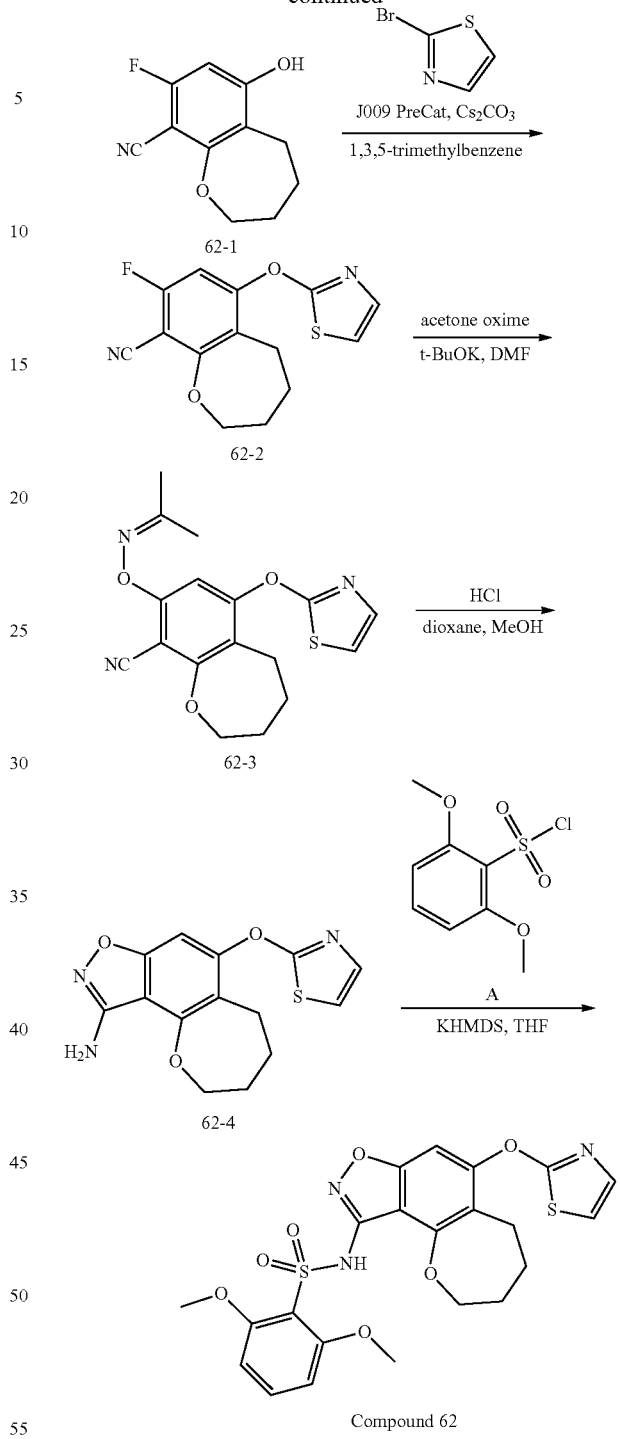

Step 1: To a solution of 19-3 (2 g, 7.4 mmol) in dioxane (20 mL) and H$_2$O (20 mL) were added KOH (1.24 g, 22.2 mmol), Pd$_2$(dba)$_3$ (2.0 g, 2.22 mmol) and t-Bu-XPhos (948 mg, 2.22 mmol). This reaction mixture was stirred at 100° C. for 18 h. The mixture was diluted with 2M HCl (20 mL) and extracted with ethyl acetate (20 ml×3). The combined organic phase was washed with brine, dried over anhydrous Na$_2$SO$_4$ and concentrated under reduced pressure. The residue was purified by flash silica gel chromatography to afford 62-1 (1.4 g, 91% yield) as a white solid. LCMS: 206.4 [M−H]$^-$.

Step 2: To a solution of 62-1 (1.4 g, 6.7 mmol) in 1,3,5-trimethylbenzene (15 mL) were added Cs$_2$CO$_3$ (6.5 g, 20.1 mmol), 2-bromothiazole (3.2 g, 20.1 mmol) and Josiphos SL-J009-1 Pd G3 (619 mg, 0.67 mmol). This reaction mixture was stirred at 160° C. for 2 h under microwave. The reaction mixture was concentrated and purified by flash silica gel chromatography to afford 62-2 (220 mg, 11% yield) as a white solid. LCMS: 291.4 [M+H]$^+$.

Step 3: To a solution of 62-2 (220 mg, 0.75 mmol) in DMF (5 mL) was added t-BuOK (101 mg, 0.9 mmol) and stirred at room temperature for 0.5 h. Then acetone oxime (66 mg, 0.9 mmol) was added. This reaction mixture was stirred at room temperature for 1 h. The reaction mixture was quenched with water (10 mL). The aqueous phase was extracted with ethyl acetate (20 mL×2). The combined organic phase was washed with brine, dried over anhydrous sodium sulfate and concentrated under reduced pressure. The residue was purified by flash silica gel chromatography to afford 62-3 (220 mg, 85% yield) as a yellow solid. LCMS: 344.4 [M+H]$^+$.

Step 4: To a solution of 62-3 (220 mg, 0.64 mmol) in MeOH (5 mL) was added 4M HCl in dioxane (5 ml). This reaction mixture was stirred at 25° C. for 18 h. The reaction mixture was concentrated in vacuum to give a residue which was purified by flash silica gel chromatography to afford 62-4 (70 mg, 35% yield) as a white solid. LCMS: 304.2 [M+H]$^+$.

Step 5: To a solution of 62-4 (70 mg, 0.23 mmol) in THF (5 mL) was added KHMDS (0.34 mL, 0.34 mmol) at −78° C. and stirred at this temperature for 30 min. Then A (66 mg, 0.28 mmol) was added. The reaction was stirred at −78° C. for 1 h. The reaction mixture was concentrated. The residue was purified by Prep-HPLC to afford Compound 62 (11 mg, 16% yield). LCMS: 504.2 [M+H]$^+$. $^1$H NMR (400 MHz, DMSO-d$_6$) δ 9.74 (s, 1H), 7.51 (t, J=8.4 Hz, 1H), 7.38 (s, 1H), 7.29-7.24 (m, 2H), 6.80 (d, J=8.8 Hz, 2H), 4.27-4.20 (m, 2H), 3.79 (s, 6H), 2.80-2.75 (m, 2H), 1.98-1.92 (m, 2H), 1.72-1.64 (m, 2H).

Example 63: Synthesis of 2-methoxy-N-(6-(thiazol-2-yloxy)-2,3,4,5,9,10-hexahydrooxepino[3',2':5,6]benzo[1,2-d]isoxazol-10-yl)benzenesulfonamide (Compound 63)

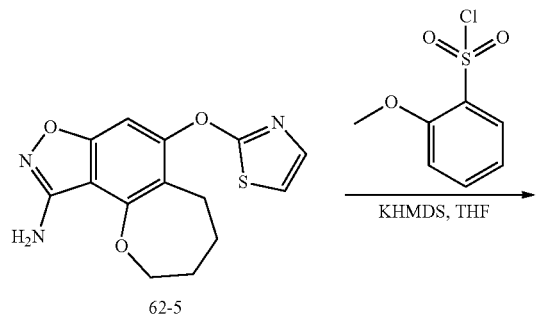

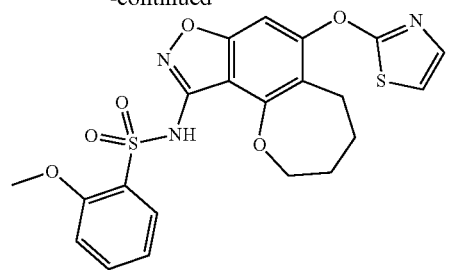

Compound 63

To a solution of 62-5 (25 mg, 0.08 mmol) in THF (5 mL) was added KHMDS (0.12 mL 0.12 mmol) at −78° C. and stirred at this temperature for 30 min. Then 2-methoxybenzenesulfonyl chloride (33 mg, 0.16 mmol) was added. The reaction was stirred at −78° C. for 1 h. The reaction mixture was concentrated. The residue was purified by Prep-HPLC to afford Compound 63 (5.5 mg, 14% yield). LCMS: 474.2 [M+H]$^+$. $^1$H NMR (400 MHz, DMSO-d$_6$) δ 10.21 (s, 1H), 7.84 (dd, J=7.6, 1.6 Hz, 1H), 7.67-7.61 (m, 1H), 7.39 (s, 1H), 7.29-7.20 (m, 3H), 7.14-7.07 (m, 1H), 4.20-4.14 (m, 2H), 3.81 (s, 3H), 2.80-2.74 (m, 2H), 1.97-1.91 (m, 2H), 1.70-1.62 (m, 2H).

Example 64: Synthesis of 2,4-dimethoxy-6-methyl-N-(6-(thiazol-2-yloxy)-2,3,4,5,9,10-hexahydrooxepino[3',2':5,6]benzo[1,2-d]isoxazol-10-yl)pyridine-3-sulfonamide (Compound 64)

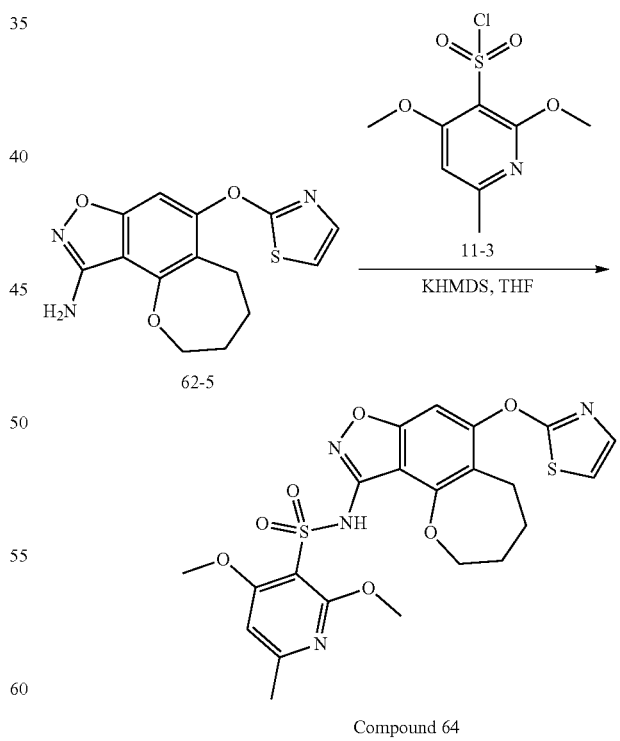

Compound 64

To a solution of 62-5 (60 mg, 0.19 mmol) in THF (5 mL) was added KHMDS (0.29 mL 0.29 mmol) at −78° C. and stirred at this temperature for 30 min. Then 11-3 (78 mg, 0.38 mmol) was added. The reaction was stirred at −78° C.

for 1 h. The reaction mixture was concentrated. The residue was purified by Prep-HPLC to afford Compound 64 (6 mg, 6% yield). LCMS: 519.2 [M+H]+. 1H NMR (400 MHz, DMSO-d6) δ 10.05 (s, 1H), 7.39 (s, 1H), 7.30-7.25 (m, 2H), 6.82 (s, 1H), 4.25-4.23 (m, 2H), 3.85 (s, 3H), 3.83 (s, 3H), 2.80-2.76 (m, 2H), 2.39 (s, 3H), 1.97-1.92 (m, 2H), 1.71-1.65 (m, 2H).

Example 65: Synthesis of N-(4-(fluoromethoxy)-6-(thiazol-2-ylmethyl)benzo[d]isoxazol-3-yl)-2,6-dimethoxybenzenesulfonamide (Compound 65)

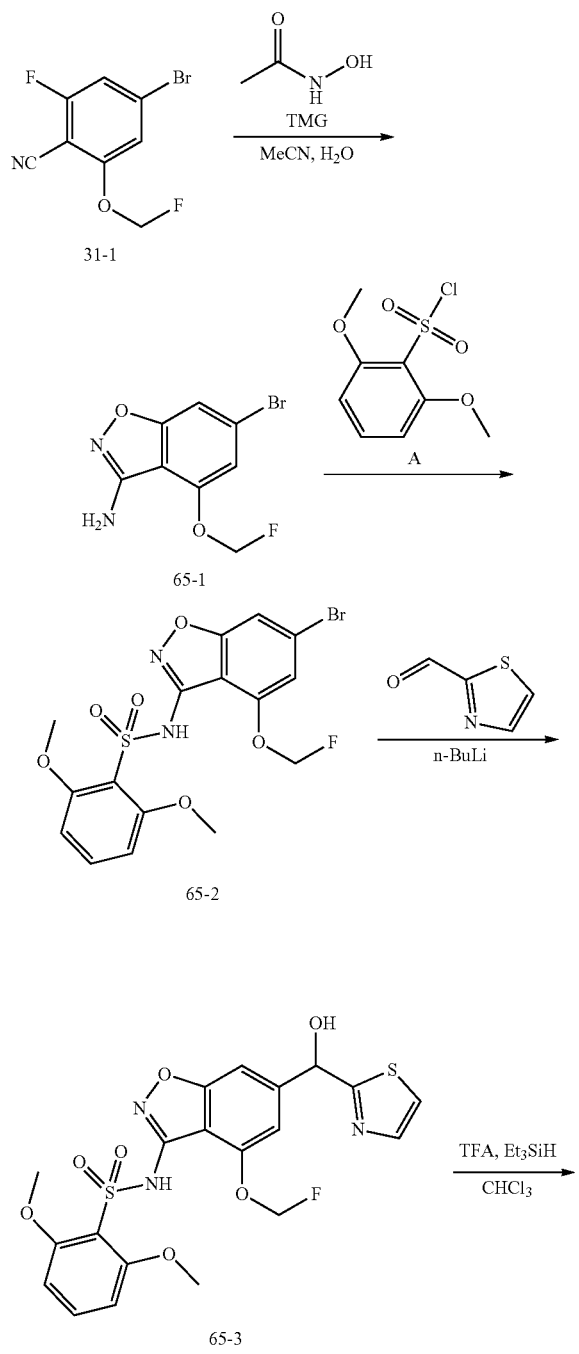

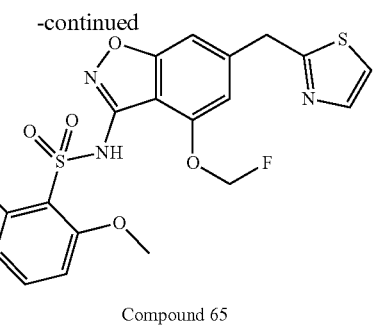

Compound 65

Step 1: To a mixture of 31-1 (500 mg, 2.0 mmol), N-hydroxyacetamide (454 mg, 6.0 mmol), and water (1 mL) in MeCN (9 mL) was added 1,1,3,3-tetramethylguanidine (1.4 g, 12.0 mmol). The mixture was stirred at 60° C. for 5 h. Water (50 mL) was added to the mixture. Following extraction with ethyl acetate (50 mL×3), the organic phase was combined, washed with brine, dried over anhydrous Na2SO4 and filtered. The filtrate was concentrated under reduced pressure and then purified by flash silica gel chromatography to afford 65-1 (280 mg, 53% yield) as a white solid. LCMS: 259.2 [M−H]−.

Step 2: To a solution of 65-1 (280 mg, 1.1 mmol) in tetrahydrofuran (10 mL) was added potassium bis(trimethylsilyl)amide (2.2 mL, 2.2 mmol, 1M) at −78° C. for 30 min. A (254 mg, 1.1 mmol) was added and the reaction mixture was stirred at −78° C. for 1.5 h. The reaction mixture was concentrated in vacuum to give a residue. The residue was purified by flash silica gel chromatography to afford 65-2 (180 mg, 36% yield) as a white solid. LCMS: 461.0 [M+H]+.

Step 3: To a solution of 65-2 (400 mg, 0.87 mmol) in tetrahydrofuran (3 mL) was added n-BuLi (1.6 mL, 2.60 mmol, 1.6 M) at −78° C. for 20 min. Then, 1,3-thiazole-2-carbaldehyde (294 mg, 2.60 mmol) was added and the reaction mixture was stirred at −78° C. for 3 h. The reaction was quenched with saturated NH4Cl (20 mL). The aqueous phase was extracted with DCM (20 mL×3). The combined organic phase was washed with brine, dried over anhydrous sodium sulfate, filtered and concentrated under reduced pressure to give a residue. The residue was purified by flash silica gel chromatography to afford 65-3 (50 mg, 12% yield) as a yellow oil. LCMS: 496.2 [M+H]+.

Step 4: To a solution of 65-3 (20 mg, 0.04 mmol) in CHCl3 (3 mL) were added TFA (22 mg, 0.20 mmol) and Et3SiH (22 mg, 0.20 mmol). This reaction mixture was stirred at 60° C. for 3 h. The reaction mixture was quenched with NaHCO3 (10 mL). The aqueous phase was extracted with DCM (20 mL×3). The combined organic phase was washed with brine, dried over anhydrous sodium sulfate and concentrated. The residue was purified by Prep-HPLC to afford Compound 65 (1.3 mg, 7% yield). LCMS: 480.2 [M+H]+. 1H NMR (400 MHz, CD3OD) δ 7.73 (d, J=3.2 Hz, 1H), 7.51-7.45 (m, 2H), 7.19 (s, 1H), 7.02 (s, 1H), 6.74 (d, J=8.4 Hz, 2H), 5.94 (d, J=53.2 Hz, 2H), 4.50 (s, 2H), 3.83 (s, 6H).

Example 66: Synthesis of 2,6-dimethoxy-N-(4-methoxy-6-(thiazol-2-ylthio)benzo[d] isoxazol-3-yl)benzenesulfonamide (Compound 66)

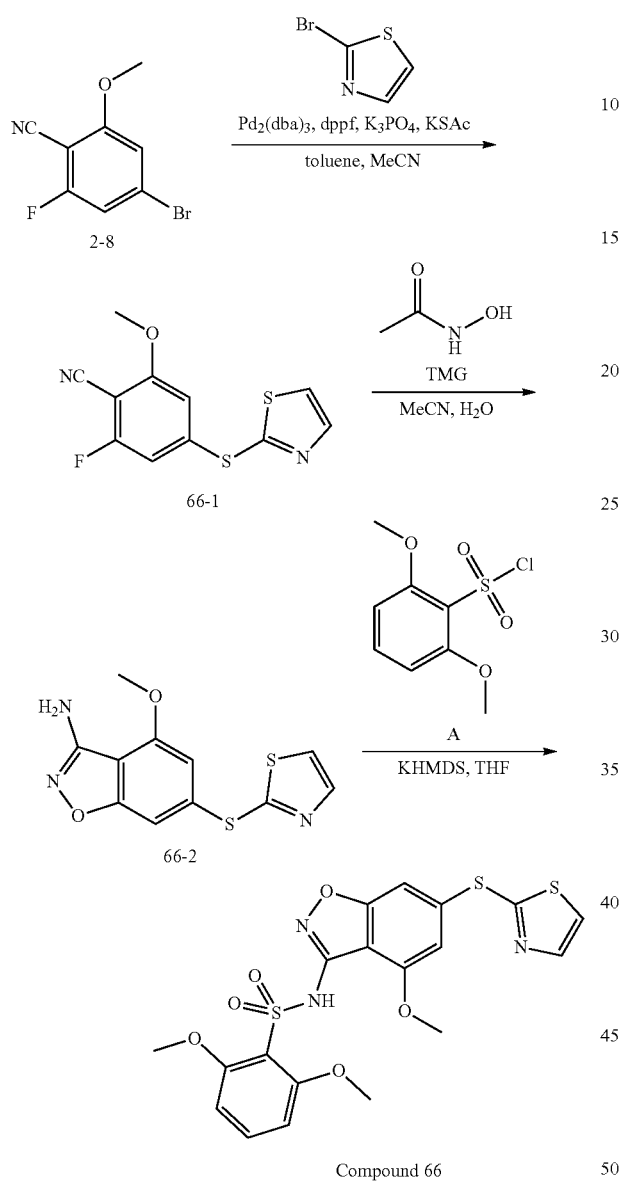

Compound 66

Step 1: To a mixture of 2-8 (5 g, 22.9 mmol) and 2-bromothiazole (3.76 g, 22.9 mmol) in toluene (60 mL) and MeCN (30 mL) were added KSAc (2.6 g, 22.9 mmol), dppf (5.08 g, 9.2 mmol), K$_3$PO$_4$ (11.7 g, 55.2 mmol) and Pd$_2$(dba)$_3$ (4.2 g, 4.6 mmol). The mixture was stirred at 110° C. for 12 h. This reaction mixture was filtered and concentrated under reduced pressure to give a residue which was purified by flash silica gel chromatography to afford 66-1 (837 mg, 13% yield) as a brown oil. LCMS: 267.2 [M+H]$^+$.

Step 2: To a solution of 66-1 (837 mg, 3.14 mmol) in MeCN (9 mL) and H$_2$O (1 mL) were added 1,1,3,3-tetramethylguanidine (2.16 g, 18.84 mmol) and N-hydroxyacetamide (706 mg, 9.42 mmol). The reaction mixture was stirred at 70° C. under N$_2$ for 12 h. The mixture was concentrated. The residue was purified by flash silica gel chromatography to afford the 66-2 (208 mg, 23%) as a white solid. LCMS: 280.2 [M+H]$^+$.

Step 3: To a solution of 66-2 (208 mg, 0.74 mmol) in THF (5 mL) was added KHMDS (1.11 mL, 1.11 mmol) at −78° C. under N$_2$ and stirred for 30 min. A (263 mg, 1.11 mmol) was added. The reaction mixture was stirred at −78° C. for 2 h. The mixture was concentrated. The residue was purified by flash silica gel chromatography to afford compound 66 (28 mg, 8% yield). LCMS: 480.1 [M+H]$^+$. $^1$H NMR (400 MHz, DMSO-d$_6$) δ 9.79 (s, 1H), 7.92 (d, J=3.2 Hz, 1H), 7.87 (d, J=3.2 Hz, 1H), 7.50 (t, J=8.8 Hz, 1H), 7.30 (s, 1H), 7.00 (s, 1H), 6.78 (d, J=8.8 Hz, 2H), 3.89 (s, 3H), 3.77 (s, 6H).

Example 67: Synthesis of 2-methoxy-N-(4-methoxy-6-(thiazol-2-ylthio)benzo[d]isoxazol-3-yl)benzenesulfonamide (Compound 67)

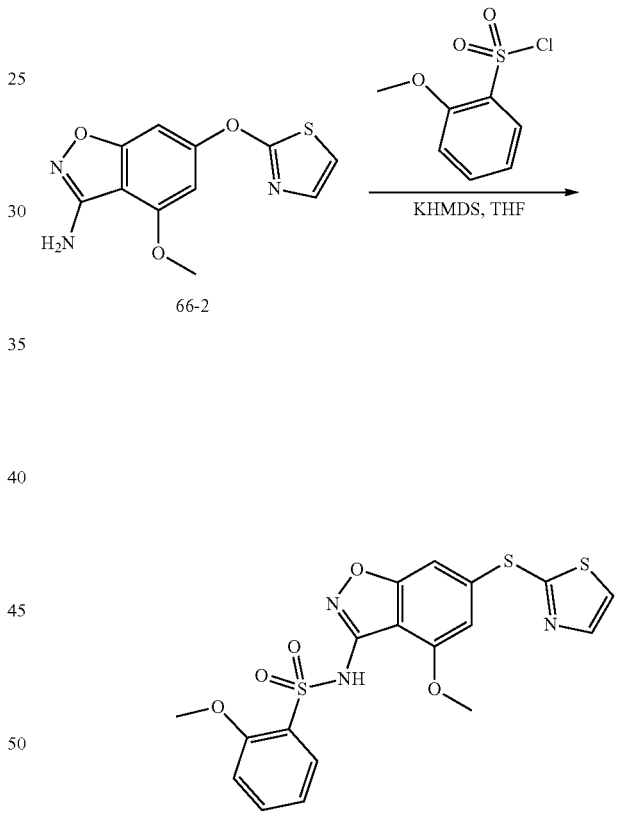

Compound 67

To a solution of 66-2 (30 mg, 0.11 mmol) in THF (5 mL) was added KHMDS (0.15 mL 0.15 mmol) at −78° C. and stirred for 0.5 h. Then 2-methoxybenzene sulfonyl chloride (27 mg, 0.13 mmol) was added. The reaction mixture was stirred at −78° C. for 1 h. The reaction mixture was concentrated. The residue was purified by Prep-HPLC to afford Compound 67 (8 mg, 18% yield). LCMS: 450.1 [M+H]$^+$. $^1$H NMR (400 MHz, DMSO-d$_6$) δ 10.32 (s, 1H), 7.94-7.78 (m, 3H), 7.63 (t, J=7.6 Hz, 1H), 7.30 (s, 1H), 7.20 (d, J=8.4 Hz, 1H), 7.10 (t, J=7.6 Hz, 1H), 6.97 (s, 1H), 3.84 (s, 3H), 3.77 (s, 3H).

Example 68: Synthesis of 2,4-dimethoxy-N-(4-methoxy-6-(thiazol-2-ylthio)benzo[d] isoxazol-3-yl)-6-methylpyridine-3-sulfonamide (Compound 68)

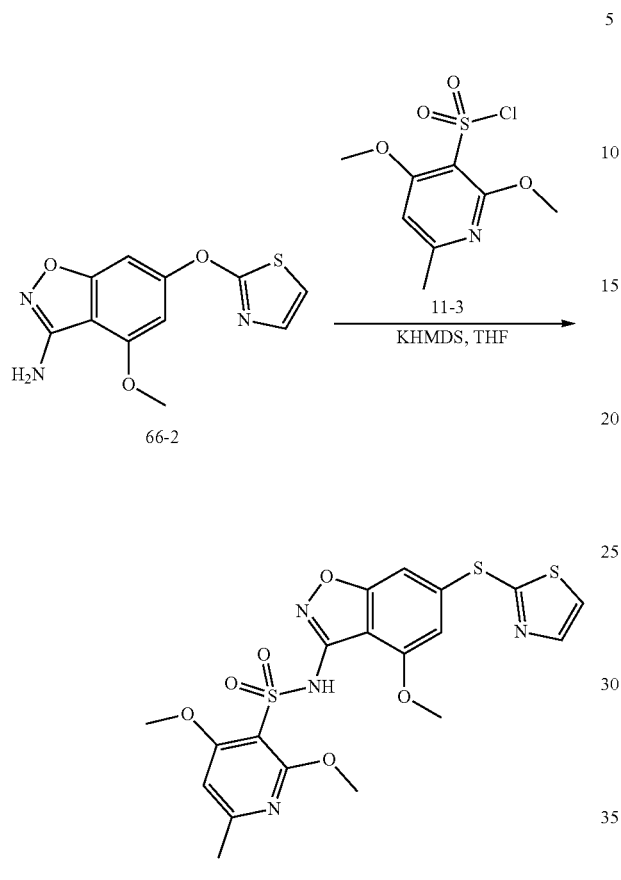

Compound 68

To a solution of 66-2 (25 mg, 0.09 mmol) in THF (5 mL) was added KHMDS (0.13 mL 0.13 mmol) at −78° C. and stirred for 0.5 h. Then 11-3 (23 mg, 0.09 mmol) was added. The reaction was stirred at −78° C. for 1 h. The reaction mixture was concentrated. The residue was purified by Prep-HPLC to afford Compound 68 (8 mg, 18% yield). LCMS: 495.1 [M+H]$^+$. $^1$H NMR (400 MHz, DMSO-d$_6$) δ 10.15 (s, 1H), 7.91 (d, J=3.2 Hz, 1H), 7.86 (d, J=3.6 Hz, 1H), 7.31 (s, 1H), 6.99 (s, 1H), 6.80 (s, 1H), 3.88 (s, 3H), 3.82 (s, 3H), 3.80 (s, 3H), 2.38 (s, 3H).

Example 69: Synthesis of N-(7-((1H-pyrazol-1-yl)methyl)-5,5a,6,6a-tetrahydro cyclopropa[3,4]chromeno[8,7-d]isoxazol-3-yl)-2,4-dimethoxy-6-methylpyridine-3-sulfonamide (Compound 69)

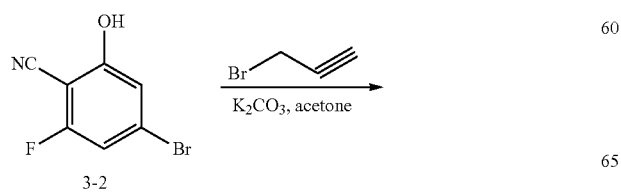

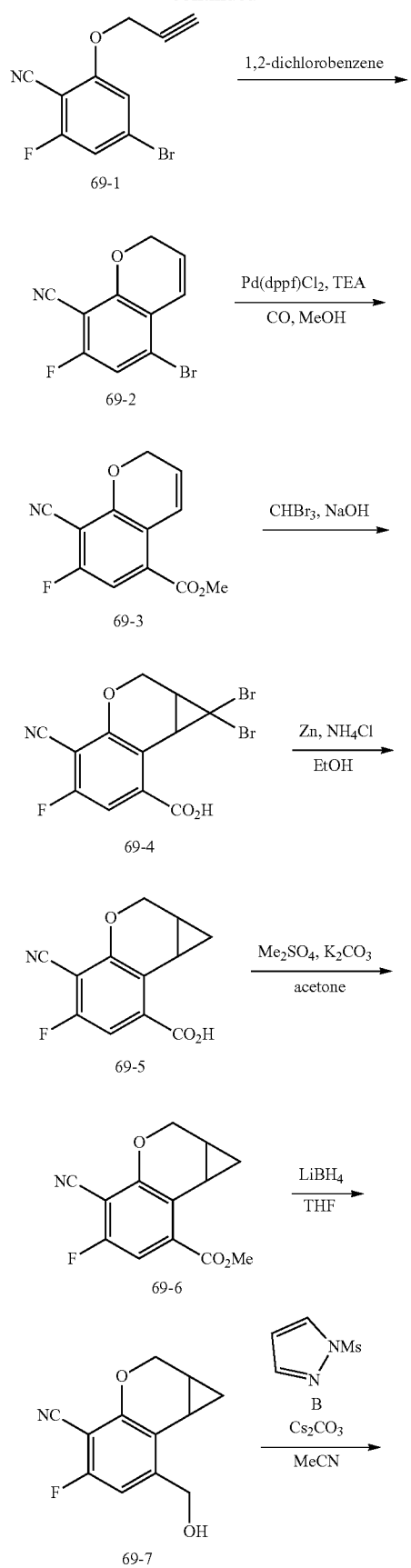

-continued

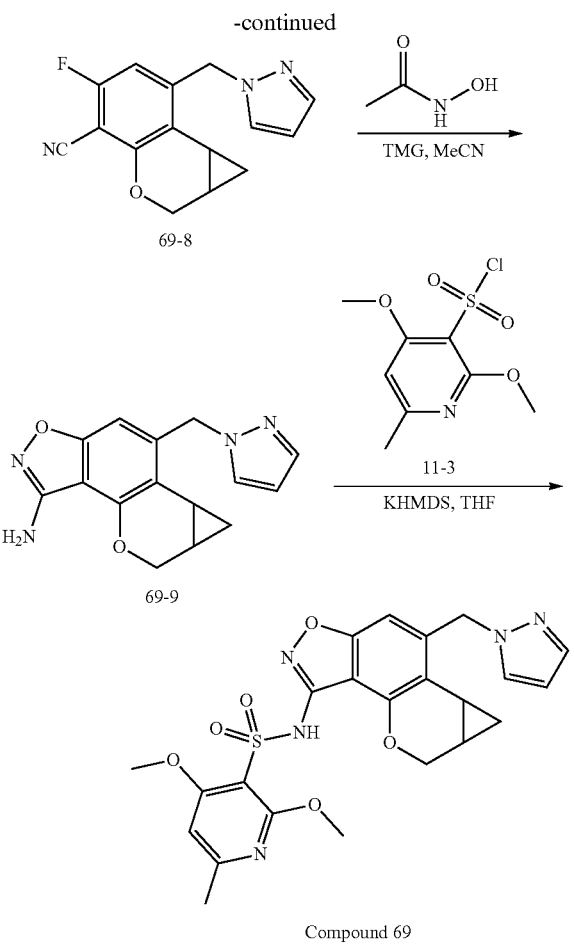

Compound 69

Step 1: To a solution of 3-2 (20.0 g, 93 mmol) in acetone (200 mL) were added K$_2$CO$_3$ (38.5 g, 279 mmol) and 3-bromopropyne (16.6 g, 140 mmol) at 0° C. The reaction mixture was stirred at 65° C. for 12 h under N$_2$. Water (300 mL) was added and the mixture was extracted with DCM (300 mL×3). The combined organic phase was washed with brine, dried over anhydrous Na$_2$SO$_4$, filtered and concentrated in vacuum to afford 69-1 (15.0 g, 64%) as a white solid.

Step 2: A solution of 69-1 (15.0 g, 59.2 mmol) in 1,2-dichlorobenzene (150 mL) was heated at 200° C. for 48 h under N$_2$. Then the reaction mixture was filtered. The filtrate was concentrated. The residue was purified by flash silica gel chromatography to give 69-2 (14 g, 93%) as a white solid.

Step 3: To a solution of 69-2 (10.0 g, 39.5 mmol) in MeOH (100 mL) were added Pd(dppf)Cl$_2$ (2.9 g, 4.0 mmol) and TEA (16.5 mL, 118.6 mmol). The reaction mixture was stirred at 100° C. for 18 h under CO (3 MPa) atmosphere. Then the reaction mixture was filtered. The filtrate was concentrated. The residue was purified by flash silica gel chromatography to give 69-3 (6.0 g, 65% yield) as a white solid.

Step 4: To a solution of 69-3 (10.0 g, 42.9 mmol) in CBr$_3$ (40 mL) and 50% NaOH in water (7.5 mL) was added benzyl triethyl ammonium chloride (976 mg, 4.3 mmol). The reaction mixture was stirred at 60° C. for 3 h. The reaction mixture was diluted with MeOH (50 mL) and filtered. The filtrate was concentrated. The residue was purified by flash silica gel chromatography to give 69-4 (11.0 g, 67% yield) as a white solid. LCMS: 388.2 [M–H]$^-$.

Step 5: To a solution of 69-4 (6.0 g, 15.4 mmol) in EtOH (100 mL) were added Zn (5.0 g, 77.0 mmol) and NH$_4$Cl (4.2 g, 77.0 mmol). The reaction mixture was stirred at 70° C. for 12 h. The reaction mixture was filtered and concentrated to give a crude monodebromo product (4.8 g). To a solution of this crude monodebromo product (4.8 g, 15.4 mmol) in EtOH (15 mL) were added Zn (5.0 g, 77.0 mmol) and NH$_4$Cl (4.2 g, 77.0 mmol). The reaction mixture was stirred at 70° C. for another 12 h. The reaction mixture was filtered and concentrated. This residue was purified by Prep-HPLC to give 69-5 (2.0 g, 55% yield for two steps) as a white solid. LCMS: 232.2 [M–H]$^-$.

Step 6: To a solution of 69-5 (500 mg, 2.14 mmol) in acetone (10 mL) were added K$_2$CO$_3$ (593 mg, 4.29 mmol) and dimethyl sulfate (406 mg, 3.22 mmol). The reaction mixture was stirred at 60° C. for 3 h. The reaction mixture was concentrated. The residue was purified by flash silica gel chromatography to give 69-6 (250 mg, 47% yield) as a white solid.

Step 7: To a solution of 69-6 (250 mg, 1.01 mmol) in THF (5 mL) were added LiBH$_4$ (67 mg, 3.04 mmol) at 0° C. The reaction mixture was stirred at 25° C. for 2 h. The reaction mixture was quenched by Na$_2$SO$_4$·10H$_2$O and filtered. The filtrate was concentrated. The residue was purified by flash silica gel chromatography to give 69-7 (180 mg, 81% yield) as a white solid. LCMS: 218.0 [M–H]$^-$.

Step 8: To a solution of 69-7 (130 mg, 0.59 mmol) in acetonitrile (5 mL) were added Compound B (103 mg, 0.71 mmol) and Cs$_2$CO$_3$ (231 g, 0.71 mmol). The reaction mixture was stirred at 70° C. for 1 h. Then the reaction mixture was concentrated. The residue was purified by flash silica gel chromatography to give 69-8 (100 mg, 63% yield) as a yellow solid. LCMS: 270.4 [M+H]$^+$.

Step 9: To a solution of 69-8 (100 mg, 0.37 mmol) in acetonitrile (4.5 mL) and water (0.5 mL) were added N-hydroxyacetamide (84 mg, 1.12 mmol) and 1,1,3,3-tetramethylguanidine (257 mg, 2.23 mmol). The reaction was stirred at 60° C. for 2 h. Then the reaction mixture was concentrated. The residue was purified by flash silica gel chromatography to give 69-9 (30 mg, 29% yield) as a white solid. LCMS: 283.2 [M+H]$^+$.

Step 10: To a solution of 69-9 (50 mg, 0.18 mmol) in THF (5 mL) was added KHMDS (0.35 mL 0.35 mmol) at –78° C. and stirred for 0.5 h. Then 11-3 (67 mg, 0.27 mmol) was added. The reaction was stirred at –78° C. for 1 h. The reaction mixture was concentrated. The residue was purified by Prep-HPLC to afford Compound 69 (3.2 mg, 4% yield). LCMS: 498.2 [M+H]$^+$. $^1$H NMR (400 MHz, DMSO-d$_6$) δ 10.04 (s, 1H), 7.82 (d, J=2.4 Hz, 1H), 7.51 (d, J=1.6 Hz, 1H), 6.79 (s, 1H), 6.62 (s, 1H), 6.31 (t, J=2.0 Hz, 1H), 5.64-5.52 (m, 2H), 4.21 (dd, J=11.2, 2.0 Hz, 1H), 4.11 (dd, J=10.8, 3.2 Hz, 1H), 3.81 (s, 3H), 3.79 (s, 3H), 2.38 (s, 3H), 2.24-2.17 (m, 1H), 1.87-1.79 (m, 1H), 1.17-1.10 (m, 1H), 0.67-0.59 (m, 1H).

Example 70: KAT6A Biochemical Assay

Inhibition of KAT6A enzymatic activity by test compounds was determined using a radiometric 384-well format assay. A 10-point serial dilution of the test compounds were conducted in DMSO and then a volume of 200 nL was transferred into 384-well assay plate by Echo (Labcyte). 10 µL of 2× enzyme solution (5 nM KAT6A (Active Motif) in assay buffer (50 mM Tris-HCl pH 8.0, 50 mM KCl, 0.1 mM EDTA, 5% glycerol, 1 mM DTT)) was dispensed into assay plate except for low control wells, in which 10 μL of assay buffer was transferred. The plate was incubated at room temperature for 15 min before addition of 10 μL of 2× [$^3$H]-acetyl coenzyme A (Ac-CoA) and substrate peptide mix solution (500 nM (KAT6A) [$^3$H]-Ac-CoA (PerkinElmer) and 800 nM (KAT6A) biotinylated H4(1-30) peptide (GL Biochem) in assay buffer) to each well to start reaction. The plate was incubated at room temperature for 60 min (KAT6A), and then the reaction was stopped by adding 10 μL of stop solution (cold Ac-CoA (Cayman) in 1× assay buffer). 25 μL of reaction in each well was transferred to Flashplate (PerkinElmer) and incubated for another 1 hour at room temperature. The plate was read on Microbeta and the inhibition percentage of each compound treated well was calculated based on the equation inh %=(Max−sample)/(Max−Min)*100 where Max is signal from high control wells with enzyme, and Min is signal from low control wells with assay buffer only. The inh % data were further fit in XL-Fit to obtain IC50 values using a 4-parameter logistic (4PL) sigmoidal curve model. KAT6A IC50s for Compounds 1 to 69 described in Examples 1 to 69 are shown in Table 2.

TABLE 2

| Compound | KAT6A IC$_{50}$ (nM) |
|---|---|
| 1 | C |
| 2 | B |
| 3 | A |
| 4 | B |
| 5 | B |
| 6 | B |
| 7 | C |
| 8 | B |
| 9 | B |
| 10 | A |
| 11 | A |
| 12 | B |
| 13 | D |
| 14 | A |
| 15 | A |
| 16 | B |
| 17 | A |
| 18 | A |
| 19 | A |
| 20 | A |
| 21 | A |
| 22 | B |
| 23 | A |
| 24 | A |
| 25 | A |
| 26 | B |
| 27 | C |
| 28 | B |
| 29 | C |
| 30 | B |
| 31 | A |
| 32 | B |
| 33 | B |
| 34 | A |
| 35 | A |
| 36 | A |
| 37 | A |
| 38 | C |
| 39 | B |
| 40 | C |
| 41 | B |
| 42 | B |
| 43 | B |
| 44 | B |
| 45 | B |
| 46 | A |
| 47 | A |
| 48 | A |

TABLE 2-continued

| Compound | KAT6A IC$_{50}$ (nM) |
|---|---|
| 49 | B |
| 50 | C |
| 51 | A |
| 52 | B |
| 53 | B |
| 54 | A |
| 55 | B |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | B |
| 68 | B |
| 69 | A |

IC50 (nM): 0 < A ≤ 10; 10 < B ≤ 100; 100 < C ≤ 1000; 1000 < D

Example 71: Kinetic Solubility

Kinetic solubility of test compounds was determined in 50 mM phosphate buffer (pH 7.4). 10 μL of 10 mM in DMSO of test and control compounds was added into lower chambers of whatman miniuniprep vials, respectively. 490 μL of 50 mM PB (pH 7.4) was added into lower chambers of the whatman miniuniprep vials, respectively. The solubility samples were vortexted for at least 2 minutes. The miniuniprep vials were shaken on a shaker for 24 hours at room temperature at the speed of 800 rpm and then centrifuged for 20 minutes (eg. 4000 rpm). The miniunipreps were compressed to prepare the filtrates for injection into HPLC system to calculate the concentration with standard curve. Kinetic solubility results of some example compounds are shown in Table 3.

TABLE 3

| Compound | Kinetic Solubility (μM) |
|---|---|
| 14 | 16.1 |
| 47 | 12.1 |
| 35 | 165 |
| 46 | 3.34 |
| 24 | 189 |

From data in Table 3, compounds (e.g., Compound 35) having X group as —O— have improved kinetic solubility than the otherwise identical compounds (e.g., Compound 47) having X group as carbon (i.e., —C(R$^6$)(R$^{6a}$)—).

Example 72: Permeability

Permeability of test compounds was determined in Caco-2 Assay. Caco-2 cells purchased from ATCC were seeded onto polyethylene membranes (PET) in 96-well Corning Insert plates at 1×105 cells/cm2, and refreshed medium every 4~5 days until to the 21st to 28th day for confluent cell monolayer formation. The transport buffer in the study was HBSS with 10.0 mM HEPES at pH 7.40±0.05. Test compound was tested at 2.00 μM bi-directionally in duplicate. Digoxin was tested at 10.0 μM bi-directionally in duplicate, while nadolol and metoprolol were tested at 2.00

μM in A to B direction in duplicate. Final DMSO concentration was adjusted to less than 1%. The plate was incubated for 2 hours in $CO_2$ incubator at 37±1° C., with 5% $CO_2$ at saturated humidity without shaking. And all samples after mixed with acetonitrile containing internal standard were centrifuged at 3200×g for 10 min. For nadolol and metoprolol, 200 μL supernatant solution was diluted with 600 μL ultra-pure water for LC-MS/MS analysis. For digoxin and test compounds, 200 μL supernatant solution was diluted with 200 μL ultra-pure water for LC-MS/MS analysis. Concentrations of test and control compounds in starting solution, donor solution, and receiver solution were quantified by LC-MS/MS methodologies, using peak area ratio of analyte/internal standard. After transport assay, lucifer yellow rejection assay was applied to determine the Caco-2 cell monolayer integrity. Permeability results of some example compounds are shown in Table 4.

TABLE 4

| Compound | Mean $P_{app}$ ($10^{-6}$ cm/s) A to B | Efflux Ratio |
|---|---|---|
| PF-9363* | 0.628 | 42.4 |
| 14 | 0.439 | 59.6 |
| 47 | 3.53 | 12.3 |
| 35 | 8.59 | 5.06 |
| 9 | 11.8 | 3.66 |
| 19 | 3.47 | 13.2 |
| 22 | 3.45 | 6.87 |
| 23 | 1.30 | 14.2 |
| 24 | 12.9 | 3.2 |
| 28 | 2.38 | 9.58 |
| 46 | 2.66 | 15.3 |
| 55 | 1.46 | 12.3 |
| 56 | 5.28 | 2.84 |
| 57 | 3.38 | 6.28 |
| 58 | 5.14 | 6.17 |
| 59 | 6.20 | 4.53 |
| 60 | 13.7 | 1.33 |
| 61 | 9.38 | 1.76 |
| 62 | 10.6 | 3.16 |
| 63 | 6.48 | 2.88 |
| 64 | 9.00 | 2.82 |
| 66 | 6.83 | 4.25 |
| 67 | 10.9 | 1.40 |
| 68 | 2.29 | 9.74 |

*PF-9363 is Example 98 in WO2020/254946 A1 having the following structure:

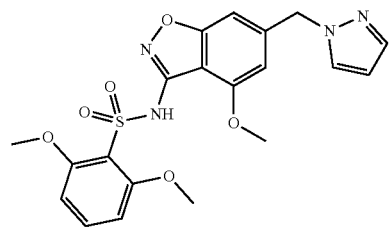 [SMILES: COc1cccc(OC)c1S(=O)(=O)Nc1noc2cc(Cn3cccn3)cc(OC)c12]

From data in Table 4, compound 35 having X group as —O— has improved permeability than the corresponding compound 47 having X group as carbon (i.e., —C($R^6$)($R^{6a}$)—). Our example compounds having X group as —O— or —S— have improved permeability than PF-9363.

What is claimed is:

1. A compound of Formula (Ia), or a pharmaceutically acceptable salt thereof:

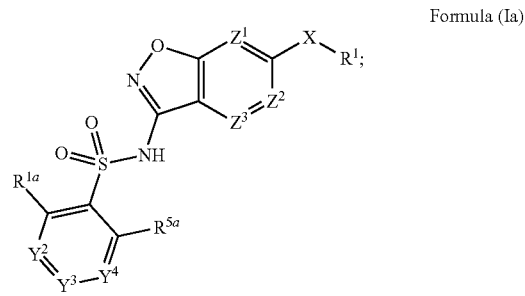

Formula (Ia)

wherein:
$Y^2$ is $CR^{2a}$ or N;
$Y^3$ is $CR^{3a}$;
$Y^4$ is $CR^{4a}$ or N;
$Z^1$ is $CR^{1b}$;
$Z^2$ is $CR^{2b}$;
$Z^3$ is $CR^{3b}$;
X is —O—;
$R^1$ is 5-membered heteroaryl;
$R^{1a}$, $R^{2a}$, $R^{3a}$, $R^{4a}$, $R^{5a}$, $R^{1b}$, $R^{2b}$, and $R^{3b}$ are independently selected from hydrogen, halogen, $C_{1-6}$alkyl, $C_{1-6}$haloalkyl, and —$OR^{10}$; and
each $R^{10}$ is independently selected from hydrogen, $C_{1-6}$alkyl, $C_{1-6}$haloalkyl, and $C_{3-6}$cycloalkyl.

2. The compound of claim 1, or a pharmaceutically acceptable salt thereof, wherein $R^{1a}$ and $R^{5a}$ are independently selected from hydrogen and —$OR^{10}$.

3. The compound of claim 2, or a pharmaceutically acceptable salt thereof, wherein $R^{1a}$ and $R^{5a}$ are —$OR^{10}$.

4. The compound of claim 3, or a pharmaceutically acceptable salt thereof, wherein $R^{10}$ is $C_{1-6}$alkyl.

5. The compound of claim 4, or a pharmaceutically acceptable salt thereof, wherein $R^{10}$ is —$CH_3$.

6. The compound of claim 1, or a pharmaceutically acceptable salt thereof, wherein:
$Y^2$ is N;
$Y^3$ is $CR^{3a}$; and
$Y^4$ is $CR^{4a}$.

7. The compound of claim 1, or a pharmaceutically acceptable salt thereof, wherein:
$Y^2$ is $CR^{2a}$;
$Y^3$ is $CR^{3a}$; and
$Y^4$ is $CR^{4a}$.

8. The compound of claim 1, or a pharmaceutically acceptable salt thereof, wherein $R^{3b}$ is —$OR^{10}$ and $R^{10}$ is $C_{1-6}$alkyl or $C_{1-6}$haloalkyl.

9. The compound of claim 1, or a pharmaceutically acceptable salt thereof, wherein $R^{2a}$, $R^{3a}$, $R^{4a}$, $R^{1b}$, and $R^{2b}$ are independently selected from hydrogen and $C_{1-6}$alkyl.

10. The compound of claim 1, or a pharmaceutically acceptable salt thereof, wherein $R^1$ is selected from

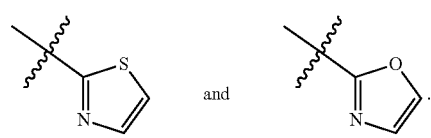 [SMILES: *c1nccs1 ; *c1ncco1]

11. The compound of claim 1, or a pharmaceutically acceptable salt thereof, wherein R¹ is

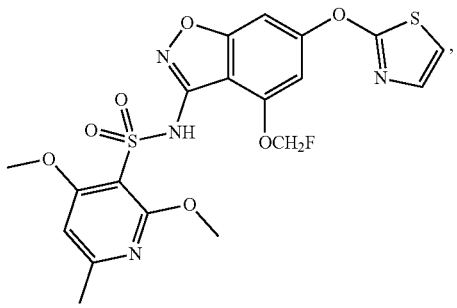

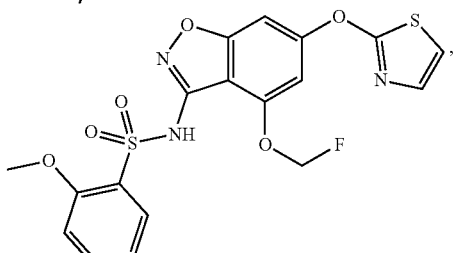

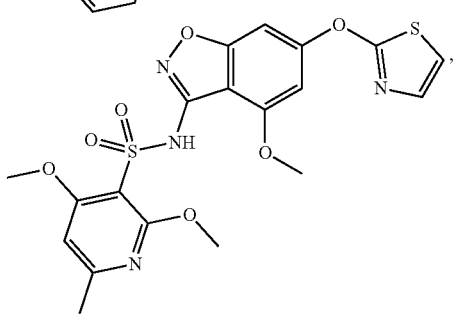

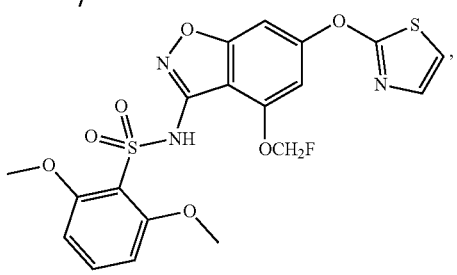

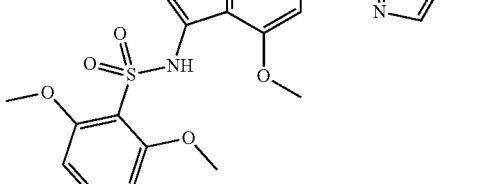 and

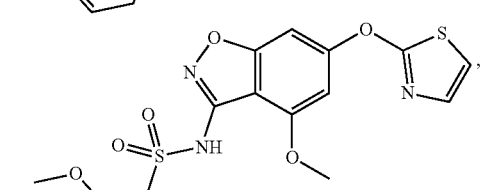

12. A compound of claim 1 selected from the group consisting of:

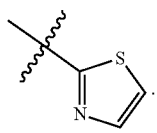

or a pharmaceutically acceptable salt thereof.

13. The compound of claim 12 that is

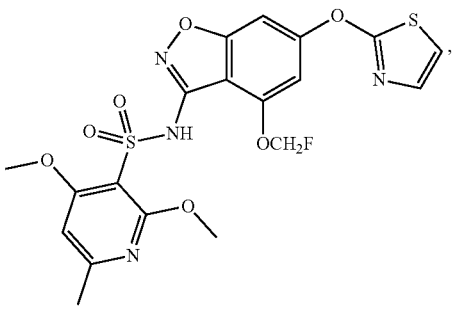

or a pharmaceutically acceptable salt thereof.

14. The compound of claim 12 that is

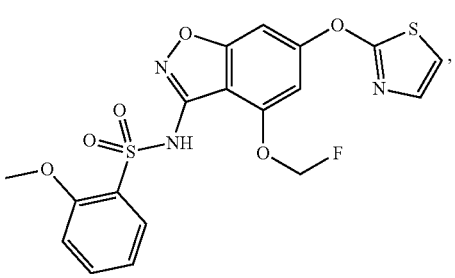 [SMILES: COc1ccccc1S(=O)(=O)Nc1noc2cc(Oc3nccs3)cc(OCF)c12]

or a pharmaceutically acceptable salt thereof.

15. The compound of claim 12 that is

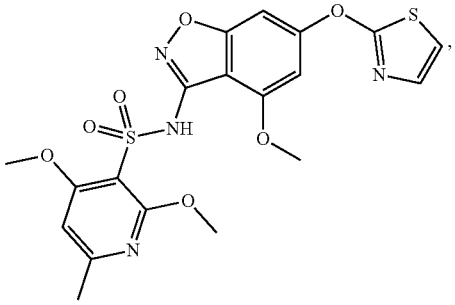 [SMILES: COc1cc(C)nc(OC)c1S(=O)(=O)Nc1noc2cc(Oc3nccs3)cc(OC)c12]

or a pharmaceutically acceptable salt thereof.

16. The compound of claim 12 that is

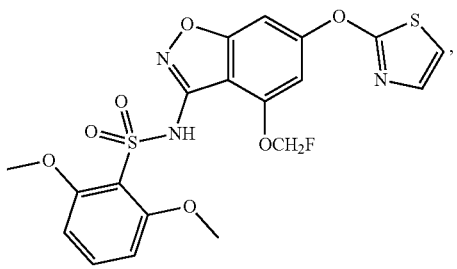

or a pharmaceutically acceptable salt thereof.

17. The compound of claim 12 that is

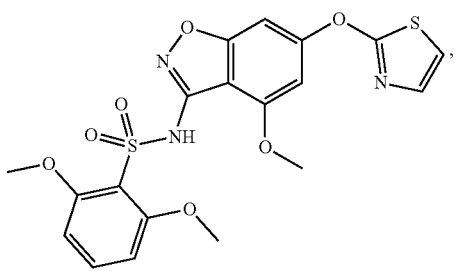 [SMILES: COc1cccc(OC)c1S(=O)(=O)Nc1noc2cc(Oc3nccs3)cc(OC)c12]

or a pharmaceutically acceptable salt thereof.

18. The compound of claim 12 that is

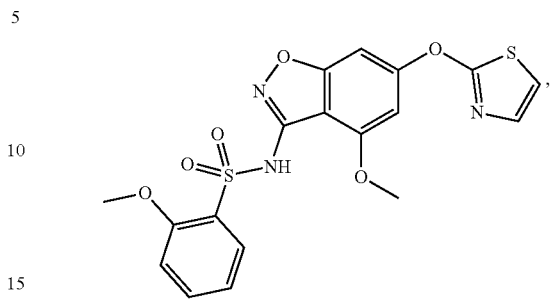

or a pharmaceutically acceptable salt thereof.

19. A pharmaceutical composition comprising a compound of claim 1, or a pharmaceutically acceptable salt thereof, and at least one pharmaceutically acceptable excipient.

20. A method of treating breast cancer in a mammal in need thereof, comprising administering to the mammal a compound of claim 1, or a pharmaceutically acceptable salt thereof.

* * * * *

UNITED STATES PATENT AND TRADEMARK OFFICE
CERTIFICATE OF CORRECTION

PATENT NO. : 12,091,406 B2
APPLICATION NO. : 18/507566
DATED : September 17, 2024
INVENTOR(S) : Xin Cheng et al.

It is certified that error appears in the above-identified patent and that said Letters Patent is hereby corrected as shown below:

In the Claims

Column 251, Claim 11, Lines 1-66:
Replace:
"11. The compound of claim 1, or a pharmaceutically acceptable salt thereof, wherein $R^1$ is

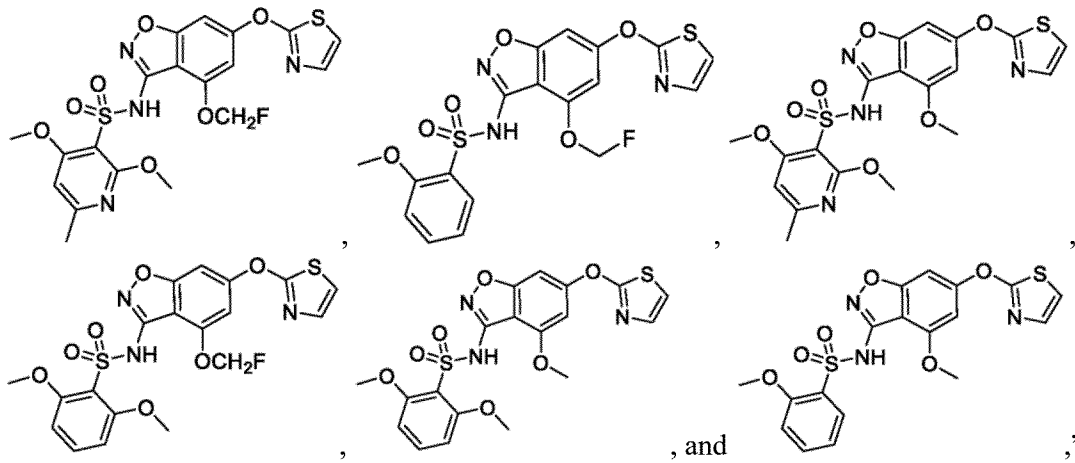

, and , ,"

with --11. The compound of claim 1, or a pharmaceutically acceptable salt thereof, wherein $R^1$ is

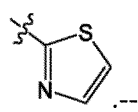 .--

Column 252, Claim 12, Lines 1-12:
Replace:
"12. A compound of claim 1 selected from the group consisting of:

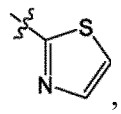 , or a pharmaceutically acceptable salt thereof."

Signed and Sealed this
Fifth Day of November, 2024

*Katherine Kelly Vidal*
Katherine Kelly Vidal
*Director of the United States Patent and Trademark Office* with --12. A compound of claim 1 selected from the group consisting of:
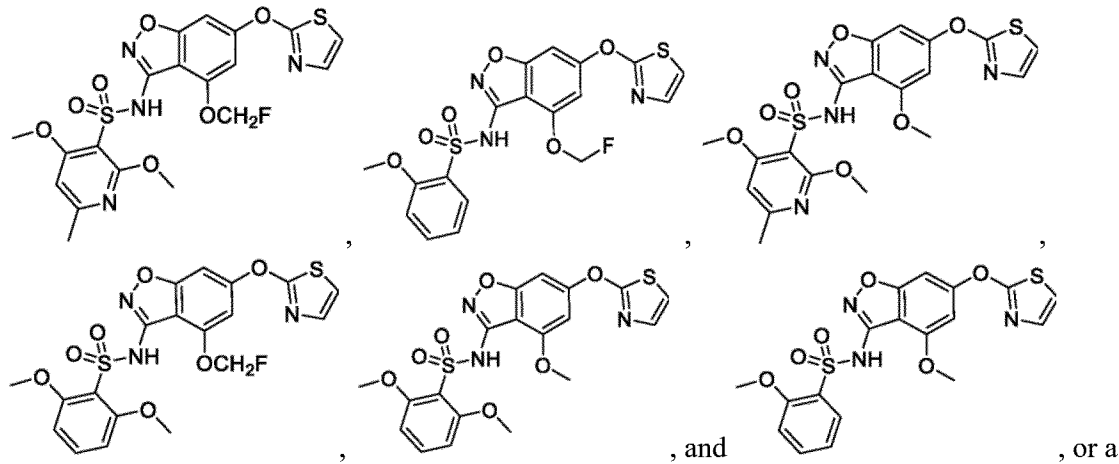
, and , or a pharmaceutically acceptable salt thereof.--